United States Patent
Pal et al.

(10) Patent No.: US 7,820,654 B2
(45) Date of Patent: Oct. 26, 2010

(54) PYRIMIDINE COMPOUNDS, PROCESS FOR THEIR PREPARATION AND COMPOSITIONS CONTAINING THEM

(75) Inventors: Manojit Pal, Andhra Pradesh (IN); Srinivas Kalleda, Andhra Pradesh (IN); Srinivas Padakanti, Andhra Pradesh (IN); Nalivela Kumara Swamy, Andhra Pradesh (IN); Koteswar Rao Yeleswarapu, Andhra Pradesh (IN); Christopher W. Alexander, Atlanta, GA (US); Ish Khanna, Alpharetta, GA (US); Javed Iqbal, Andhra Pradesh (IN); Sivaram Pillarisetti, Norcross, GA (US); Deepak Barange, Andhra Pradesh (IN)

(73) Assignee: Dr. Reddy's Laboratories Ltd., Ameerpet, Hyderabad (IN)

( * ) Notice: Subject to any disclaimer, the term of this patent is extended or adjusted under 35 U.S.C. 154(b) by 652 days.

(21) Appl. No.: 11/234,695

(22) Filed: Sep. 23, 2005

(65) Prior Publication Data
US 2006/0084645 A1 Apr. 20, 2006

Related U.S. Application Data

(60) Provisional application No. 60/612,374, filed on Sep. 23, 2004.

(51) Int. Cl.
A61K 31/54 (2006.01)
A61K 31/535 (2006.01)
A61K 31/497 (2006.01)
A61K 31/505 (2006.01)
C07D 417/00 (2006.01)
C07D 413/00 (2006.01)
C07D 403/00 (2006.01)
C07D 239/02 (2006.01)

(52) U.S. Cl. ............ 514/227.8; 514/235.5; 514/252.14; 514/275; 544/60; 544/122; 544/295; 544/329; 544/330

(58) Field of Classification Search .................. None
See application file for complete search history.

(56) References Cited

U.S. PATENT DOCUMENTS

| 5,728,704 | A | 3/1998 | Mylari et al. |
| 5,863,924 | A | 1/1999 | Berger et al. |
| 5,977,117 | A | 11/1999 | Chan et al. |
| 2004/0198728 | A1 | 10/2004 | Hong et al. |
| 2004/0204386 | A1 | 10/2004 | Bhatt et al. |

FOREIGN PATENT DOCUMENTS

| EP | 1321169 A1 | 6/2003 |
| WO | WO 97/25321 A2 | 7/1997 |
| WO | WO 01/62233 A2 | 8/2001 |
| WO | WO0172745 | * 10/2001 |
| WO | WO02/22608 | * 3/2002 |
| WO | WO 02/47690 A1 | 6/2002 |
| WO | WO02/088079 | * 11/2002 |
| WO | WO02/088080 | * 11/2002 |
| WO | WO 03/030909 A1 | 4/2003 |
| WO | WO 03/063794 A2 | 8/2003 |
| WO | WO 03/075828 A2 | 9/2003 |
| WO | WO 04/000820 A2 | 12/2003 |
| WO | WO 2004/014382 A1 | 2/2004 |
| WO | WO 2004/048365 A1 | 6/2004 |
| WO | WO 2004/089286 A2 | 10/2004 |
| WO | WO 2005/009977 A1 | 2/2005 |
| WO | WO 2005/012262 A1 | 2/2005 |
| WO | WO 2005/047268 A2 | 5/2005 |

OTHER PUBLICATIONS

Dorwald F. A. Side Reactions in Organic Synthesis, 2005, Wiley: VCH, Weinheim p. IX of Preface.*
Banker, et. al., Modern Pharmaceuticals, 3$^{rd}$ Ed. p. 596 (1996).*
Wolff, Manfred E. Burger's Medicinal Chemistry, 5th Ed. Part 1, pp. 975-977 (1995).*
Sedova, et. al., Khimiya Geterotsiklicheskikh Soedinenii (1977), (5), 678-83.*
Katritzky, et. al., Journal of the Chemical Society, Perkin Transactions 1: Organic and Bio-Organic Chemistry (1972-1999) (1982), (1), 153-8.*
Herschlag, D., et al., "Phosphoryl Transfer to Anionic Oxygen Nucleophiles. Nature of the Transition State and Electrostatic Repulsion," Journal of the American Chemical Society, 1989, 7587-7596, 111, American Chemical Society, Washington, D.C., U.S.A.
Jaeger, F., et al., "List of Rare Chemicals," Jul. 28, 2005, 25-31, Synchem Laborgemeinschaft OHG, Kassel, Germany.
http://www.chembuyersguide.com/partners/ischem.html, printed Jul. 28, 2005.
Farhanullah et al., Journal of Organic Chemistry, 2003, vol. 68, No. 7, pp. 2983-2985.

* cited by examiner

*Primary Examiner*—James O Wilson
*Assistant Examiner*—Jeffrey H Murray
(74) *Attorney, Agent, or Firm*—Nelson Mullins Riley & Scarborough, LLP

(57) ABSTRACT

The present invention is directed to a compounds, methods and compositions for making the compounds and methods of treating a variety of diseases and disease states including atherosclerosis, arthritis, restenosis, diabetic nephropathy, or dyslipidemia, or disease states mediated by the low expression of Perlecan, comprising the administration of new heterocyclic compounds, particularly substituted pyrimidines. The present invention is directed to novel compounds represented by the general formula:

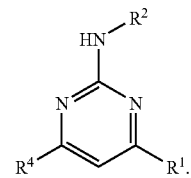

9 Claims, No Drawings

PYRIMIDINE COMPOUNDS, PROCESS FOR THEIR PREPARATION AND COMPOSITIONS CONTAINING THEM

RELATED APPLICATION DATA

This application claims the benefit of U.S. Provisional Patent Application Ser. No. 60/612,374, filed Sep. 23, 2004, which is incorporated herein by reference in its entirety.

FIELD OF THE INVENTION

The present invention relates to substituted pyrimidine compounds, methods and compositions for making and using substituted pyrimidine compounds, and methods for preventing or treating diseases in humans or animals employing such compounds and compositions.

BACKGROUND OF THE INVENTION

Novel compounds for new therapeutic interventions are needed for many areas of medicine and disease treatment. For example, chronic and acute inflammatory conditions form the basis for diseases affecting all organ systems including, but not limited to, asthma, acute inflammatory diseases, vascular inflammatory disease, chronic inflammation, atherosclerosis, angiopathy, myocarditis, nephritis, Crohn's disease, arthritis, type I and II diabetes and associated vascular pathologies. The incidence of these inflammatory conditions is on the rise in the population as a whole, with diabetes alone affecting 16 million people. Therefore, synthesis of novel compounds leads to new possibilities for discovery of novel therapeutic interventions.

While inflammation in and of itself is a normal immune response, chronic inflammation leads to complications and ongoing system damage due to the interactions of unknown cellular factors. In particular, chronic inflammation can cause endothelial damage resulting in vascular complications. Coronary artery, cerbrovascular and peripheral vascular disease resulting from atherosclerotic and thromboembolic macroangiopathy are the primary causes of mortality in chronic inflammatory diseases.

Many humans and animals have limited lifespans and lifestyles because of conditions relating to lifestyle choices, such as diet and exercise, or because of genetic predispositions to develop a disease. For example, vascular smooth muscle cell proliferation is a common consequence of endothelial injury and is believed to be an early pathogenetic event in the formation of atherosclerotic plaques or complications related to vascular injury or as a result surgical interventions. Abnormal vascular smooth muscle cell (SMC) proliferation is thought to contribute to the pathogenesis of vascular occlusive lesions, including arteriosclerosis, atherosclerosis, restenosis, and graft atherosclerosis after organ transplantation.

One disease that rapidly growing in the industrialized countries is the occurrence of diabetes and all of its attendant sequellae. One of the factors important in the damage associated with diabetes is the presence of glycated proteins. Glycated proteins and advanced glycation end products (AGE) contribute to cellular damage, particularly, diabetic tissue injury. One potential mechanism by which hyperglycemia can be linked to microangiopathies is through the process of non-enzymatic glycation of critical proteins. These are a highly reactive group of molecules whose interaction with specific receptors on the cell-surface which are thought to lead to pathogenic outcomes.

Another major area of unwanted cellular growth, that is unchecked by the body's regulatory systems, is cancer or oncological conditions. Many therapies have been used and are being used in an effort to restore health or at least stop the unwanted cell growth. Many times, therapeutic agents can have an effect individually, but often, therapeutic regimes require combinations of different pharmacological agents with treatments such as surgery or radiation.

There is a present need for treatments of chronic or acute diseases, such as atherosclerosis, unwanted cellular growth or cellular proliferation, diabetes, inflammatory conditions and vascular occlusive pathologic conditions. Because of occurrence is frequent, the currently available treatments are costly and the conditions are refractory to many pharmacological therapies. The mechanisms involved in the control or prevention of such diseases are not clear and there exists a need for preventive and therapeutic treatments of these and other diseases. Thus, what is presently needed are novel compounds that find utility in methods and compositions for treatment and prevention of chronic and acute diseases, to which the present invention is directed.

SUMMARY OF THE INVENTION

The present invention is directed to novel pyrimidines, novel compositions comprising pyrimidines, and novel methods employing such pyrimidines and compositions. Disclosed herein are methods for making pyrimidines, compositions comprising pyrimidines, and methods and compositions for using pyrimidines. The pyrimidine compounds and compositions comprising the compounds have utility in treatment of a variety of diseases.

In one aspect, compounds in accordance with the present invention, and compositions comprising these compounds, comprise nitrogen heterocyclic compounds of formula (II):

In one aspect, this disclosure provides for compounds and compositions comprising these compounds, wherein the compounds have the following formula (II):

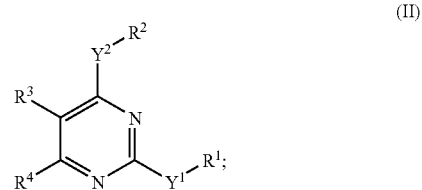

or a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ and $Y^2$, in each occurrence, are independently $>NR^5$, —(CH$_2$)n-, —(CH$_2$)p-(CH=CH)(CH$_2$)q-, $>CR^5R^6$, —(CH$_2$)p(C≡C)(CH$_2$)q-, —O—, >CO, —S—, >SO or $>SO_2$; wherein n, p, and q are independently an integer from 0 to 3;

$R^5$ and $R^6$, in each occurrence, are independently: 1) a substituted or an unsubstituted alkyl, aryl, alkoxyalkyl, heteroaryl, cycloalkyl, or heterocyclyl, any of which having up to about 10 carbon atoms; wherein any heteroaryl or heterocyclyl comprises at least one heteroatom or heterogroup selected from —O—, >N—, —S—, $>SO_2$, or >CO; or 2) hydrogen;

wherein when $Y^1$ or $Y^2$ is independently $>NR^5$;
1) the corresponding $R^z$, wherein z is 1 or 2, in each occurrence is independently selected from: a) a substituted or an unsubstituted alkyl, aryl, alkoxyalkyl, cycloalkyl, —$COR^9$, aryl, aralkyl, heterocyclyl or heteroaryl comprising at least one heteroatom or heterogroup selected from —O—, >N—, —S—, >$SO_2$, or >CO; any of which having up to about 10 carbon atoms; or b) hydrogen; or
2) the corresponding $Y^zR^z$, wherein z is 1 or 2, is a cyclic structure selected from: a) a substituted or an unsubstituted cyclic ring, which optionally comprises at least one additional heteroatom or heterogroup selected from —O—, >N—, —S—, >$SO_2$, or >CO; or b) a substituted or an unsubstituted morpholinyl, piperazinyl, thiomorpholinyl, pyrrolidinyl, or piperidinyl; any of which having up to about 10 carbon atoms; wherein the optional substituents on the cyclic $Y^zR^z$ structure are independently selected from at least one of: i) hydroxyl or halogen; or ii) alkyl, alkoxy, haloalkyl, cycloalkyl, aryl, or heteroaryl any of which having up to about 6 carbon atoms;
wherein when $Y^zR^z$ is piperazinyl, the piperazine nitrogen is optionally substituted by an alkyl, a cycloalkyl, an acyl, a haloalkyl, an alkoxyalkyl, $SO_2R^7$, $SO_2NR^7_2$, or $CO_2R^7$, wherein $R^7$ is independently selected from: a) an alkyl or an aryl having up to about 8 carbon atoms; or b) hydrogen;
wherein when $Y^1$ or $Y^2$ is independently —O— or —S—; the corresponding $R^z$, wherein z is 1 or 2, in each occurrence is independently selected from: 1) a substituted or an unsubstituted alkyl, aryl, alkoxyalkyl, cycloalkyl, —$COR^9$, aryl, aralkyl, heterocyclyl or heteroaryl comprising at least one heteroatom or heterogroup selected from —O—, >N—, —S—, >$SO_2$, or >CO; any of which having up to about 10 carbon atoms; or 2) hydrogen;
wherein when $Y^1$ or $Y^2$ is independently —$(CH_2)n$-, —$(CH_2)p(CH=CH)(CH_2)q$-, >$CR^5R^6$, —$(CH_2)p(C\equiv C)(CH_2)q$-, >CO, >SO or >$SO_2$; the corresponding $R^z$, wherein z is 1 or 2, in each occurrence is independently selected from: 1) a substituted or an unsubstituted alkyl, haloalkyl, cycloalkyl, —$COR^9$, aryl, aralkyl, alkoxy, alkenyl, alkynyl, alkoxyalkyl, aryl, —$CO_2R^5$, —$COR^5$, heterocyclyl or heteroaryl comprising at least one heteroatom or heterogroup selected from —O—, >N—, —S—, >$SO_2$, or >CO; any of which having up to about 10 carbon atoms; or 2) hydrogen, halogen, cyano, or hydroxyl;
wherein $R^3$ and $R^4$, in each occurrence, are independently: 1) a substituted or an unsubstituted alkyl, alkenyl, alkynyl, alkoxy, cycloalkyl, haloalkyl, alkylthio, alkylsufonyl, aryl, —$CO_2R^5$,—$COR^5$,—$NR^5R^6$,—$SO_2NR^5R^6$,—$SO_3R^5$, heterocyclyl or heteroaryl comprising at least one heteroatom or heterogroup selected from —O—, >N—, —S—, >$SO_2$, or >CO; any of which having up to about 10 carbon atoms; 2) hydrogen; halogen; hydroxyl; or cyano; or 3) $Y^1R^1$;
wherein any of $R^1$, $R^2$, $R^5$, or $R^6$ is optionally substituted with at least one group independently selected from: 1) alkyl, alkoxy, alkylthio, haloalkyl, haloalkoxy, cycloalkyl, aryl, heteroaryl, heterocyclyl, $N(R^8)_2$, —$COR^9$, —$OCOR^9$, —$CON(R^8)_2$, —$(CH_2)_b$—$CO_2R^8$ wherein b is an integer from 0 to 3, —$SO_2R^9$, —$OCO(CH_2)_bCOOR^{10}$, —$NHSO_2R^9$ or —$SO_2N(R^8)_2$, any of which having up to about 10 carbon atoms; or 2) hydrogen, halogen, hydroxyl, or cyano;
wherein $R^8$, in each occurrence, is independently: 1) an alkyl, a haloalkyl, or an aryl having up to about 6 carbon atoms; or 2) hydrogen;
wherein $R^9$, in each occurrence, is independently an alkyl, a haloalkyl, an aryl, or a heteroaryl having up to about 8 carbon atoms $R^9$ is optionally substituted with halogen, hydroxyl, alkyl, alkoxy, carboxylic acid or its esters; and
wherein any of $R^3$ or $R^4$ is optionally substituted with at least one group independently selected from halogen, hydroxyl, alkyl, alkoxy, haloalkyl, cycloalkyl, aryl, heteroaryl, heterocyclyl, alkenyl, alkynyl, —$COR^{10}$, —$CO_2R^{10}$, —$CON(R^{10})_2$, —$SR^{10}$, —$SO_2R^{10}$, —$SO_2N(R^{10})_2$, or —$N(R^{10})_2$, any of which having up to about 10 carbon atoms; and
wherein $R^{10}$, in each occurrence, is independently: 1) an alkyl or an aryl having up to about 6 carbon atoms; or hydrogen.

In another aspect, compounds in accordance with the present invention, and compositions comprising these compounds, comprise nitrogen heterocyclic compounds of formula (II):

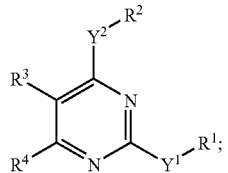

(II-α)

or a salt, including a pharmaceutically acceptable or a non-pharmaceutically acceptable salt, a prodrug, a diastereomeric mixture, an enantiomer, a tautomer, or a racemic mixture thereof;

$Y^1$ and $Y^2$, in each occurrence, are independently represents —O—, —S—, >$NR^5$, —$(CH_2)n$-, —$(CH_2)p(C\equiv C)(CH_2)q$-, wherein n, p, and q are independently represent 0; The corresponding $R^z$, wherein z is 1 or 2, in each occurrence is independently selected from: a) a substituted or an unsubstituted alkyl, alkoxyalkyl, cycloalkyl, —$COR^9$, aryl, aralkyl, heterocyclyl or heteroaryl comprising at least one heteroatom or heterogroup selected from —O—, >N—, —S—, >CO or >$SO_2$, or b) hydrogen;

$R^5$ is hydrogen or alkyl;

$R^3$ is hydrogen;

$R^4$ is a substituted or an unsubstituted alkyl, aryl, heterocyclyl or heteroaryl comprising at least one heteroatom or heterogroup selected from —O—, >N—, —S—, or >CO, or 2) hydrogen, halogen, hydroxyl;

$R^1$ and $R^2$ are optionally substituted with at least one group independently selected from: 1) alkyl, alkoxy, haloalkyl, haloalkoxy, —$COR^9$, —$OCOR^9$, —$CON(R^8)_2$, —$(CH_2)_bCO_2R^8$, —$OCO(CH_2)_bCOOR^{10}$, wherein b is an integer from 0 to 3, —$SO_2R^9$, —$NHSO_2R^9$, or —$SO_2N(R^8)_2$, or 2) hydrogen, halogen or hydroxyl;

$R^8$, in each occurrence, is independently: 1) an alkyl, a haloalkyl, or an aryl having up to about 6 carbon atoms, or 2) hydrogen;

$R^9$, in each occurrence, is independently an alkyl, a haloalkyl, an aryl, or a heteroaryl. $R^9$ is optionally substituted with halogen, hydroxyl, alkyl, alkoxy, carboxylic acid or its esters;

$R^4$ is optionally substituted with at least one group independently selected from halogen, hydroxyl, alkyl, alkoxy, —$COR^{10}$, —$SR^{10}$, —$SO_2R^{10}$, —$SO_2N(R^{10})_2$, or —$N(R^{10})_2$; and $R^{10}$, in each occurrence, is independently hydrogen, an alkyl, an aryl, heteroaryl or heterocyclyl.

The present invention is directed to methods and compositions comprising compounds that have utility in treatment of pathological conditions. One aspect of the present invention comprises pyrimidines and compositions comprising pyrimidines in methods for treating diseases related to unwanted cellular proliferation. Vascular diseases, such as cardiovascular diseases, organ transplant sequellae, vascular occlusive conditions including, but not limited to, neointimal hyperplasia, restenosis, transplant vasculopathy, cardiac allograft vasculopathy, atherosclerosis, and arteriosclerosis, are caused by or have collateral damage due to unwanted cellular proliferation, such as smooth muscle cell (SMC) hyperplasia. At least one activity of one or more of these compounds is that the compound has the activity of affecting the synthesis of proteoglycans including induction and synthesis of proteoglycans and active fragments of proteoglycans. Methods comprise administration of compositions comprising compounds that have at least the activity of affecting cellular proliferation and affecting proteoglycan synthesis and activity. Further, the pyrimidines and compositions comprising pyrimidines disclosed herein can be employed to prevent or treat the aforementioned diseases.

The present invention also comprises methods and compositions comprising pyrimidines described herein that have an activity associated with modulation of glycosidase enzymes and thus, affecting the substrates for such enzymes. Glycosidase enzymes and their activity with their substrates, such as proteoglycans or glycated proteins, are aspects of a variety of diseases such as vascular conditions, proteoglycan-associated diseases, kidney disease, autoimmune disease and inflammatory diseases. Pyrimidines described herein that have an activity that affects the concentrations of substrates of glycosidase enzymes are used in methods of treatment of such vascular, inflammatory, metastatic and systemic diseases.

Another aspect of the present invention comprises methods and compositions comprising pyrimidines of the present invention for the treatment and prevention of conditions or diseases that have as an aspect of the disease or condition, inflammation. An aspect of the present invention is directed to methods and compositions comprising pyrimidines that are effective in inhibiting inflammation, particularly inflammation associated with the accumulation or presence of glycated proteins or AGE. Methods of treatment comprise administration of compositions comprising pyrimidines having at least the activity of modulating inflammatory reactions that are components of biological conditions including, but not limited to, vascular complications of type I and type II diabetic-induced vasculopathies, other vasculopathies, microangiopathies, renal insufficiency, Alzheimer's syndrome, and inflammation-induced diseases such as atherosclerosis. An aspect of the present invention also comprises methods and compositions for the treatment of diseases, preconditions or pathologies associated with inflammatory cytokines and other inflammation related molecules.

The present invention also comprises pharmaceutical compositions comprising the compounds disclosed herein. Routes of administration and dosages of effective amounts of the compounds and pharmaceutical compositions are also disclosed. For example, the compounds of the present invention can be administered in combination with other pharmaceutical agents in a variety of protocols for effective treatment of disease.

In another aspect, the present invention relates to drug delivering or eluting medical devices that contain or are coated with at least one compound disclosed herein. The medical device suitable for use with the compounds of the present invention include, but are not limited to, stents and other medical devices that can provide a substrate for delivery of at least one compound.

DETAILED DESCRIPTION OF THE INVENTION

In accordance with the present invention, novel pyrimidine compounds and novel compositions comprising pyrimidine compounds are described herein. In one aspect, compounds in accordance with the present invention, and compositions comprising these compounds, comprise substituted pyrimidine compounds of formula (II):

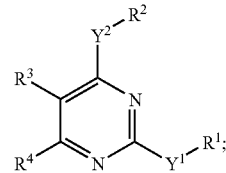

(II)

or a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ and $Y^2$, in each occurrence, are independently $>NR^5$, —$(CH_2)n$-, —$(CH_2)p$-$(CH=CH)(CH_2)q$-, $>CR^5R^6$, —$(CH_2)p(C\equiv C)(CH_2)q$-, —O—, >CO, —S—, >SO or $>SO_2$; wherein n, p, and q are independently an integer from 0 to 3;

$R^5$ and $R^6$, in each occurrence, are independently: 1) a substituted or an unsubstituted alkyl, aryl, alkoxyalkyl, heteroaryl, cycloalkyl, or heterocyclyl, any of which having up to about 10 carbon atoms; wherein any heteroaryl or heterocyclyl comprises at least one heteroatom or heterogroup selected from —O—, >N—, —S—, $>SO_2$, or >CO; or 2) hydrogen;

wherein when $Y^1$ or $Y^2$ is independently $>NR^5$;

1) the corresponding $R^z$, wherein z is 1 or 2, in each occurrence is independently selected from: a) a substituted or an unsubstituted alkyl, aryl, alkoxyalkyl, cycloalkyl, —$COR^9$, aryl, aralkyl, heterocyclyl or heteroaryl comprising at least one heteroatom or heterogroup selected from —O—, >N—, —S—, $>SO_2$, or >CO; any of which having up to about 10 carbon atoms; or b) hydrogen; or 2) the corresponding $Y^zR^z$, wherein z is 1 or 2, is a cyclic structure selected from: a) a substituted or an unsubstituted cyclic ring, which optionally comprises at least one additional heteroatom or heterogroup selected from —O—, >N—, —S—, $>SO_2$, or >CO; or b) a substituted or an unsubstituted morpholinyl, piperazinyl, thiomorpholinyl, pyrrolidinyl, or piperidinyl; any of which having up to about 10 carbon atoms; wherein the optional substituents on the cyclic $Y^zR^z$ structure are independently selected from at least one of: i) hydroxyl or halogen; or ii) alkyl, alkoxy, haloalkyl, cycloalkyl, aryl, or heteroaryl any of which having up to about 6 carbon atoms;

wherein when $Y^zR^z$ is piperazinyl, the piperazine nitrogen is optionally substituted by an alkyl, a cycloalkyl, an acyl, a haloalkyl, an alkoxyalkyl, $SO_2R^7$, $SO_2NR^7_2$, or $CO_2R^7$, wherein $R^7$ is independently selected from: a) an alkyl or an aryl having up to about 8 carbon atoms; or b) hydrogen;

wherein when $Y^1$ or $Y^2$ is independently —O— or —S—; the corresponding $R^z$, wherein z is 1 or 2, in each occurrence is independently selected from: 1) a substituted or an unsubstituted alkyl, aryl, alkoxyalkyl, cycloalkyl, —COR$^9$, aryl, aralkyl, heterocyclyl or heteroaryl comprising at least one heteroatom or heterogroup selected from —O—, >N—, —S—, >SO$_2$, or >CO; any of which having up to about 10 carbon atoms; or 2) hydrogen;

wherein when $Y^1$ or $Y^2$ is independently —(CH$_2$)n-, —(CH$_2$)p(CH=CH)(CH$_2$)q-, >CR$^5$R$^6$, —(CH$_2$)p(C≡C)(CH$_2$)q-, >CO, >SO or >SO$_2$; the corresponding $R^z$, wherein z is 1 or 2, in each occurrence is independently selected from: 1) a substituted or an unsubstituted alkyl, haloalkyl, cycloalkyl, —COR$^9$, aryl, aralkyl, alkoxy, alkenyl, alkynyl, alkoxyalkyl, aryl, —CO$_2$R$^5$, —COR$^5$, heterocyclyl or heteroaryl comprising at least one heteroatom or heterogroup selected from —O—, >N—, —S—, >SO$_2$, or >CO; any of which having up to about 10 carbon atoms; or 2) hydrogen, halogen, cyano, or hydroxyl;

wherein $R^3$ and $R^4$, in each occurrence, are independently: 1) a substituted or an unsubstituted alkyl, alkenyl, alkynyl, alkoxy, cycloalkyl, haloalkyl, alkylthio, alkylsufonyl, aryl, —CO$_2$R$^5$, —COR$^5$, —NR$^5$R$^6$, —SO$_2$NR$^5$R$^6$, —SO$_3$R, heterocyclyl or heteroaryl comprising at least one heteroatom or heterogroup selected from —O—, >N—, —S—, >SO$_2$, or >CO; any of which having up to about 10 carbon atoms; 2) hydrogen; halogen; hydroxyl; or cyano; or 3) $Y^1R^1$;

wherein any of $R^1$, $R^2$, $R^5$, or $R^6$ is optionally substituted with at least one group independently selected from: 1) alkyl, alkoxy, alkylthio, haloalkyl, haloalkoxy, cycloalkyl, aryl, heteroaryl, heterocyclyl, N(R$^8$)$_2$, —COR$^9$, —OCOR$^9$, —CON(R$^8$)$_2$, —(CH$_2$)$_b$—CO$_2$R$^8$ wherein b is an integer from 0 to 3, —SO$_2$R$^9$, —OCO(CH$_2$)$_b$COOR$^{10}$, —NHSO$_2$R$^9$ or —SO$_2$N(R$^8$)$_2$, any of which having up to about 10 carbon atoms; or 2) hydrogen, halogen, hydroxyl, or cyano;

wherein $R^8$, in each occurrence, is independently: 1) an alkyl, a haloalkyl, or an aryl having up to about 6 carbon atoms; or 2) hydrogen;

wherein $R^9$, in each occurrence, is independently an alkyl, a haloalkyl, an aryl, or a heteroaryl having up to about 8 carbon atoms $R^9$ is optionally substituted with halogen, hydroxyl, alkyl, alkoxy, carboxylic acid or its esters; and wherein any of $R^3$ or $R^4$ is optionally substituted with at least one group independently selected from halogen, hydroxyl, alkyl, alkoxy, haloalkyl, cycloalkyl, aryl, heteroaryl, heterocyclyl, alkenyl, alkynyl, —COR$^{10}$, —CO$_2$R$^{10}$, —CON(R$^{10}$)$_2$, —SR$^{10}$, —SO$_2$R$^{10}$, —SO$_2$N(R$^{10}$)$_2$, or —N(R$^{10}$)$_2$, any of which having up to about 10 carbon atoms; and wherein $R^{10}$, in each occurrence, is independently: 1) an alkyl or an aryl having up to about 6 carbon atoms; or hydrogen.

In another aspect, this disclosure provides for compounds and compositions comprising these compounds, wherein the compounds have the following formula (IIi):

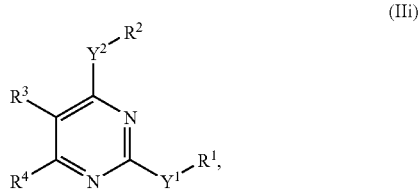

(IIi)

or a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ and $Y^2$, in each occurrence, are independently >NR$^5$, —(CH$_2$)n- wherein n is 0 or 1, —S—, —O—, >CO, or >SO$_2$;

$R^5$, in each occurrence, is independently: 1) a substituted or an unsubstituted alkyl, aryl, alkoxyalkyl, heteroaryl, cycloalkyl, or heterocyclyl, any of which having up to about 10 carbon atoms; wherein any heteroaryl or heterocyclyl comprises at least one heteroatom or heterogroup selected from —O—, >N—, —S—, >SO$_2$, or >CO; or 2) hydrogen;

wherein when $Y^1$ or $Y^2$ is independently >NR$^5$;

1) the corresponding $R^z$, wherein z is 1 or 2, in each occurrence is independently selected from: a) a substituted or an unsubstituted alkyl, aryl, alkoxyalkyl, cycloalkyl, —COR$^9$, aryl, aralkyl, heterocyclyl or heteroaryl comprising at least one heteroatom or heterogroup selected from —O—, >N—, —S—, >SO$_2$, or >CO; any of which having up to about 10 carbon atoms; or b) hydrogen; or 2) the corresponding $Y^zR^z$, wherein z is 1 or 2, is selected from a morpholinyl, a piperazinyl, or a piperidinyl; any of which having up to about 10 carbon atoms, wherein when $Y^zR^z$ is piperazinyl, the piperazine nitrogen is optionally substituted by an alkyl, a cycloalkyl, an acyl, a haloalkyl, an alkoxyalkyl, SO$_2$R$^7$, SO$_2$NR$^7_2$, or CO$_2$R$^7$, wherein $R^7$ is independently selected from: a) an alkyl or an aryl having up to about 8 carbon atoms; or b) hydrogen;

wherein when $Y^1$ or $Y^2$ is independently —O— or —S—; the corresponding $R^z$, wherein z is 1 or 2, in each occurrence is independently selected from: 1) a substituted or an unsubstituted alkyl, aryl, alkoxyalkyl, cycloalkyl, —COR$^9$, aryl, aralkyl, heterocyclyl or heteroaryl comprising at least one heteroatom or heterogroup selected from —O—, >N—, —S—, >SO$_2$, or >CO; any of which having up to about 10 carbon atoms; or 2) hydrogen;

wherein when $Y^1$ or $Y^2$ is independently —(CH$_2$)n-, >CO, or >SO$_2$; the corresponding $R^z$, wherein z is 1 or 2, in each occurrence is independently selected from: 1) a substituted or an unsubstituted alkyl, haloalkyl, cycloalkyl, —COR$^9$, aryl, aralkyl, alkoxy, alkenyl, alkynyl, alkoxyalkyl, aryl, —CO$_2$R$^5$, —COR$^5$, heterocyclyl or heteroaryl comprising at least one heteroatom or heterogroup selected from —O—, >N—, —S—, >SO$_2$, or >CO; any of which having up to about 10 carbon atoms; or 2) hydrogen, halogen, cyano, or hydroxyl;

wherein $R^3$ and $R^4$, in each occurrence, are independently: 1) haloalkyl having less than 3 carbon atoms; 2) alkyl, aryl, cycloalkyl, heteroaryl, or heterocyclyl having up to about 10 carbon atoms, wherein any heteroaryl or heterocyclyl comprises at least one heteroatom or heterogroup selected from —O—, >N—, —S—, >SO$_2$, or >CO; 3) hydrogen; or 4) $Y^1R^1$;

wherein any of $R^1$, $R^2$, or $R^5$ is optionally substituted with at least one group independently selected from: 1) alkyl, alkoxy, haloalkyl, N(R$^8$)$_2$, —SO$_2$R$^9$, or —SO$_2$N(R$^8$)$_2$, any of which having up to about 10 carbon atoms; or 2) hydrogen, halogen, or cyano;

wherein $R^8$, in each occurrence, is independently: 1) an alkyl, a haloalkyl, or an aryl having up to about 6 carbon atoms; or 2) hydrogen;

wherein $R^9$, in each occurrence, is independently an alkyl, a haloalkyl, an aryl, or a heteroaryl having up to about 8 carbon atoms; and wherein any of R³ or R⁴ is optionally substituted with at least one group independently selected from halogen, hydroxyl, alkyl, alkoxy, haloalkyl, cycloalkyl, aryl, heteroaryl, heterocyclyl, alkenyl, alkynyl, —COR¹⁰, —CO₂R¹⁰, —CON(R¹⁰)₂, —SR¹⁰, —SO₂R¹⁰, —SO₂N(R¹⁰)₂, or —N(R¹⁰)₂, any of which having up to about 10 carbon atoms; and wherein R¹⁰, in each occurrence, is independently: 1) an alkyl or an aryl having up to about 6 carbon atoms; or hydrogen.

In still another aspect, this disclosure provides for compounds and compositions comprising these compounds, wherein the compounds have the following formula (IIii):

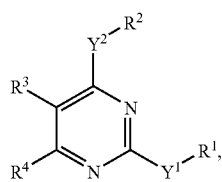

(IIii)

or a salt, including a pharmaceutically acceptable or a non-pharmaceutically acceptable salt, a prodrug, a diastereomeric miixture, an enantiomer, a tautomer, or a racemic mixture thereof;
wherein:
Y¹ and Y² are, in each occurrence, independently selected from >NR⁵, >(CH₂)ₙ wherein n is 0 or 1, —O—, >CO, or >SO₂;
R⁵, in each occurrence, is independently: 1) a substituted or an unsubstituted alkyl, aryl, alkoxyalkyl, heteroaryl, cycloalkyl, or heterocyclyl, any of which having up to about 10 carbon atoms; wherein any heteroaryl or heterocyclyl comprises at least one heteroatom or heterogroup selected from —O—, >N—, —S—, >SO₂, or >CO; or 2) hydrogen;
wherein when Y¹ or Y² is independently >NR⁵;
1) the corresponding Rᶻ, wherein z is 1 or 2, in each occurrence is independently selected from: a) a substituted or an unsubstituted alkyl, aryl, cycloalkyl, —COR⁹, aryl, aralkyl, heterocyclyl or heteroaryl comprising at least one heteroatom or heterogroup selected from —O—, >N—, —S—, >SO₂, or >CO; any of which having up to about 10 carbon atoms; or b) hydrogen; or
2) the corresponding YᶻRᶻ, wherein z is 1 or 2, is selected from a morpholinyl, a piperazinyl, or a piperidinyl; wherein when YᶻRᶻ is piperazinyl, the piperazine nitrogen is optionally substituted by an alkyl, a cycloalkyl, an acyl, a haloalkyl, an alkoxyalkyl, SO₂R⁷, SO₂NR⁷₂, or CO₂R⁷, wherein R⁷ is independently selected from: a) an alkyl or an aryl having up to about 8 carbon atoms; or b) hydrogen;
wherein when Y¹ or Y² is independently —O—; the corresponding Rᶻ, wherein z is 1 or 2, in each occurrence is independently selected from: 1) a substituted or an unsubstituted alkyl, aryl, cycloalkyl, —COR⁹, aryl, aralkyl, heterocyclyl or heteroaryl comprising at least one heteroatom or heterogroup selected from —O—, >N—, —S—, >SO₂, or >CO; any of which having up to about 10 carbon atoms; or 2) hydrogen; and
wherein when Y¹ or Y² is independently —(CH₂)n-, >CO, or >SO₂; the corresponding Rᶻ, wherein z is 1 or 2, in each occurrence is independently selected from: 1) a substituted or an unsubstituted alkyl, haloalkyl, cycloalkyl, —COR⁹, aryl, aralkyl, alkoxy, aryl, or heterocyclyl or heteroaryl comprising at least one heteroatom or heterogroup selected from —O—, >N—, —S—, >SO₂, or >CO; any of which having up to about 10 carbon atoms; or 2) hydrogen, halogen, cyano, or hydroxyl;
wherein R³ and R⁴ in each occurrence, are independently: 1) haloalkyl having less than 3 carbon atoms; 2) alkyl, aryl, cycloalkyl, heteroaryl, or heterocyclyl having up to about 10 carbon atoms, wherein any heteroaryl or heterocyclyl comprises at least one heteroatom or heterogroup selected from —O—, >N—, —S—, >SO₂, or >CO; 3) hydrogen; or 4) Y¹R¹;
wherein any of R¹, R², or R⁵ is optionally substituted with at least one group independently selected from: 1) alkyl, alkoxy, haloalkyl, N(R⁸)₂, —SO₂R⁹, or —SO₂N(R⁸)₂, any of which having up to about 10 carbon atoms; 2) hydrogen, halogen, or cyano;
wherein any of R³ or R⁴ is optionally substituted with at least one group independently selected from halogen, hydroxyl, alkyl, haloalkyl, —SO₂R¹⁰, —SR¹⁰, —SO₂N(R¹⁰)₂, or —N(R¹⁰)₂, any of which having up to about 10 carbon atoms; and
wherein R⁸, R⁹, and R¹⁰, in each occurrence, are independently: 1) an alkyl or an aryl having up to about 6 carbon atoms; or 2) hydrogen.

In yet another aspect, the present invention provides for compounds and compositions comprising these compounds, wherein the compounds have the following formula (IIiii):

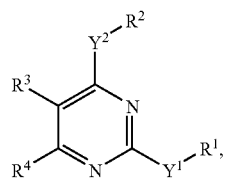

(IIiii)

or a salt, including a pharmaceutically acceptable or a non-pharmaceutically acceptable salt, a prodrug, a diastereomeric mixture, an enantiomer, a tautomer, or a racemic mixture thereof;
wherein:
Y¹ and Y² are, in each occurrence, independently >NR⁵, >(CH₂)n wherein n is 0 or 1, or —O—;
R⁵, in each occurrence, is independently: 1) an alkyl, an aryl, an alkoxyalkyl, a heteroaryl, a cycloalkyl, or a heterocyclyl, any of which having up to about 10 carbon atoms; wherein any heteroaryl or heterocyclyl comprises at least one heteroatom or heterogroup selected from —O—, >N—, —S—, >SO₂, or >CO; or 2) hydrogen;
wherein when Y¹ or Y² is independently >NR⁵;
1) the corresponding Rᶻ, wherein z is 1 or 2, in each occurrence is independently selected from: a) a substituted or an unsubstituted alkyl, aryl, cycloalkyl, —COR⁹, aryl, aralkyl, or heterocyclyl or heteroaryl comprising at least one heteroatom or heterogroup selected from —O—, >N—, —S—, >SO₂, or >CO; any of which having up to about 10 carbon atoms; or b) hydrogen; or
2) the corresponding YᶻRᶻ, wherein z is 1 or 2, is selected from a morpholinyl, a piperazinyl, or a piperidinyl; wherein when YᶻRᶻ is piperazinyl, the piperazine nitrogen is optionally substituted by an alkyl, a cycloalkyl, an acyl, a haloalkyl, an alkoxyalkyl, SO₂R⁷, SO₂NR⁷₂, or CO$_2$R$^7$, wherein R$^7$ is independently selected from: a) an alkyl or an aryl having up to about 8 carbon atoms; or b) hydrogen;

wherein when Y$^1$ or Y$^2$ is independently —O—; the corresponding R$^z$, wherein z is 1 or 2, in each occurrence is independently selected from: 1) a substituted or an unsubstituted alkyl, aryl, cycloalkyl, —COR$^9$, aryl, aralkyl, heterocyclyl or heteroaryl comprising at least one heteroatom or heterogroup selected from —O—, >N—, —S—, >SO$_2$, or >CO; any of which having up to about 10 carbon atoms; or 2) hydrogen; and wherein when Y$^1$ or Y$^2$ is independently —(CH$_2$)n-; the corresponding R$^z$, wherein z is 1 or 2, in each occurrence is independently selected from: 1) a substituted or an unsubstituted alkyl, haloalkyl, cycloalkyl, —COR$^9$, aryl, aralkyl, alkoxy, aryl, or heterocyclyl or heteroaryl comprising at least one heteroatom or heterogroup selected from —O—, >N—, —S—, >SO$_2$, or >CO; any of which having up to about 10 carbon atoms; or 2) hydrogen, halogen, cyano, or hydroxyl;

wherein any of R$^1$, R$^2$, or R$^5$ is optionally substituted with at least one group independently selected from: 1) alkyl, alkoxy, haloalkyl, N(R$^8$)$_2$, —SO$_2$R$^9$, or —SO$_2$N(R$^8$)$_2$, any of which having up to about 10 carbon atoms; or 2) hydrogen, halogen, or cyano;

wherein R$^8$ and R$^9$, in each occurrence, are independently: 1) an alkyl or an aryl having up to about 6 carbon atoms; or 2) hydrogen;

wherein R$^3$ is hydrogen or halogen; and wherein R$^4$, in each occurrence, is independently: 1) haloalkyl having less than 3 carbon atoms; 2) alkyl, aryl, —COR$^5$, cycloalkyl, heteroaryl, or heterocyclyl having up to about 10 carbon atoms, wherein any heteroaryl or heterocyclyl comprises at least one heteroatom or heterogroup selected from —O—, >N—, —S—, >SO$_2$, or >CO; 3) hydrogen; or 4) Y$^1$R$^1$.

In still another aspect, the present invention provides for compounds and compositions comprising these compounds, wherein the compounds have the following formula (IIiv):

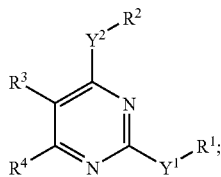

(IIiv)

or a salt, including a pharmaceutically acceptable or a non-pharmaceutically acceptable salt, a prodrug, a diastereomeric mixture, an enantiomer, a tautomer, or a racemic mixture thereof;

wherein:

Y$^1$ and Y$^2$ are, in each occurrence, independently >NR$^5$, >(CH$_2$), wherein n is 0 or 1,or —O—;

R$^5$, in each occurrence, is independently: 1) an alkyl, an aryl, a cycloalkyl, or a heteroaryl or a heterocyclyl comprising at least one heteroatom or heterogroup selected from —O—, >N—, —S—, >SO$_2$, or >CO; any of which having up to about 10 carbon atoms; or 2) hydrogen;

wherein when Y$^1$ or Y$^2$ is independently >NR$^5$;

1) the corresponding R$^z$, wherein z is 1 or 2, in each occurrence is independently selected from: a) a substituted or an unsubstituted alkyl, aryl, cycloalkyl, —COR$^9$, aryl, aralkyl, heterocyclyl or heteroaryl comprising at least one heteroatom or heterogroup selected from —O—, >N—, —S—, >SO$_2$, or >CO; any of which having up to about 10 carbon atoms; or b) hydrogen; or 2) the corresponding Y$^z$R$^z$, wherein z is 1 or 2, is selected from a morpholinyl, a piperazinyl, or a piperidinyl; wherein when Y$^z$R$^z$ is piperazinyl, the piperazine nitrogen is optionally substituted by an alkyl, a cycloalkyl, a haloalkyl, an alkoxyalkyl, SO$_2$R$^7$, SO$_2$NR$^7_2$, or CO$_2$R$^7$, wherein R$^7$ is independently selected from: a) an alkyl or an aryl having up to about 8 carbon atoms; or b) hydrogen;

wherein when y$^1$ or Y$^2$ is independently —(CH$_2$)n- or —O—; the corresponding R$^z$, wherein z is 1 or 2, in each occurrence is independently selected from: 1) a substituted or an unsubstituted alkyl, aryl, cycloalkyl, —COR$^9$, aryl, aralkyl, heterocyclyl or heteroaryl comprising at least one heteroatom or heterogroup selected from —O—, >N—, —S—, >SO$_2$, or >CO; any of which having up to about 10 carbon atoms; or 2) hydrogen;

wherein any of R$^1$, R$^2$, or R$^5$ is optionally substituted with at least one group independently selected from: 1) alkyl, alkoxy, haloalkyl, N(R$^8$)$_2$, —SO$_2$R$^9$, or —SO$_2$N(R$^8$)$_2$, any of which having up to about 10 carbon atoms; or 2) hydrogen, halogen, or cyano;

wherein R$^8$ and R$^9$, in each occurrence, are independently: 1) an alkyl or an aryl having up to about 6 carbon atoms; or 2) hydrogen; and wherein R$^3$ and R$^4$ are, in each occurrence, independently: 1) R$^1$ or 2) Y$^1$R$^1$.

Another aspect of the present invention encompasses compounds and compositions comprising these compounds, wherein the compounds have the following formula (IIv):

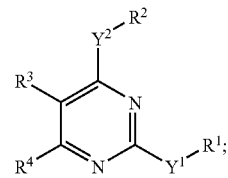

(IIv)

or a salt, including a pharmaceutically acceptable or a non-pharmaceutically acceptable salt, a prodrug, a diastereomeric mixture, an enantiomer, a tautomer, or a racemic mixture thereof;

wherein:

Y$^1$ and Y$^2$ are, in each occurrence, independently >NR$^5$, >CH$_2$, or —O—;

R$^5$, in each occurrence, is independently: 1) an alkyl, an aryl, a cycloalkyl, or a heteroaryl or a heterocyclyl comprising at least one heteroatom or heterogroup selected from —O—, >N—, —S—, >SO$_2$, or >CO; any of which having up to about 10 carbon atoms; or 2) hydrogen;

wherein when Y$^1$ or Y$^2$ is independently >NR$^5$;

1) the corresponding R$^z$, wherein z is 1 or 2, in each occurrence is independently selected from an alkyl, an aryl, a cycloalkyl, —COR$^9$, aryl, aralkyl, a heterocyclyl or a heteroaryl comprising at least one heteroatom or heterogroup selected from —O—, >N—, —S—, >SO$_2$, or >CO; any of which having up to about 10 carbon atoms; or 2) the corresponding Y$^z$R$^z$, wherein z is 1 or 2, is selected from a morpholinyl, a piperazinyl, or a piperidinyl;

wherein when $Y^1$ or $Y^2$ is independently $>CH_2$ or —O—; the corresponding $R^z$, wherein z is 1 or 2, in each occurrence is independently selected from: 1) a substituted or an unsubstituted alkyl, aryl, cycloalkyl, —$COR^9$, aryl, aralkyl, heterocyclyl or heteroaryl comprising at least one heteroatom or heterogroup selected from —O—, >N—, —S—, >$SO_2$, or >CO; any of which having up to about 10 carbon atoms; or 2) hydrogen; and wherein $R^3$ and $R^4$, in each occurrence, are independently: 1) $R^1$ or 2) $Y^1R^1$.

In another aspect, this invention provides compounds and compositions comprising these compounds, wherein the compounds have the following formula (IIvi):

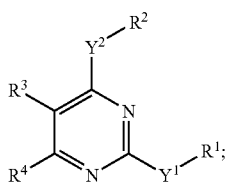

(IIvi)

or a salt, including a pharmaceutically acceptable or a non-pharmaceutically acceptable salt, a prodrug, a diastereomeric mixture, an enantiomer, a tautomer, or a racemic mixture thereof;
wherein:
one of $Y^z$, wherein z is 1 or 2, is >NH, and the other of $Y^z$, wherein z is 2 or 1, respectively, is >$(CH_2)_n$ wherein n is 0 or 1;

wherein when $Y^z$ is >$(CH_2)_n$, the corresponding $R^z$, wherein z is 2 or 1, is selected from a substituted or an unsubstituted: 1) aryl; or 2) heterocyclyl or heteroaryl comprising at least one heteroatom or heterogroup selected from —O—, >N—, —S—, >$SO_2$, or >CO; any of which having up to about 10 carbon atoms;

wherein when $Y^z$ is >NH, the corresponding $R^z$, wherein z is 1 or 2, is selected from a substituted or an unsubstituted: 1) aryl; or 2) heteroaryl comprising at least one heteroatom or heterogroup selected from —O—, >N—, —S—; any of which having up to about 10 carbon atoms;

wherein any of $R^1$ or $R^2$ is optionally substituted with at least one group independently selected from: 1) alkyl, alkoxy, haloalkyl, haloalkoxy, N($R^8$)$_2$, —$COR^9$, —$OCOR^9$, —CON($R^8$)$_2$, —$CO_2R^9$, —$SO_2R^9$, —$OCO(CH_2)_bCOOR^{10}$, —$NHSO_2R^9$ or —$SO_2N(R^8)_2$, any of which having up to about 10 carbon atoms; or 2) hydrogen, halogen, or cyano;

wherein $R^8$ and $R^9$, in each occurrence, are independently: 1) an alkyl or an aryl having up to about 6 carbon atoms; or 2) hydrogen; and $R^3$ is hydrogen; and
$R^4$ is $R^1$ or $Y^1R^1$.

In this aspect, the compound of formula (IIvi) above can have the following substituents:
when $Y^z$ is >NH, wherein z is 1 or 2, the corresponding $R^z$ can be phenyl, naphthyl, pyridyl, or benzoxazolyl; and
when $Y^z$ is >$(CH_2)_n$, wherein z is 2 or 1, respectively, the corresponding $R^z$ can be phenyl, naphthyl, benzoxazolyl, pyridyl, pyrazolyl, isoxazolyl, pyrazinyl, imidazopyridinyl, benzdioxolanyl, morpholinyl, piperazinyl, or piperidinyl.

In another aspect, this disclosure encompasses compounds and compositions comprising these compounds, wherein the compounds have the following formula (IIvii):

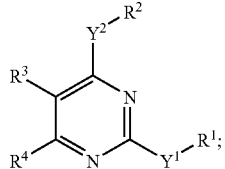

(IIvii)

or a salt, including a pharmaceutically acceptable or a non-pharmaceutically acceptable salt, a prodrug, a diastereomeric mixture, an enantiomer, a tautomer, or a racemic mixture thereof;
wherein:
$Y^1$ and $Y^2$ are, in each occurrence, independently >$(CH_2)n$ wherein n is 0 or 1;
wherein $R^1$ and $R^2$ are independently selected from a substituted or an unsubstituted: 1) aryl; or 2) heterocyclyl or heteroaryl comprising at least one heteroatom or heterogroup selected from —O—, >N—, —S—, >$SO_2$, or >CO; any of which having up to about 10 carbon atoms;

wherein any of $R^1$ or $R^2$ is optionally substituted with at least one group independently selected from: 1) alkyl, alkoxy, haloalkyl, haloalkoxy, N($R^8$)$_2$, —$COR^9$, —$OCOR^9$, —CON($R^8$)$_2$, —$CO_2R^9$, —$SO_2R^9$, —$OCO(CH_2)_bCOOR^{10}$, —$NHSO_2R^9$ or —$SO_2N(R^8)_2$, any of which having up to about 10 carbon atoms; or 2) hydrogen, halogen, or cyano;

wherein $R^8$ and $R^9$, in each occurrence, are independently: 1) an alkyl or an aryl having up to about 6 carbon atoms; or 2) hydrogen; and $R^3$ is hydrogen or halogen; and
$R^4$ is $R^1$ or $Y^1R^1$.

In this aspect, $R^1$ and $R^2$ of the formula (IIvii) can be independently phenyl, naphthyl, benzoxazolyl, pyridyl, pyrazolyl, isoxazolyl, pyrazinyl, imidazopyridinyl, benzdioxolanyl, morpholinyl, piperazinyl, or piperidinyl.

In another aspect, this disclosure further provides compounds, and compositions comprising the compounds, wherein the compounds have the following formula (IIviii):

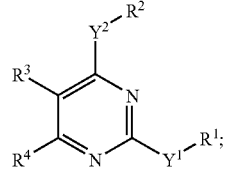

(IIviii)

or a salt, including a pharmaceutically acceptable or a non-pharmaceutically acceptable salt, a prodrug, a diastereomeric mixture, an enantiomer, a tautomer, or a racemic mixture thereof;
wherein:
$Y^1$ and $Y^2$, in each occurrence, are independently represents —O—, —S—, >$NR^5$, —$(CH_2)n$-, —$(CH_2)p(C \equiv C)(CH_2)q$-, wherein n, p, and q are independently represent 0; The corresponding $R^z$, wherein z is 1 or 2, in each occurrence is independently selected from: a) a substituted or an unsubstituted alkyl, alkoxyalkyl, cycloalkyl, —$COR^9$, aryl, aralkyl, heterocyclyl or heteroaryl comprising at least one heteroatom or heterogroup selected from —O—, >N—, —S—, >CO or >$SO_2$, or b) hydrogen;

$R^5$ is hydrogen or alkyl;

$R^3$ is hydrogen;

$R^4$ is a substituted or an unsubstituted alkyl, aryl, heterocyclyl or heteroaryl comprising at least one heteroatom or heterogroup selected from —O—, >N—, —S—, or >CO, or 2) hydrogen, halogen, hydroxyl;

$R^1$ and $R^2$ are optionally substituted with at least one group independently selected from: 1) alkyl, alkoxy, haloalkyl, haloalkoxy, —COR$^9$, —OCOR$^9$, —CON(R$^8$)$_2$, —(CH$_2$)$_b$CO$_2$R$^8$, —OCO(CH$_2$)$_b$COOR$^{10}$, wherein b is an integer from 0 to 3, —SO$_2$R$^9$, —NHSO$_2$R$^9$, or —SO$_2$N(R$^8$)$_2$, or 2) hydrogen, halogen or hydroxyl;

$R^8$, in each occurrence, is independently: 1) an alkyl, a haloalkyl, or an aryl having up to about 6 carbon atoms, or 2) hydrogen;

$R^9$, in each occurrence, is independently an alkyl, a haloalkyl, an aryl, or a heteroaryl. $R^9$ is optionally substituted with halogen, hydroxyl, alkyl, alkoxy, carboxylic acid or its esters;

$R^4$ is optionally substituted with at least one group independently selected from halogen, hydroxyl, alkyl, alkoxy, —COR$^{10}$, —SR$^{10}$, —SO$_2$R$^{10}$, —SO$_2$N(R$^{10}$)$_2$, or —N(R$^{10}$)$_2$; and $R^{10}$, in each occurrence, is independently hydrogen, an alkyl, an aryl, heteroaryl or heterocyclyl.

Further, in this aspect, the compound of formula (IIviii) above can have the following substituents:

$Y^1$ and $Y^2$, in each occurrence, can be independently >NR$^5$, —(CH$_2$)n-, —(CH$_2$)p-(C≡C)(CH$_2$)q-, wherein n, p, and q are independently represent 0; $R^1$ and $R^2$, in each occurrence is independently selected from a substituted or an unsubstituted cycloalkyl, aryl, heterocyclyl or heteroaryl comprising at least one heteroatom or heterogroup selected from —O—, >N—, —S— or >CO;

$R^5$ is hydrogen;

$R^3$ is hydrogen;

$R^4$ is a substituted or an unsubstituted aryl, heterocyclyl or heteroaryl comprising at least one heteroatom or heterogroup selected from —O—, >N—, —S—, or >CO;

$R^1$ and $R^2$ are optionally substituted with at least one group independently selected from: 1) alkyl, alkoxy, haloalkyl, haloalkoxy, —COR$^9$, —OCOR$^9$, —CON(R$^8$)$_2$, —(CH$_2$)$_b$CO$_2$R, —OCO(CH$_2$)$_b$COOR$^{10}$, wherein b is an integer from 0 to 3, —SO$_2$R$^9$, —NHSO$_2$R$^9$, or —SO$_2$N(R$^8$)$_2$; or 2) hydrogen, halogen or hydroxyl;

$R^8$, in each occurrence, is independently: 1) an alkyl, a haloalkyl, or an aryl having up to about 6 carbon atoms, or 2) hydrogen;

$R^9$, in each occurrence, is independently an alkyl, a haloalkyl, an aryl, or a heteroaryl. $R^9$ is optionally substituted with halogen, hydroxyl, alkyl, alkoxy, carboxylic acid or its esters;

$R^4$ is optionally substituted with at least one group independently selected from halogen, hydroxyl, alkyl, alkoxy, —COR$^{10}$, —SR$^{10}$, —SO$_2$R$^{10}$ or —SO$_2$N(R$^{10}$)$_2$; and $R^{10}$, in each occurrence, is independently hydrogen, an alkyl, an aryl or heterocyclyl.

In addition, in this aspect, the formula (IIviii) illustrated above can also have the following substitutents:

$Y^1$ and $Y^2$, in each occurrence, can independently represents —(CH$_2$)n-, wherein n is 0;

$R^1$ is a substituted or an unsubstituted aryl, heteroaryl or heterocycle comprising at least one heteroatom selected from —O—, >N— or —S—; where in the carbon atom of the said heterocycle or heteroaryl is connected to the carbon atom of the pyrimidine ring;

$R^2$ is a substituted or an unsubstituted nitrogen containing heterocyclyl, which may optionally further contain at least one more heteroatom selected from —O—, >N— or —S—, wherein the nitrogen atom of the said heterocycle is connected to the carbon atom of the pyrimidine ring;

$R^4$ is a substituted or an unsubstituted aryl or heteroaryl;

$R^1$ and $R^2$ are optionally substituted with at least one group independently selected from halogen, hydroxyl, alkoxy, haloalkyl, haloalkoxy;

$R^4$ is optionally substituted with at least one group independently selected from halogen, hydroxyl, alkyl, alkoxy or —SO$_2$R$^{10}$; and $R^{10}$ is an alkyl or an aryl having up to about 6 carbon atoms.

Further regarding this aspect of the present invention, the compound of formula (IIviii) illustrated above can also have the following substituents:

$Y^1$ and $Y^2$, in each occurrence, can be independently represents —(CH$_2$)n-, wherein n is 0;

$R^1$ is a substituted or an unsubstituted nitrogen containing heterocyclyl, which may optionally further contain at least one more heteroatom selected from —O—, >N— or —S—, wherein the nitrogen atom of the said heterocycle is connected to the carbon atom of the pyrimidine ring;

$R^2$ is a substituted or an unsubstituted aryl, heteroaryl or heterocyclyl comprising at least one heteroatom selected from —O—, >N— or —S—, wherein the carbon atom of the said heteroaryl or heterocycle is connected to the carbon atom of the pyrimidine ring;

$R^4$ is a substituted or an unsubstituted aryl or heteroaryl;

$R^1$ and $R^2$ are optionally substituted with at least one group independently selected from halogen, hydroxyl, alkyl, alkoxy, haloalkyl or haloalkoxy;

$R^4$ is optionally substituted with at least one group independently selected from halogen, hydroxyl, alkyl, alkoxy, or —SO$_2$R$^{10}$; and $R^{10}$ is an alkyl or an aryl.

Yet further to this aspect of the present invention, the compound of formula (IIviii) illustrated above can also have the following substituents:

$Y^1$ represents —(CH$_2$)n-, wherein n is 0;

$Y^2$ represents NH;

$R^1$ and $R^2$, in each occurrence is independently selected from a substituted or an unsubstituted aryl or heteroaryl;

$R^4$ is a substituted or an unsubstituted nitrogen containing heterocyclyl, which may optionally further contain at least one more heteroatom selected from —O—, >N— or —S—, wherein the nitrogen atom of the heterocycle ring is connected to the carbon atom of the pyrimidine ring;

$R^1$ and $R^2$ are optionally substituted with at least one group independently selected from halogen, hydroxyl, alkyl, alkoxy, haloalkyl, haloalkoxy, —SO$_2$R$^9$, or —SO$_2$N(R$^8$)$_2$;

$R^4$ is optionally substituted with at least one group independently selected from halogen, hydroxyl, alkyl or alkoxy;

$R^8$ is hydrogen, an alkyl, a haloalkyl, or an aryl;

$R^9$ is an alkyl, a haloalkyl, an aryl, or a heteroaryl.

In a further aspect, this disclosure also provides compounds, and compositions comprising the compounds, wherein the compounds have the following formula:

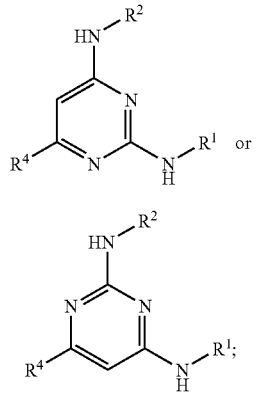

(II-A1)

(II-A2)

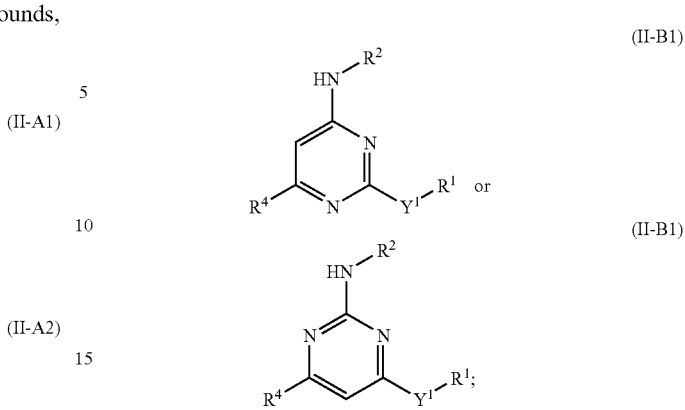

(II-B1)

(II-B1)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^1$ and $R^2$, in each occurrence is independently selected from a substituted or an unsubstituted cycloalkyl, aryl, aralkyl, heterocyclyl or heteroaryl comprising at least one heteroatom or heterogroup selected from —O—, >N— or —S—;

$R^4$ is a substituted or an unsubstituted nitrogen containing heterocyclyl or heteroaryl, which may optionally firther contain at least one more heteroatom selected from —O—, >N— or —S—, wherein the nitrogen atom of the said heterocycle or heteroaryl is connected to the carbon atom of the pyrimidine ring;

$R^1$ and $R^2$ are optionally substituted with at least one group independently selected from halogen, hydroxyl, alkyl, alkoxy, haloalkyl or haloalkoxy; and $R^4$ is optionally substituted with at least one group independently selected from halogen, hydroxyl, alkyl or alkoxy.

In this aspect, the compounds shown as formulas (II-A1) and (II-A2) illustrated above can have the following substituents:

$R^1$ and $R^2$, in each occurrence can be independently selected from a substituted or an unsubstituted cycloalkyl or aryl;

$R^4$ can be a substituted or an unsubstituted nitrogen containing heterocyclyl, which may optionally further contain at least one more heteroatom selected from —O—, >N— or —S—, wherein the nitrogen atom of the said heterocycle is connected to the carbon atom of the pyrimidine ring;

$R^1$ and $R^2$ is optionally substituted with at least one group independently selected from halogen, hydroxyl, alkyl or alkoxy; and $R^4$ is optionally substituted with at least one group independently selected from hydroxyl or alkoxy.

In yet a further aspect, this invention provides compounds, and compositions comprising the compounds, wherein the compounds have the following formula:

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ represents NH or —$(CH_2)n$-, wherein n is 0;

$R^1$ and $R^2$, in each occurrence is independently selected from a substituted or an unsubstituted alkyl, cycloalkyl, aryl, aralkyl, heterocyclyl or heteroaryl comprising at least one heteroatom or heterogroup selected from —O—, >N— or —S—;

$R^4$ is a substituted or an unsubstituted aryl;

$R^1$ and $R^2$ are optionally substituted with at least one group independently selected from halogen, hydroxyl, alkyl, alkoxy, haloalkyl, haloalkoxy, —$SO_2R^9$ or —$SO_2N(R^8)_2$;

$R^4$ is optionally substituted with at least one group independently selected from halogen, hydroxyl, alkyl, alkoxy, haloalkoxy, —$COR^9$, —$SR^9$ or —$SO_2R^9$;

$R^8$, in each occurrence, is independently hydrogen, an alkyl, a haloalkyl, or an aryl;

$R^9$ is an alkyl, a haloalkyl, an aryl or a heteroaryl.

Regarding this particular aspect, the compounds of formulas (II-B1) and (II-B2) illustrated above can have the following substituents:

$Y^1$ can be —$(CH_2)n$-, wherein n is 0;

$R^1$ is a substituted or an unsubstituted nitrogen containing heterocyclyl, which may optionally further contain at least one more heteroatom selected from —O—, >N— or —S—, wherein the nitrogen atom of the said heterocycle is connected to the carbon atom of the pyrimidine ring;

$R^2$ is a substituted or an unsubstituted aryl, aralkyl, heteroaryl, heterocyclyl, which may optionally further contain at least one more heteroatom comprising at least one heteroatom selected from —O—, >N— or —S—;

$R^4$ is a substituted or an unsubstituted aryl, heterocyclyl or heteroaryl comprising at least one heteroatom selected from —O—, >N— or —S—;

$R^1$ and $R^2$ are optionally substituted with at least one group independently selected from halogen, hydroxyl, alkyl, alkoxy, haloalkyl, haloalkoxy, —$SO_2R^9$ or —$SO_2N(R^8)_2$;

$R^4$ is optionally substituted with at least one group independently selected from halogen, hydroxyl, alkyl, alkoxy, haloalkoxy or —$SO_2R^9$;

$R^8$, in each occurrence, is independently hydrogen, an alkyl, a haloalkyl, or an aryl; and $R^9$ is an alkyl, a haloalkyl, an aryl, or a heteroaryl.

Further regarding this aspect of the present invention, the compounds of formuls (II-B1) and (II-B2) illustrated above can also have the following substituents:

$Y^1$ can represent —$(CH_2)n$-, wherein n is 0;

$R^1$ is morpholinyl or hydroxyl substituted piperidinyl, thiomorpholinyl, piperazinyl, wherein the nitrogen atom of the said heterocycle is connected to the carbon atom of the pyrimidine ring;

$R^2$ is a substituted or an unsubstituted aryl;

$R^4$ is a substituted or an unsubstituted aryl;

$R^1$ and $R^2$ are optionally substituted with at least one group independently selected from halogen, hydroxyl, alkoxy, haloalkyl or haloalkoxy;

$R^4$ is optionally substituted with at least one group independently selected from halogen, alkoxy or haloalkoxy.

In yet a further aspect, this invention provides compounds, and compositions comprising the compounds, wherein the compounds have the following formulas:

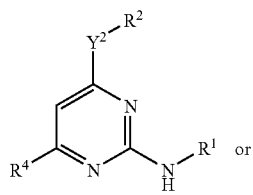

(II-C1)

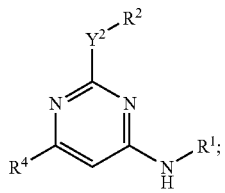

(II-C2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$Y^2$ represents NH or —$(CH_2)n$-, wherein n is 0;

$R^1$ and $R^2$, in each occurrence is independently selected from a substituted or an unsubstituted alkyl, cycloalkyl, aryl, aralkyl, heterocyclyl or heteroaryl comprising at least one heteroatom or heterogroup selected from —O—, >N—, —S—, >CO or >$SO_2$;

$R^4$ is a substituted or an unsubstituted aryl;

$R^1$ and $R^2$ are optionally substituted with at least one group independently selected from halogen, hydroxyl, alkyl, alkoxy, haloalkyl, haloalkoxy, —$COR^9$, —$SO_2R^9$ or —$SO_2N(R^8)_2$;

$R^4$ is optionally substituted with at least one group independently selected from halogen, hydroxyl, alkyl or alkoxy;

$R^8$ is hydrogen, an alkyl, a haloalkyl, or an aryl; and $R^9$ is an alkyl, a haloalkyl, an aryl, or a heteroaryl.

Regarding this aspect of the present invention, the compounds of formulas (II-C1) or (II-C2) illustrated above can also have the following substituents:

$Y^2$ represents —$(CH_2)n$-, wherein n is 0;

$R^1$ is a substituted or an unsubstituted aryl, aralkyl, heteroaryl, heterocyclyl, which may optionally further contain at least one more heteroatom comprising at least one heteroatom selected from —O—, >N—, —S— or >$SO_2$;

$R^2$ is a substituted or an unsubstituted nitrogen containing heterocyclyl, heteroaryl which may optionally further contain at least one more heteroatom selected from —O—, >N— or —S—, wherein the nitrogen atom of the said heterocycle is connected to the carbon atom of the pyrimidine ring;

$R^4$ is a substituted or an unsubstituted aryl;

$R^1$ and $R^2$ are optionally substituted with at least one group independently selected from halogen, hydroxyl, alkyl, alkoxy, haloalkyl, haloalkoxy, —$COR^9$, —$SO_2R^9$ or —$SO_2N(R^8)_2$;

$R^4$ is optionally substituted with at least one group independently selected from halogen, hydroxyl, alkyl or alkoxy;

$R^8$ is hydrogen, an alkyl, a haloalkyl, or an aryl; and $R^9$ is an alkyl, a haloalkyl, an aryl, or a heteroaryl.

Further regarding this aspect of the present invention, the compounds of formulas (II-C1) or (II-C2) illustrated above can also have the following substituents:

$Y^2$ represents —$(CH_2)n$-, wherein n is 0;

$R^1$ is a substituted or an unsubstituted aryl;

$R^2$ is a morpholinyl, piperazinyl, thiomorpholinyl, piperidinyl, wherein the nitrogen atom of the said heterocycle is connected to the carbon atom of the pyrimidine ring;

$R^4$ is a substituted or an unsubstituted aryl;

$R^1$ and $R^2$ are optionally substituted with at least one group independently selected from halogen, hydroxyl, alkyl, alkoxy, haloalkyl, haloalkoxy, —$COR^9$, —$SO_2R^9$ or —$SO_2N(R^8)_2$;

$R^4$ is optionally substituted with at least one group independently selected from halogen or alkoxy;

$R^8$ is hydrogen, an alkyl, a haloalkyl, or an aryl; and $R^9$ is an alkyl, a haloalkyl, an aryl, or a heteroaryl.

In still another aspect, this invention provides compounds, and compositions comprising the compounds, wherein the compounds have the following formula:

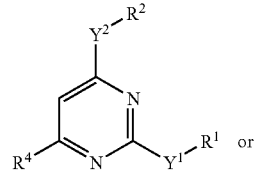

(II-D1)

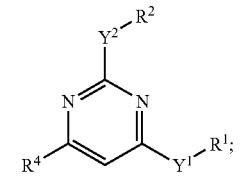

(II-D2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ and $Y^2$ are selected independently from >$NR^5$, —O—, —S—, or —$(CH_2)n$- wherein n is 0 or 1;

$R^5$ in each occurrence, is independently: 1) a substituted or an unsubstituted alkyl, aryl, heteroaryl, cycloalkyl, or heterocyclyl, any of which having up to 10 carbon atoms; wherein any heteroaryl or heterocyclyl comprises at least one heteroatom or heterogroup selected from —O—, >N—, —S—, >$SO_2$, or >CO; or 2) hydrogen;

wherein when $Y^1$ or $Y^2$ is independently >$NR^5$;

1) the corresponding $R^z$, wherein z is 1 or 2, in each occurrence is independently selected from: a) a substituted or an unsubstituted alkyl, aryl, cycloalkyl, heterocyclyl or heteroaryl comprising at least one heteroatom or heterogroup selected from —O—, >N—, —S—, >SO$_2$, or >CO; any of which having up to 10 carbon atoms; or b) hydrogen; or 2) the corresponding $Y^zR^z$, wherein z is 1 or 2, is a cyclic structure selected from: a) a substituted or an unsubstituted cyclic ring, which optionally comprises at least one additional heteroatom or heterogroup selected from —O—, >N—, —S—, >SO$_2$, or >CO; or b) a substituted or an unsubstituted morpholinyl, piperazinyl, thiomorpholinyl, pyrrolidinyl, or piperidinyl; any of which having up to 10 carbon atoms; wherein the optional substituents on the cyclic $Y^zR^z$ structure are independently selected from at least one of: a) hydroxyl; or b) alkyl, alkoxy, haloalkyl, aryl, or heteroaryl any of which having up to 6 carbon atoms;

wherein when $Y^zR^z$ is piperazinyl, the piperazine nitrogen is optionally substituted by an alkyl, a cycloalkyl, an acyl, a haloalkyl, an alkoxyalkyl, SO$_2$R$^7$, SO$_2$NR$^7{}_2$, or CO$_2$R$^7$, wherein R$^7$ is independently selected from: a) an alkyl or an aryl having up to 8 carbon atoms; or b) hydrogen;

wherein when $Y^1$ or $Y^2$ is independently —(CH$_2$)n-; the corresponding $R^z$, wherein z is 1 or 2, in each occurrence is independently selected from: 1) alkyl, haloalkyl, —COR$^9$, alkoxy, alkenyl, alkynyl, alkoxyalkyl, aryl, —CO$_2$R$^5$, —COR$^5$, heterocyclyl or heteroaryl comprising at least one heteroatom or heterogroup selected from —O—, >N—, —S—, >SO$_2$, or >CO; any of which having up to 10 carbon atoms; or 2) hydrogen, halogen, cyano, or hydroxyl;

wherein R$^4$ is selected independently from: 1) alkyl, alkenyl, alkynyl, alkoxy, haloalkyl, alkylsufonyl, aryl, —CO$_2$R$^5$, —COR$^5$, —NR$^5$R$^6$, —SO$_2$NR$^5$R$^6$, heterocyclyl or heteroaryl comprising at least one heteroatom or heterogroup selected from —O—, >N—, —S—, >SO$_2$, or >CO; any of which having up to 10 carbon atoms; or 2) hydrogen, halogen, hydroxyl, or cyano;

wherein any R$^1$ or R$^2$ are optionally substituted with at least one group independently selected from: 1) alkyl; alkoxy; alkylthio; haloalkyl; cycloalkyls; aryl; heterocyclyl or heteroaryl comprising at least one heteroatom or heterogroup selected from —O—, >N—, —S—, >SO$_2$, or >CO; haloalkoxy; —NR$^8{}_2$; —COR$^9$; —CONR$^8{}_2$; —SO$_2$R$^9$; —NHSO$_2$R$^9$; or —SO$_2$NR$^8{}_2$; any of which having up to 10 carbon atoms; or 2) hydrogen, halogen, hydroxyl, cyano, or —OCH$_2$O—;

wherein R$^8$, in each occurrence, is independently: 1) an alkyl or a haloalkyl having up to 10 carbon atoms; or 2) hydrogen;

wherein R$^9$, in each occurrence, is independently: 1) an alkyl or haloalkyl having up to 10 carbon atoms; or 2) hydrogen or hydroxyl; and wherein any of R$^4$ is optionally substituted with at least one group independently selected from: 1) alkyl, alkoxy, haloalkyl, haloalkoxy, cycloalkyl, aryl, heteroaryl, heterocyclyl, alkenyl, alkynyl, —COR$^{10}$, —CO$_2$R$^{10}$, —CONR$^{10}{}_2$, —SO$_2$R$^{10}$, —SO$_2$NR$^{10}{}_2$, or —NR$^{10}{}_2$, any of which having up to 10 carbon atoms; 2) halogen; or 3) hydroxyl; and wherein R$^{10}$, in each occurrence, is independently: 1) an alkyl or an aryl having up to 6 carbon atoms; or 2) hydrogen.

In another aspect, this invention provides compounds, and compositions comprising the compounds, wherein the compounds have the following formula:

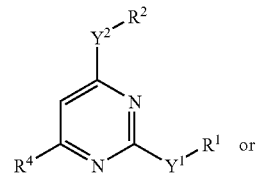

(II-D1i)

or

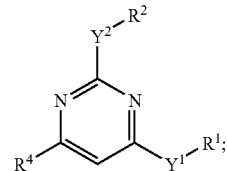

(II-D2i)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ and $Y^2$ are selected independently from >NR$^5$, —O—, or —CH$_2$—;

R$^5$, in each occurrence, is independently hydrogen or methyl;

wherein when $Y^1$ or $Y^2$ is independently >NR$^5$;

1) the corresponding $R^z$, wherein z is 1 or 2, in each occurrence is independently selected from: a) alkyl, aryl, cycloalkyl, heterocyclyl or heteroaryl comprising at least one heteroatom or heterogroup selected from —O—, >N—, —S—, >SO$_2$, or >CO; any of which having up to 10 carbon atoms; or b) hydrogen; or 2) the corresponding $Y^zR^z$, wherein z is 1 or 2, is selected from a morpholinyl, a piperazinyl, a piperidinyl, or a pyrrolidinyl; wherein when $Y^zR^z$ is piperazinyl, the piperazine nitrogen is optionally substituted by an alkyl, a cycloalkyl, an acyl, a haloalkyl, an alkoxyalkyl, SO$_2$R$^7$, or SO$_2$NR$^7{}_2$, wherein R$^7$ is independently selected from: a) an alkyl or an aryl having up to 8 carbon atoms; or b) hydrogen;

wherein when any $Y^zR^z$ is selected from a piperidinyl or a pyrrolidinyl, the piperidinyl or pyrrolidinyl ring is optionally substituted with: 1) an alkyl or a haloalkyl having up to 10 carbon atoms; or 2) a hydroxyl;

wherein when $Y^1$ or $Y^2$ is independently —CH$_2$—, the corresponding $R^z$, wherein z is 1 or 2, in each occurrence is independently selected from an alkyl, a haloalkyl, an alkoxy, an aryl, or a heterocyclyl or heteroaryl comprising at least one heteroatom or heterogroup selected from —O—, >N—, —S—, >SO$_2$, or >CO; any of which having up to 10 carbon atoms;

wherein R$^4$ is selected independently from: 1) an alkyl, a haloalkoxy, an aryl, or a heteroaryl or heterocyclyl having up to 10 carbon atoms, wherein any heteroaryl or heterocyclyl comprises at least one heteroatom or heterogroup selected from —O—, >N—, —S—, >SO$_2$, or >CO; or 2) Y$^1$R$^1$;

wherein any of R$^1$, R$^2$, or R$^5$ is optionally substituted with at least one group independently selected from: 1) an alkyl, an alkoxy, a haloalkyl, a haloalkoxy, —NR$^8{}_2$, —SO$_2$R$^9$, or —SO$_2$NR$^8{}_2$, any of which having up to 10 carbon atoms; or 2) hydrogen, halogen, cyano, or —OCH$_2$O—;

wherein R$^8$, in each occurrence, is independently: 1) alkyl, haloalkyl, or aryl, any of which having up to 6 carbon atoms; or 2) hydrogen;

wherein $R^9$, in each occurrence, is independently an alkyl, a haloalkyl, or an aryl, any of which having up to 10 carbon atoms; and wherein $R^4$ is optionally substituted with at least one group independently selected from: 1) alkyl, alkoxy, haloalkyl, haloalkoxy, cycloalkyl, aryl, heteroaryl, heterocyclyl, —$COR^{10}$, —$CO_2R^{10}$, —$CONR^{10}_2$, —$SO_2R^{10}$, —$SO_2NR^{10}_2$, or —$NR^{10}_2$, any of which having up to 10 carbon atoms; or 2) halogen or hydroxyl; and wherein $R^{10}$, in each occurrence, is independently: 1) an alkyl or an aryl having up to 6 carbon atoms; or 2) hydrogen.

Yet another aspect, this invention provides compounds, and compositions comprising the compounds, wherein the compounds have the following formula:

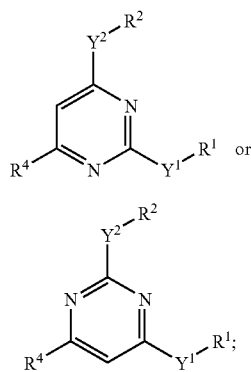

(II-D1ii)

(II-D2ii)

or respectively, a salt, including a pharmaceutically acceptable or a non-pharmaceutically acceptable salt, a prodrug, a diastereomeric mixture, an enantiomer, a tautomer, or a racemic mixture thereof, wherein:

$Y^1$ and $Y^2$ are selected independently from >NR5 or —$CH_2$—;

$R^5$, in each occurrence, is independently methyl or hydrogen;

wherein when $Y^1$ or $Y^2$ is independently >$NR^5$;

1) the corresponding $R^z$, wherein z is 1 or 2, in each occurrence is independently selected from an aryl, or a heterocyclyl or heteroaryl comprising at least one heteroatom or heterogroup selected from —O—, >N—, —S—, >$SO_2$, or >CO; any of which having up to 10 carbon atoms; or 2) the corresponding $Y^zR^z$, wherein z is 1 or 2, is selected from a morpholinyl, a piperazinyl, a pyrrolidinyl or a piperidinyl; wherein $Y^zR^z$ is optionally substituted by: a) an alkyl or an acyl having up to 10 carbon atoms; or b) hydroxyl or hydrogen;

wherein when $Y^1$ or $Y^2$ is independently —$CH_2$—; the corresponding $R^z$, wherein z is 1 or 2, in each occurrence is independently selected from a substituted or an unsubstituted aryl, or a substituted or an unsubstituted heterocyclyl or heteroaryl comprising at least one heteroatom or heterogroup selected from —O—, >N—, —S—, >$SO_2$, or >CO; any of which having up to 10 carbon atoms;

wherein any $R^1$ or $R^2$ are optionally substituted with at least one group independently selected from: 1) alkyl, alkoxy, haloalkyl, haloalkoxy, —O—$CH_2$—O—, —$OCOR^9$, $NR^8_2$, —$SO_2R^9$, or —$SO_2NR^8_2$, any of which having up to 10 carbon atoms; or 2) hydrogen, halogen, or cyano;

wherein $R^8$ and $R^9$, in each occurrence, are independently selected from: 1) an alkyl or an aryl having up to 10 carbon atoms; or 2) hydrogen; and wherein $R^4$, in each occurrence, is selected independently from a substituted or an unsubstituted: alkyl, aryl, or heteroaryl or heterocyclyl having up to 10 carbon atoms, wherein any heteroaryl or heterocyclyl comprises at least one heteroatom or heterogroup selected from —O—, >N—, —S—, >$SO_2$, or >CO;

wherein $R^4$ is optionally substituted with at least one group independently selected from: 1) an alkyl, a haloalkoxy, an alkoxy, —$COR^{10}$, —$CONR^8_2$, —$SO_2R^{10}$, —$SO_2NR^{10}_2$, or —$NR^{10}_2$, any of which having up to 10 carbon atoms; or 2) halogen or hydroxyl; and wherein $R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

Still another aspect of this invention provides compounds, and compositions comprising the compounds, wherein the compounds have the following formula:

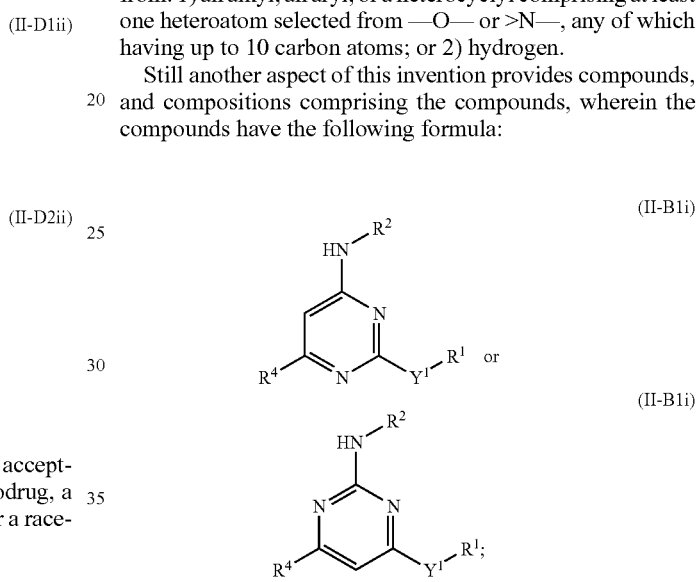

(II-B1i)

(II-B1i)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ is selected from >$NR^5$, or —$CH_2$—;

$R^1$ and $R^2$ are selected independently from a substituted or an unsubstituted cycloalkyl, aryl, or heterocyclyl or heteroaryl comprising at least one heteroatom or heterogroup selected from —O—, >N—, —S—, >CO or >$SO_2$, any of which having up to 10 carbon atoms;

$R^5$ is selected from methyl or hydrogen;

$R^4$ is selected from a substituted or an unsubstituted alkyl, aryl, or heterocyclyl or heteroaryl comprising at least one heteroatom or heterogroup selected from —O—, >N—, —S—, or >CO, any of which having up to 10 carbon atoms;

$R^1$ and $R^2$ are optionally substituted with at least one group independently selected from: 1) an alkyl, an alkoxy, a haloalkyl, a haloalkoxy, —$COR^9$, -cyano, —$CONR^8_2$, —$SO_2R^9$, —$NHSO_2R^9$, or —$SO_2NR^8_2$, any of which having up to 10 carbon atoms; or 2) halogen, hydroxyl, or —$OCH_2O$—;

$R^8$, in each occurrence, is selected independently from: 1) alkyl, haloalkyl, or aryl having up to 6 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

R$^4$ is optionally substituted with at least one group independently selected from: 1) alkyl, haloalkoxy, alkoxy, —COR$^{10}$, —CONR$^8{}_2$, —SO$_2$R$^{10}$, —SO$_2$NR$^{10}{}_2$, or —NR$^{10}{}_2$, any of which having up to 10 carbon atoms; or 2) halogen or hydroxyl; and R$^{10}$, in each occurrence, is selected independently from: 1) alkyl, aryl, or heterocyclyl comprising at least one heteroatom selected from —O— or >N—, any of which having up to 10 carbon atoms; or 2) hydrogen.

Another aspect of the present invention provides compounds, and compositions comprising the compounds, wherein the compounds have the following formula:

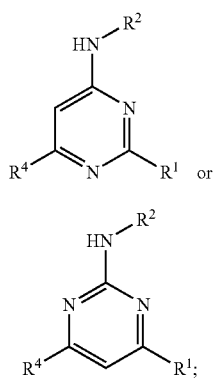

(II-E1)

or (II-E2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

R$^1$ and R$^2$ are selected independently from a substituted or an unsubstituted aryl or heteroaryl comprising at least one heteroatom or heterogroup selected from —O—, >N—, —S—, >SO$_2$, or >CO, any of which having up to 10 carbon atoms;

R$^4$ is selected from a substituted or an unsubstituted aryl, or a substituted or an unsubstituted heterocyclyl or heteroaryl comprising at least one heteroatom or heterogroup selected from —O—, >N—, —S—, or >CO, any of which having up to 10 carbon atoms;

R$^1$ and R$^2$ are optionally substituted with at least one group independently selected from: 1) an alkyl, an alkoxy, a haloalkyl, a haloalkoxy, —COR$^9$, —CO$_2$R$^8$, —CONR$^8{}_2$, SO$_2$R$^9$, —NHSO$_2$R$^9$, or —SO$_2$NR$^8{}_2$, any of which having up to 10 carbon atoms; or 2) halogen, hydroxyl, cyano, or —OCH$_2$O—;

R$^8$, in each occurrence, is selected independently from: 1) an alkyl, a haloalkyl, or an aryl having up to 6 carbon atoms; or 2) hydrogen;

R$^9$, in each occurrence, is selected independently from an alkyl, a haloalkyl, an aryl, or a heterocyclyl or a heteroaryl comprising at least one heteroatom selected from —O— or >N—, any of which having up to 10 carbon atoms;

R$^4$ is optionally substituted with at least one group independently selected from: 1) an alkyl, a haloalkyl, an alkoxy, —COR$^{10}$, —CO$_2$R$^8$, —CONR$^8{}_2$, —SO$_2$R$^9$, —SO$_2$NR$^{10}{}_2$, or —NR$^{10}{}_2$, any of which having up to 10 carbon atoms; or 2) halogen or hydroxyl; and R$^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

Still another aspect of this invention provides compounds, and compositions comprising the compounds, wherein the compounds have the formula:

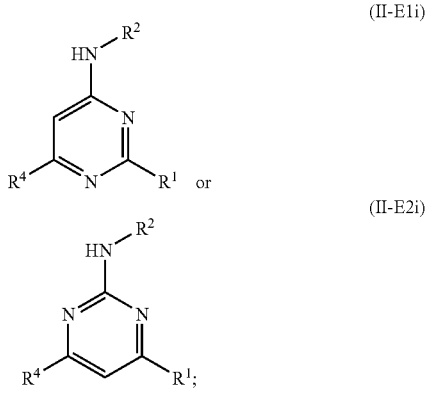

(II-E1i)

or (II-E2i)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

R$^1$, R$^2$, and R$^4$ are selected independently from a substituted or an unsubstituted aryl, or a substituted or an unsubstituted heterocyclyl or heteroaryl comprising at least one heteroatom selected from —O—, >N—, —S—, >SO$_2$, or >CO, any of which having up to 10 carbon atoms;

R$^1$, R$^2$, and R$^4$ are optionally substituted with at least one group independently selected from: 1) an alkyl, an alkoxy, a haloalkyl, a haloalkoxy, —COR$^9$, —COR$^{10}$, —CO$_2$R$^8$, —CONR$^8{}_2$, —SO$_2$R$^9$, —SR$^8$, —NHSO$_2$R$^9$, —SO$_2$NR$^8{}_2$, —SO$_2$N$^{10}{}_2$, or —NR$^{10}{}_2$, any of which having up to 10 carbon atoms; or 2) halogen, hydroxyl, cyano, or —OCH$_2$O—;

R$^8$, in each occurrence, is selected independently from: 1) an alkyl, a haloalkyl, or an aryl having up to 6 carbon atoms; or 2) hydrogen;

R$^9$, in each occurrence, is selected independently from an alkyl, a haloalkyl, an aryl, or a heterocyclyl or a heteroaryl comprising at least one heteroatom selected from —O— or >N—, any of which having up to 10 carbon atoms; and R$^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

Another aspect of this invention provides compounds, and compositions comprising the compounds, wherein the compounds have the formula:

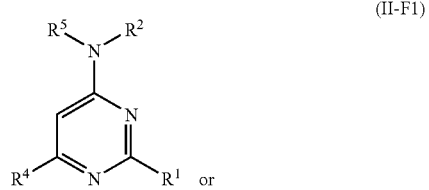

(II-F1)

or

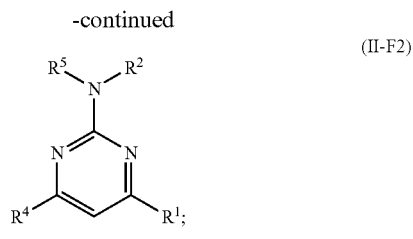

(II-F2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^1$ and $R^2$ are selected independently from: a) a substituted or an unsubstituted aryl or heteroaryl comprising at least one heteroatom or heterogroup selected from —O—, >N—, —S—, any of which having up to 10 carbon atoms; b) hydrogen, or c) halogen or hydroxy;

$R^4$ is selected from a substituted or unsubstituted aryl or heteroaryl comprising at least one heteroatom or heterogroup selected from —O—, >N—, —S—, any of which having up to 10 carbon atoms;

$R^5$ is an alkyl having up to 3 carbon atoms or hydrogen;

$R^1$ and $R^2$ are optionally substituted with at least one group independently selected from: 1) an alkyl, an alkoxy, a haloalkyl, a haloalkoxy, —COR$^9$, —CONR$^8_2$, —SO$_2$R$^9$, —NHSO$_2$R$^9$, or —SO$_2$NR$^8_2$, any of which having up to 10 carbon atoms; or 2) halogen, hydroxyl, or —OCH$_2$O—;

$R^8$, in each occurrence, is selected independently from: 1) an alkyl, a haloalkyl, or an aryl having up to 6 carbon atoms; or 2) hydrogen;

$R^9$, in each occurrence, is independently an alkyl, a haloalkyl, an aryl, or a heterocyclyl or heteroaryl comprising at least one heteroatom selected from —O— or >N—, any of which having up to 10 carbon atoms;

$R^4$ is optionally substituted with at least one group independently selected from: 1) alkyl, haloalkoxy, alkoxy, —COR$^{10}$, —CONR$^8_2$, —SO$_2$R$^{10}$, —SO$_2$NR$^{10}_2$, or —NR$^{10}_2$, any of which having up to 10 carbon atoms; 2) halogen; or 3) hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

Yet another aspect of this invention provides compounds, and compositions comprising the compounds, wherein the compounds have the formula:

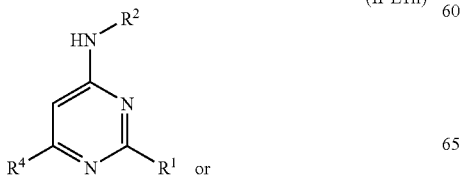

(II-E1ii)

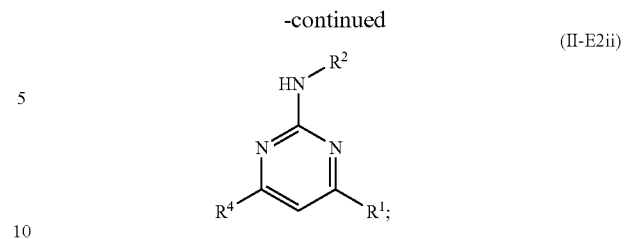

(II-E2ii)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^1$ and $R^2$ are selected independently from: a) a substituted or an unsubstituted aryl or heteroaryl comprising at least one heteroatom or heterogroup selected from —O—, >N—, —S—, any of which having up to 10 carbon atoms; b) hydrogen, or c) halogen or hydroxy;

$R^4$ is selected from: 1) a substituted or an unsubstituted alkyl or heterocyclyl comprising at least one heteroatom or heterogroup selected from —O—, >N—, —S—, or >CO, any of which having up to 10 carbon atoms;

$R^1$ and $R^2$ are optionally substituted with at least one group independently selected from: 1) an alkyl, an alkoxy, a haloalkyl, a haloalkoxy, —COR$^9$, —CONR$^8_2$, —SO$_2$R$^9$, —NHSO$_2$R$^9$, or —SO$_2$NR$^8_2$, any of which having up to 10 carbon atoms; or 2) halogen, cyano, hydroxyl, or —OCH$_2$O—;

$R^8$, in each occurrence, is selected independently from: 1) an alkyl, a haloalkyl, or an aryl having up to 6 carbon atoms; or 2) hydrogen;

$R^9$, in each occurrence, is independently an alkyl, a haloalkyl, an aryl, or a heterocyclyl or heteroaryl comprising at least one heteroatom selected from —O— or >N—, any of which having up to 10 carbon atoms;

$R^4$ is optionally substituted with at least one group independently selected from: 1) alkyl, haloalkoxy, alkoxy, —COR$^{10}$, —CONR$^8_2$, —SO$_2$R$^{10}$, —SO$_2$NR$^{10}_2$, or —NR$^{10}_2$, any of which having up to 10 carbon atoms; 2) halogen; or 3) hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

In still another aspect, this invention provides compounds, and compositions comprising the compounds, wherein the compounds have the following formula:

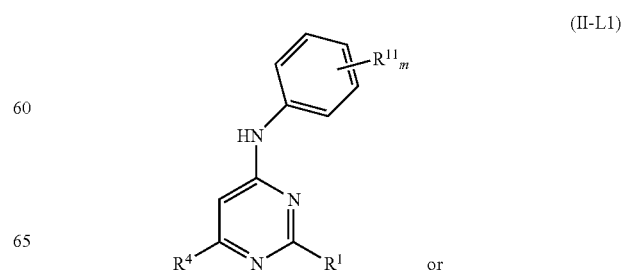

(II-L1)

-continued

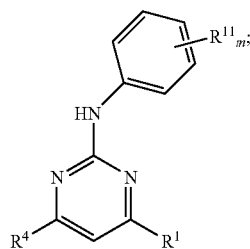

(II-L2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^1$ and $R^4$ are selected independently from a substituted or an unsubstituted aryl or a substituted or an unsubstituted heterocyclyl or heteroaryl comprising at least one heteroatom selected from —O—, >N—, or —S—, any of which having up to 10 carbon atoms;

$R^{11}$, in each occurrence, is selected independently from: 1) an alkyl, an alkoxy, a haloalkyl, a haloalkoxy, —COR$^9$, —CO$_2$R$^8$, —CONR$^8_2$, —SO$_2$R$^9$, —NHSO$_2$R$^9$, or —SO$_2$NR$^8_2$, any of which having up to 10 carbon atoms; or 2) halogen, hydroxyl, or —OCH$_2$O—;

m is an integer from 0 to 3, inclusive;

$R^1$ and $R^4$ are optionally substituted with at least one group independently selected from: 1) an alkyl, an alkoxy, a haloalkyl, a haloalkoxy, —COR$^9$, —CO$_2$R$^8$, —CONR$^8_2$, —SO$_2$R$^9$, —NHSO$_2$R$^9$, or —SO$_2$NR$^8_2$, any of which having up to 10 carbon atoms or 2) halogen, hydroxyl, or —OCH$_2$O—;

$R^8$, in each occurrence, is selected independently from: 1) an alkyl, a haloalkyl, or an aryl, any of which having up to 6 carbon atoms; or 2) hydrogen; and $R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms.

In yet another aspect, this invention provides compounds, and compositions comprising the compounds, wherein the compounds have the following formula:

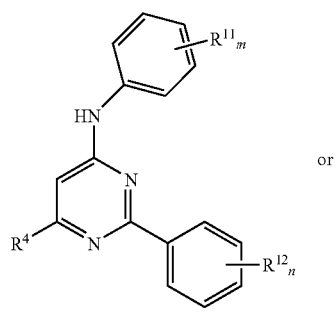

(II-G1)

or

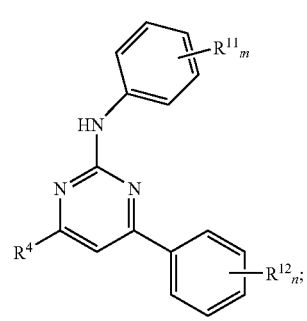

(II-G2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^4$ is selected from a substituted or an unsubstituted heterocyclyl comprising at least one heteroatom or heterogroup selected from —O—, >N—, —S—, or >CO, any of which having up to 10 carbon atoms;

n and m are independently an integer from 0 to 3, inclusive;

$R^{11}$ and $R^{12}$, in each occurrence, are selected independently from: 1) an alkyl, an alkoxy, a haloalkyl, a haloalkoxy, —COR$^9$, —CONR$^8_2$, —CO$_2$R$^8$, —SO$_2$R$^9$, —SR$^8$, —NHSO$_2$R$^9$, or —SO$_2$NR$^8_2$, any of which having up to 10 carbon atoms; or 2) halogen, hydroxyl, or —OCH$_2$O—;

$R^8$, in each occurrence, is selected independently from: 1) an alkyl, a haloalkyl, or an aryl having up to 6 carbon atoms; or 2) hydrogen;

$R^9$, in each occurrence, is selected independently from: 1) an alkyl, a haloalkyl, an aryl, or a heterocyclyl or heteroaryl comprising at least one heteroatom selected from —O— or >N—, any of which having up to 10 carbon atoms; or 2) hydrogen;

$R^4$ is optionally substituted with at least one group independently selected from: 1) an alkyl, —COR$^9$, —CO$_2$R$^8$, —CONR$^8_2$, —SO$_2$R$^9$, or —SO$_2$NR$^{10}_2$, any of which having up to 10 carbon atoms; or 2) hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

In this aspect, $R^4$ can be selected from or

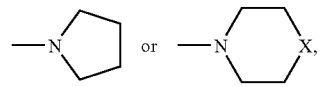

wherein X is selected from CH$_2$, O, NH, NMe, NEt, S, SO$_2$, or CH(OH); and $R^{11}$ and $R^{12}$, in each occurrence, can be selected independently from OCF$_3$, OMe, Cl, F, SO$_2$Me, CF$_3$, Me, COMe, SMe, CONHMe, NHSO$_2$Me, SO$_2$NH$_2$, SO$_2$NHMe, SO$_2$NMe$_2$, CONH$_2$, CONMe$_2$, CO$_2$Me, CO$_2$H, —OCH$_2$O—, or OH.

In still another aspect, this invention provides compounds, and compositions comprising the compounds, wherein the compounds have the formula:

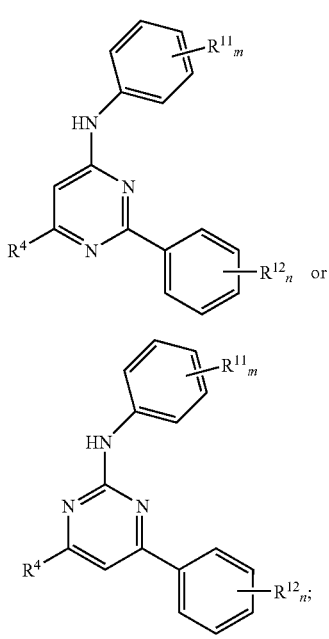

(II-G1i)

(II-G2i)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^4$ is selected from: 1) hydrogen, chloro, or hydroxy; or 2) a substituted or an unsubstituted aryl, heteroaryl, or alkoxy, any of which having up to 10 carbon atoms;

n and m are independently an integer from 0 to 3, inclusive;

$R^{11}$ and $R^{12}$, in each occurrence, are selected independently from: 1) alkyl, alkoxy, haloalkyl, haloalkoxy, —$COR^9$, —$CONR^8_2$, —$SO_2R^9$, —$NHSO_2R^9$, or —$SO_2NR^8_2$, any of which having up to 10 carbon atoms; or 2) halogen, hydroxyl, or —$OCH_2O$—;

$R^8$, in each occurrence, is selected independently from: 1) an alkyl, a haloalkyl, or an aryl having up to 6 carbon atoms; or 2) hydrogen;

$R^9$, in each occurrence, is independently selected from: 1) an alkyl, a haloalkyl, an aryl, or a heterocyclyl or heteroaryl comprising at least one heteroatom selected from —O— or >N—, any of which having up to 10 carbon atoms; or 2) hydrogen;

wherein when $R^4$ is aryl or heteroaryl, $R^4$ is optionally substituted with at least one group independently selected from: 1) alkyl, haloalkoxy, alkoxy, —$COR^{10}$, —$CONR^8_2$, —$SO_2R^{10}$, —$SO_2NR^{10}_2$, or —$NR^{10}_2$, any of which having up to 10 carbon atoms; or 2) halogen or hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

Another aspect of this invention provides compounds, and compositions comprising the compounds, wherein the compounds have the following formula:

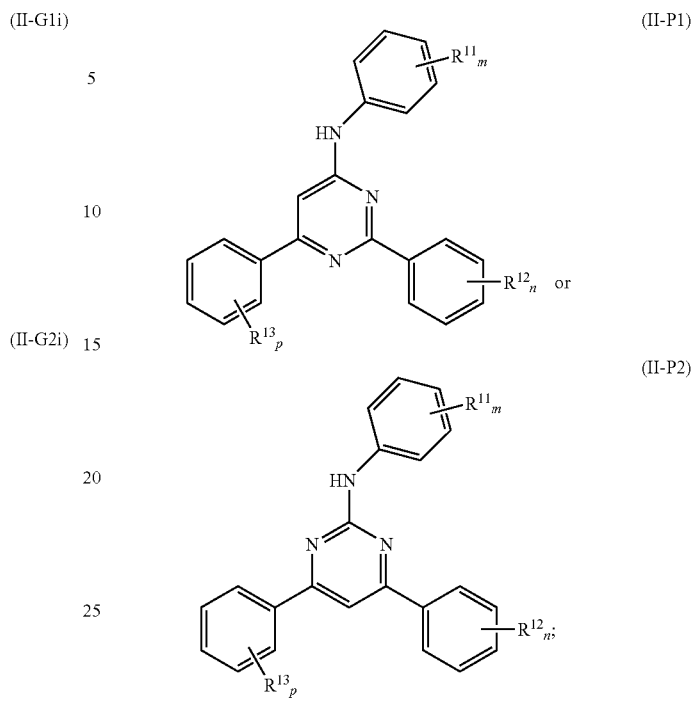

(II-P1)

(II-P2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^{11}$, $R^{12}$, and $R^{13}$, in each occurrence, are selected independently from: 1) an alkyl, an alkoxy, a haloalkyl, a haloalkoxy, —$COR^9$, $CO_2R^8$, —$CONR^8_2$, —$SO_2R^9$, —$NHSO_2R^9$, or —$SO_2NR^8_2$, any of which having up to 10 carbon atoms; or 2) halogen, hydroxyl, or —$OCH_2O$—;

m, n, and p are selected independently from an integer from 0 to 3, inclusive;

$R^8$, in each occurrence, is selected independently from: 1) an alkyl, a haloalkyl, or an aryl, any of which having up to 6 carbon atoms; or 2) hydrogen; and $R^9$, in each occurrence, is selected independently from: 1) an alkyl, a haloalkyl, an aryl, or a heterocyclyl or heteroaryl comprising at least one heteroatom selected from —O— or >N—, any of which having up to 10 carbon atoms; or 2) hydrogen.

Still another aspect of this invention provides compounds, and compositions comprising the compounds, wherein the compounds have the following formula:

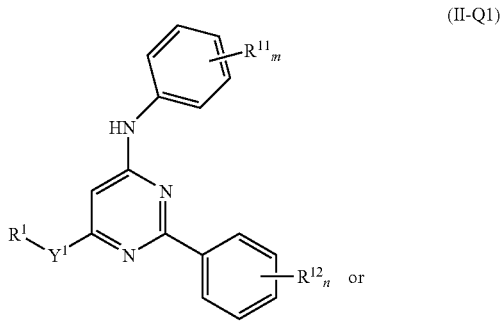

(II-Q1)

-continued

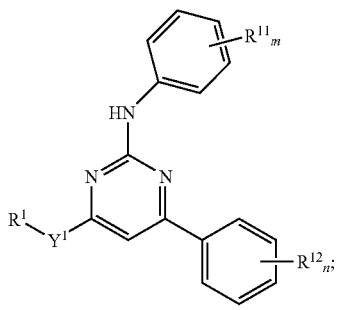
(II-Q2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ is selected from >NH or —O—;

$R^1$ is selected from a substituted or an unsubstituted alkyl, cycloalkyl, aryl, benzyl, or heterocyclyl or heteroaryl comprising at least one heteroatom selected from —O— or >N—, any of which having up to 10 carbon atoms;

$R^{11}$ and $R^{12}$, in each occurrence, are selected independently from: 1) an alkyl, an alkoxy, a haloalkyl, a haloalkoxy, —COR$^9$, —CO$_2$R$^8$, —CONR$^8{}_2$, —SO$_2$R$^9$, —NHSO$_2$R$^9$, or —SO$_2$NR$^8{}_2$, any of which having up to 10 carbon atoms; or 2) —OCH$_2$O—, halogen, or hydroxyl;

n and m are selected independently from an integer from 0 to 3, inclusive; and $R^8$, in each occurrence, is selected independently from: 1) an alkyl, a haloalkyl, or an aryl, any of which having up to 6 carbon atoms; or 2) hydrogen; and $R^9$, in each occurrence, is selected independently from: 1) an alkyl, a haloalkyl, an aryl, or a heterocyclyl or heteroaryl comprising at least one heteroatom selected from —O— or >N—, any of which having up to 10 carbon atoms; or 2) hydrogen; and wherein $R^1$ is optionally substituted with at least one group independently selected from: 1) an alkyl, an alkoxy, a haloalkyl, or a haloalkoxy, any of which having up to 10 carbon atoms; or 2) hydroxyl, CO$_2$H, or CO$_2$Et.

Another aspect of the present invention provides compounds, and compositions comprising the compounds, wherein the compounds have the following formula:

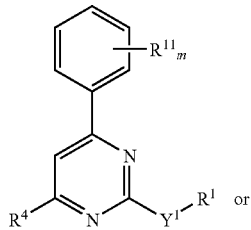
(II-M1)

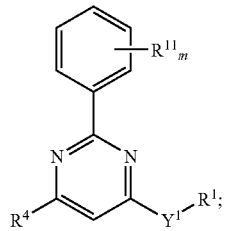
(II-M2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ is selected from >NR$^5$ or —(CH$_2$)n- wherein n is 0;

$R^5$ is selected from methyl or hydrogen;

$R^1$ and $R^4$ are selected independently from a substituted or an unsubstituted aryl, or a substituted or an unsubstituted heteroaryl or heterocyclyl comprising at least one heteroatom selected from —O—, >N—, —S—, >CO, or >SO$_2$, any of which having up to 10 carbon atoms;

m is an integer from 0 to 3, inclusive;

$R^{11}$, in each occurrence, is selected independently from: 1) an alkyl, an alkoxy, a haloalkyl, a haloalkoxy, —COR$^9$, —CO$_2$R$^8$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, or —OCH$_2$O—;

$R^1$ and $R^4$ are optionally substituted with at least one group selected independently from: 1) an alkyl, an alkoxy, a haloalkyl, a haloalkoxy, —COR$^9$, —CO$_2$R$^8$, —CONR$^8{}_2$, —SO$_2$R$^9$, —SO$_2$R$^{10}$, —SR$^8$, —NHSO$_2$R$^9$, —SO$_2$NR$^8{}_2$, or —SO$_2$NR$^{10}{}_2$, any of which having up to 10 carbon atoms; or 2) halogen, hydroxyl, or —OCH$_2$O—;

$R^8$, in each occurrence, is selected independently from: 1) an alkyl, a haloalkyl, or an aryl, any of which having up to 6 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms; and $R^{10}$, in each occurrence, is independently selected from: 1) an alkyl, an aryl, or a heterocyclyl comprising at least one heteroatom selected from —O— or >N—, any of which having up to 10 carbon atoms; or 2) hydrogen.

In one aspect of the formula (II-M2); when $Y^1R^1$ is

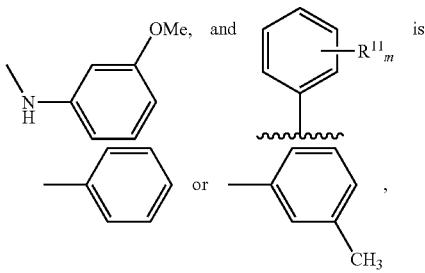

then one option for $R^4$ is that $R^4$ is not

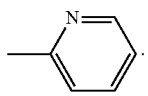

Another aspect of this invention provides compounds, and compositions comprising the compounds, wherein the compounds have the formula:

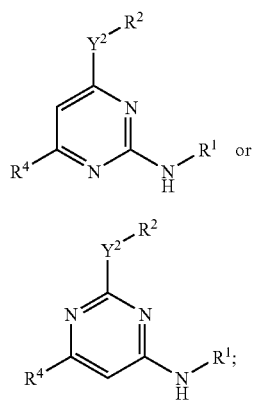

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$Y^2$ is selected from $>NR^5$ or $>(CH_2)n$ wherein n is 0 or 1;

$R^1$ and $R^2$ are selected independently from: a) a substituted or an unsubstituted alkyl, cycloalkyl, aryl, heterocyclyl or heteroaryl comprising at least one heteroatom or heterogroup selected from —O—, >N—, —S—, >CO or >SO$_2$, any of which having up to 10 carbon atoms; b) hydrogen, or c) halogen or hydroxy;

$R^5$ is an alkyl having up to 3 carbon atoms or hydrogen;

$R^4$ is selected from: 1) a substituted or an unsubstituted alkyl, aryl, heterocyclyl or heteroaryl comprising at least one heteroatom or heterogroup selected from —O—, >N—, —S—, or >CO, any of which having up to 10 carbon atoms; 2) hydrogen; or 3) halogen;

$R^1$ and $R^2$ are optionally substituted with at least one group independently selected from: 1) an alkyl, an alkoxy, a haloalkyl, a haloalkoxy, —COR$^9$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, cyano, or —OCH$_2$O—;

$R^8$, in each occurrence, is selected independently from: 1) an alkyl, a haloalkyl, or an aryl having up to 6 carbon atoms; or 2) hydrogen;

$R^9$, in each occurrence, is independently an alkyl, a haloalkyl, an aryl, or a heterocyclyl or heteroaryl comprising at least one heteroatom selected from —O— or >N—, any of which having up to 10 carbon atoms;

wherein when $R^4$ is a alkyl, an aryl, a heterocyclyl, or a heteroaryl, $R^4$ is optionally substituted with at least one group independently selected from: 1) alkyl, haloalkoxy, alkoxy, —COR$^{10}$, —CONR$^8{}_2$, —SO$_2$R$^{10}$, —SO$_2$NR$^{10}{}_2$, or —NR$^{10}{}_2$, any of which having up to 10 carbon atoms; 2) halogen; or 3) hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

Still another aspect of this invention provides compounds, and compositions comprising the compounds, wherein the compounds have the formula:

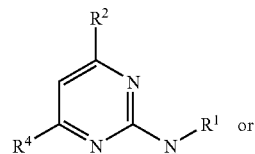

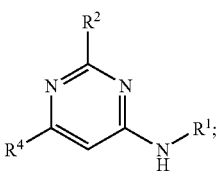

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^1$ and $R^2$ are selected independently from: a) a substituted or an unsubstituted aryl or heteroaryl comprising at least one heteroatom or heterogroup selected from —O—, >N—, —S—, any of which having up to 10 carbon atoms; b) hydrogen; or c) halogen or hydroxy;

$R^4$ is selected from: 1) a substituted or an unsubstituted alkyl, aryl, heterocyclyl or heteroaryl comprising at least one heteroatom or heterogroup selected from —O—, >N—, —S—, or >CO, any of which having up to 10 carbon atoms; 2) hydrogen; or 3) halogen;

$R^1$ and $R^2$ are optionally substituted with at least one group independently selected from: 1) an alkyl, an alkoxy, a haloalkyl, a haloalkoxy, —COR$^9$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, or —OCH$_2$O—;

$R^8$, in each occurrence, is selected independently from: 1) an alkyl, a haloalkyl, or an aryl having up to 6 carbon atoms; or 2) hydrogen;

$R^9$, in each occurrence, is independently an alkyl, a haloalkyl, an aryl, or a heterocyclyl or heteroaryl comprising at least one heteroatom selected from —O— or >N—, any of which having up to 10 carbon atoms;

Wherein when $R^4$ is an alkyl, an aryl, a heterocyclyl, or a heteroaryl, $R^4$ is optionally substituted with at least one group independently selected from: 1) alkyl, haloalkoxy, alkoxy, —COR$^{10}$, —CONR$^8{}_2$, —SO$_2$R$^{10}$, —SO$_2$NR$^{10}{}_2$, or —NR$^{10}{}_2$, any of which having up to 10 carbon atoms; 2) halogen; or 3) hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

Yet another aspect of this invention provides compounds, and compositions comprising the compounds, wherein the compounds have the formula:

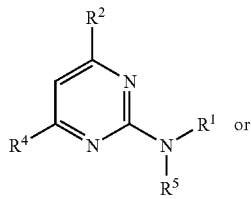

(II-I1)

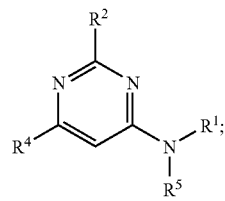

(II-I2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^1$ and $R^2$ are selected independently from: a) a substituted or an unsubstituted aryl or heteroaryl comprising at least one heteroatom or heterogroup selected from —O—, >N—, —S—, >CO or >SO$_2$, any of which having up to 10 carbon atoms; b) hydrogen, or c) halogen or hydroxy;

$R^4$ is selected from a substituted or unsubstituted aryl or heteroaryl, any of which having up to 10 carbon atoms;

$R^5$ is an alkyl having up to 3 carbon atoms or hydrogen;

$R^1$ and $R^2$ are optionally substituted with at least one group independently selected from: 1) an alkyl, an alkoxy, a haloalkyl, a haloalkoxy, —COR$^9$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, or —OCH$_2$O—;

$R^8$, in each occurrence, is selected independently from: 1) an alkyl, a haloalkyl, or an aryl having up to 6 carbon atoms; or 2) hydrogen;

$R^9$, in each occurrence, is independently an alkyl, a haloalkyl, an aryl, a heterocyclyl or heteroaryl comprising at least one heteroatom selected from —O— or >N—, any of which having up to 10 carbon atoms;

$R^4$ is optionally substituted with at least one group independently selected from: 1) alkyl, haloalkoxy, alkoxy, —COR$^{10}$, —CONR$^8{}_2$, —SO$_2$R$^{10}$, —SO$_2$NR$^{10}{}_2$, or —NR$^{10}{}_2$, any of which having up to 10 carbon atoms; 2) halogen; or 3) hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

Another aspect of the present invention provides compounds, and compositions comprising the compounds, wherein the compounds have the formula:

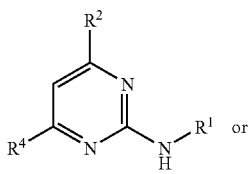

(II-H1i)

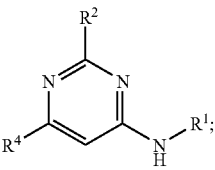

(II-H2i)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^1$ and $R^2$ are selected independently from: 1) a substituted or an unsubstituted aryl or heteroaryl comprising at least one heteroatom or heterogroup selected from —O—, >N—, —S—, any of which having up to 10 carbon atoms; or 2) hydrogen, halogen, or hydroxyl;

$R^4$ is selected from: 1) a substituted or an unsubstituted alkyl or heterocyclyl comprising at least one heteroatom or heterogroup selected from —O—, >N—, —S—, or >CO, any of which having up to 10 carbon atoms;

$R^1$ and $R^2$ are optionally substituted with at least one group independently selected from: 1) an alkyl, an alkoxy, a haloalkyl, a haloalkoxy, —COR$^9$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, or —OCH$_2$O—;

$R^8$, in each occurrence, is selected independently from: 1) an alkyl, a haloalkyl, or an aryl having up to 6 carbon atoms; or 2) hydrogen;

$R^9$, in each occurrence, is independently an alkyl, a haloalkyl, an aryl, or a heterocyclyl or heteroaryl comprising at least one heteroatom selected from —O— or >N—, any of which having up to 10 carbon atoms;

$R^4$ is optionally substituted with at least one group independently selected from: 1) alkyl, haloalkoxy, alkoxy, —COR$^{10}$, —CONR$^8{}_2$, —SO$_2$R$^{10}$, —SO$_2$NR$^{10}{}_2$, or —NR$^{10}{}_2$, any of which having up to 10 carbon atoms; 2) halogen; or 3) hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

Yet another aspect of this invention provides compounds, and compositions comprising the compounds, wherein the compounds have the formula:

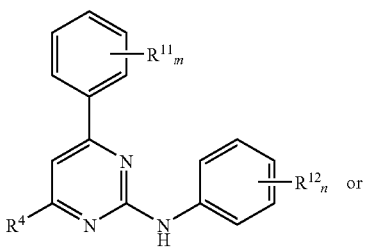

(II-J1)

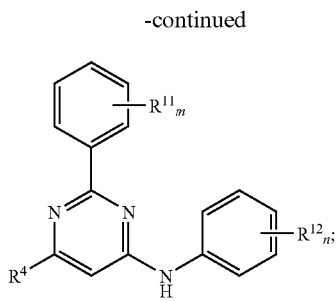

(II-J2)

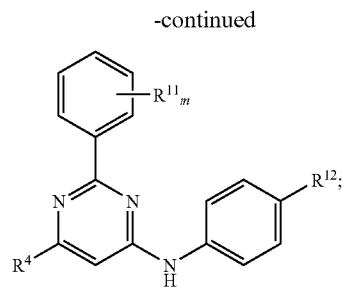

(II-R2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^4$ is a substituted or an unsubstituted heterocyclyl comprising at least one heteroatom or heterogroup selected from —O—, >N—, —S—, or >CO, and having up to 10 carbon atoms;

n and m are independently an integer from 0 to 3, inclusive;

$R^{11}$ and $R^{12}$, in each occurrence, are selected independently from: 1) an alkyl, an alkoxy, a haloalkyl, a haloalkoxy, —$COR^9$, —$CONR^8{}_2$, —$SO_2R^9$, —$NHSO_2R^9$, or —$SO_2NR^8{}_2$, any of which having up to 10 carbon atoms; or 2) halogen, hydroxyl, or —$OCH_2O$—;

$R^8$, in each occurrence, is selected independently from: 1) an alkyl, a haloalkyl, or an aryl having up to 6 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

wherein $R^4$ is optionally substituted with at least one group selected independently from: 1) alkyl, —$COR^{10}$, —$CONR^8{}_2$, —$SO_2R^{10}$, —$SO_2NR^{10}{}_2$, any of which having up to 10 carbon atoms; or 2) hydroxyl; and $R^{10}$, in each occurrence, is independently selected from: 1) an alkyl, an aryl, or a heterocyclyl comprising at least one heteroatom selected from —O— or >N—, any of which having up to 10 carbon atoms; or 2) hydrogen.

In still another aspect, this invention provides compounds, and compositions comprising the compounds, wherein the compounds have the following formula:

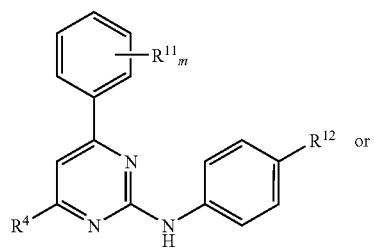

(II-R1)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^4$ is selected from a substituted or an unsubstituted aryl, or a substituted or an unsubstituted heteroaryl or heterocyclyl comprising at least one heteroatom or heterogroup selected from —O—, >N—, —S—, or >CO, any of which having up to 10 carbon atoms;

$R^{11}$, in each occurrence, are selected independently from: 1) an alkyl, an alkoxy, a haloalkyl, a haloalkoxy, —$COR^9$, —$CONR^8{}_2$, —$CO_2R^8$, —$SO_2R^9$, —$NHSO_2R^9$, or —$SO_2NR^8{}_2$, any of which having up to 10 carbon atoms; or 2) halogen, hydroxyl, or —$OCH_2O$—;

m is an integer from 0 to 3, inclusive;

$R^{12}$ is selected from $OCF_3$, SMe, $SO_2Me$, or $SO_2NHMe$;

$R^8$, in each occurrence, is selected independently from: 1) an alkyl, a haloalkyl, or an aryl having up to 6 carbon atoms; or 2) hydrogen;

$R^9$, in each occurrence, is selected independently from: 1) an alkyl, a haloalkyl, an aryl, or a heterocyclyl or heteroaryl comprising at least one heteroatom selected from —O— or >N—, any of which having up to 10 carbon atoms; or 2) hydrogen;

wherein $R^4$ is optionally substituted with at least one group selected independently from: 1) an alkyl, —$COR^9$, —$CO_2R^8$, —$CONR^8{}_2$, —$SO_2R^{10}$, —$SO_2NR^{10}{}_2$, any of which having up to 10 carbon atoms; or 2) hydroxyl; and $R^{10}$, in each occurrence, is independently selected from: 1) an alkyl, an aryl, or a heterocyclyl comprising at least one heteroatom selected from —O— or >N—, any of which having up to 10 carbon atoms; or 2) hydrogen.

In ths aspect, $R^4$ can be selected from

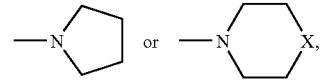

wherein X is selected from $CH_2$, O, NH, NMe, NEt, S, $SO_2$, or CH(OH); and $R^{11}$, in each occurrence, can be selected independently from $OCF_3$, OMe, Cl, F, $SO_2Me$, $CF_3$, Me, COMe, CONHMe, $NHSO_2Me$, $SO_2NH_2$, $SO_2NHMe$, $SO_2NMe_2$, $CONH_2$, $CONMe_2$, $CO_2Me$, $CO_2H$, —$OCH_2O$—, or OH.

Yet another aspect of this invention provides compounds, and compositions comprising the compounds, wherein the compounds have the formula:

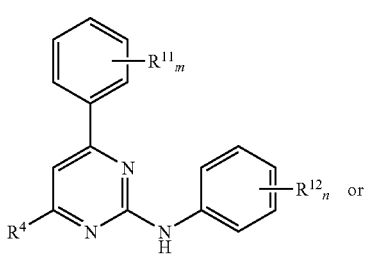

(II-J1i)

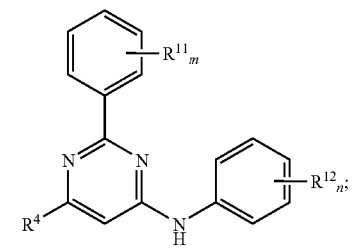

(II-J2i)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^4$ is selected from: 1) a substituted or unsubstituted alkoxy, aryl, or heteroaryl comprising at least one heteroatom selected from —O—, —S—, >N—, or >NH, any of which having up to 10 carbon atoms; 2) hydrogen; or 3) chloro or hydroxyl;

n and m are independently an integer from 0 to 3, inclusive;

$R^{11}$ and $R^{12}$, in each occurrence, are selected independently from: 1) an alkyl, an alkoxy, a haloalkyl, a haloalkoxy, —COR$^9$, —CONR$^8_2$, —SO$_2$R$^9$, —NHSO$_2$R$^9$, or —SO$_2$NR$^8_2$, any of which having up to 10 carbon atoms; or 2) halogen, hydroxyl, —OCH$_2$O—;

$R^8$, in each occurrence, is selected independently from: 1) an alkyl, a haloalkyl, or an aryl having up to 6 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

$R^4$ is optionally substituted with at least one group independently selected from: 1) alkyl, haloalkoxy, alkoxy, —COR$^{10}$, —CONR$^8_2$, —SO$_2$R$^{10}$, —SO$_2$NR$^{10}_2$, or —NR$^{10}_2$, any of which having up to 10 carbon atoms; 2) halogen; or 3) hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

In another aspect, this invention provides compounds, and compositions comprising the compounds, wherein the compounds have the following formula:

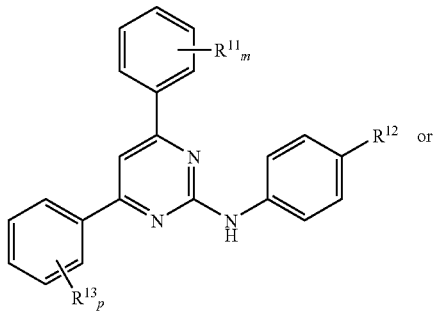

(II-S1)

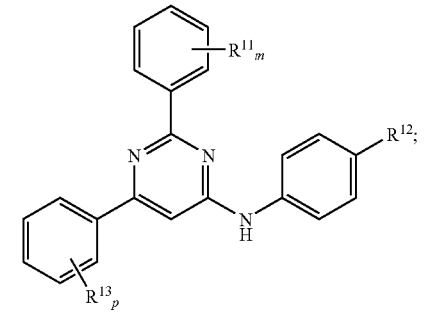

(II-S2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^{11}$ and $R^{13}$, in each occurrence, are selected independently from: 1) an alkyl, an alkoxy, a haloalkyl, a haloalkoxy, —COR$^9$, —CO$_2$R$^8$, —CONR$^8_2$, —SO$_2$R$^9$, —NHSO$_2$R$^9$, or —SO$_2$NR$^8_2$, any of which having up to 10 carbon atoms; or 2) halogen, hydroxyl, or —OCH$_2$O—;

m and p are selected independently from an integer from 0 to 3, inclusive;

$R^{12}$ is selected from OCF$_3$, SMe, SO$_2$Me, or SO$_2$NHMe;

$R^8$, in each occurrence, is selected independently from: 1) an alkyl, a haloalkyl, or an aryl, any of which having up to 6 carbon atoms; or 2) hydrogen; and $R^9$, in each occurrence, is independently selected from an alkyl, a haloalkyl, an aryl, or a heterocyclyl or heteroaryl comprising at least one heteroatom selected from —O— or >N—, any of which having up to 10 carbon atoms.

Still another aspect of this invention provides compounds, and compositions comprising the compounds, wherein the compounds have the following formula:

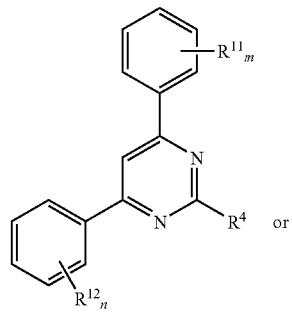

(II-T1)

-continued (II-T2)

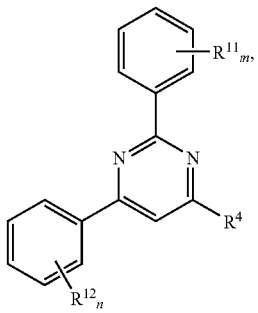

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^4$ is selected from

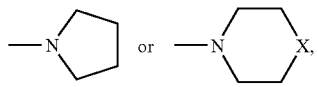

wherein X is selected from $CH_2$, O, NH, NMe, NEt, S, $SO_2$, or CH(OH);

$R^{11}$ and $R^{12}$, in each occurrence, are selected independently from: 1) an alkyl, an alkoxy, a haloalkyl, a haloalkoxy, —$COR^9$, —$CO_2R^8$, —$CONR^8{}_2$, —$SO_2R^9$, —$NHSO_2R^9$, or —$SO_2NR^8{}_2$, any of which having up to 10 carbon atoms; or 2) halogen, hydroxyl, or —$OCH_2O$—;

n and m are selected independently from an integer from 0 to 3, inclusive;

$R^8$, in each occurrence, is selected independently from: 1) an alkyl, a haloalkyl, or an aryl, any of which having up to 6 carbon atoms; or 2) hydrogen; and $R^9$, in each occurrence, is independently selected from an alkyl, a haloalkyl, an aryl, or a heterocyclyl or heteroaryl comprising at least one heteroatom selected from —O— or >N—, any of which having up to 10 carbon atoms.

Yet another aspect of this invention provides compounds, and compositions comprising the compounds, wherein the compounds have the following formula:

(II-J1ii)

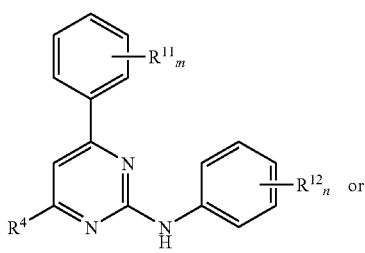

(II-J2ii)

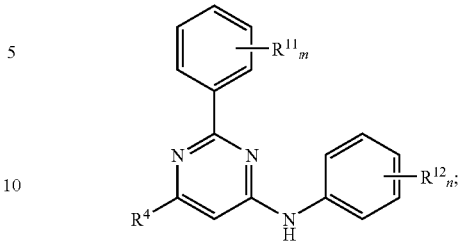

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^4$ is selected from: 1) a substituted or an unsubstituted alkoxy, aryl, or heteroaryl comprising at least one heteroatom selected from —O—, >N—, or —S—, any of which having up to 10 carbon atoms; or 2) hydrogen, chloro, or hydroxyl;

$R^{11}$ and $R^{12}$, in each occurrence, are selected independently from: 1) an alkyl, an alkoxy, a haloalkyl, a haloalkoxy, —$COR^9$, —$CONR^8{}_2$, —$SO_2R^9$, —$NHSO_2R^9$, or —$SO_2NR^8{}_2$, any of which having up to 10 carbon atoms; or 2) halogen, hydroxyl, or —$OCH_2O$—;

n and m are selected independently from an integer from 0 to 3, inclusive;

$R^8$, in each occurrence, is selected independently from: 1) an alkyl, a haloalkyl, or an aryl, any of which having up to 6 carbon atoms; or 2) hydrogen;

$R^9$, in each occurrence, is independently selected from an alkyl, a haloalkyl, an aryl, or a heterocyclyl or heteroaryl comprising at least one heteroatom selected from —O— or >N—, any of which having up to 10 carbon atoms;

$R^4$ is optionally substituted with at least one group independently selected from: 1) an alkyl, an alkoxy, a haloalkoxy, —$COR^{10}$, —$CONR^8{}_2$, —$SO_2R^{10}$, —$SO_2NR^{10}{}_2$, or $NR^{10}{}_8$, any of which having up to 10 carbon atoms; or 2) halogen or hydroxyl; and $R^{10}$, in each occurrence, is independently selected from: 1) an alkyl, an aryl, or a heterocyclyl comprising at least one heteroatom selected from —O— or >N—, any of which having up to 10 carbon atoms; or 2) hydrogen.

In another aspect, this invention provides compounds, and compositions comprising the compounds, wherein the compounds have the following formula:

(II-N1)

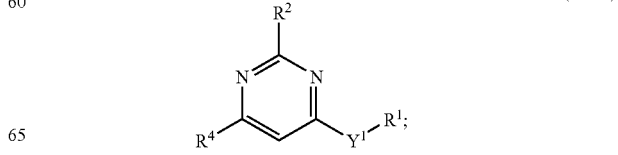

(II-N2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ is selected independently from >NRW or —(CH$_2$)n— wherein n is 0 or 1;

$R^1$ and $R^4$ are selected independently from: 1) a substituted or an unsubstituted alkyl, cycloalkyl, aryl, or heterocyclyl or heteroaryl comprising at least one heteroatom or heterogroup selected from —O—, >N—, —S—, >CO, or >SO$_2$, any of which having up to 10 carbon atoms; or 2) hydrogen, halogen, or hydroxyl;

$R^5$ is selected from an alkyl having up to 3 carbon atoms or hydrogen;

$R^2$ is selected from a heterocyclyl or heteroaryl comprising at least one heteroatom or heterogroup selected from —O—, >N—, —S—, >CO, or >SO$_2$, any of which having up to 10 carbon atoms;

$R^1$ and $R^4$ are optionally substituted with at least one group independently selected from: 1) an alkyl, an alkoxy, a haloalkyl, a haloalkoxy, —COR$^9$, —CONR$^8{}_2$, SO$_2$R$^9$, —NHSO$_2$R$^9$, or —SO$_2$NR$^8{}_2$, any of which having up to 10 carbon atoms; or 2) halogen, cyano, hydroxyl, or —OCH$_2$O—;

$R^8$, in each occurrence, is selected independently from: 1) an alkyl, a haloalkyl, or an aryl, any of which having up to 6 carbon atoms; or 2) hydrogen; and $R^9$, in each occurrence, is independently selected from an alkyl, a haloalkyl, an aryl, or a heterocyclyl or heteroaryl comprising at least one heteroatom selected from —O— or >N—, any of which having up to 10 carbon atoms.

In yet another aspect, this invention provides compounds, and compositions comprising the compounds, wherein the compounds have the formula:

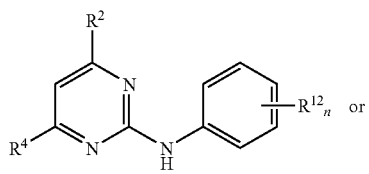

(II-O1)

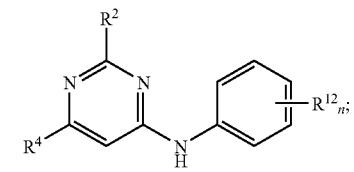

(II-O2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^2$ is selected from a heterocyclyl or heteroaryl comprising at least one heteroatom or heterogroup selected from —O—, >N—, —S—, >CO or >SO$_2$, having up to 10 carbon atoms;

$R^4$ is selected from: 1) a substituted or an unsubstituted alkyl, cycloalkyl, aryl, heterocyclyl or heteroaryl comprising at least one heteroatom or heterogroup selected from —O—, >N—, —S—, >CO or >SO$_2$, any of which having up to 10 carbon atoms; or 2) hydrogen, halogen; or hydroxyl;

n is an integer from 0 to 3, inclusive;

$R^{12}$, in each occurrence, is selected independently from: 1) an alkyl, an alkoxy, a haloalkyl, a haloalkoxy, —COR$^9$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, or —OCH$_2$O—;

$R^4$ is optionally substituted with at least one group selected independently from: 1) an alkyl, an alkoxy, a haloalkyl, a haloalkoxy, —COR$^9$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, cyano, or —OCH$_2$O—;

$R^8$, in each occurrence, is selected independently from: 1) an alkyl, a haloalkyl, or an aryl having up to 6 carbon atoms; or 2) hydrogen; and $R^9$, in each occurrence, is selected independently from an alkyl, a haloalkyl, an aryl, a heterocyclyl or heteroaryl comprising at least one heteroatom selected from —O— or >N—, any of which having up to 10 carbon atoms.

In another aspect, this invention provides compounds, and compositions comprising the compounds, wherein the compounds have the formula:

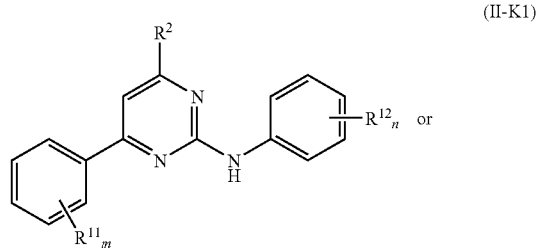

(II-K1)

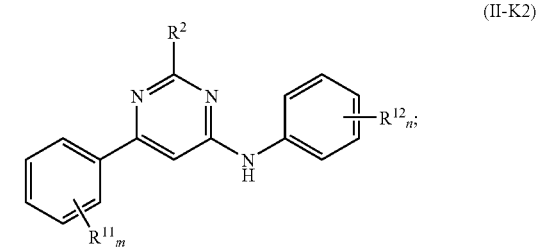

(II-K2)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^2$ is selected from a substituted or an unsubstituted heterocyclyl or heteroaryl comprising at least one heteroatom or heterogroup selected from —O—, >N—, —S—, >CO, or >SO$_2$, any of which having up to 10 carbon atoms;

n and m are independently an integer from 0 to 3, inclusive;

$R^{11}$ and $R^{12}$, in each occurrence, are selected independently from: 1) an alkyl, an alkoxy, a haloalkyl, a haloalkoxy, —COR$^9$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, or —OCH$_2$O—;

$R^8$, in each occurrence, is selected independently from: 1) an alkyl, a haloalkyl, or an aryl, having up to 6 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

$R^2$ is optionally substituted with at least one group independently selected from: 1) alkyl, —COR$^{10}$, —CONR$^8{}_2$, —SO$_2$R$^{10}$, or —SO$_2$NR$^{10}{}_2$, any of which having up to 10 carbon atoms; or 2) hydroxyl; and $R^{10}$, in each occurrence, is independently: 1) an alkyl, an aryl, or a heterocyclyl comprising at least one heteroatom selected from —O— or >N—, any of which having up to 10 carbon atoms; or 2) hydrogen.

Another aspect of this invention provides compounds, and compositions comprising the compounds, wherein the compounds have the following formula:

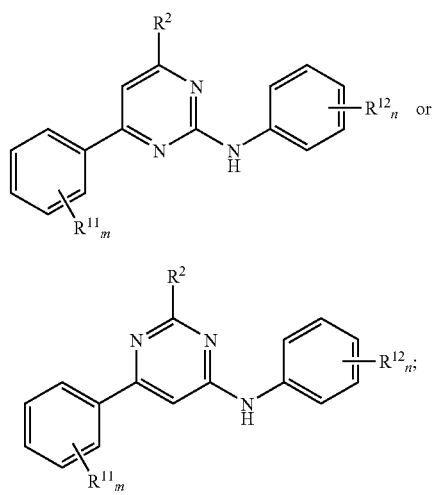

(II-K1i)

(II-K2i)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^2$ is selected from a heterocyclyl or a heteroaryl comprising at least one heteroatom or heterogroup selected from —O—, >N—, —S—, >CO, or >SO$_2$, any of which having up to 10 carbon atoms;

n and m are independently an integer from 0 to 3, inclusive;

$R^{11}$ and $R^{12}$, in each occurrence, are selected independently from: 1) an alkyl, an alkoxy, a haloalkyl, a haloalkoxy, —COR$^9$, —CO$_2$R$^8$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, or —OCH$_2$O—;

$R^8$, in each occurrence, is selected independently from: 1) an alkyl, a haloalkyl, or an aryl having up to 6 carbon atoms; or 2) hydrogen; and $R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms.

In this aspect, $R^2$ can be selected from

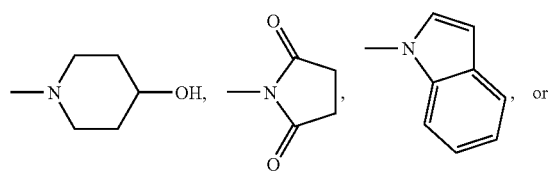

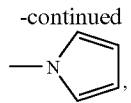

or the like.

Another aspect of this invention provides compounds, and compositions comprising the compounds, wherein the compounds have the following formula:

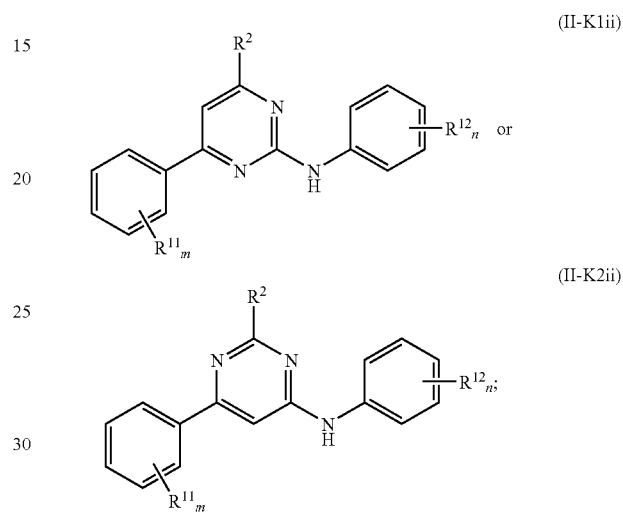

(II-K1ii)

(II-K2ii)

or respectively, a salt, including a pharmaceutically acceptable or a non-pharmaceutically acceptable salt, a prodrug, a diastereomeric mixture, an enantiomer, a tautomer, or a racemic mixture thereof;

wherein:

$R^2$ is selected from a substituted or an unsubstituted heterocyclyl or heteroaryl comprising at least one heteroatom or heterogroup selected from —O—, >N—, —S—, >CO, or >SO$_2$, any of which having up to 10 carbon atoms;

$R^2$ is optionally substituted with at least one group independently selected from: 1) an alkyl, an alkoxy, a haloalkyl, a haloalkoxy, —COR$^9$, —COR$^{10}$, —CO$_2$R$^8$, —CONR$^8{}_2$, —SO$_2$R$^9$, —SR$^8$, —NHSO$_2$R$^9$, —SO$_2$NR$^8{}_2$, —SO$_2$NR$^{02}$, or —NR$^{10}{}_2$, any of which having up to 10 carbon atoms; or 2) halogen, oxo, hydroxyl, cyano, or —OCH$_2$O—;

n and m are independently an integer from 0 to 3, inclusive;

$R^{11}$ and $R^{12}$, in each occurrence, are selected independently from: 1) an alkyl, an alkoxy, a haloalkyl, a haloalkoxy, —COR$^9$, —CO$_2$R$^8$, —CONR$^8{}_2$, —SO$_2$R$^9$, —NHSO$_2$R$^9$, or —SO$_2$NR$^8{}_2$, any of which having up to 10 carbon atoms; or 2) halogen, hydroxyl, or —OCH$_2$O—;

$R^8$, in each occurrence, is selected independently from: 1) an alkyl, a haloalkyl, or an aryl having up to 6 carbon atoms; or 2) hydrogen; and $R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms.

One aspect of this invention provides compounds, and compositions comprising the compounds, wherein the compounds have the following formula:

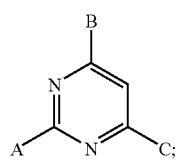
wherein the pyrimidine substituents A, B, and C are as defined herein, but wherein the following provisos regarding the definitions of substituents A, B, and C are applicable:
1. when B or C is CF$_3$, A is not
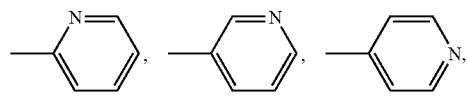
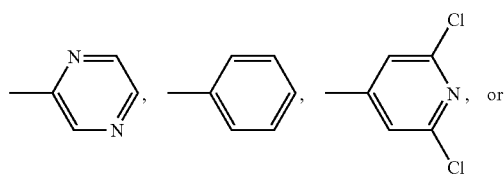
2. when B is
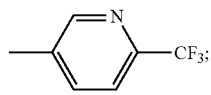
and A is
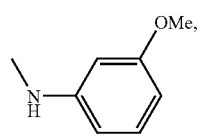
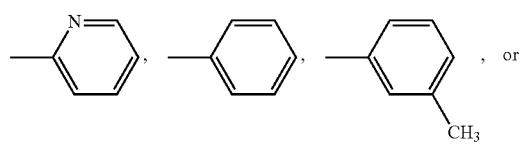
C is not CH$_3$, CH$_2$OCH$_3$,
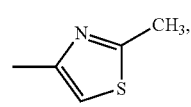
3. when B is
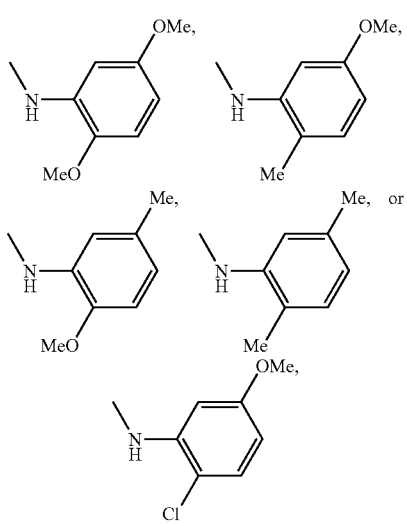
and C is CH$_3$, CH$_2$OCH$_3$, or
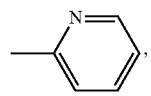
A is not
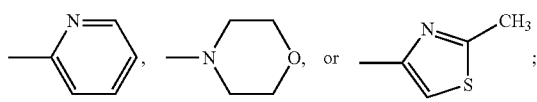
4. when A is
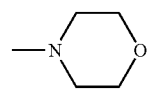
and B is
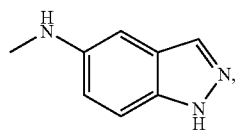
C is not
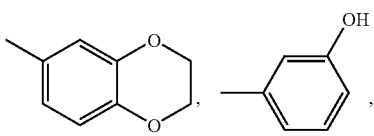

-continued
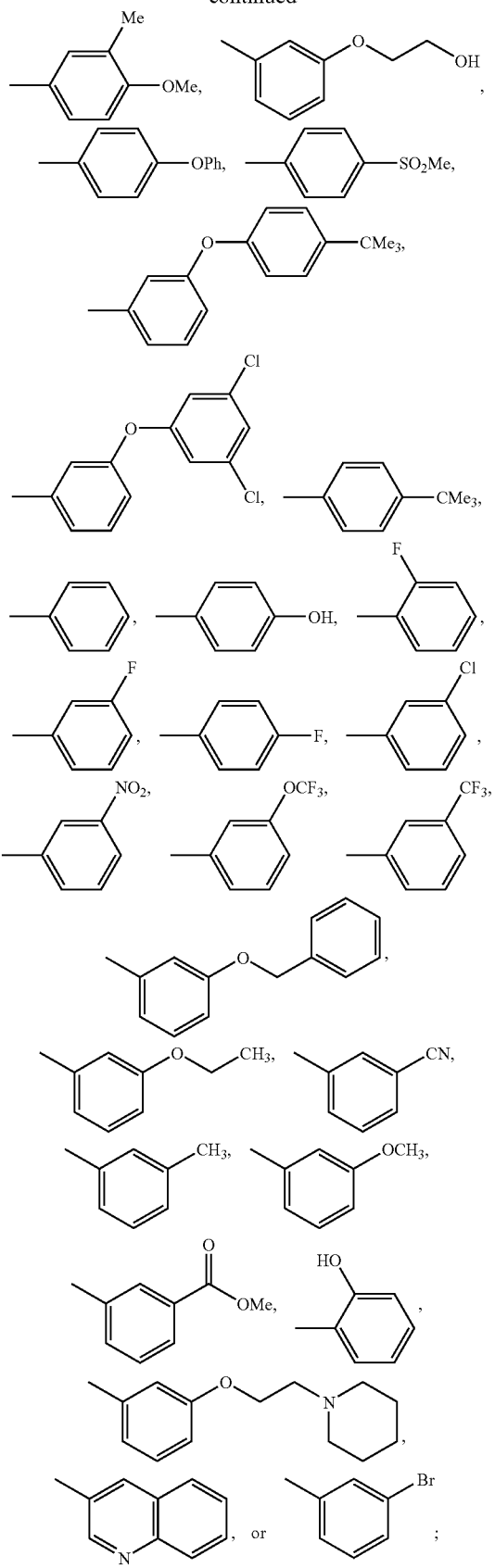
5. when A is
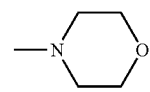
and B is
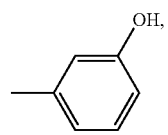
C is not OH, NH$_2$,
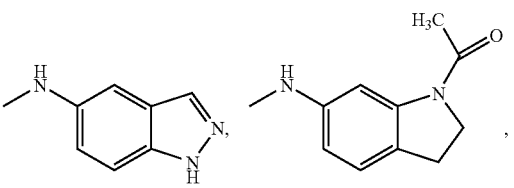
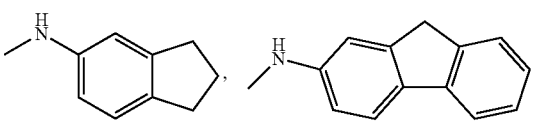
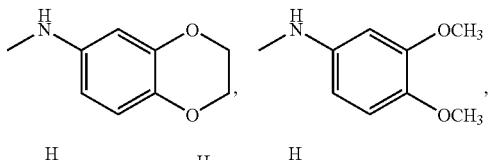
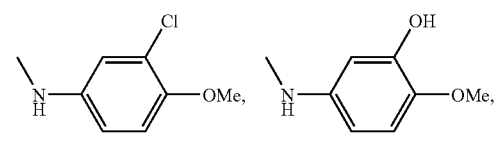
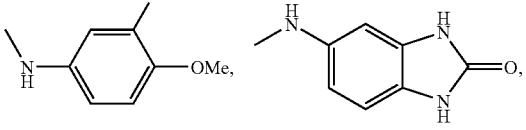
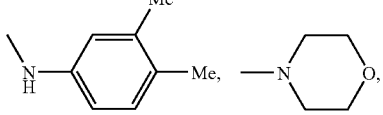
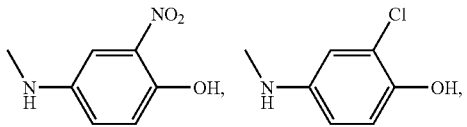

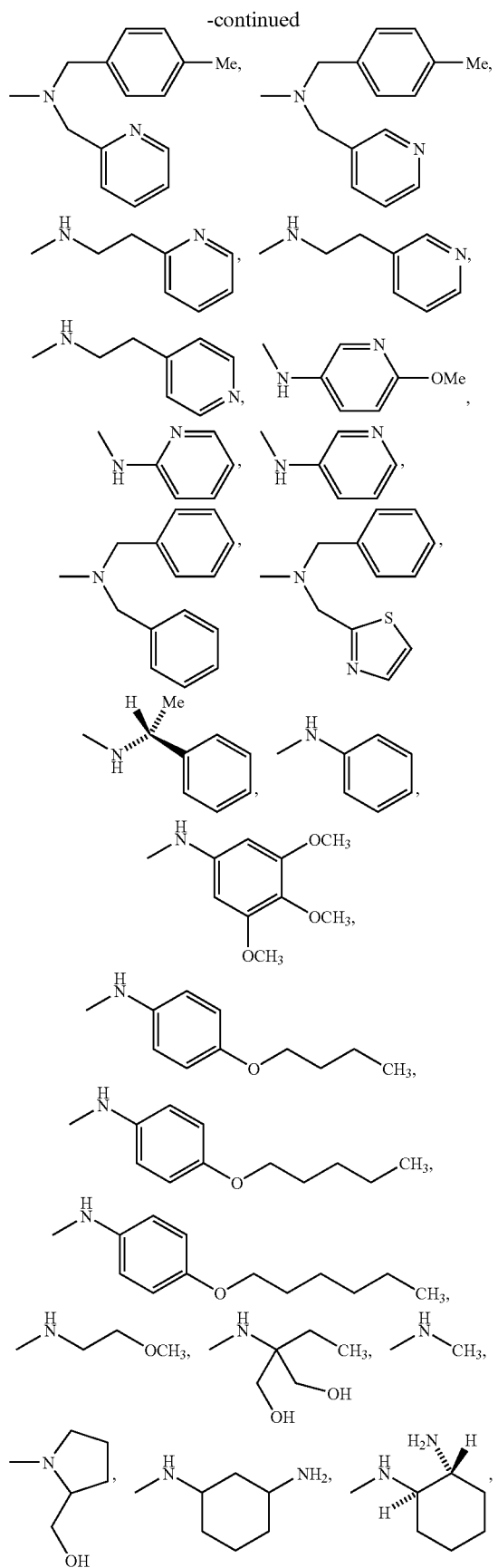
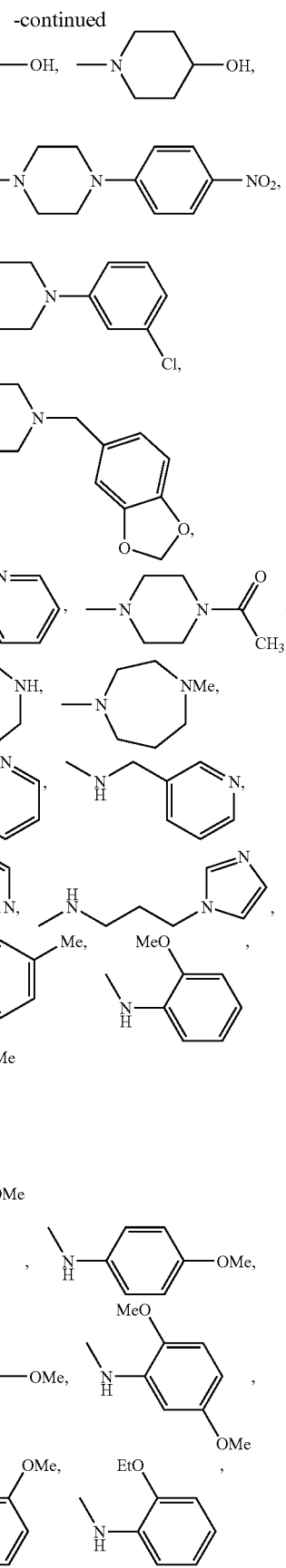

-continued
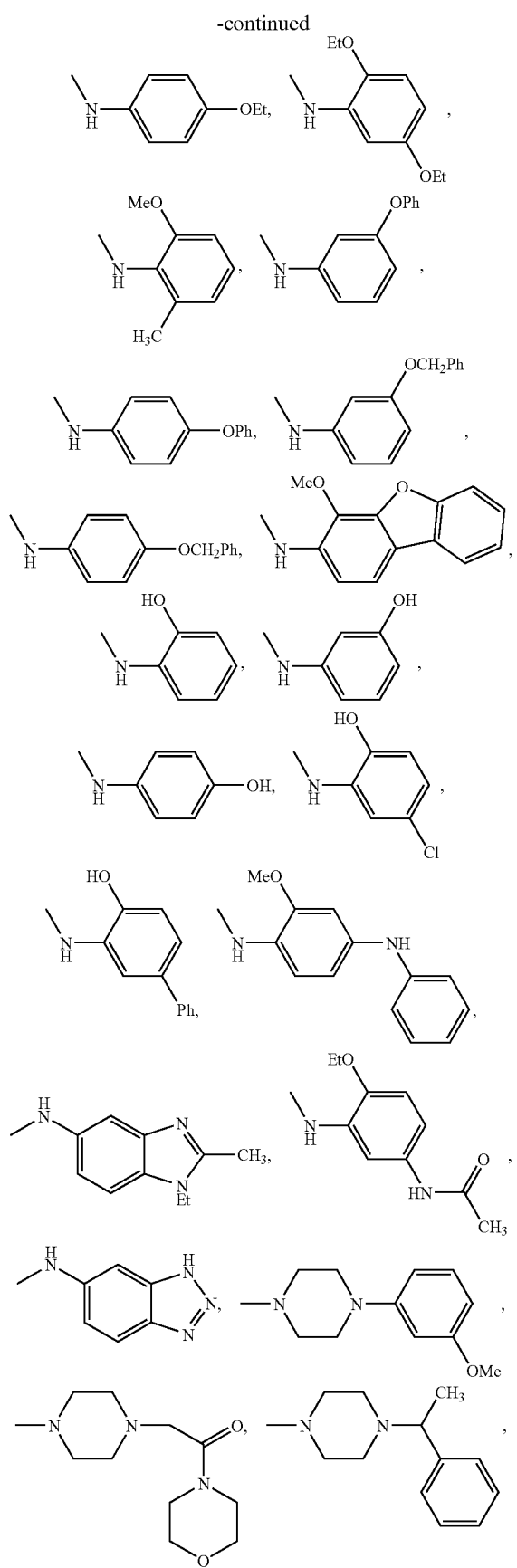
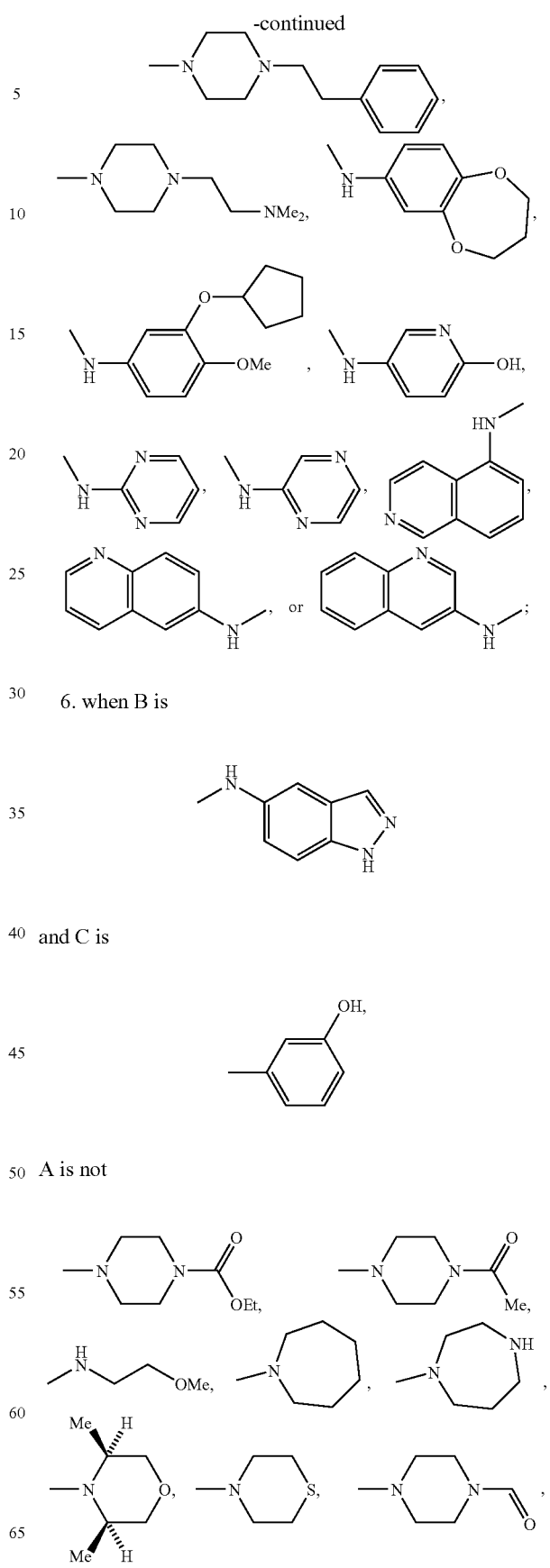
6. when B is
and C is
A is not

-continued

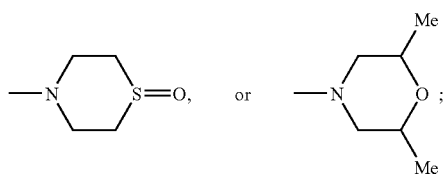

7. when A is

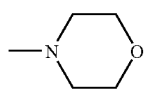

and B is

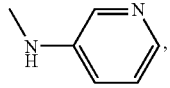

C is not

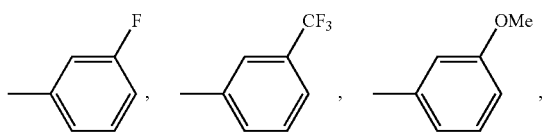

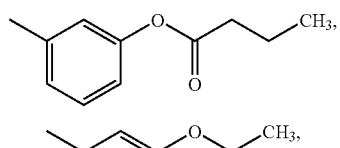

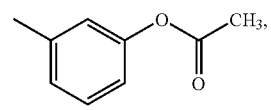

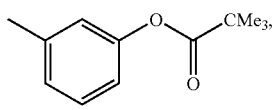

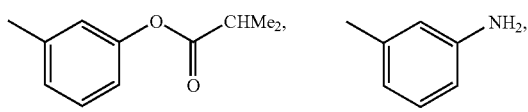

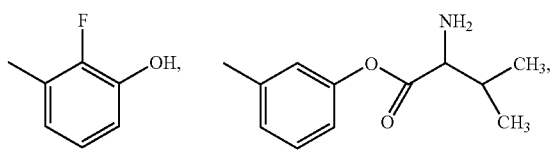

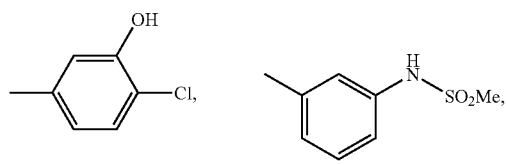

-continued

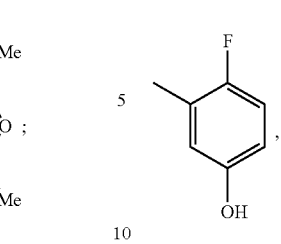

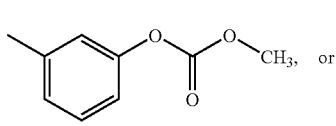

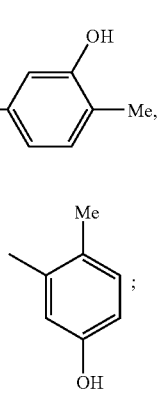

8. wherein when A is

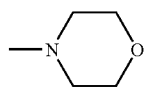

and B is

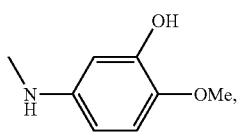

C is not

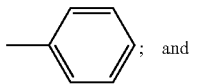; and 9. wherein when A and B are

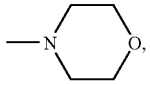

C is not

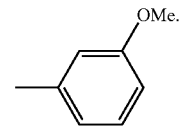

Definitions

The groups defined for various symbols used in the formulas of this disclosure, as well as the optional substituents defined on those groups, may be defined in the detailed manner as follows. Further definitions related to the more biological aspects of this disclosure are provided further below in their respective sections. Unless otherwise specified, any recitation of the number of carbon atoms in a particular group is intended to refer to the unsubstituted "base" group, therefore, any substituent recited on a base group is described by its own definition, including its own limitation of the number of carbon atoms. Unless otherwise specified, all structural isomers of a given structure, for example, all enantiomers, diasteriomers, and regioisomers, are included within this definition.

The terms 'halogen' or 'halo' includes fluorine, chlorine, bromine, or iodine.

The term 'alkyl' group is used to refer to both linear or branched alkyl groups. Exemplary alkyl groups include, but are not limited to, methyl, ethyl, propyl, butyl, pentyl, pentyl, hexyl, heptyl, octyl, nonyl, or decyl, and the like. Unless otherwise specified, an alkyl group has from 1 to 10 carbon atoms. Also unless otherwise specified, all structural isomers of a given structure, for example, all enantiomers and all diasteriomers, are included within this definition. For example, unless otherwise specified, the term propyl is meant to include n-propyl and iso-propyl, while the term butyl is meant to include n-butyl, iso-butyl, t-butyl, sec-butyl, and so forth.

'Haloalkyl' is a group containing at least one halogen and an alkyl portion as define above. Unless otherwise specified, all structural isomers of a given structure, for example, all enantiomers and all diasteriomers, are included within this definition. Exemplary haloalkyl groups include fluoromethyl, chloromethyl, fluoroethyl, chloroethyl, trifluoromethyl, and the like. Unless otherwise specified, a haloalkyl group has from 1 to 10 carbon atoms.

'Acyl' is used to refer to an H—CO— or an alkyl-CO— group, where alkyl is defined herein. Exemplary acyl groups include, but are not limited to, acetyl, propionyl, iso-propionyl, tert-butionyl, and the like.

'Cycloalkyl' group refers to a cyclic alkyl group which may be mono or polycyclic. Exemplary cycloalkyl groups include cyclopropyl, cyclobutyl, cyclopentyl, cyclohexyl, cycloheptyl, cyclooctyl, cyclononyl, and cyclodecyl. Unless otherwise specified, a cycloalkyl group has from 3 to 10 carbon atoms.

'Alkoxy' refers to an —O(alkyl) group, where alkyl is as defined above. Therefore, unless otherwise specified, all isomers of a given structure are included within a definition. Exemplary alkyl groups include methoxy, ethoxy, n-propoxy, iso-propoxy, n-butoxy, iso-butoxy, t-butoxy, and the like. Unless otherwise specified, an alkoxy group has from 1 to 10 carbon atoms.

'Alkoxyalkyl' is an alkyl group with an alkoxy substituent, where alkoxy and alkyl groups are as defined above. Exemplary alkoxyalkyl groups include methoxymethyl, methoxyethyl, methoxypropyl, ethoxymethyl, ethoxyethyl, propoxymethyl, isopropoxymethyl isopropoxyethyl, isopropoxypropyl, t-butoxymethyl, t-butoxymethyl, t-butoxypropyl, and the like. Unless otherwise specified, an alkoxyalkyl group typically has from 1 to 10 carbon atoms.

'Haloalkoxy' is an alkoxy group with a halo substituent, where alkoxy and halo groups are as defined above. Exemplary haloalkoxy groups include chloromethoxy, trichloroethoxy, trifloroethoxy, perfluoroethoxy (—OCF$_2$CF$_3$), trifluoro-t-butoxy, hexafluoro-t-butoxy, perfluoro-t-butoxy (—OC(CF$_3$)$_3$), and the like. Unless otherwise specified, an haloalkoxy group typically has from 1 to 10 carbon atoms.

'Alkylthio' refers to an —S(alkyl) goup, where alkyl group is as defined above. Exemplary alkyl groups include methylthio, ethylthio, propylthio, butylthio, iso-propylthio, iso-butylthio, and the like. Unless otherwise specified, an alkylthio group typically has from 1 to 10 carbon atoms.

'Alkylsulfonyl' refers to a —SO$_2$(alkyl) group, where alkyl group is as defined above. Exemplary alkylsulfonyl groups include methylsulfonyl, ethylsulfonyl, and the like. Unless otherwise specified, an alkylsulfonyl group typically has from 1 to 10 carbon atoms.

'Alkenyl' is an unsaturated aliphatic group containing a C═C double bond. Exemplary alkenyl groups include ethenyl, propenyl, prop-1-enyl, isopropenyl, butenyl, but-1-enyl, isobutenyl, pentenyl, pent-1-enyl, hexenyl, pent-2-enyl, 2-methyl-but-2-ene, 2-methyl-pent-2-enyl, and the like. Unless otherwise specified, an alkenyl group typically has from 2 to 10 carbon atoms.

'Alkynyl' is an unsaturated aliphatic group containing a C≡C triple bond. Exemplary alkynyl groups include ethenyl, propynyl, prop-1-ynyl, butynyl, butaynyl, and the like. Unless otherwise specified, an alkynyl group typically has from 2 to 10 carbon atoms.

'Aryl' is optionally substituted monocylic or polycyclic aromatic ring system of 6 to 14 carbon atoms. Exemplary groups include phenyl, naphthyl, and the like. Unless otherwise specified, an aryl group typically has from 6 to 14 carbon atoms.

'Aralkyl' is an alkyl group with an aryl substituent, where alkyl and aryl groups are as defined above. Exemplary aralkyl groups include, but are not limited to, benzyl, phenethyl (for example, 2-phenethyl), phenylpropyl (for example, 3-phenylpropyl), naphthylmethyl (for example, 1-naphthylmethyl and 2-naphthylmethyl), and the like.

'Heteroaryl' is an aromatic monocyclic or polycyclic ring system of 4 to 10 carbon atoms, having at least one heteroatom or heterogroup selected from —O—, >N—, —S—, >NH or NR, and the like, wherein R is a substituted or unstubstituted alkyl, aryl, or acyl, as defined herein. In this aspect, >NH or NR are considered to be included when the heteroatom or heterogroup can be >N—. Exemplary heteroaryl groups include pyrazinyl, isothiazolyl, oxazolyl, pyrazolyl, pyrrolyl, pyridazinyl, thienopyrimidyl, furanyl, indolyl, isoindolyl, benzo[1,3]dioxolyl, 1,3-benzoxathiole, quinazolinyl, pyridyl, thiophenyl, and the like. Unless otherwise specified, a heteroaryl group typically has from 4 to 10 carbon atoms. Moreover, the heteroaryl group can be bonded to the pyrimidine core structure at a ring carbon atom, or, if applicable for a N-substituted heteroaryl such as pyrrole, can be bonded to the pyrimidine core structure through the heteroatom that is formally deprotonated to form a direct heteroatom-pyrimdine ring bond.

'Heterocyclyl' is a non-aromatic saturated monocyclic or polycyclic ring system of 3 to 10 member having at least one heteroatom or heterogroup selected from —O—, >N—, —S—, >SO$_2$, or >CO. Exemplary heterocyclyl groups include aziridinyl, pyrrolidinyl, piperdinyl, piperazinyl, morpholinyl, thiomorpholinyl, thiazolidinyl, 1,3-dioxolanyl, 1,4-dioxanyl, and the like. Unless otherwise specified, a heterocyclyl group typically has from 2 to 10 carbon atoms. A heterocyclyl group can be bonded through a heteroatom that is formally deprotonated or a heterocyclyl group can be bonded through a carbon atom of the heterocyclyl group.

'Carboxylic acid or its derivatives' may be amides or esters. Exemplary carboxylic acid groups include CONH$_2$, CONHMe, CONMe$_2$, CONHEt, CONEt$_2$, CONHPh, COOH, COOCH$_3$, COOC$_2$H$_5$, or COOC$_3$H$_7$.

'Cyclic amines' means nitrogen containing heteroaryl or heterocyclyl groups.

According to one aspect of the present invention, compounds and compositions comprising these compounds are provided, wherein the compounds have the following formula:

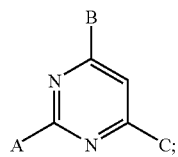
wherein A is selected from —NH₂, —SEt, —OH,
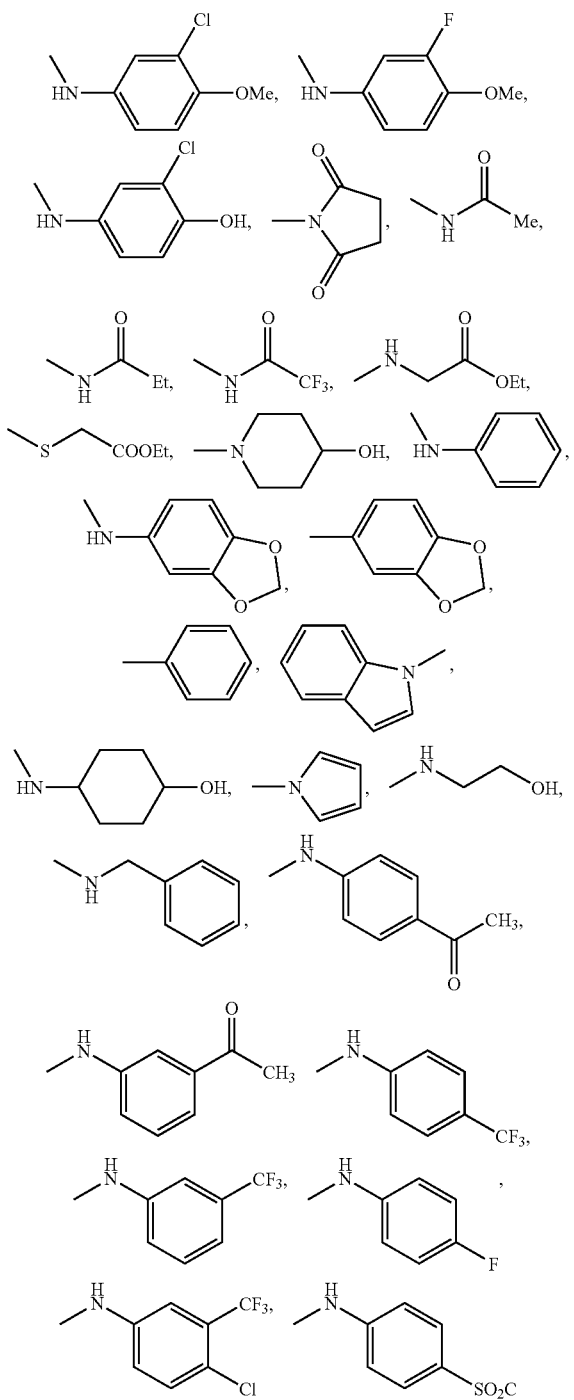
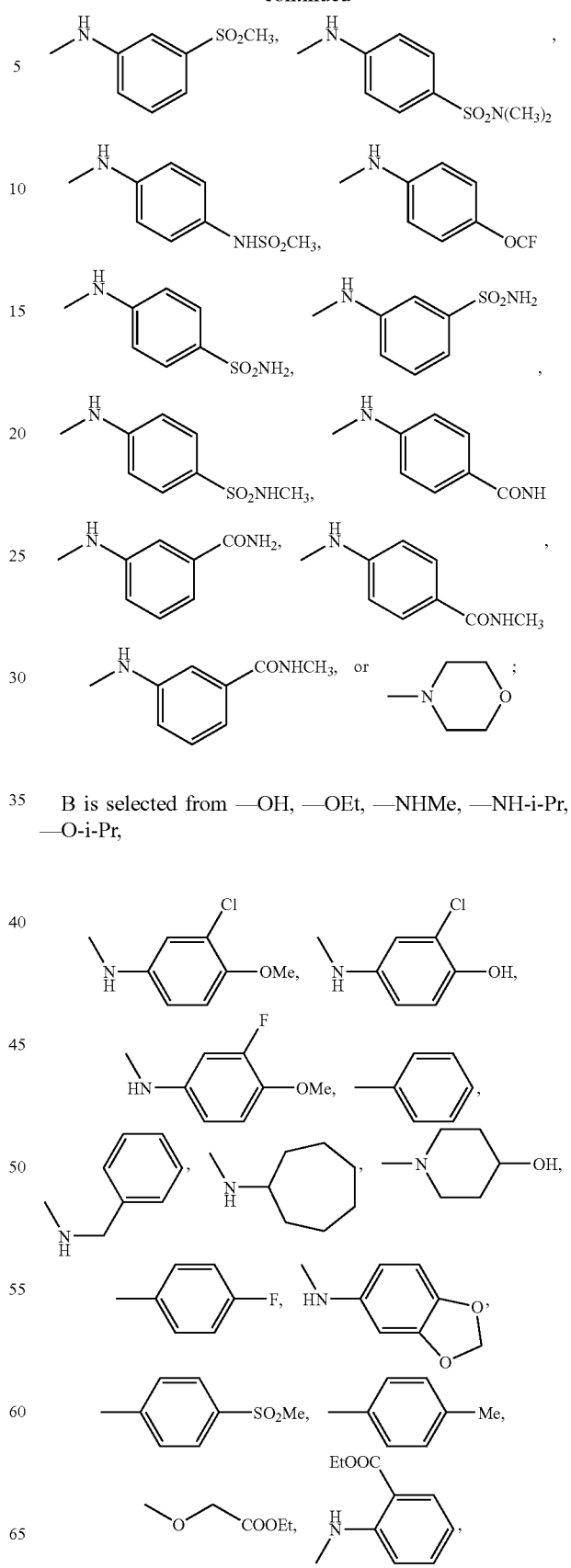
B is selected from —OH, —OEt, —NHMe, —NH-i-Pr, —O-i-Pr, and C is selected from —Cl, —OH, —CH₃,

or a salt, including a pharmaceutically acceptable or a non-pharmaceutically acceptable salt, a prodrug, a diastereomeric mixture, an enantiomer, a tautomer, or a racemic mixture thereof.

In yet a further aspect, this invention provides compounds, and compositions comprising the compounds, wherein the compounds have the formula or a salt, including a pharmaceutically acceptable or a non-pharmaceutically acceptable salt, a prodrug, a diastereomeric mixture, an enantiomer, a tautomer, or a racemic mixture wherein:

A is selected from A1, A2, or A3, wherein:

A1 is

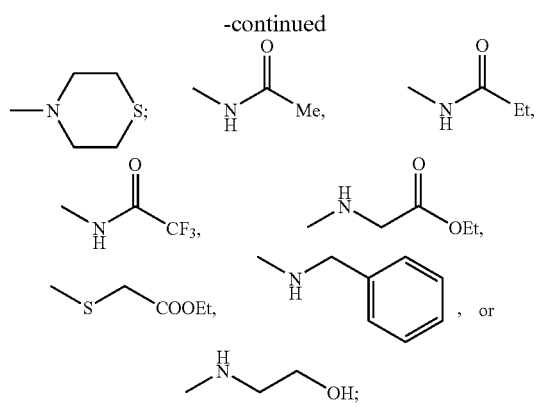

A2 is

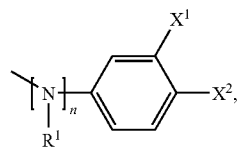

wherein n is 0 or 1;

R[1] is H or CH$_3$;

X[1] is H, F, Cl, OCH$_3$, SO$_2$CH$_3$, SO$_2$NH$_2$, SO$_2$NHCH$_3$, SO$_2$N(CH$_3$)$_2$, CF$_3$, C(O)CH$_3$, C(O)NH$_2$, C(O)NHCH$_3$, or C(O)N(CH$_3$)$_2$; and X[2] is H, F, Cl, OH, OCH$_3$, OCH$_2$CH$_3$, SCH$_3$, CH$_3$, CF$_3$, OCF$_3$, SO$_2$CH$_3$, SO$_2$NH$_2$, SO$_2$NHCH$_3$, SO$_2$N(CH$_3$)$_2$, C(O)CH$_3$, C(O)NH$_2$, C(O)NHCH$_3$, C(O)N(CH$_3$)$_2$, NHSO$_2$CH$_3$, or X[1] and X[2] form a fused 1,3-dioxolane ring; and A3 is H, Cl, NH$_2$, SH, SMe, SEt, or OH; and B and C are selected independently from:

1) A1 or A2;

2)

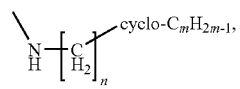

wherein n is 0 or 1, and m is 5, 6, 7, or 8; or

3) Cl, OH, NH$_2$, SH, SMe, SEt, OEt, NHMe, NH-i-Pr, O-i-Pr, CH$_3$,

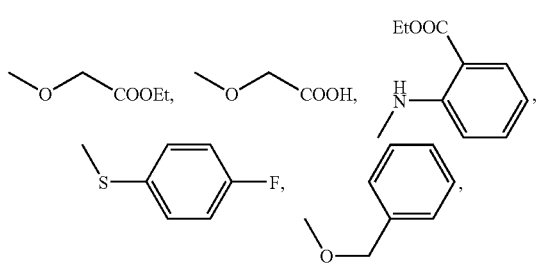

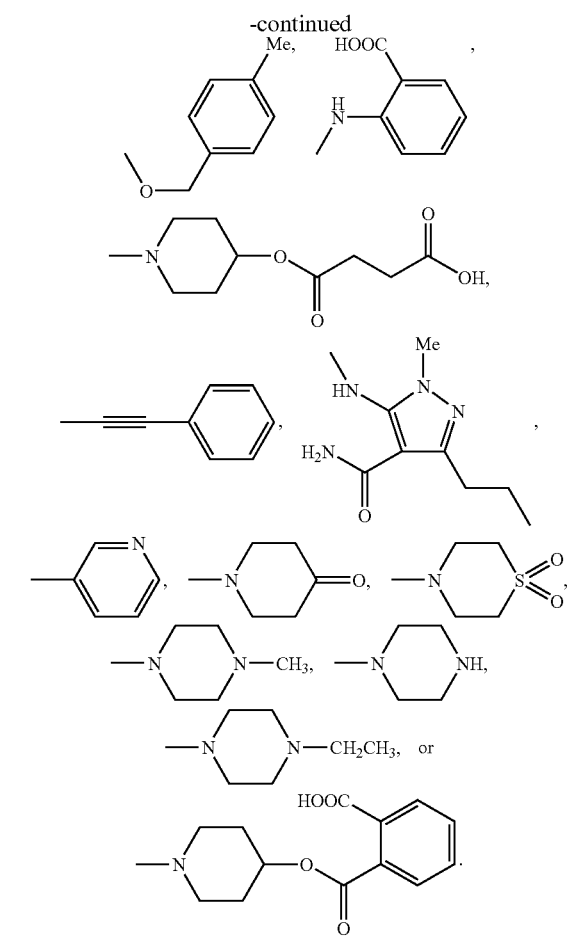

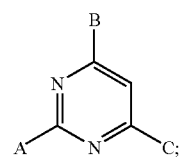

In another aspect, this invention provides compounds, and compositions comprising the compounds, wherein the compounds have the formula:

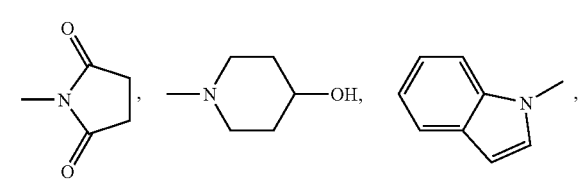

or a salt, including a pharmaceutically acceptable or a non-pharmaceutically acceptable salt, a prodrug, a diastereomeric mixture, an enantiomer, a tautomer, or a racemic mixture thereof, wherein:

A is selected from A1, A2, or A3, wherein:

A1 is

A2 is wherein
 n is 0 or 1;
 $R^1$ is H or $CH_3$;
 $X^1$ is H, F, Cl, $OCH_3$, $SO_2CH_3$, $SO_2NH_2$, $SO_2NHCH_3$, $SO_2N(CH_3)_2$, $CF_3$, $C(O)CH_3$, $C(O)NH_2$, $C(O)NHCH_3$, or $C(O)N(CH_3)_2$; and
 $X^2$ is H, F, Cl, OH, $OCH_3$, $OCH_2CH_3$, $SCH_3$, $CH_3$, $CF_3$, $OCF_3$, $SO_2CH_3$, $SO_2NH_2$, $SO_2NHCH_3$, $SO_2N(CH_3)_2$, $C(O)CH_3$, $C(O)NH_2$, $C(O)NHCH_3$, $C(O)N(CH_3)_2$, $NHSO_2CH_3$, or $X^1$ and $X^2$ form a fused 1,3-dioxolane ring; and
 A3 is H, Cl, $NH_2$, SH, SMe, SEt, or OH;
B is selected from:
 1) A1 or A2;
 2)

wherein n is 0 or 1, and m is 5, 6, 7, or 8; or
 3) Cl, OH, $NH_2$, SH, SMe, SEt, OEt, NHMe, NH-i-Pr, O-i-Pr, $CH_3$, C is selected from:
 1) Cl, OH, $CH_3$,

2)

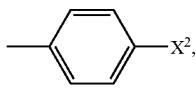

wherein $X^2$ is H, F, OCH$_3$, OCH$_2$CH$_3$, SCH$_3$, CH$_3$, CF$_3$, OCF$_3$, or SO$_2$CH$_3$.

In yet a further aspect, this invention provides compounds, and compositions comprising the compounds, wherein the compounds have the formula:

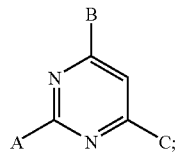

or a salt, including a pharmaceutically acceptable or a non-pharmaceutically acceptable salt, a prodrug, a diastereomeric mixture, an enantiomer, a tautomer, or a racemic mixture thereof, wherein:
A is selected from A1 or A2, and
B and C are selected independently from A2 or A3, wherein:
 A1 is

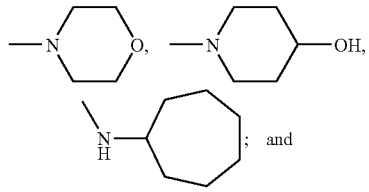

A2 is

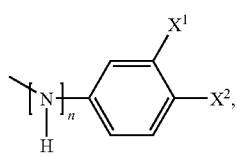

wherein:
 n is 0 or 1;
 $X^1$ is H, Cl, F, CF$_3$, SO$_2$CH$_3$, C(O)CH$_3$, or SO$_2$NH$_2$; and
 $X^2$ is H, Cl, F, OCH$_3$, OCF$_3$, CF$_3$, SO$_2$CH$_3$, C(O)CH$_3$, SO$_2$N(CH$_3$)$_2$, or SO$_2$NHCH$_3$, or $X^1$ and $X^2$ form a fused 1,3-dioxolane ring; and
 A3 is

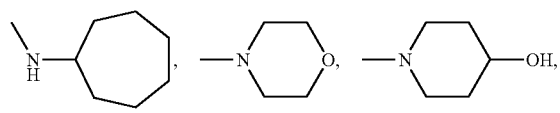

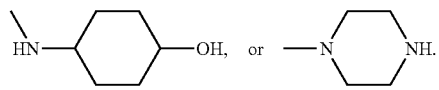

Also in another aspect, this invention provides compounds, and compositions comprising the compounds, wherein the compounds have the formula:

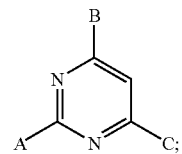

or a salt, including a pharmaceutically acceptable or a non-pharmaceutically acceptable salt, a prodrug, a diastereomeric mixture, an enantiomer, a tautomer, or a racemic mixture thereof, wherein:
 A is selected from

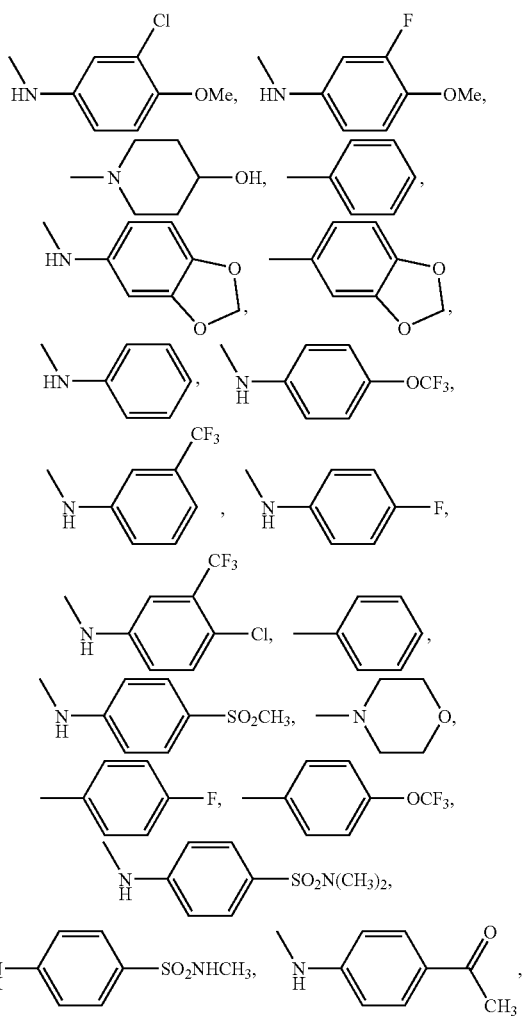

-continued

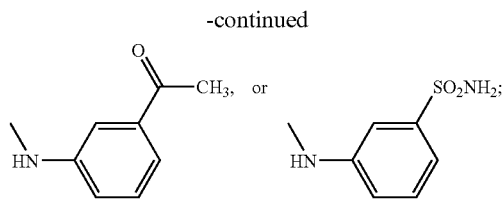

B is selected from

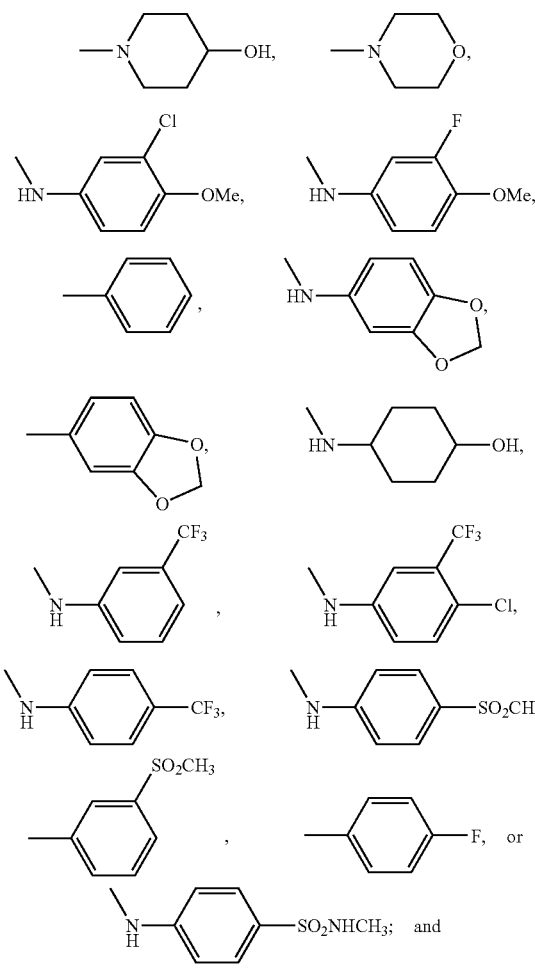

C is selected from

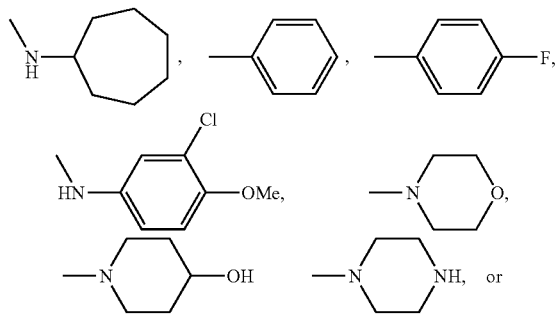

-continued

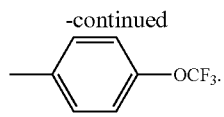

In still another aspect, this invention provides compounds, and compositions comprising the compounds, wherein the compounds have the formula:

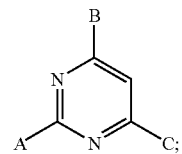

or a salt, including a pharmaceutically acceptable or a non-pharmaceutically acceptable salt, a prodrug, a diastereomeric mixture, an enantiomer, a tautomer, or a racemic mixture thereof, wherein:

A and B are selected independently from

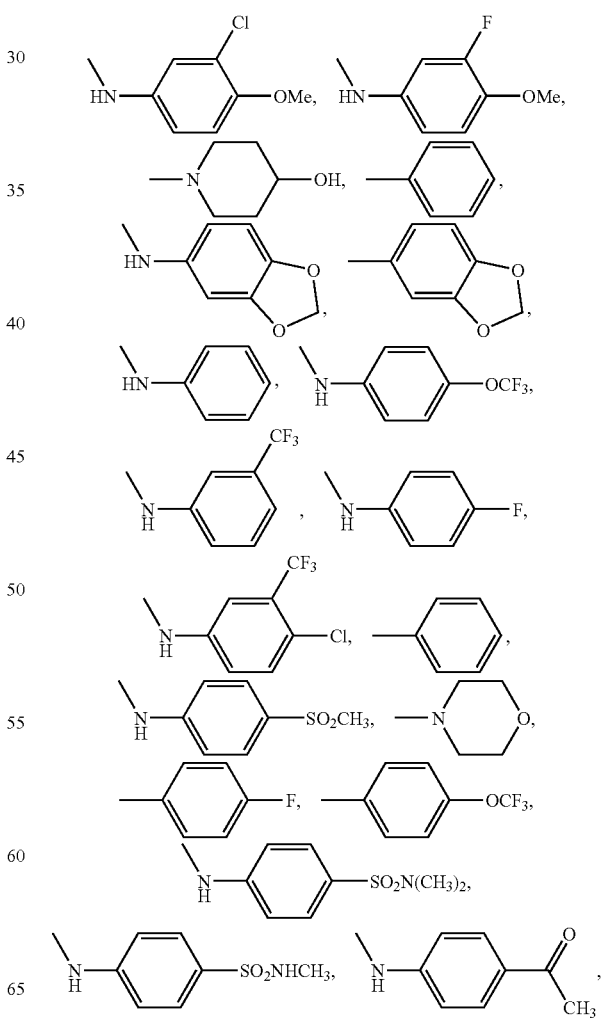

-continued

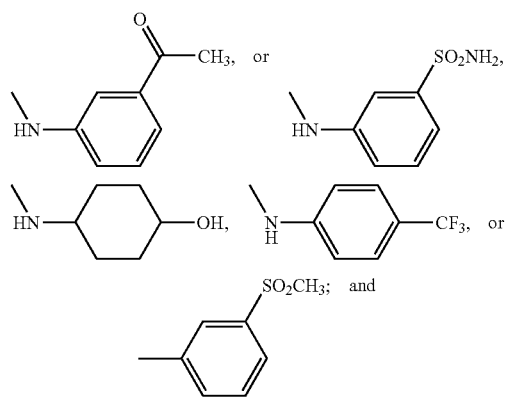

C is selected from

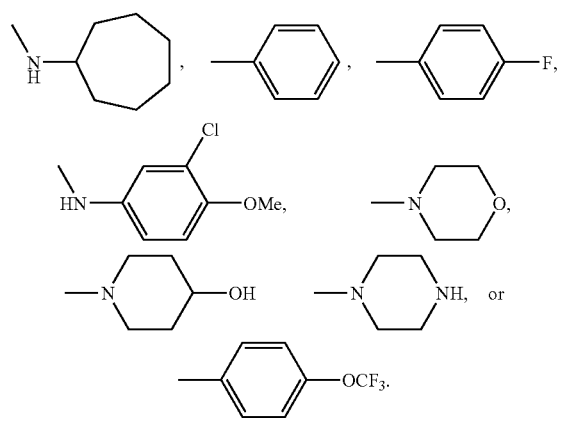

Another aspect of this invention provides compounds, and compositions comprising the compounds, wherein the compounds have the formula:

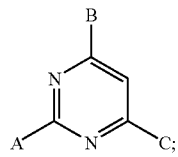

or a salt, including a pharmaceutically acceptable or a non-pharmaceutically acceptable salt, a prodrug, a diastereomeric mixture, an enantiomer, a tautomer, or a racemic mixture thereof, wherein:

A is selected from —H, —Cl, —NH$_2$, —SH, —SEt, —OH,

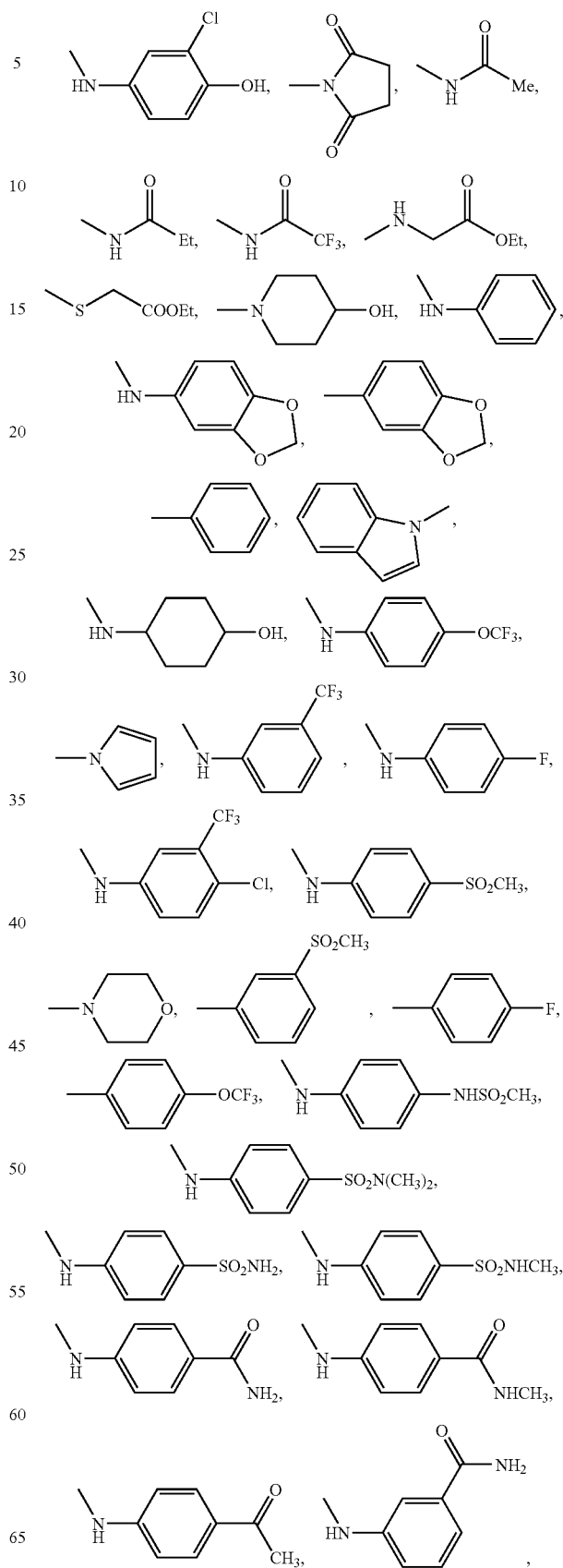

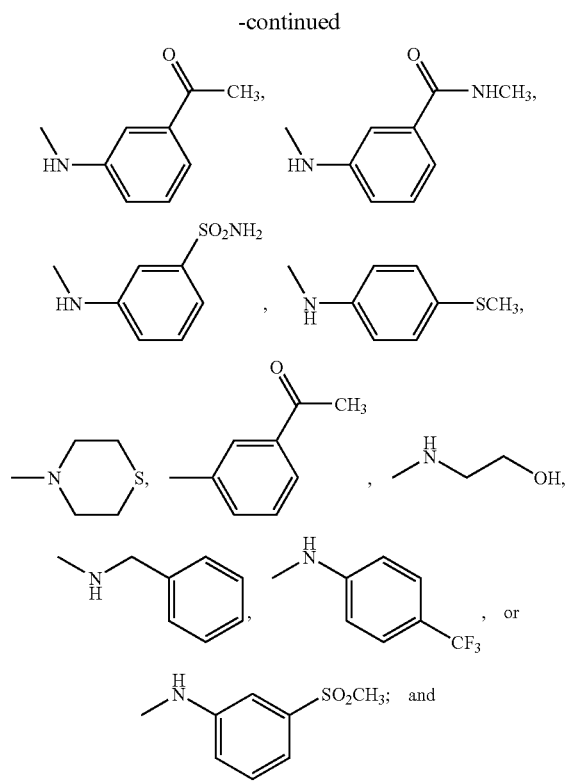
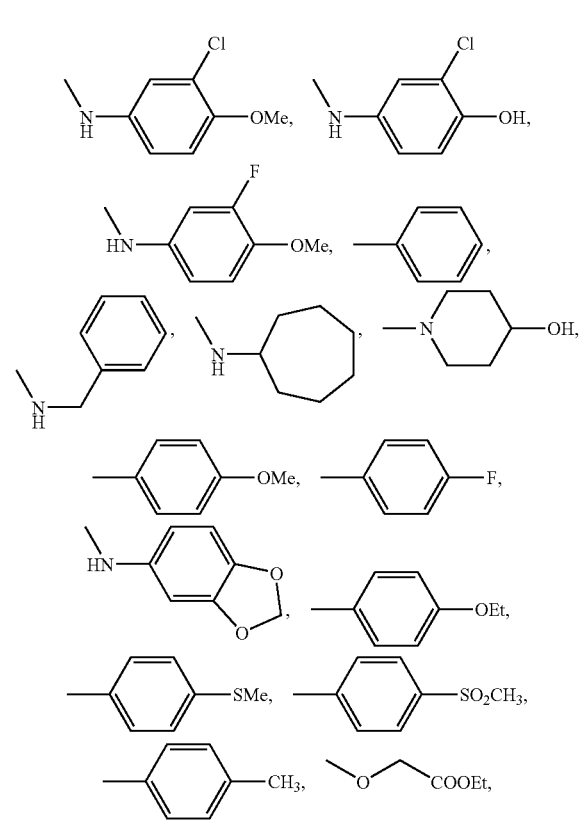
B and C are independently selected from —Cl, —OH, —OEt, —NHMe, —NH-i-Pr, —O-i-Pr, Pr, —CH₃,
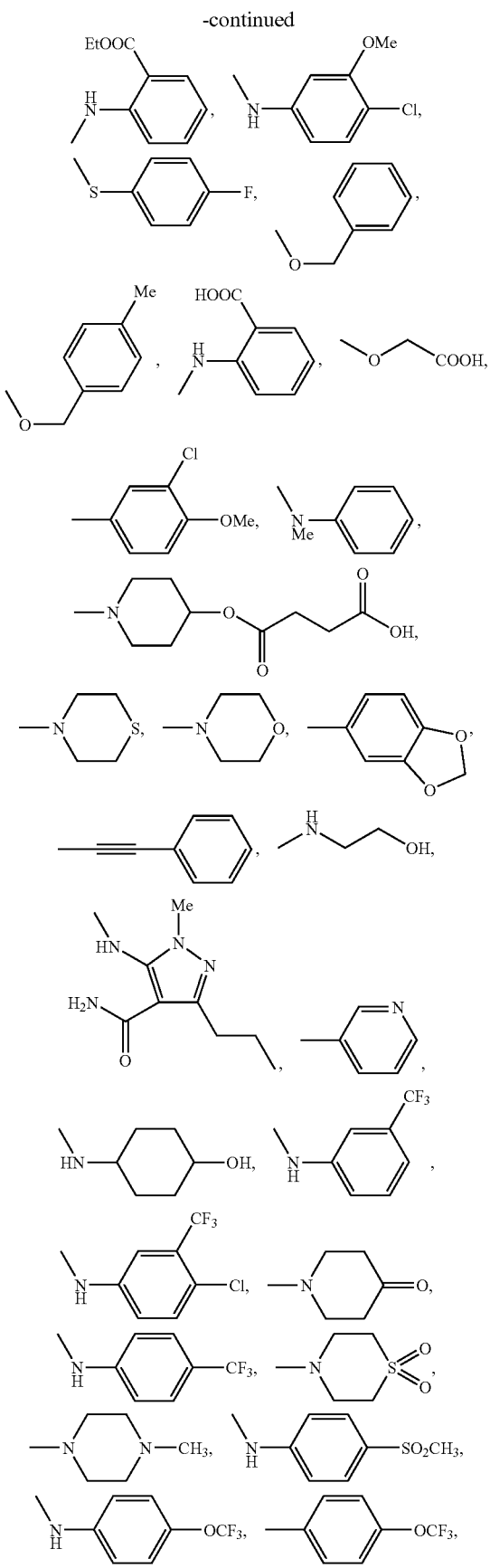

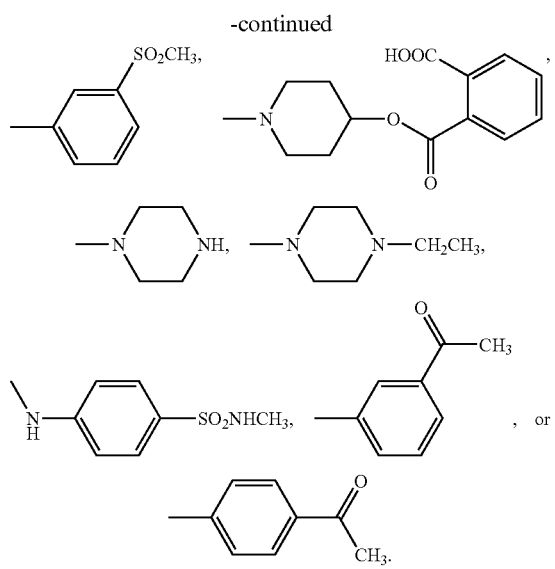

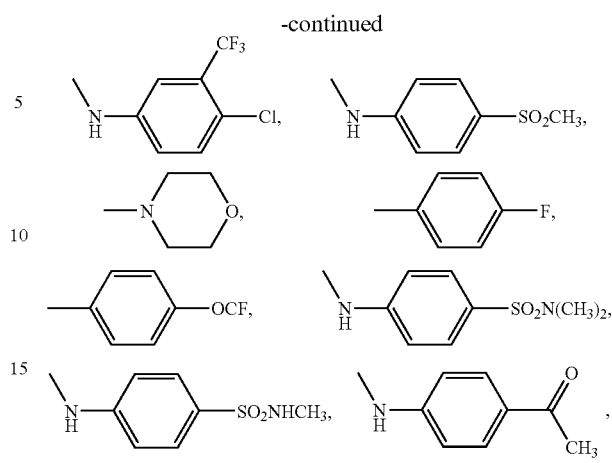

In yet still another aspect, this invention provides compounds, and compositions comprising the compounds, wherein the compounds have the formula:

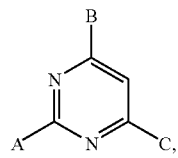

or a salt, including a pharmaceutically acceptable or a non-pharmaceutically acceptable salt, a prodrug, a diastereomeric mixture, an enantiomer, a tautomer, or a racemic mixture thereof, wherein:

A and B are selected independently from

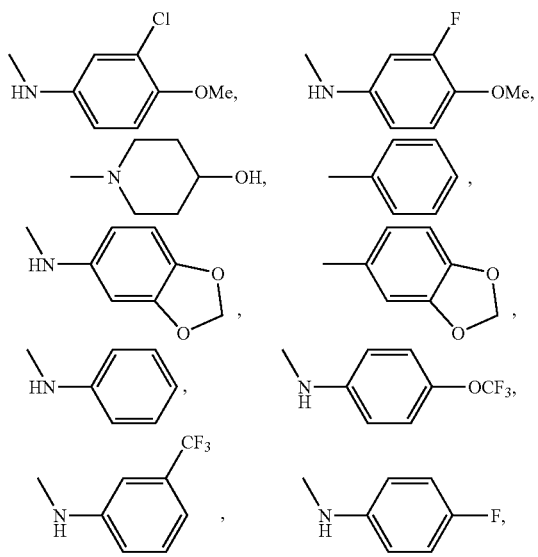

C is selected from

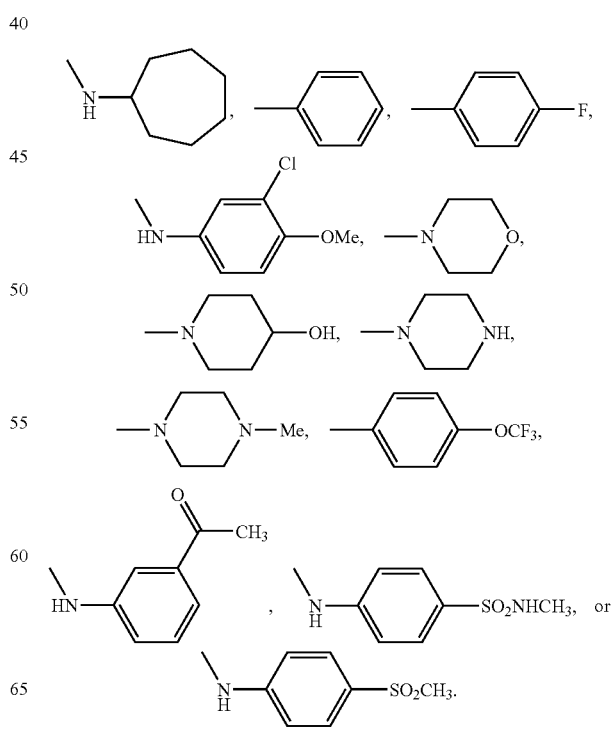

In another aspect of the present invention, this invention provides compounds, and compositions comprising the compounds, wherein the compounds have the formula:

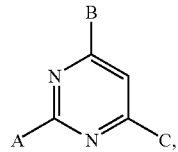

or a salt, including a pharmaceutically acceptable or a non-pharmaceutically acceptable salt, a prodrug, a diastereomeric mixture, an enantiomer, a tautomer, or a racemic mixture thereof, wherein:

A and B are selected independently from

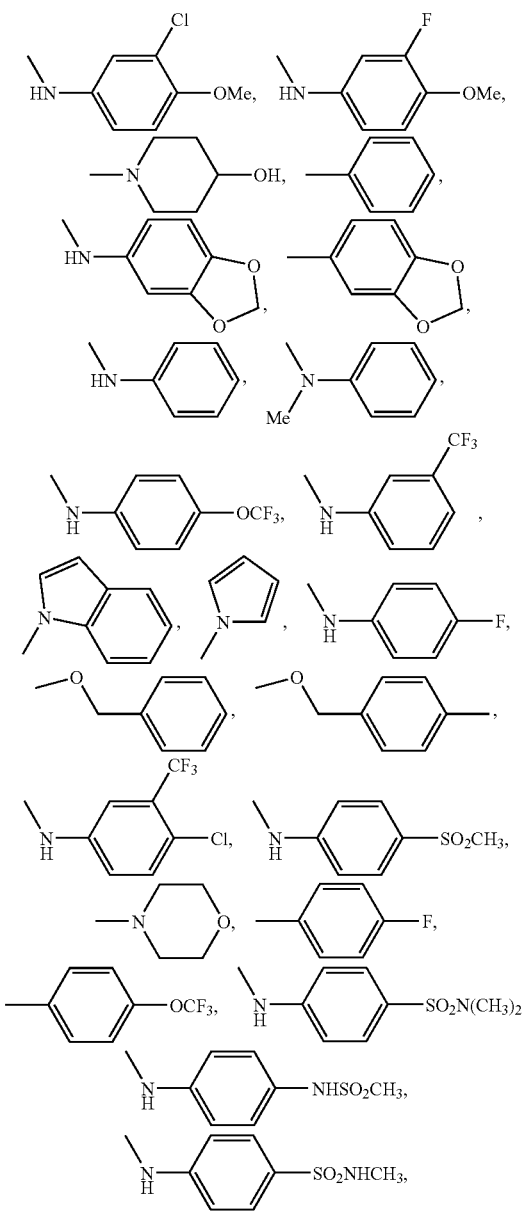

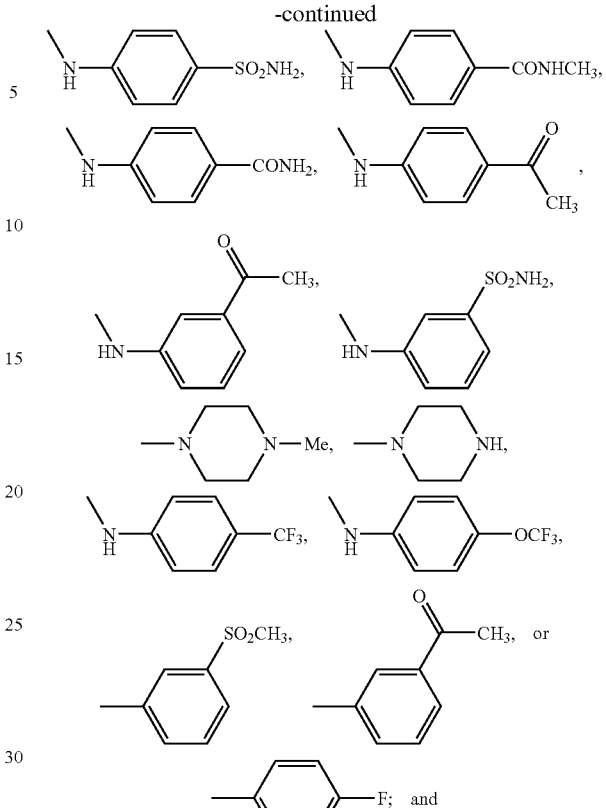

C is selected from

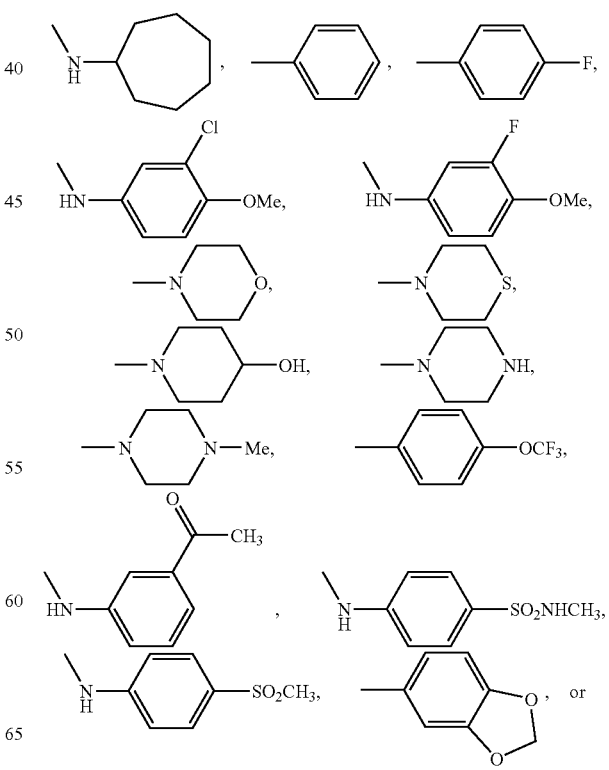

-continued

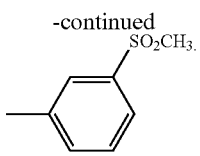

In another aspect, this invention provides substituted pyrimidine compounds, wherein the compound can be: 1-(2,6-Diphenyl-pyrimidin-4-yl)-piperidin-4-ol; 1-[2-(4-Methanesulfonyl-phenylamino)-6-phenyl-pyrimidin-4-yl]-piperidin-4-ol; 1-[4-(4-Methanesulfonyl-phenylamino)-6-phenyl-pyrimidin-2-yl]-piperidin-4-ol; (6-Morpholin-4-yl-2-phenyl-pyrimidin-4-yl)-(4-trifluoromethoxy-phenyl)-amine; (4-Morpholin-4-yl-6-phenyl-pyrimidin-2-yl)-(4-trifluoromethoxy-phenyl)-amine; 4-[4-(4-Hydroxy-piperidin-1-yl)-6-phenyl-pyrimidin-2-ylamino]-benzenesulfonamide; 4-(2,6-Diphenyl-pyrimidin-4-ylamino)-N-methyl-benzenesulfonamide; 1-{4-[4-(4-Hydroxy-piperidin-1-yl)-6-phenyl-pyrimidin-2-ylamino]-phenyl}-ethanone. hydro chloride; 1-[4-(3-Fluoro-4-methoxy-phenylamino)-6-phenyl-pyrimidin-2-yl]-piperidin-4-ol; 1-[2-(3-Fluoro-4-methoxy-phenylamino)-6-phenyl-pyrimidin-4-yl]-piperidin-4-ol; (3—Chloro-4-methoxy-phenyl)-(4-morpholin-4-yl-6-phenyl-pyrimidin-2-yl)-amine; Benzo[1,3]dioxol-5-yl-(4-morpholin-4-yl-6-phenyl-pyrimidin-2-yl)-amine; (3-Fluoro-4-methoxy-phenyl)-(4-morpholin-4-yl-6-phenyl-pyrimidin-2-yl)-amine; 1-(2-Benzo[1,3]dioxol-5-yl-6-phenyl-pyrimidin-4-yl)-piperidin-4-ol; 1-(6-Phenyl-2-phenylamino-pyrimidin-4-yl)-piperidin-4-ol; 1-(4,6-Diphenyl-pyrimidin-2-yl)-piperidin-4-ol; 1-(4-Benzo[1,3]dioxol-5-yl-6-phenyl-pyrimidin-2-yl)-piperidin-4-ol; 4-[2-(3-Chloro-4-methoxy-phenylamino)-6-phenyl-pyrimidin-4-ylamino]-cyclohexanol; 1-[6-Phenyl-2-(4-trifluoromethoxy-phenylamino)-pyrimidin-4-yl]-piperidin-4-ol; 4-(2-Benzo[1,3]dioxol-5-yl-6-phenyl-pyrimidin-4-yl)-morpholine; 1-[6-Phenyl-2-(3-trifluoromethyl-phenylamino)-pyrimidin-4-yl]-piperidin-4-ol; 1-[4-Phenyl-6-(3-trifluoromethyl-phenylamino)-pyrimidin-2-yl]-piperidin-4-ol; 1-[4-(4-Chloro-3-trifluoromethyl-phenylamino)-6-phenyl-pyrimidin-2-yl]-piperidin-4-ol; Benzo[1,3]dioxol-5-yl-[4-(4-fluoro-phenyl)-6-morpholin-4-yl-pyrimidin-2-yl]-amine; 1-[4-(Benzo[1,3]dioxol-5-ylamino)-6-phenyl-pyrimidin-2-yl]-piperidin-4-ol; 1-[2-(Benzo[1,3]dioxol-5-ylamino)-6-phenyl-pyrimidin-4-yl]-piperidin-4-ol; [4-(4-Fluoro-phenyl)-6-morpholin-4-yl-pyrimidin-2-yl]-(3-trifluoromethyl-phenyl)-amine; (4-Fluoro-phenyl)-[4-(4-fluoro-phenyl)-6-morpholin-4-yl-pyrimidin-2-yl]-amine; 1-[2-(4-Chloro-3-trifluoromethyl-phenylamino)-6-phenyl-pyrimidin-4-yl]-piperidin-4-ol; 1-[4-Phenyl-6-(4-trifluoromethyl-phenylamino)-pyrimidin-2-yl]-piperidin-4-ol; 1-[6-(3-Chloro-4-methoxy-phenylamino)-2-phenyl-pyrimidin-4-yl]-piperidin-4-ol; Benzo[1,3]dioxol-5-yl-(6-morpholin-4-yl-2-phenyl-pyrimidin-4-yl)-amine; 1-(6-Benzo[1,3]dioxol-5-yl-2-phenyl-pyrimidin-4-yl)-piperidin-4-ol; (2-Morpholin-4-yl-6-phenyl-pyrimidin-4-yl)-(3-rifluoromethyl-phenyl)-amine; (4-Morpholin-4-yl-6-phenyl-pyrimidin-2-yl)-(3-trifluoromethyl-phenyl)-amine; Phthalic acid mono-[1-(2,6-diphenyl-pyrimidin-4-yl)-piperidin-4-yl]ester; 1-[2-(4-Fluoro-phenyl)-6-phenyl-pyrimidin-4-yl]-piperidin-4-ol; N-{4-[4-(4-Hydroxy-piperidin-1-yl)-6-phenyl-pyrimidin-2-ylamino]-phenyl}; (3-Chloro-4-methoxy-phenyl)-[4-(4-methyl-piperazin-1-yl)-6-phenyl-pyrimidin-2-yl]-amine; N-[4-(4-Morpholin-4-yl-6-phenyl-pyrimidin-2-ylamino)-phenyl]-methanesulfonamide. hydrochloride; 4- [4-(4-Hydroxy-piperidin-1-yl)-6-phenyl-pyrimidin-2-ylamino]-N-methyl-benzenesulfonamide; 4-[4-(4-Fluoro-phenyl)-6-(4-hydroxy-piperidin-1-yl)-pyrimidin-2-ylamino]-N-methyl-benzenesulfonamide; (2,6-Diphenyl-pyrimidin-4-yl)-(4-trifluoromethoxy-phenyl)-amine; (4-Methanesulfonyl-phenyl)-(6-morpholin-4-yl-2-phenyl-pyrimidin-4-yl)-amine; [4,6-Bis-(4-fluoro-phenyl)-pyrimidin-2-yl]-(4-trifluoromethoxy-phenyl)-amine; (2,6-Diphenyl-pyrimidin-4-yl)-(4-methanesulfonyl-phenyl)-amine; N-Methyl-4-(4-morpholin-4-yl-6-phenyl-pyrimidin-2-ylamino)-benzenesulfonamide; 1-{3-[4-(4-Hydroxy-piperidin-1-yl)-6-phenyl-pyrimidin-2-ylamino]-phenyl}-ethanone; 3-(4-Morpholin-4-yl-6-phenyl-pyrimidin-2-ylamino)-benzenesulfonamide; 1-[2-(3-Chloro-4-methoxy-phenylamino)-6-cycloheptylamino-pyrimidin-4-yl]-piperidin-4-ol; 1-[6-(3-Methanesulfonyl-phenyl)-2-phenyl-pyrimidin-4-yl]-piperidin-4-ol; 1-[6-(4-Methanesulfonyl-phenylamino)-2-phenyl-pyrimidin-4-yl]-piperidin-4-ol; (4-Methanesulfonyl-phenyl)-[2-phenyl-6-(4-trifluoromethoxy-phenyl)-pyrimidin-4-yl]-amine; or any mixture thereof, including a salt, including a pharmaceutically acceptable or a non-pharmaceutically acceptable salt, a prodrug, a diastereomeric mixture, an enantiomer, a tautomer, or a racemic mixture thereof.

According to another aspect of this invention, and consistent with the definitions provided herein, the present invention also provides for compounds of the following general structure II:

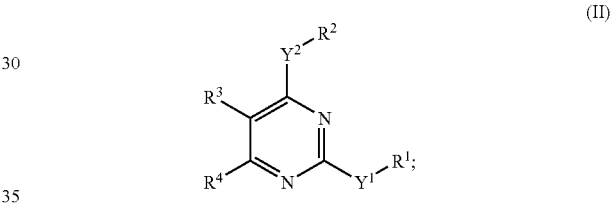

wherein within structure II, the substituents $Y^1$, $R^1$, $Y^2$, $R^2$, $R^3$ and $R^4$ can be selected according to the following listings, wherein each substituent is defined in Table 1.

The substituent $Y^1$ and $Y^2$ can be selected independently from $Y^A$, $Y^B$, $Y^C$, $Y^D$, $Y^E$, $Y^F$, $Y^G$, $Y^H$, $Y^I$, or $Y^J$.

The substituent $R^1$ can be selected independently from $R^{1A}$, $R^{1B}$, $R^{1C}$, $R^{1D}$, $R^{1E}$, $R^{1F}$, $R^{1G1}$, $R^{1G2}$, $R^{1G3}$, $R^{1G4}$, $R^{1G5}$, $R^{1H1}$, $R^{1H2}$, $R^{1H3}$, $R^{1H4}$, $R^{1H5}$, $R^{1I}$, $R^{1J}$, $R^{1K}$, $R^{1L}$, $R^{1M}$, $R^{1N}$, $R^{1O}$, $R^{1P}$, or $R^{1Q}$.

The substituent $R^2$ can be selected independently from $R^{2A}$, $R^{2B}$, $R^{2C}$, $R^{2D}$, $R^{2E}$, $R^{2F}$, $R^{2G1}$, $R^{2G2}$, $R^{2G3}$, $R^{2G4}$, $R^{2G5}$, $R^{2H1}$, $R^{2H2}$, $R^{2H3}$, $R^{2H4}$, $R^{2H5}$, $R^{2I}$, $R^{2J}$, $R^{2K}$, $R^{2L}$, $R^{2M}$, $R^{2N}$, $R^{2O}$, $R^{2P}$, or $R^{2Q}$.

Alternatively, the moieties $Y^1R^1$ and $Y^2R^2$ can be selected independently from $YR^A$, $YR^B$, $YR^C$, $YR^D$, $YR^E$, $YR^F$, $YR^G$, $YR^H$, $YR^I$, $YR^J$, or $YR^K$, as defined herein.

The substituent $R^3$ can be selected independently from $R^{3A}$, $R^{3B}$, $R^{3C}$, $R^{3D}$, $R^{3E}$, $R^{3F}$, $R^{3G}$, $R^{3H}$, $R^{3I}$, $R^{3J}$, $R^{3K}$, $R^{3L}$, $R^{3M}$, $R^{3N}$, $R^{3O}$, $R^{3P1}$, $R^{3P2}$, $R^{3P3}$, $R^{3P4}$, $R^{3P5}$, $R^{3Q1}$, $R^{3Q2}$, $R^{3Q3}$, $R^{3Q4}$, $R^{3Q5}$, $R^{3R}$, $R^{3S}$, $R^{3T}$, $R^{3U}$, or $R^{3V}$.

The substituent $R^4$ can be selected independently from $R^{4A}$, $R^{4B}$, $R^{4C}$, $R^{4D}$, $R^{4E}$, $R^{4F}$, $R^{4G}$, $R^{4H}$, $R^{4I}$, $R^{4J}$, $R^{4K}$, $R^{4L}$, $R^{4M}$, $R^{4N}$, $R^{4O}$, $R^{4P1}$, $R^{4P2}$, $R^{4P3}$, $R^{4P4}$, $R^{4P5}$, $R^{4Q1}$, $R^{4Q2}$, $R^{4Q3}$, $R^{4Q4}$, $R^{4Q5}$, $R^{4R}$, $R^{4S}$, $R^{4T}$, $R^{4U}$, or $R^{4V}$.

The substituents recited above are defined as follows, consistent with the definitions provided herein.

TABLE 1

Substituent abbreviations.

| | |
|---|---|
| $Y^A$ | >$NR^5$, wherein $R^5$ is selected from $R^{5A}$ through $R^{5G}$ |
| $Y^B$ | —$(CH_2)n$—, n is 0 to 3 |

TABLE 1-continued

Substituent abbreviations.

| | |
|---|---|
| $Y^C$ | —(CH$_2$)p(CH═CH)(CH$_2$)q—, p and q are independently 0 to 3 |
| $Y^D$ | >CR$^5$R$^6$, wherein R$^5$ is selected from R$^{5A}$ through R$^{5G}$, and R$^6$ is selected from R$^{6A}$ through R$^{6G}$ |
| $Y^E$ | —(CH$_2$)p(C≡C)(CH$_2$)q—, p and q are independently 0 to 3 |
| $Y^F$ | —O— |
| $Y^G$ | >CO |
| $Y^H$ | —S— |
| $Y^I$ | >SO |
| $Y^J$ | >SO$_2$ |
| $YR^A$ | saturated or unsaturated carbocyclic or N-heterocyclic ring having up to 10 carbon atoms |
| $YR^B$ | saturated or unsaturated carbocyclic or N-heterocyclic ring having up to 10 carbon atoms, further comprising —O— in the ring |
| $YR^C$ | saturated or unsaturated carbocyclic or N-heterocyclic ring having up to 10 carbon atoms, further comprising —S— in the ring |
| $YR^D$ | saturated or unsaturated carbocyclic or N-heterocyclic ring having up to 10 carbon atoms, further comprising >N— in the ring |
| $YR^E$ | saturated or unsaturated carbocyclic or N-heterocyclic ring having up to 10 carbon atoms, further comprising >SO$_2$ in the ring |
| $YR^F$ | saturated or unsaturated carbocyclic or N-heterocyclic ring having up to 10 carbon atoms, further comprising >CO in the ring |
| $YR^G$ | substituted or an unsubstituted morpholinyl |
| $YR^H$ | substituted or an unsubstituted piperazinyl |
| $YR^I$ | substituted or an unsubstituted thiomorpholinyl |
| $YR^J$ | substituted or an unsubstituted pyrrolidinyl |
| $YR^K$ | substituted or an unsubstituted piperidinyl |
| $R^{1A}, R^{2A}$ | Alkyl having up to 10 carbon atoms |
| $R^{1B}, R^{2B}$ | Aryl having up to 10 carbon atoms |
| $R^{1C}, R^{2C}$ | Alkoxyalkyl having up to 10 carbon atoms |
| $R^{1D}, R^{2D}$ | Cycloalky having up to 10 carbon atoms |
| $R^{1E}, R^{2E}$ | —COR$^9$ having up to 10 carbon atoms |
| $R^{1F}, R^{2F}$ | Aralkyl having up to 10 carbon atoms |
| $R^{1G1}, R^{2G1}$ | Heterocyclyl having up to 10 carbon atoms, comprising —O— |
| $R^{1G2}, R^{2G2}$ | Heterocyclyl having up to 10 carbon atoms, comprising >N— |
| $R^{1G3}, R^{2G3}$ | Heterocyclyl having up to 10 carbon atoms, comprising —S— |
| $R^{1G4}, R^{2G4}$ | Heterocyclyl having up to 10 carbon atoms, comprising >SO$_2$ |
| $R^{1G5}, R^{2G5}$ | Heterocyclyl having up to 10 carbon atoms, comprising >CO |
| $R^{1H1}, R^{2H1}$ | Heteroaryl having up to 10 carbon atoms, comprising —O— |
| $R^{1H2}, R^{2H2}$ | Heteroaryl having up to 10 carbon atoms, comprising >N— |
| $R^{1H3}, R^{2H3}$ | Heteroaryl having up to 10 carbon atoms, comprising —S— |
| $R^{1H4}, R^{2H4}$ | Heteroaryl having up to 10 carbon atoms, comprising >SO$_2$ |
| $R^{1H5}, R^{2H5}$ | Heteroaryl having up to 10 carbon atoms, comprising >CO |
| $R^{1I}, R^{2I}$ | hydrogen |
| $R^{1J}, R^{2J}$ | Halogen |
| $R^{1K}, R^{2K}$ | Cyano |
| $R^{1L}, R^{2L}$ | Hydroxyl |
| $R^{1M}, R^{2M}$ | Alkoxy having up to 10 carbon atoms |
| $R^{1N}, R^{2N}$ | Alkenyl having up to 10 carbon atoms |
| $R^{1O}, R^{2O}$ | Alkynyl having up to 10 carbon atoms |
| $R^{1P}, R^{2P}$ | —CO$_2$R$^5$ having up to 10 carbon atoms |
| $R^{1Q}, R^{2Q}$ | —COR$^5$ having up to 10 carbon atoms |
| $R^{3A}, R^{4A}$ | Alkyl having up to 10 carbon atoms |
| $R^{3B}, R^{4B}$ | Alkenyl having up to 10 carbon atoms |
| $R^{3C}, R^{4C}$ | Alkynyl having up to 10 carbon atoms |
| $R^{3D}, R^{4D}$ | Alkoxy having up to 10 carbon atoms |
| $R^{3E}, R^{4E}$ | Cycloalkyl having up to 10 carbon atoms |
| $R^{3F}, R^{4F}$ | Haloalkyl having up to 10 carbon atoms |
| $R^{3G}, R^{4G}$ | Haloalkoxy having up to 10 carbon atoms |
| $R^{3H}, R^{4H}$ | Alkylthio having up to 10 carbon atoms |
| $R^{3I}, R^{4I}$ | Alkylsufonyl having up to 10 carbon atoms |
| $R^{3J}, R^{4J}$ | Aryl having up to 10 carbon atoms |
| $R^{3K}, R^{4K}$ | —CO$_2$R$^5$ having up to 10 carbon atoms |
| $R^{3L}, R^{4L}$ | —COR$^5$ having up to 10 carbon atoms |
| $R^{3M}, R^{4M}$ | —NR$^5$R$^6$ having up to 10 carbon atoms |
| $R^{3N}, R^{4N}$ | —SO$_2$NR$^5$R$^6$ having up to 10 carbon atoms |
| $R^{3O}, R^{4O}$ | —SO$_3$R$^5$ having up to 10 carbon atoms |
| $R^{3P1}, R^{4P1}$ | Heterocyclyl having up to 10 carbon atoms, comprising —O— |
| $R^{3P2}, R^{4P2}$ | Heterocyclyl having up to 10 carbon atoms, comprising >N— |
| $R^{3P3}, R^{4P3}$ | Heterocyclyl having up to 10 carbon atoms, comprising —S— |
| $R^{3P4}, R^{4P4}$ | Heterocyclyl having up to 10 carbon atoms, comprising >SO$_2$ |
| $R^{3P5}, R^{4P5}$ | Heterocyclyl having up to 10 carbon atoms, comprising >CO |
| $R^{3Q1}, R^{4Q1}$ | Heteroaryl having up to 10 carbon atoms, comprising —O— |
| $R^{3Q2}, R^{4Q2}$ | Heteroaryl having up to 10 carbon atoms, comprising >N— |
| $R^{3Q3}, R^{4Q3}$ | Heteroaryl having up to 10 carbon atoms, comprising —S— |
| $R^{3Q4}, R^{4Q4}$ | Heteroaryl having up to 10 carbon atoms, comprising >SO$_2$ |
| $R^{3Q5}, R^{4Q5}$ | Heteroaryl having up to 10 carbon atoms, comprising >CO |
| $R^{3R}, R^{4R}$ | Hydrogen |

TABLE 1-continued

Substituent abbreviations.

| | |
|---|---|
| $R^{3S}$, $R^{4S}$ | Halogen |
| $R^{3T}$, $R^{4T}$ | Hydroxyl |
| $R^{3U}$, $R^{4U}$ | Cyano |
| $R^{3V}$, $R^{4V}$ | $Y^1R^1$, independent of the selection of $Y^1R^1$ |
| $R^{5A}$, $R^{6A}$ | Alkyl having up to 10 carbon atoms |
| $R^{5B}$, $R^{6B}$ | Aryl having up to 10 carbon atoms |
| $R^{5C}$, $R^{6C}$ | Alkoxyalkyl having up to 10 carbon atoms |
| $R^{5D1}$, $R^{6D1}$ | Heteroaryl having up to 10 carbon atoms, comprising —O— |
| $R^{5D2}$, $R^{6D2}$ | Heteroaryl having up to 10 carbon atoms, comprising >N— |
| $R^{5D3}$, $R^{6D3}$ | Heteroaryl having up to 10 carbon atoms, comprising —S— |
| $R^{5D4}$, $R^{6D4}$ | Heteroaryl having up to 10 carbon atoms, comprising >$SO_2$ |
| $R^{5D5}$, $R^{6D5}$ | Heteroaryl having up to 10 carbon atoms, comprising >CO |
| $R^{5E}$, $R^{6E}$ | Cycloalkyl having up to 10 carbon atoms |
| $R^{5F1}$, $R^{6F1}$ | Heterocyclyl having up to 10 carbon atoms, comprising —O— |
| $R^{5F2}$, $R^{6F2}$ | Heterocyclyl having up to 10 carbon atoms, comprising >N— |
| $R^{5F3}$, $R^{6F3}$ | Heterocyclyl having up to 10 carbon atoms, comprising —S— |
| $R^{5F4}$, $R^{6F4}$ | Heterocyclyl having up to 10 carbon atoms, comprising >$SO_2$ |
| $R^{5F5}$, $R^{6F5}$ | Heterocyclyl having up to 10 carbon atoms, comprising >CO |
| $R^{5G}$, $R^{6G}$ | Hydrogen |

In these selections, unless otherwise indicated, the number of carbon atoms on the substituents refers to the carbon atoms on the base chemical moiety, and does not include the carbon atoms in any optional substituent. Again, unless otherwise indicated, any substituents are limited in size by the carbon atoms listed in the definitions of the substitutents.

In these selections, the following features are applicable. Any carbocyclic ring, N-heterocyclic ring, morpholinyl, piperazinyl, thiomorpholinyl, pyrrolidinyl, or piperidinyl can be optionally substituted with at least one hydroxyl, halogen, alkyl, alkoxy, haloalkyl, cycloalkyl, aryl, or heteroaryl any of which having up to 6 carbon atoms. Further any when a piperazinyl moiety is present in the substituted pyrimidine compound, the piperazine nitrogen is optionally substituted by an alkyl, a cycloalkyl, an acyl, a haloalkyl, an alkoxyalkyl, $SO_2R^7$, $SO_2NR^7_2$, or $CO_2R^7$, wherein $R^7$ is independently selected from: a) an alkyl or an aryl having up to 8 carbon atoms; or b) hydrogen.

Any of the $R^1$, $R^2$, $R^5$, or $R^6$ moieties that do not constitute hydrogen, halogen, cyano, or hydroxyl (for example, $R^{1A}$ through $R^{1H}$, $R^{1M}$ through $R^{1Q}$, $R^{2A}$ through $R^{2H}$, $R^{2M}$ through $R^{2Q}$, $R^{3A}$ through $R^{3Q}$ and $R^{3V}$, $R^{4A}$ through $R^{4Q}$ and $R^{4V}$, $R^{5A}$ through $R^{5F}$, and $R^{6A}$ through $R^{6F}$) can be optionally substituted with at least one group independently selected from: 1) alkyl; alkoxy; alkylthio; haloalkyl; cycloalkyls; aryl; heterocyclyl or heteroaryl comprising at least one heteroatom or heterogroup selected from —O—, >N—, —S—, >$SO_2$ or >CO; haloalkoxy; —$OCH_2O$—; —$OCOR^9$; $N(R^8)_2$; —$COR^9$; —$CON(R^8)_2$; —$(CH_2)_b$—$CO_2R^8$ wherein b is an integer from 0 to 3; —$OCO(CH_2)_b CO_2R^{10}$ wherein b is an integer from 0 to 3; —$SO_2R^9$; —$NHSO_2R^9$; or —$SO_2N(R^8)_2$; any of which having up to 10 carbon atoms; or 2) hydrogen, halogen, hydroxyl, or cyano. In these groups, $R^8$, in each occurrence, is independently: 1) an alkyl; a haloalkyl; a heterocyclyl or heteroaryl comprising at least one heteroatom or heterogroup selected from —O—, >N—, —S—, >$SO_2$, or >CO; or an aryl having up to 6 carbon atoms; or 2) hydrogen. Further, in these moieties, $R^9$, in each occurrence, is independently an alkyl; a haloalkyl; an aryl; or a heterocyclyl or heteroaryl comprising at least one heteroatom or heterogroup selected from —O—, >N—, —S—, >$SO_2$, or >CO; having up to 8 carbon atoms; wherein $R^9$ is optionally substituted with: 1) an alkyl, an alkoxy, a carboxylic acid, or a carboxylic acid ester, any of which having up to 8 carbon atoms; 2) halogen; or 3) hydroxyl.

Any of the $R^3$ or $R^4$ moieties that do not constitute hydrogen, halogen, cyano, or hydroxyl can be optionally substituted with at least one group independently selected from: 1) alkyl, alkoxy, haloalkyl, haloalkoxy, cycloalkyl, aryl, heteroaryl, heterocyclyl, alkenyl, alkynyl, —$COR^{10}$, —$CO_2R^{10}$, —$CON(R^{10})_2$, —$SO_2R^{10}$, —$SO_2N(R^{10})_2$, or —$N(R^{10})_2$, any of which having up to 10 carbon atoms; 2) halogen; or 3) hydroxyl; wherein $R^{10}$, in each occurrence, is independently: 1) an alkyl or an aryl having up to 6 carbon atoms; or 2) hydrogen.

Representative compounds in accordance with the present invention are presented in the Table 2. This table is not intended to be exclusive of the compounds of the present invention, but rather exemplary of the heterocyclic compounds that are encompassed by this invention.

TABLE 2

Representative compounds in accordance with the present invention.

$N^4$-(3-Chloro-4-methoxy-phenyl)-6-(4-methoxy-phenyl)-pyrimidine-2,4-diamine;

TABLE 2-continued

Representative compounds in accordance with the present invention.

| Structure | Name |
|---|---|
| (3-chloro-4-methoxyphenyl)-NH on pyrimidine-2,4-diamine with 6-phenyl | $N^4$-(3-Chloro-4-methoxy-phenyl)-6-phenyl-pyrimidine-2,4-diamine; |
| (3-chloro-4-methoxyphenyl)-NH on pyrimidine-2,4-diamine with 6-(4-fluorophenyl) | $N^4$-(3-Chloro-4-methoxy-phenyl)-6-(4-fluoro-phenyl)-pyrimidine-2,4-diamine; |
| (3-chloro-4-methoxyphenyl)-NH on pyrimidine-2,4-diamine with 6-(4-ethoxyphenyl) | $N^4$-(3-Chloro-4-methoxy-phenyl)-6-(4-ethoxy-phenyl)-pyrimidine-2,4-diamine; |
| (3-chloro-4-methoxyphenyl)-NH on pyrimidine-2,4-diamine with 6-(p-tolyl) | $N^4$-(3-Chloro-4-methoxy-phenyl)-6-p-tolyl-pyrimidine-2,4-diamine; |
| (3-chloro-4-methoxyphenyl)-NH on pyrimidine-2,4-diamine with 6-(4-methylsulfanylphenyl) | $N^4$-(3-Chloro-4-methoxy-phenyl)-6-(4-methylsulfanyl-phenyl)-pyrimidine-2,4-diamine; |

TABLE 2-continued
Representative compounds in accordance with the present invention.
| | |
|---|---|
| 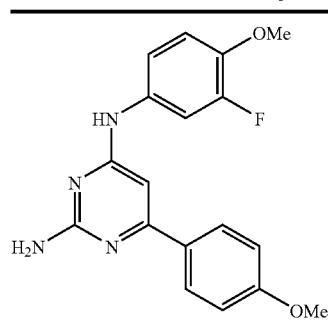 | $N^4$-(3-Fluoro-4-methoxy-phenyl)-6-(4-methoxy-phenyl)-pyrimidine-2,4-diamine; |
| 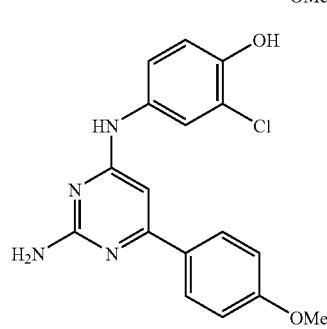 | 4-[2-Amino-6-(4-methoxy-phenyl)-pyrimidin-4-ylamino]-2-chloro-phenol; |
| 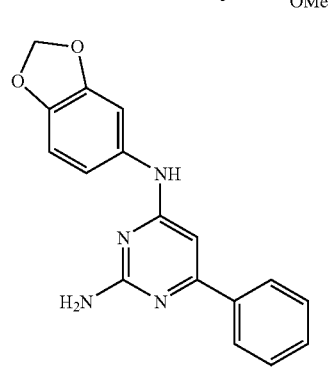 | $N^4$-Benzo[1,3]dioxol-5-yl-6-phenyl-pyrimidine-2,4-diamine; |
| 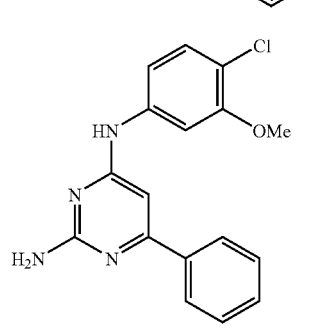 | $N^4$-(4-Chloro-3-methoxy-phenyl)-6-phenyl-pyrimidine-2,4-diamrne; |
| 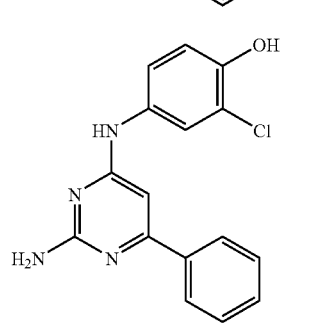 | 4-(2-Amino-6-phenyl-pyrimidin-4-ylamino)-2-chloro-phenol; |

TABLE 2-continued

Representative compounds in accordance with the present invention.

| Structure | Name |
|---|---|
| 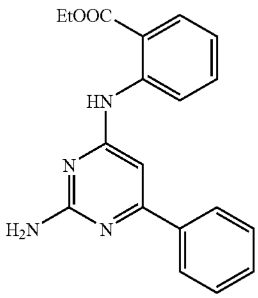 | 2-(2-Amino-6-phenyl-pyrimidin-4-ylamino)-benzoic acid ethyl ester; |
| | N[4]-(3-Chloro-4-methoxy-phenyl)-6-methyl-pyrimidine-2,4-diamine, |
| 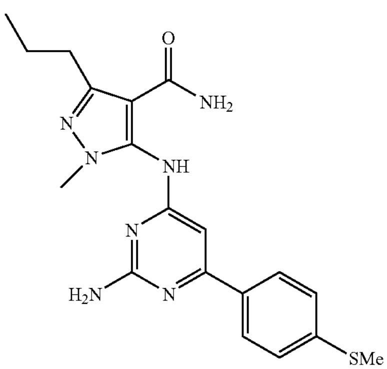 | 5-[2-Amino-6-(4-methylsulfanylphenyl)pyrimidin-4-ylamino]-1-methyl-3-propyl-1H-pyrazole-4-carboxylic acid amide; |
| | 6-Chloro-N[2]-(3-chloro-4-methoxy-phenyl)-N[4]-cycloheptyl-pyrimidine-2,4-diamine; |
| 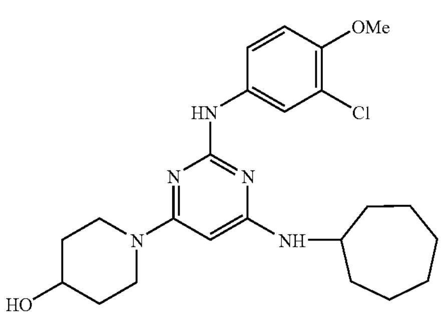 | 1-[2-(3-Chloro-4-methoxy-phenylamino)-6-cycloheptylamino-pyrimidin-4-yl]-piperidin-4-ol; |

TABLE 2-continued

Representative compounds in accordance with the present invention.

| Structure | Name |
|---|---|
| (structure) | $N^2,N^4$-Bis-(3-chloro-4-methoxy-phenyl)-6-phenyl-pyrimidine-2,4-diamine; |
| (structure) | N-[4-(3-Chloro-4-methoxy-phenylamino)-6-(4-ethoxy-phenyl)-pyrimidin-2-yl]-acetamide; |
| (structure) | N-[4-(3-Chloro-4-methoxy-phenylamino)-6-(4-methoxy-phenyl)-pyrimidin-2-yl]-acetamide; |
| (structure) | N-[4-(3-Chloro-4-methoxy-phenylamino)-6-(4-methoxy-phenyl)-pyrimidin-2-yl]-propionamide; |
| (structure) | [4-(3-Chloro-4-methoxy-phenylamino)-6-phenyl-pyrimidin-2-ylamino]-acetic acid ethyl ester; |

TABLE 2-continued

Representative compounds in accordance with the present invention.

N-[4-(3-Chloro-4-methoxy-phenylamino)-6-phenyl-pyrimidin-2-yl]-2,2,2-trifluoro-acetamide;

2,2,2-Trifluoro-N-(4-hydroxy-6-phenyl-pyrimidin-2-yl)-acetamide;

4-(4-Fluoro-phenylsulfanyl)-6-phenyl-pyrimidin-2-ylamine;

(3-Chloro-4-methoxy-phenyl)-(2-ethylsulfanyl-6-phenyl-pyrimidin-4-yl)-amine;

4-(3-Chloro-4-hydroxy-phenylamino)-6-phenyl-pyrimidin-2-ol;

TABLE 2-continued

*Representative compounds in accordance with the present invention.*

| Structure | Name |
|---|---|
| | $N^2$-(3-Chloro-4-methoxy-phenyl)-$N^4$-methyl-6-phenyl-pyrimidine-2,4-diamine; |
| | $N^2$-(3-Chloro-4-methoxy-phenyl)-$N^4$-isopropyl-6-phenyl-pyrimidine-2,4-diamine; |
| | $N^2$-(3-Chloro-4-methoxy-phenyl)-$N^4$-cycloheptyl-6-phenyl-pyrimidine-2,4-diamine; |
| | $N^4$-Benzyl-$N^2$-(3-chloro-4-methoxy-phenyl)-6-phenyl-pyrimidine-2,4-diamine; |
| | 2-(3-Chloro-4-methoxy-phenylamino)-6-(4-methoxy-phenyl)-pyrimidin-4-ol; |

TABLE 2-continued
Representative compounds in accordance with the present invention.
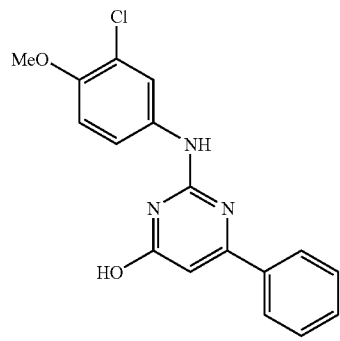
2-(3-Chloro-4-methoxy-phenylamino)-6-phenyl-pyrimidin-4-ol;
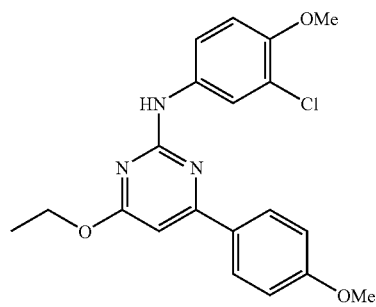
(3-Chloro-4-methoxy-phenyl)-[4-ethoxy-6-(4-methoxy-phenyl)-pyrimidin-2-yl]-amine;
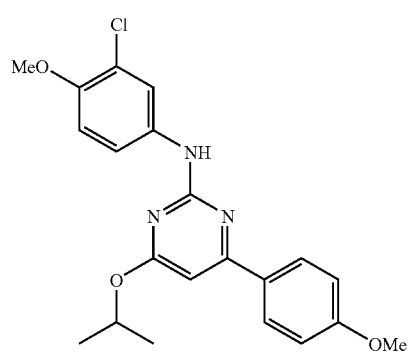
(3-Chloro-4-methoxy-phenyl)-[4-isopropoxy-6-(4-methoxy-phenyl)-pyrimidin-2-yl]-amine;
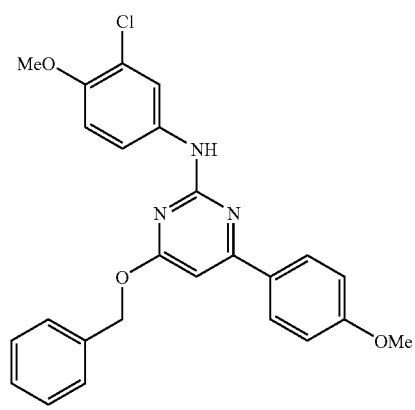
[4-Benzyloxy-6-(4-methoxy-phenyl)-pyrimidin-2-yl]-(3-chloro-4-methoxy-phenyl)-amine;

TABLE 2-continued

Representative compounds in accordance with the present invention.

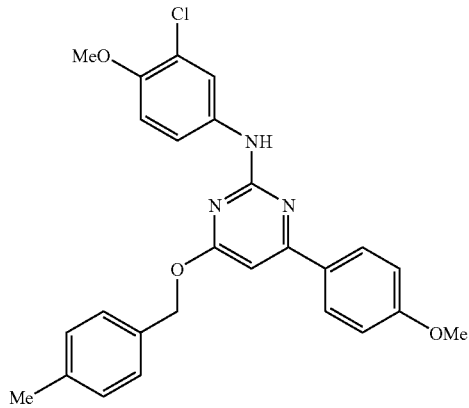
(3-Chloro-4-methoxy-phenyl)-[4-(4-methoxy-phenyl)-6-(4-methyl-benzyloxy)-pyrimidin-2-yl]-amine;

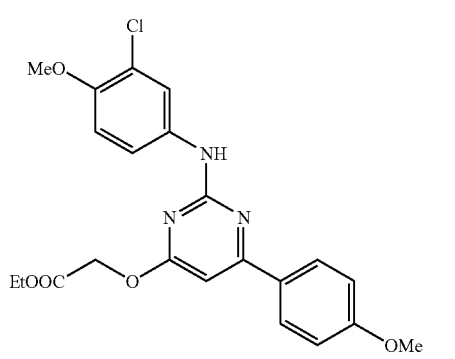
[2-(3-Chloro-4-methoxy-phenylamino)-6-(4-methoxy-phenyl)-pyrimidin-4-yloxy]-acetic acid ethyl ester;

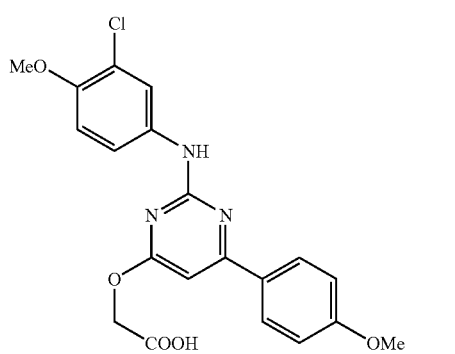
[2-(3-Chloro-4-methoxy-phenylamino)-6-(4-methoxy-phenyl)-pyrimidin-4-yloxy]-acetic acid;

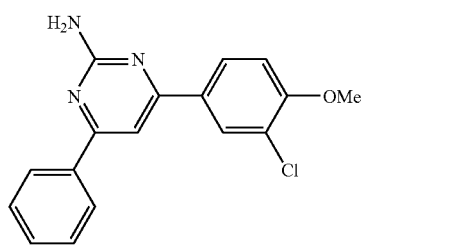
4-(3-Chloro-4-methoxy-phenyl)-6-phenyl-pyrimidin-2-ylamine;

TABLE 2-continued

Representative compounds in accordance with the present invention.

| | |
|---|---|
| 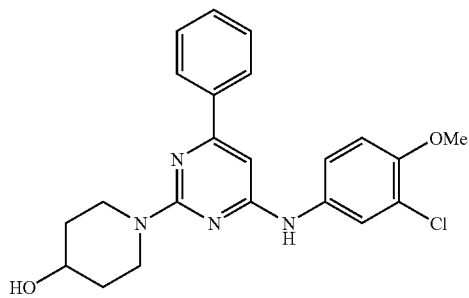 | 1-[4-(3-Chloro-4-methoxy-phenylamino)-6-phenyl-pyrimidin-2-yl]-piperidin-4-ol; |
| 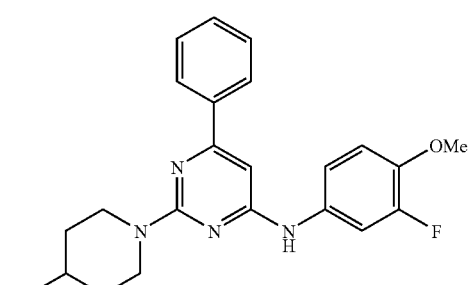 | 1-[4-(3-Fluoro-4-methoxy-phenylamino)-6-phenyl-pyrimidin-2-yl]-piperidin-4-ol; |
| 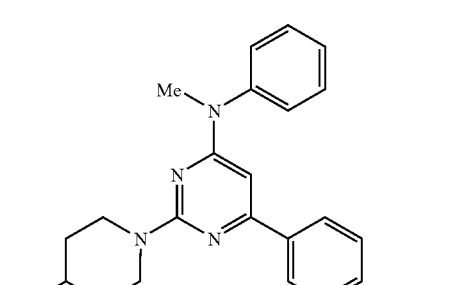 | 1-[4-(Methyl-phenyl-amino)-6-phenyl-pyrimidin-2-yl]-piperidin-4-ol; |
| 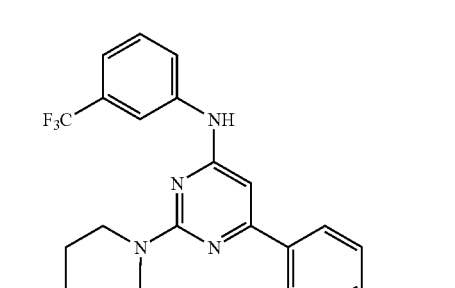 | 1-[4-Phenyl-6-(3-trifluoromethyl-phenylamino)-pyrimidin-2-yl]-piperidin-4-ol; |
| 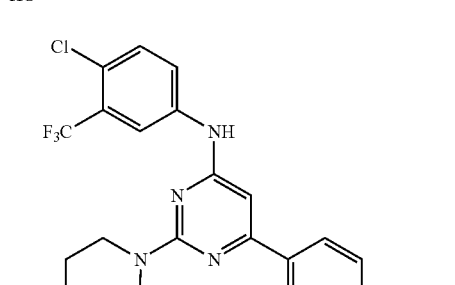 | 1-[4-(4-Chloro-3-trifluoromethyl-phenylamino)-6-phenyl-pyrimidin-2-yl]-piperidin-4-ol; |

TABLE 2-continued
Representative compounds in accordance with the present invention.
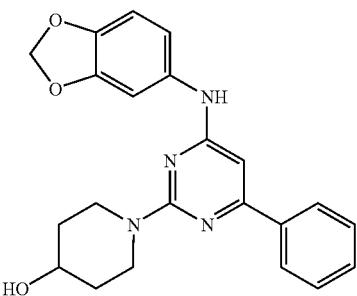
1-[4-(Benzo[1,3]dioxol-5-ylamino)-6-phenyl-pyrimidin-2-yl]-piperidin-4-ol;
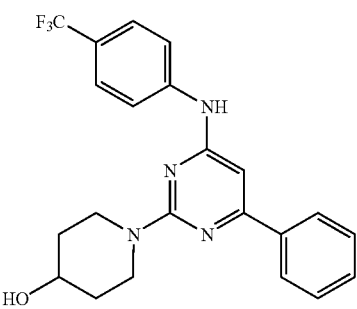
1-[4-Phenyl-6-(4-trifluoromethyl-phenylamino)-pyrimidin-2-yl]-piperidin-4-ol;
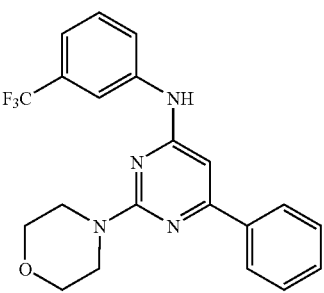
(2-Morpholin-4-yl-6-phenyl-pyrimidin-4-yl)-(3-rifluoromethyl-phenyl)-amine;
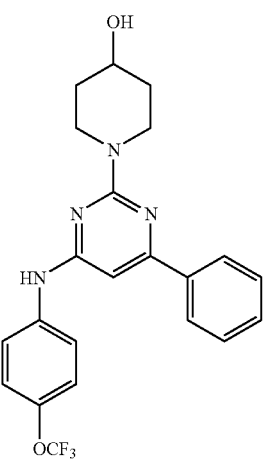
1-[4-Phenyl-6-(4-trifluoromethoxy-phenylamino)-pyrimidin-2-yl]-piperidin-4-ol;

TABLE 2-continued

Representative compounds in accordance with the present invention.

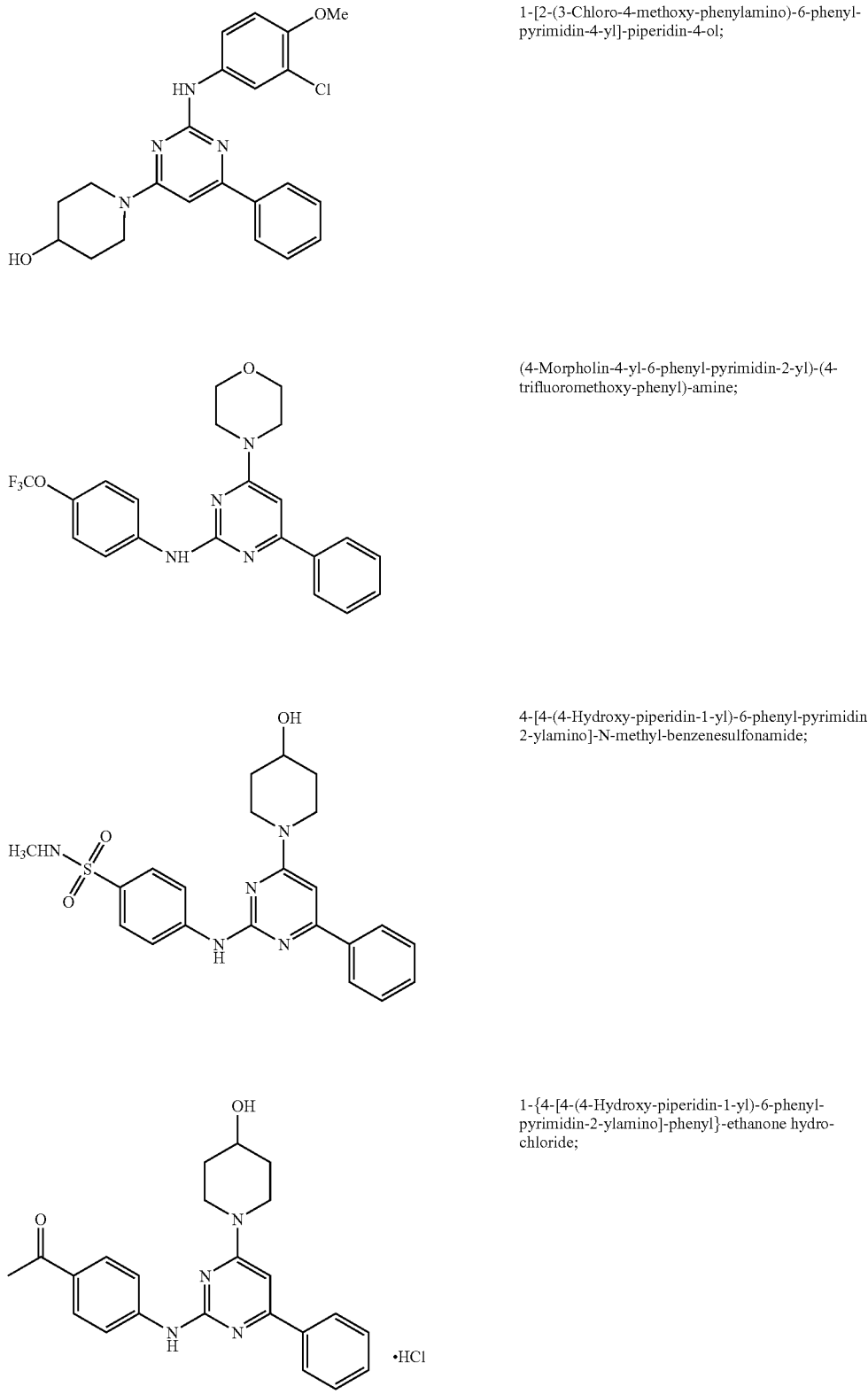

1-[2-(3-Chloro-4-methoxy-phenylamino)-6-phenyl-pyrimidin-4-yl]-piperidin-4-ol;

(4-Morpholin-4-yl-6-phenyl-pyrimidin-2-yl)-(4-trifluoromethoxy-phenyl)-amine;

4-[4-(4-Hydroxy-piperidin-1-yl)-6-phenyl-pyrimidin-2-ylamino]-N-methyl-benzenesulfonamide;

1-{4-[4-(4-Hydroxy-piperidin-1-yl)-6-phenyl-pyrimidin-2-ylamino]-phenyl}-ethanone hydrochloride;

TABLE 2-continued

Representative compounds in accordance with the present invention.

| Structure | Name |
|---|---|
| | 1-[2-(3-Chloro-4-hydroxy-phenylamino)-6-phenyl-pyrimidin-4-yl]-piperidin-4-ol; |
| | 1-[2-(3-Fluoro-4-methoxy-phenylamino)-6-phenyl-pyrimidin-4-yl]-piperidin-4-ol; |
| | 1-(6-Phenyl-2-phenylamino-pyrimidin-4-yl)-pipendin-4-ol; |
| | (3-Chloro-4-methoxy-phenyl)-(4-phenyl-6-thiomorpholin-4-yl-pyrimidin-2-yl)-amine; |
| | Benzo[1,3]dioxol-5-yl-(4-phenyl-6-thiomorpholin-4-yl-pyrimidin-2-yl)-amine; |

TABLE 2-continued

Representative compounds in accordance with the present invention.

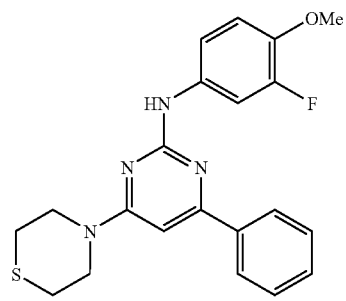

(3-Fluoro-4-methoxy-phenyl)-(4-phenyl-6-thiomorpholin-4-yl-pyrimidin-2-yl)-amine;

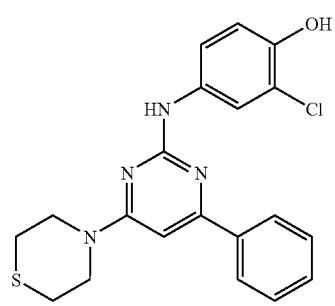

2-Chloro-4-(4-phenyl-6-thiomorpholin-4-yl-pyrimidin-2-ylamino)-phenol;

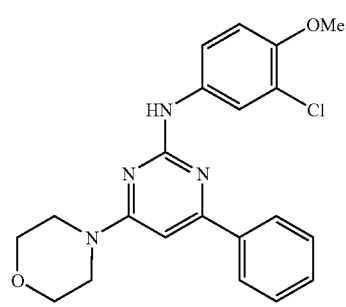

(3-Chloro-4-methoxy-phenyl)-(4-morpholin-4-yl-6-phenyl-pyrimidin-2-yl)-amine;

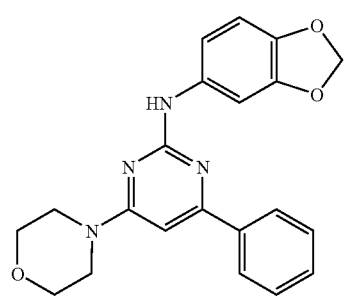

Benzo[1,3]dioxol-5-yl-(4-morpholin-4-yl-6-phenyl-pyrimidin-2-yl)-amine;

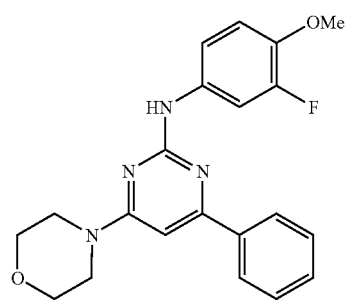

(3-Fluoro-4-methoxy-phenyl)-(4-morpholin-4-yl-6-phenyl-pyrimidin-2-yl)-amine;

TABLE 2-continued

Representative compounds in accordance with the present invention.

| | |
|---|---|
| 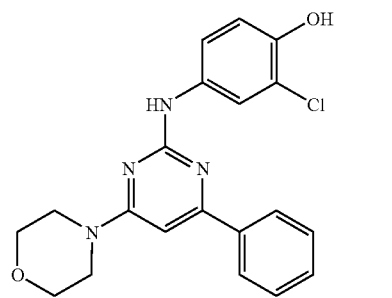 | 2-Chloro-4-(4-morpholin-4-yl-6-phenyl-pyrimidin-2-ylamino)-phenol; |
| 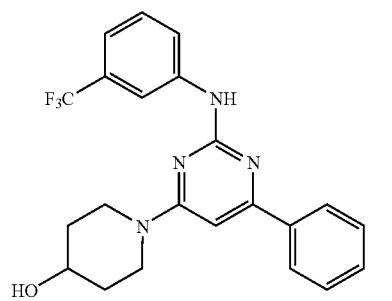 | 1-[6-Phenyl-2-(3-trifluoromethyl-phenylamino)-pyrimidin-4-yl]-piperidin-4-ol; |
| 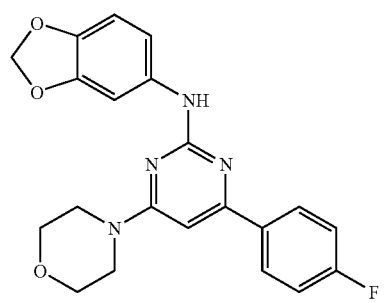 | Benzo[1,3]dioxol-5-yl-[4-(4-fluoro-phenyl)-6-morpholin-4-yl-pyrimidin-2-yl]-amine; |
| 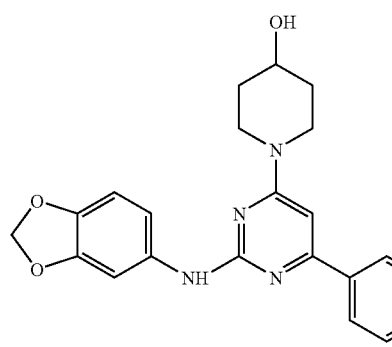 | 1-[2-(Benzo[1,3]dioxol-5-ylamino)-6-phenyl-pyrimidin-4-yl]-piperidin-4-ol; |
| 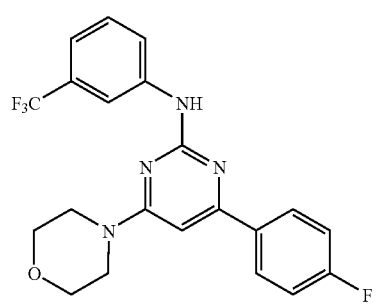 | [4-(4-Fluoro-phenyl)-6-morpholin-4-yl-pyrimidin-2-yl]-(3-trifluoromethyl-phenyl)-amine; |

TABLE 2-continued

Representative compounds in accordance with the present invention.

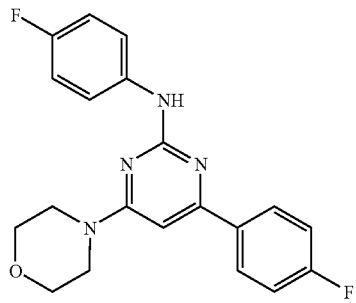

(4-Fluoro-phenyl)-[4-(4-fluoro-phenyl)-6-morpholin-4-yl-pyrimidin-2-yl]-amine;

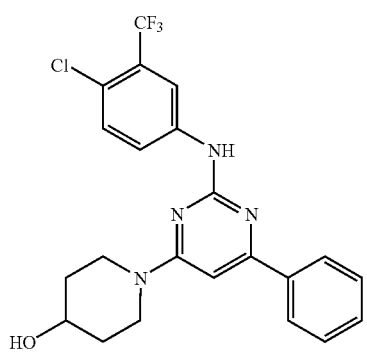

1-[2-(4-Chloro-3-trifluoromethyl-phenylamino)-6-phenyl-pyrimidin-4-yl]-piperidin-4-ol;

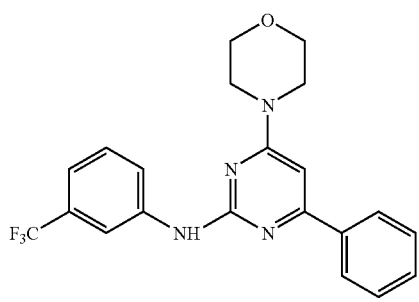

(4-Morpholin-4-yl-6-phenyl-pyrimidin-2-yl)-(3-trifluoromethyl-phenyl)-amine;

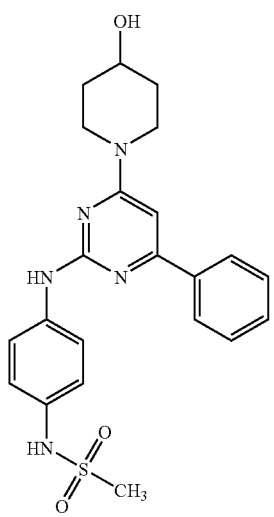

N-{4-[4-(4-Hydroxy-piperidin-1-yl)-6-phenyl-pyrimidin-2-ylamino]-phenyl}-methanesulfonamide;

TABLE 2-continued

Representative compounds in accordance with the present invention.

| | |
|---|---|
| 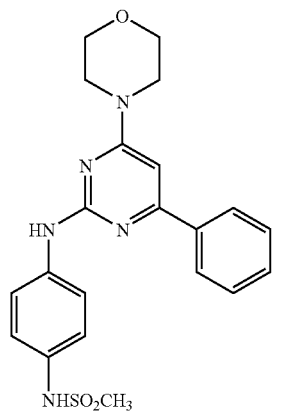 | N-[4-(4-Morpholin-4-yl-6-phenyl-pyrimidin-2-ylamino)-phenyl]-methanesulfonamide hydrochloride; |
| 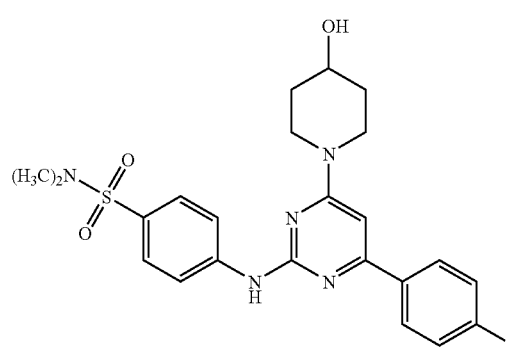 | 4-[4-(4-Fluoro-phenyl)-6-(4-hydroxy-piperidin-1-yl)-pyrimidin-2-ylamino]-N,N-dimethyl-benzenesulfonamide; |
| 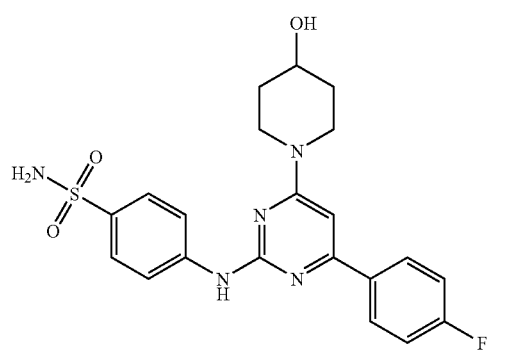 | 4-[4-(4-Fluoro-phenyl)-6-(4-hydroxy-piperidin-1-yl)-pyrimidin-2-ylamino]-benzenesulfonamide; |
| 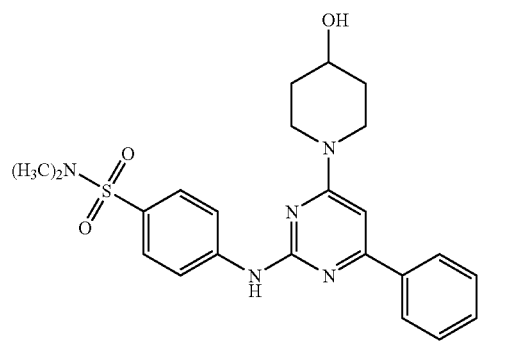 | 4-[4-(4-Hydroxy-piperidin-1-yl)-6-phenyl-pyrimidin-2-ylamino]-N,N-dimethyl-benzenesulfonamide; |

TABLE 2-continued

Representative compounds in accordance with the present invention.

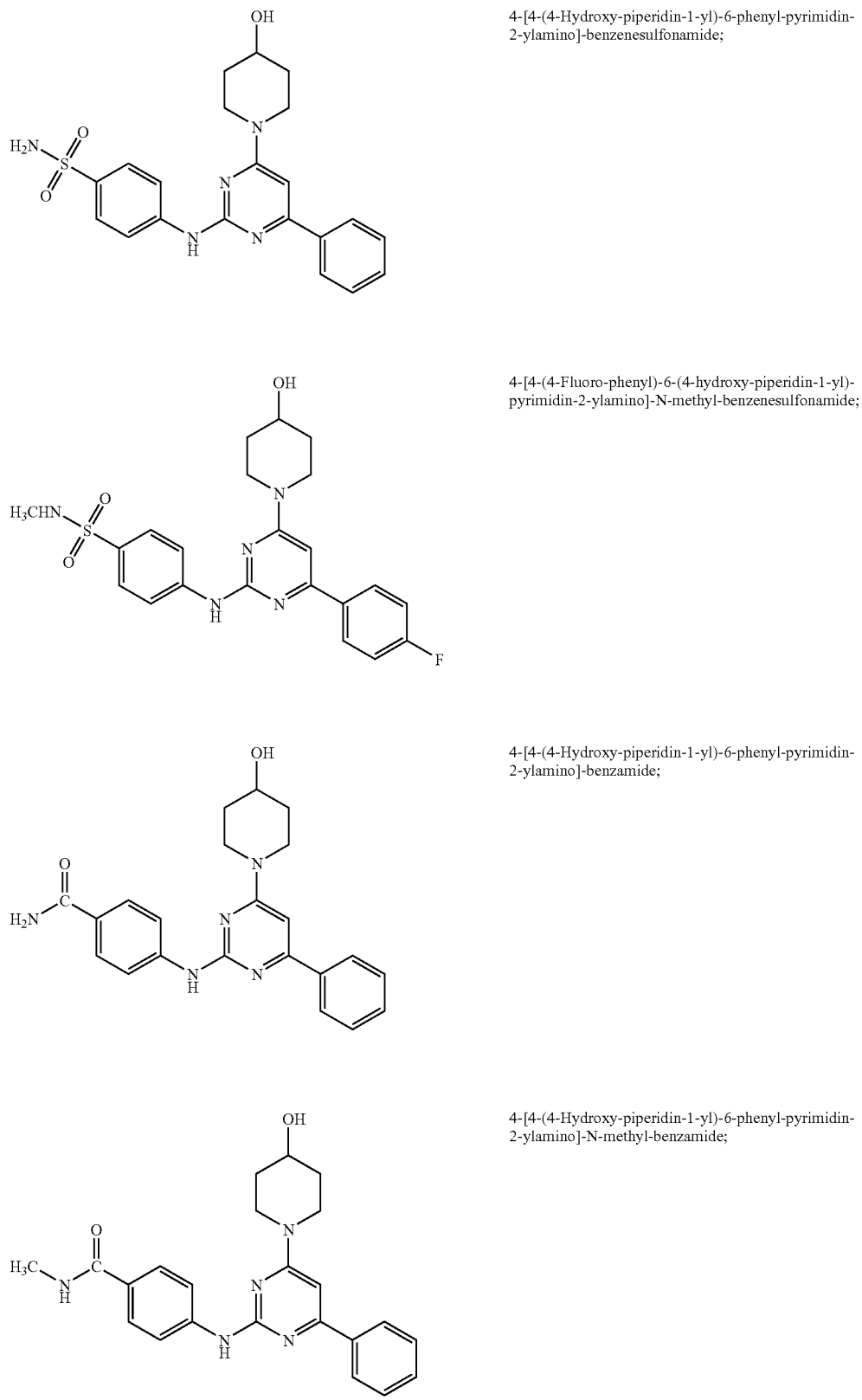

4-[4-(4-Hydroxy-piperidin-1-yl)-6-phenyl-pyrimidin-2-ylamino]-benzenesulfonamide;

4-[4-(4-Fluoro-phenyl)-6-(4-hydroxy-piperidin-1-yl)-pyrimidin-2-ylamino]-N-methyl-benzenesulfonamide;

4-[4-(4-Hydroxy-piperidin-1-yl)-6-phenyl-pyrimidin-2-ylamino]-benzamide;

4-[4-(4-Hydroxy-piperidin-1-yl)-6-phenyl-pyrimidin-2-ylamino]-N-methyl-benzamide;

TABLE 2-continued

Representative compounds in accordance with the present invention.

N-Methyl-4-(4-morpholin-4-yl-6-phenyl-pyrimidin-2-ylamino)-benzenesulfonamide;

N-Methyl-4-(4-morpholin-4-yl-6-phenyl-pyrimidin-2-ylamino)-benzamide;

3-[4-(4-Hydroxy-piperidin-1-yl)-6-phenyl-pyrimidin-2-ylamino]-benzamide;

1-{3-[4-(4-Hydroxy-piperidin-1-yl)-6-phenyl-pyrimidin-2-ylamino]-phenyl}-ethanone;

TABLE 2-continued

Representative compounds in accordance with the present invention.

| Structure | Name |
|---|---|
| | 3-[4-(4-Hydroxy-piperidin-1-yl)-6-phenyl-pyrimidin-2-ylamrno]-N-methyl-benzamide; |
| | N-Methyl-3-(4-morpholin-4-yl-6-phenyl-pyrimidin-2-ylamino)-benzamide; |
| | 1-[4-(4-Morpholin-4-yl-6-phenyl-pyrimidin-2-ylamino)-phenyl]-ethanone; |
| | 3-(4-Morpholin-4-yl-6-phenyl-pyrimidin-2-ylamino)-benzamide; |
| | 1-[3-(4-Morpholin-4-yl-6-phenyl-pyrimidin-2-ylamino)-phenyl]-ethanone; |

TABLE 2-continued

Representative compounds in accordance with the present invention.

| Structure | Name |
|---|---|
| | 3-[4-(4-Hydroxy-piperidin-1-yl)-6-phenyl-pyrimidin-2-ylamino]-benzenesulfonamide; |
| | 3-(4-Morpholin-4-yl-6-phenyl-pyrimidin-2-ylamino)-benzenesulfonamide; |
| | 1-{4-[4-(4-Fluoro-phenyl)-6-morpholin-4-yl-pyrimidin-2-ylaminol-phenyl}-ethanone; |
| | 1-{4-[4-(4-Fluoro-phenyl)-6-(4-hydroxy-piperidin-1-yl)-pyrimidin-2-ylamino]-phenyl}-ethanone; |

TABLE 2-continued
Representative compounds in accordance with the present invention.
| | |
|---|---|
| 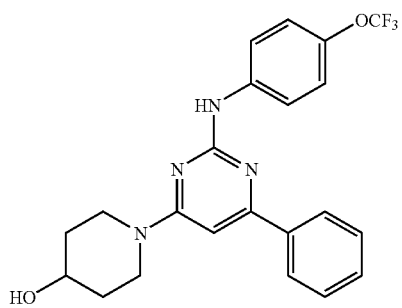 | 1-[6-Phenyl-2-(4-trifluoromethoxy-phenyl amino)-pyrimidin-4-yl]-piperidin-4-ol; |
| 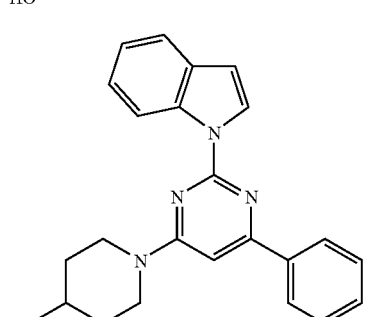 | 1-(2-Indol-1-yl-6-phenyl-pyrimidin-4-yl)-piperidin-4-ol; |
| 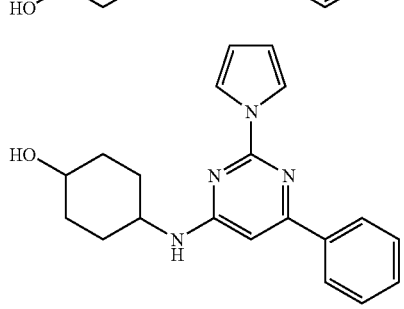 | 4-(6-Phenyl-2-pyrrol-1-yl-pyrimidin-4-ylamino)-cyclohexanol; |
| 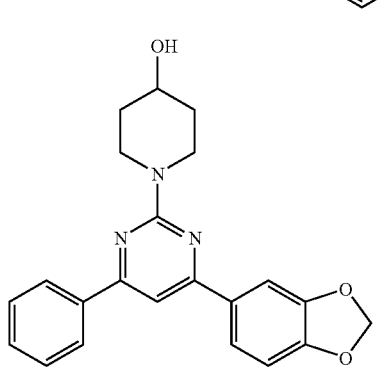 | 1-(4-Benzo[1,3]dioxol-5-yl-6-phenyl-pyrimidin-2-yl)-piperidin-4-ol; |
| 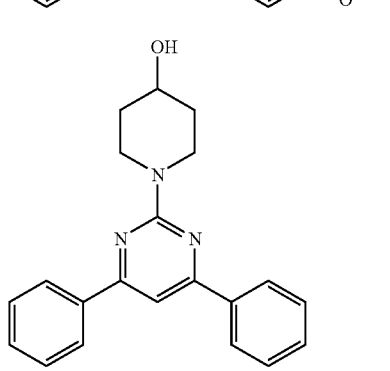 | 1-(4,6-Diphenyl-pyrimidin-2-yl)-piperidin-4-ol; |

TABLE 2-continued
Representative compounds in accordance with the present invention.
| | |
|---|---|
| 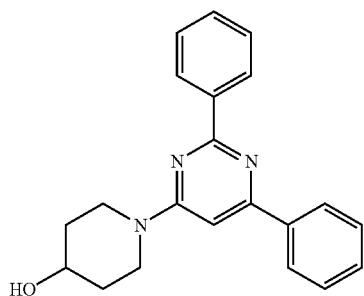 | 1-(2,6-Diphenyl-pyrimidin-4-yl)-piperidin-4-ol; |
| 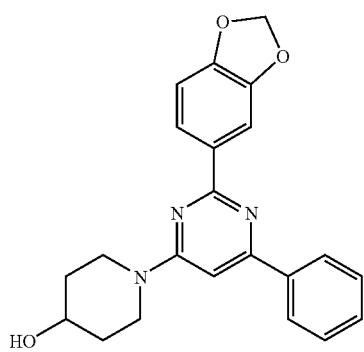 | 1-(2-Benzo[1,3]dioxol-5-yl-6-phenyl-pyrimidin-4-yl)-piperidin-4-ol; |
| 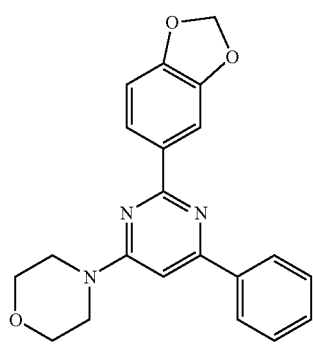 | 4-(2-Benzo[1,3]dioxol-5-yl-6-phenyl-pyrimidin-4-yl)-morpholine; |
| 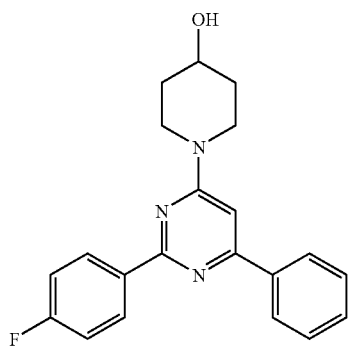 | 1-[2-(4-Fluoro-phenyl)-6-phenyl-pyrimidin-4-yl]-piperidin-4-ol; |

TABLE 2-continued
Representative compounds in accordance with the present invention.
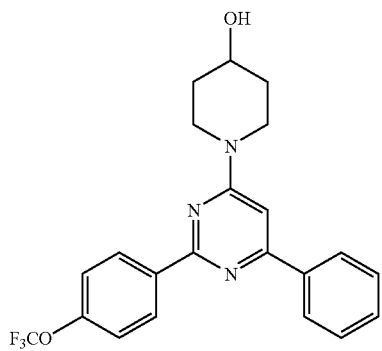
1-[6-Phenyl-2-(4-trifluoromethoxy-phenyl)-pyrimidin-4-yl]-piperidin-4-ol;
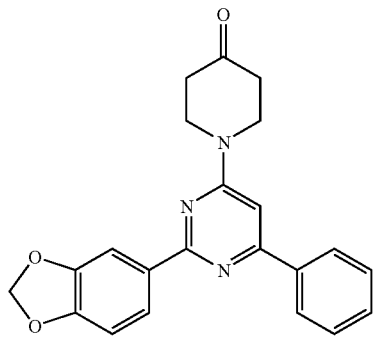
1-(2-Benzo[1,3]dioxol-5-yl-6-phenyl-pyrimidin-4-yl)-piperidin-4-one;
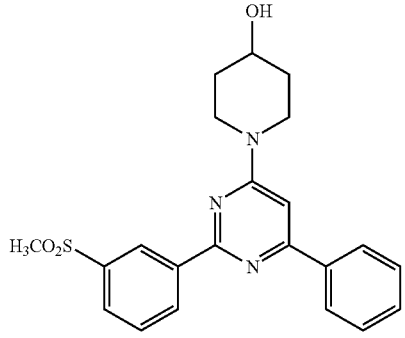
1-[2-(3-Methanesulfonyl-phenyl)-6-phenyl-pyrimidin-4-yl]-piperidin-4-ol;
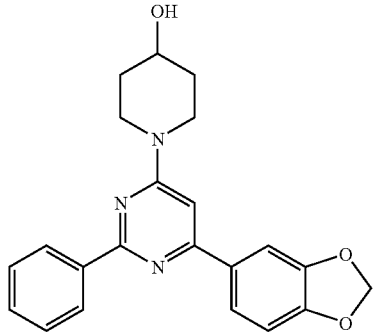
1-(6-Benzo[1,3]dioxol-5-yl-2-phenyl-pyrimidin-4-yl)-piperidin-4-ol;

TABLE 2-continued
Representative compounds in accordance with the present invention.
| | |
|---|---|
| 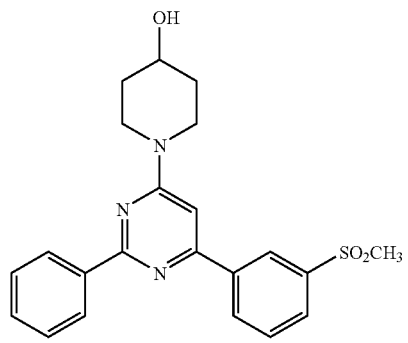 | 1-[6-(3-Methanesulfonyl-phenyl)-2-phenyl-pyrimidin-4-yl]-piperidin-4-ol; |
| 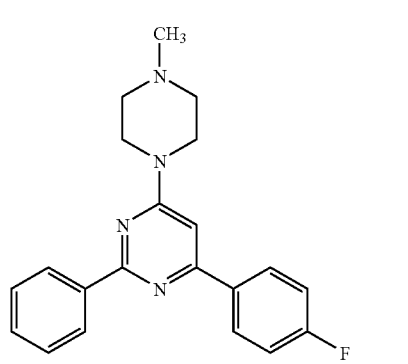 | 4-(4-Fluoro-phenyl)-6-(4-methyl-piperazin-1-yl)-2-phenyl-pyrimidine; |
| 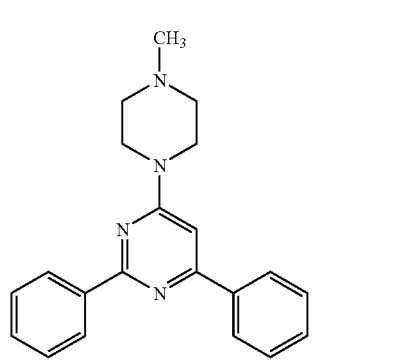 | 4-(4-Methyl-piperazin-1-yl)-2,6-diphenyl-pyrimidine; |
| 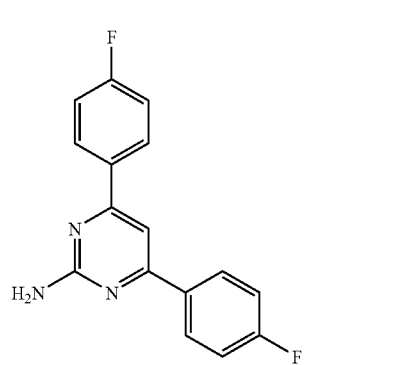 | 4,6-Bis-(4-fluoro-phenyl)-pyrimidin-2-ylamine; |

TABLE 2-continued
Representative compounds in accordance with the present invention.
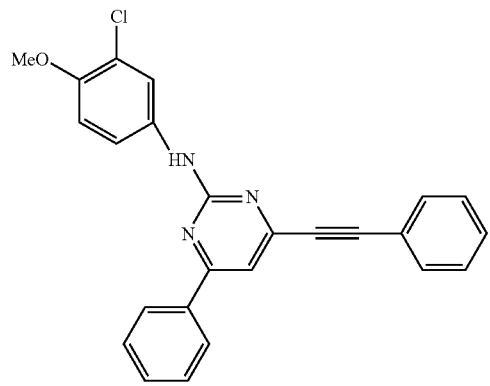
(3-Chloro-4-methoxy-phenyl)-(4-phenyl-6-phenylethynyl-pyrimidin-2-yl)-amine;
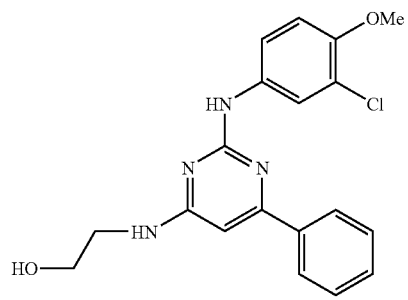
2-[2-(3-Chloro-4-methoxy-phenylamino)-6-phenyl-pyrimidin-4-ylamino]-ethanol;
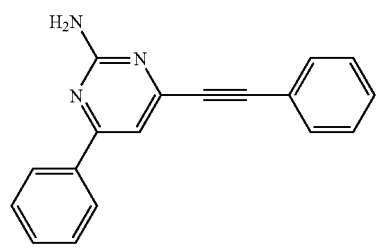
4-Phenyl-6-phenylethynyl-pyrimidin-2-ylamine;
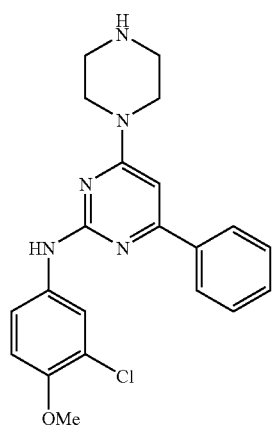
(3-Chloro-4-methoxy-phenyl)-(4-phenyl-6-piperazin-1-yl-pyrimidin-2-yl)-amine;

TABLE 2-continued
Representative compounds in accordance with the present invention.
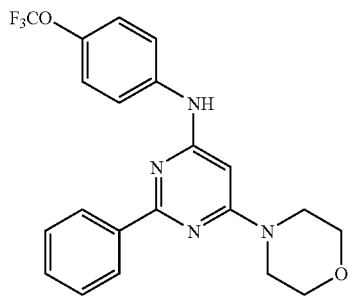
(6-Morpholin-4-yl-2-phenyl-pyrimidin-4-yl)-(4-trifluoromethoxy-phenyl)-amine;
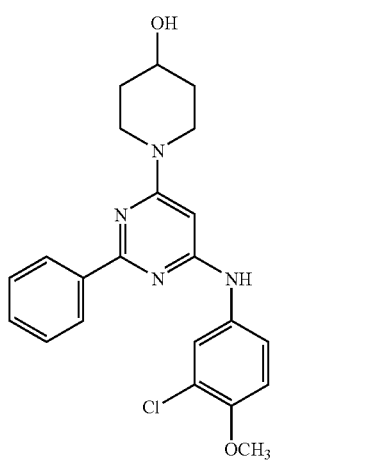
1-[6-(3-Chloro-4-methoxy-phenylamino)-2-phenyl-pyrimidin-4-yl]-piperidin-4-ol;
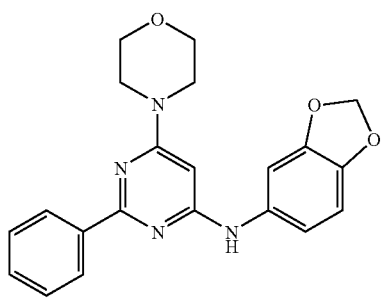
Benzo[1,3]dioxol-5-yl-(6-morpholin-4-yl-2-phenyl-pyrimidin-4-yl)-amine;
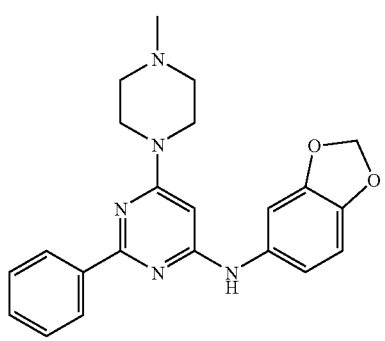
Benzo[1,3]dioxol-5-yl-[6-(4-methyl-piperazin-1-yl)-2-phenyl-pyrimidin-4-yl]-amine;

TABLE 2-continued
Representative compounds in accordance with the present invention.
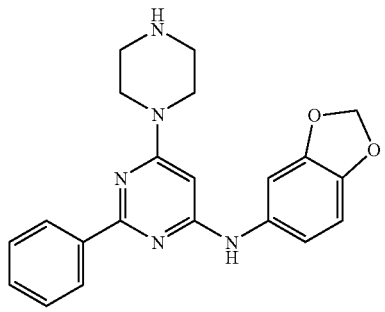
(2-Phenyl-6-piperazin-1-yl-pyrimidin-4-yl)-(4-trifluoromethoxy-phenyl)-amine;
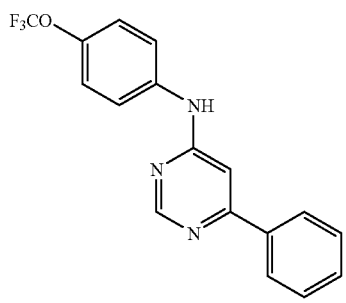
(6-Phenyl-pyrimidin-4-yl)-(4-trifluoromethoxy-phenyl)-amine;
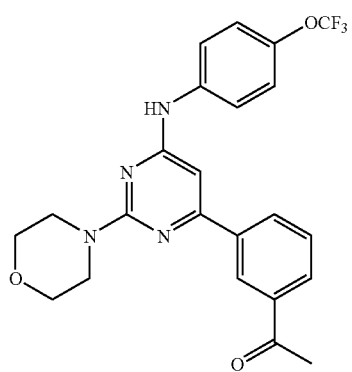
1-{3-[2-Morpholin-4-yl-6-(4-trifluoromethoxy-phenylamino)-pyrimidin-4-yl]-phenyl}-ethanone;
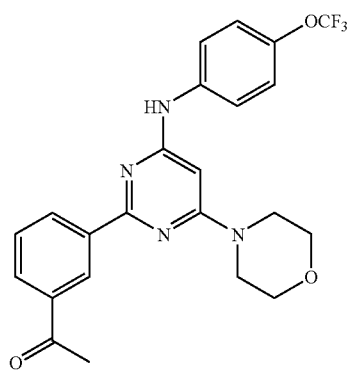
1-{3-[4-Morpholin-4-yl-6-(4-trifluoromethoxy-phenylamino)-pyrimidin-2-yl]-phenyl}-ethanone;

TABLE 2-continued
Representative compounds in accordance with the present invention.
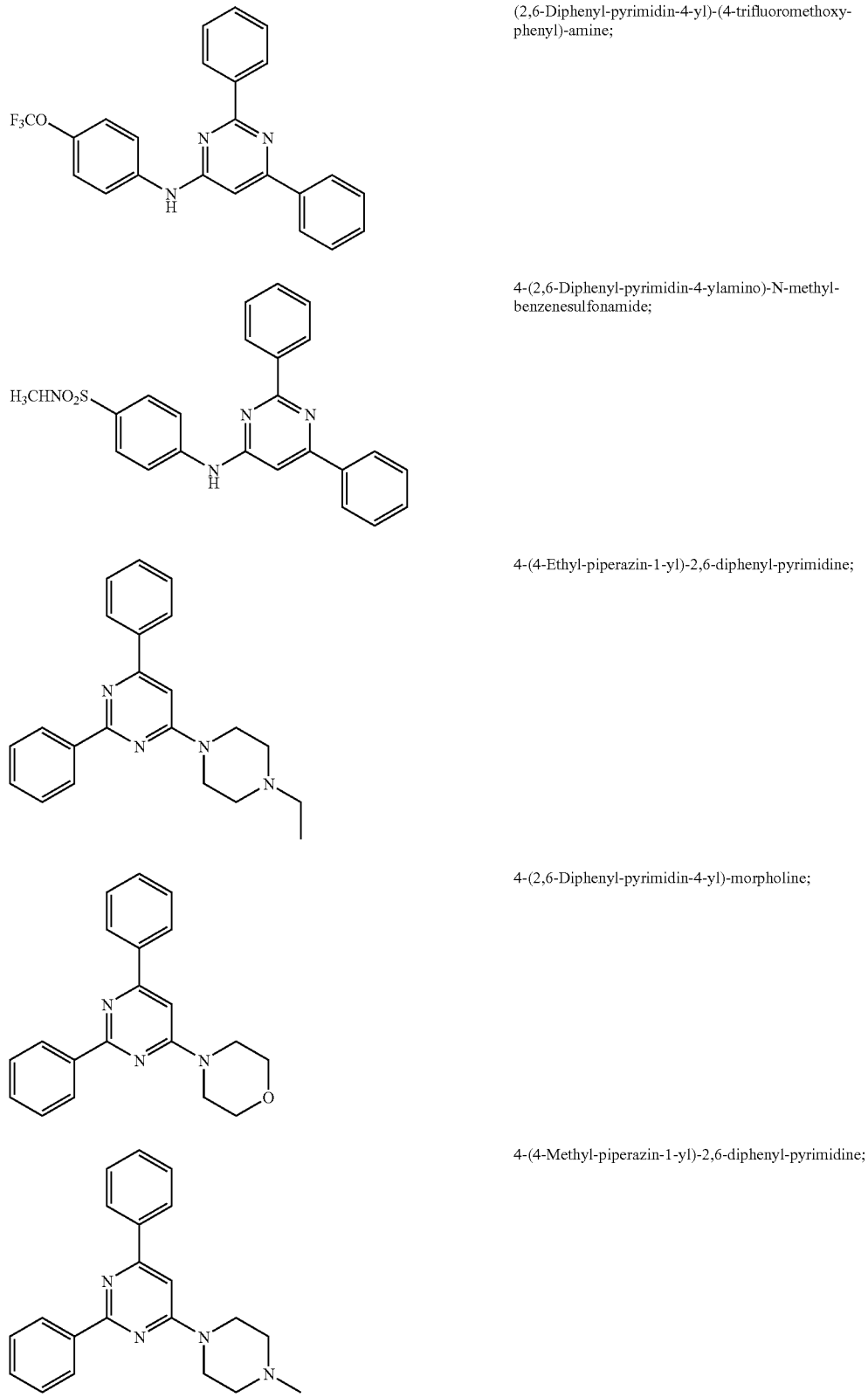
(2,6-Diphenyl-pyrimidin-4-yl)-(4-trifluoromethoxy-phenyl)-amine;
4-(2,6-Diphenyl-pyrimidin-4-ylamino)-N-methyl-benzenesulfonamide;
4-(4-Ethyl-piperazin-1-yl)-2,6-diphenyl-pyrimidine;
4-(2,6-Diphenyl-pyrimidin-4-yl)-morpholine;
4-(4-Methyl-piperazin-1-yl)-2,6-diphenyl-pyrimidine;

TABLE 2-continued

Representative compounds in accordance with the present invention.

| | |
|---|---|
| 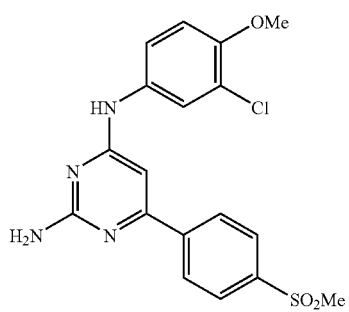 | $N^4$-(3-Chloro-4-methoxy-phenyl)-6-(4-methanesulfonyl-phenyl)-pyrimidine-2,4-diamine; |
| 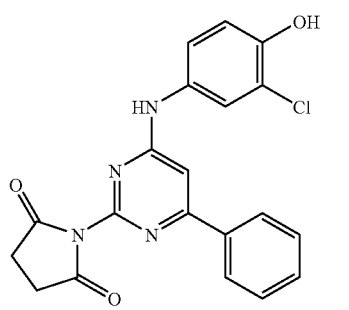 | 1-[4-(3-Chloro-4-hydroxy-phenylamino)-6-phenyl-pyrimidin-2-yl]-pyrrolidine-2,5-dione; |
| 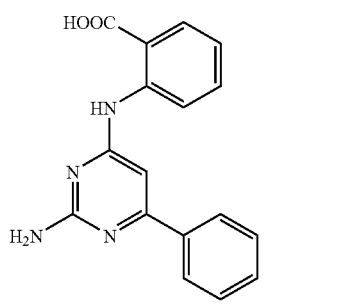 | 2-(2-Amino-6-phenyl-pyrimidin-4-ylamino)-benzoic acid; |
| 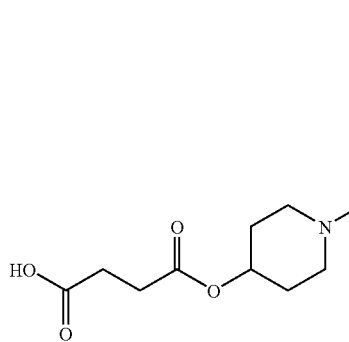 | Succinic acid mono-{1-[2-(3-chloro-4-methoxy-phenylamino)-6-phenyl-pyrimidin-4-yl]-piperidin-4-yl}ester; |

TABLE 2-continued

Representative compounds in accordance with the present invention.

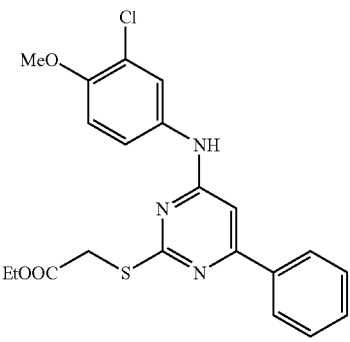

[4-(3-Chloro-4-methoxy-phenylamino)-6-phenyl-pyrimidin-2-ylsulfanyl]-acetic acid ethyl ester;

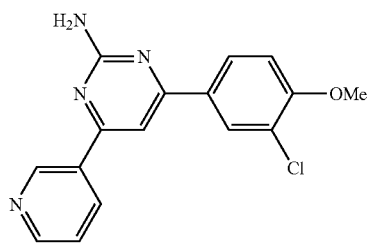

4-(3-Chloro-4-methoxy-phenyl)-6-pyridin-3-yl-pyrimidin-2-ylamine;

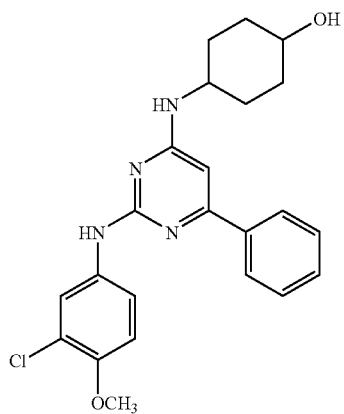

4-[2-(3-Chloro-4-methoxy-phenylamino)-6-phenyl-pyrimidin-4-ylamino]-cyclohexanol;

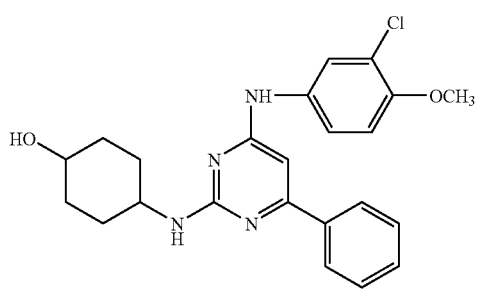

4-[4-(3-Chloro-4-methoxy-phenylamino)-6-phenyl-pyrimidin-2-ylamino]-cyclohexanol;

TABLE 2-continued
Representative compounds in accordance with the present invention.
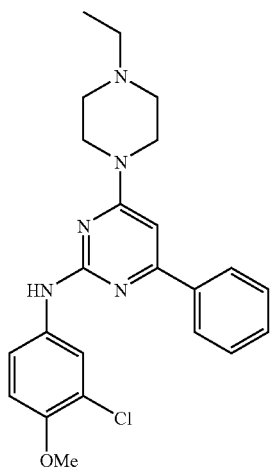
(3-Chloro-4-methoxy-phenyl)-[4-(4-ethyl-piperazin-1-yl)-6-phenyl-pyrimidin-2-yl]-amine;
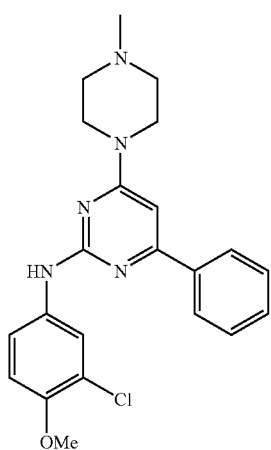
(3-Chloro-4-methoxy-phenyl)-[4-(4-methyl-piperazin-1-yl)-6-phenyl-pyrimidin-2-yl]-amine;
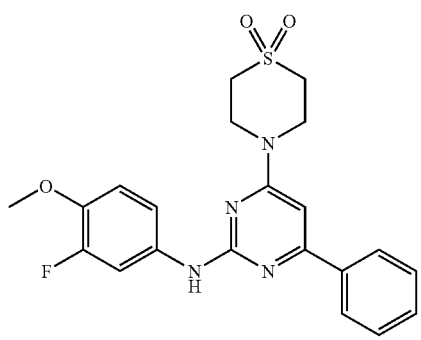
[4-(1,1-Dioxo-1-lambda-6-thiomorpholin-4-yl)-6-phenyl-pyrimidin-2-yl]-(3-fluoro-4-methoxy-phenyl)-amine;

TABLE 2-continued
Representative compounds in accordance with the present invention.
| | |
|---|---|
| 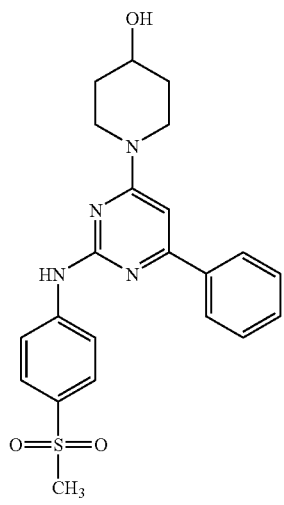 | 1-[2-(4-Methanesulfonyl-phenylamino)-6-phenyl-pyrimidin-4-yl]-piperidin-4-ol; |
| 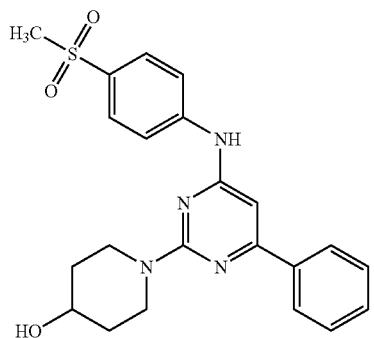 | 1-[4-(4-Methanesulfonyl-phenylamino)-6-phenyl-pyrimidin-2-yl]-piperidin-4-ol; |
| 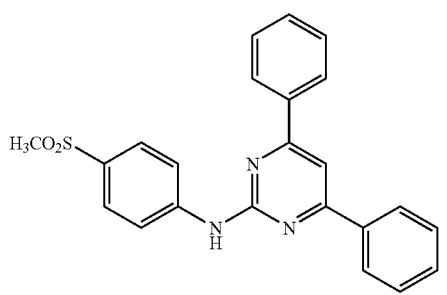 | (2,6-Diphenyl-pyrimidin-4-yl)-(4-methanesulfonyl-phenyl)-amine; |
| 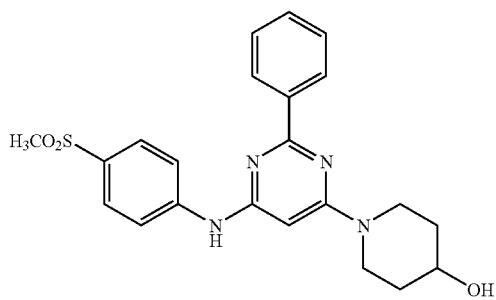 | 1-[6-(4-Methanesulfonyl-phenylamino)-2-phenyl-pyrimidin-4-yl]-piperidin-4-ol; |

TABLE 2-continued

Representative compounds in accordance with the present invention.

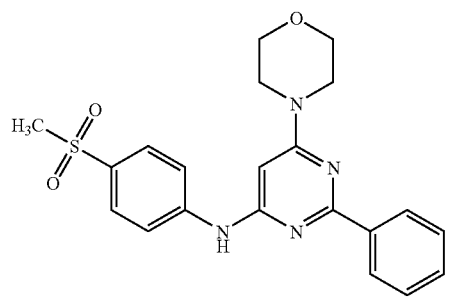
(4-Methanesulfonyl-phenyl)-(6-morpholin-4-yl-2-phenyl-pyrimidin-4-yl)-amine;

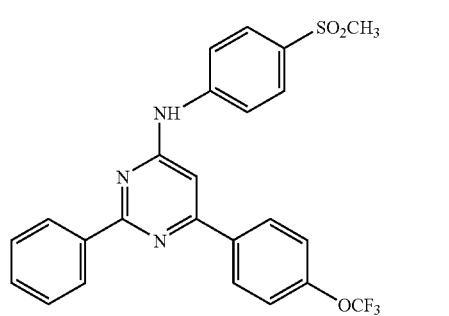
(4-Methanesulfonyl-phenyl)-[2-phenyl-6-(4-trifluoromethoxy-phenyl)-pyrimidin-4-yl]-amine;

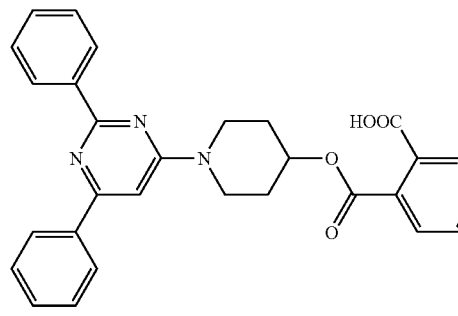
Plithalic acid mono-[1-(2,6-diphenyl-pyrimidin-4-yl)-piperidin-4-yl]ester;

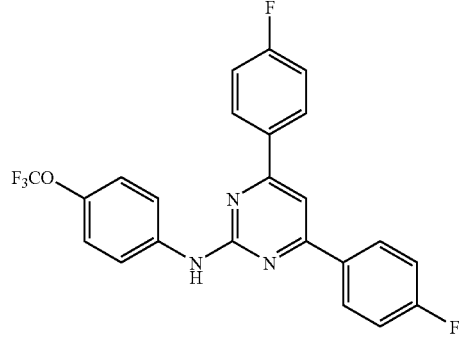
[4,6-Bis-(4-fluoro-phenyl)-pyrimidin-2-yl]-(4-trifluoromethoxy-phenyl)-amine;

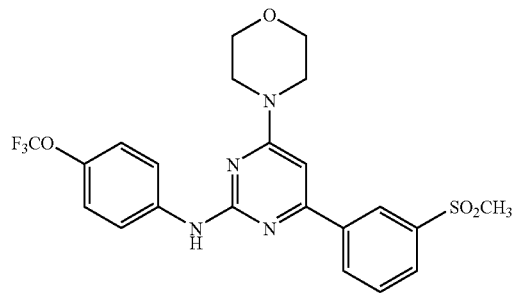
[4-(3-Methanesulfonyl-phenyl)-6-morpholin-4-yl-pyrimidin-2-yl]-(4-trifluoromethoxy-phenyl)-amine TABLE 2-continued
Representative compounds in accordance with the present invention.
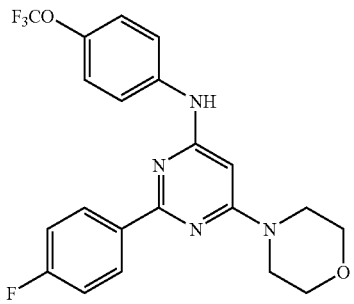
[2-(4-Fluoro-phenyl)-6-morpholin-4-yl-pyrimidin-4-yl]-(4-trifluoromethoxy-phenyl)-amine;
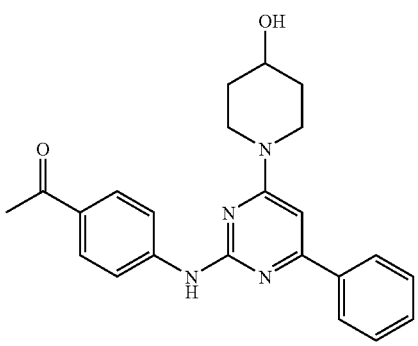
1-{4-[4-(4-Hydroxy-piperidin-1-yl)-6-phenyl-pyrimidin-2-ylamino]-phenyl}-ethanone;
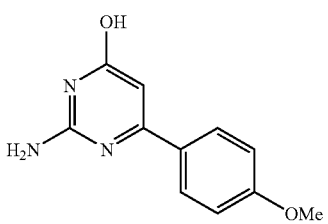
2-amino-6-(4-methoxy-phenyl)-pyrimidin-4-ol;
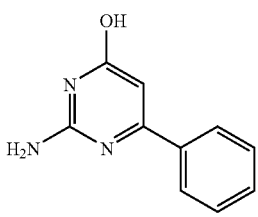
2-Amino-6-phenyl-pyrimidin-4-ol;
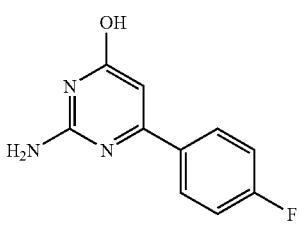
2-Amino-6-(4-fluoro-phenyl)-pyrimidin-4-ol;
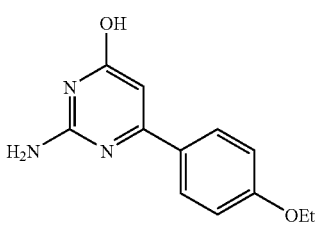
2-Amino-6-(4-ethoxy-phenyl)-pyrimidin-4-ol;

TABLE 2-continued

Representative compounds in accordance with the present invention.

| Structure | Name |
|---|---|
| (2-amino-6-(4-methylphenyl)pyrimidin-4-ol structure) | 2-Amino-6-p-tolyl-pyrimidin-4-ol; |
| (2-amino-6-(4-methylsulfanylphenyl)pyrimidin-4-ol structure) | 2-Amino-6-(4-methylsulfanyl-phenyl)-pyrimidin-4-ol; |
| (2-amino-6-(4-methoxyphenyl)pyrimidin-4-ol structure) | 4-chloro-6-(4-methoxy-phenyl)-pyrimidin-2-ylamine |
| (2-amino-6-phenylpyrimidin-4-ol structure) | 4-Chloro-6-phenyl-pyrimidin-2-ylamine; |
| (2-amino-4-chloro-6-(4-fluorophenyl)pyrimidine structure) | 4-Chloro-6-(4-fluoro-phenyl)-pyrimidin-2-ylamine; |
| (2-amino-4-chloro-6-(4-ethoxyphenyl)pyrimidine structure) | 4-chloro-6-(4-ethoxy-phenyl)-pyrimidin-2-ylamine; |
| (2-amino-4-chloro-6-(4-methylphenyl)pyrimidine structure) | 4-Chloro-6-p-tolyl-pyrimidin-2-ylamine; |

TABLE 2-continued
Representative compounds in accordance with the present invention.
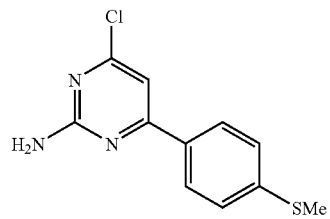 4-chloro-6-(4-methylsulfanylphenyl)pyrimidin-2-ylamine;
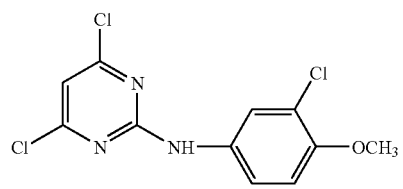 (3-chloro-4-methoxy-phenyl)-(4,6-dichloro-pyrimidin-2-yl)-amine;
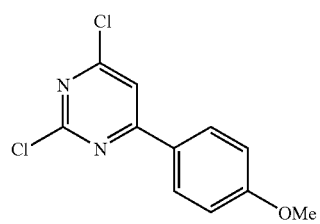 2,4-Dichloro-6-(4-methoxy-phenyl)-pyrimidine;
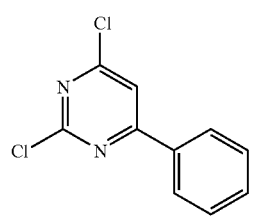 2,4-Dichloro-6-phenyl-pyrimidine;
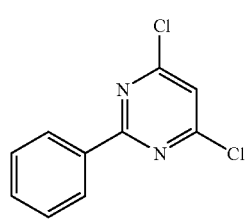 4,6-dichloro-2-phenyl-pyrimidine;
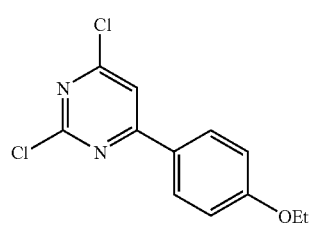 2,4-Dichloro-6-(4-ethoxy-phenyl)-pyrimidine;
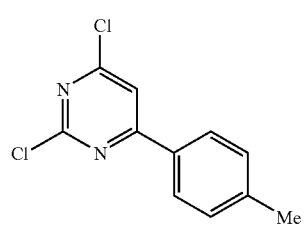 2,4-Dichloro-6-p-tolyl-pyrimidine;

TABLE 2-continued

Representative compounds in accordance with the present invention.

| | |
|---|---|
| 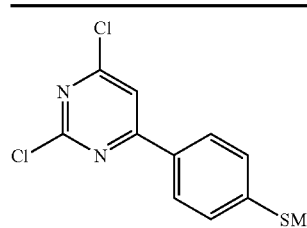 | 2,4-Dichloro-6-(4-methylsulfanyl-phenyl)-pyrimidine; |
| 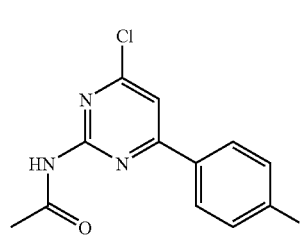 | N-[4-chloro-6-(4-ethoxy-phenyl)-pyrimidin-2-yl]-formamide; |
| 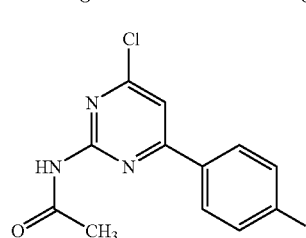 | N-[4-Chloro-6-(4-methoxy-phenyl)-pyrimidin-2-yl]-acetamide; |
| 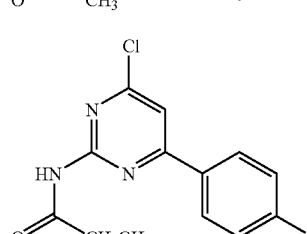 | N-[4-Chloro-6-(4-methoxy-phenyl)-pyrimidin-2-yl]-propionamide; |
| 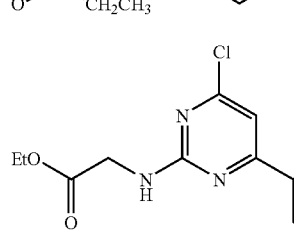 | (4-Chloro-6-phenyl-pyrimidin-2-ylamino)-acetic acid ethyl ester; |
| 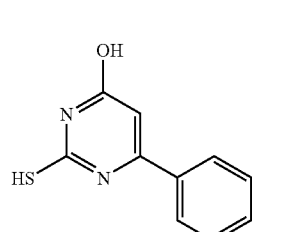 | 2-mercapto-6-phenyl-pyrimidin-4-ol; |
| 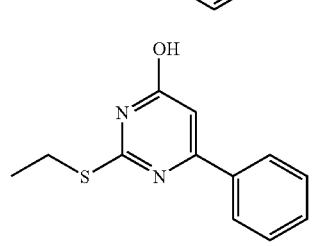 | 2-ethylsulfanyl-6-arylpyrimidin-4-ol; |

TABLE 2-continued

Representative compounds in accordance with the present invention.

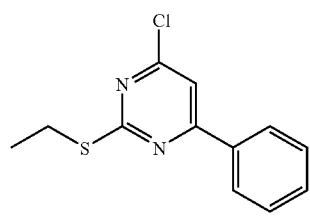
4-chloro-2-ethylsulfanyl-6-phenylpyrimidine;

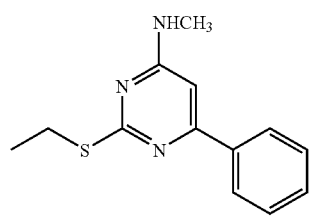
(2-ethylsulfanyl-6-phenylpyrimidin-4-yl)methylamine;

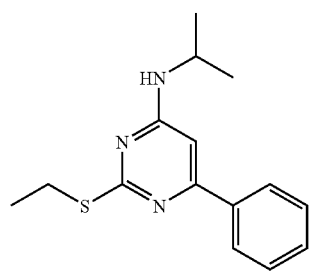
(2-Ethylsulfanyl-6-phenyl-pyrimidin-4-yl)-isopropyl-amine;

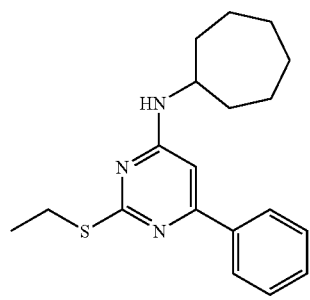
Cycloheptyl-(2-ethylsulfanyl-6-phenyl-pyrimidin-4-yl)-amine;

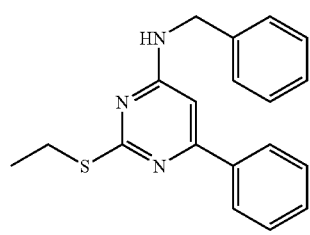
Benzyl-(2-ethylsulfanyl-6-phenyl-pyrimidin-4-yl)-amine;

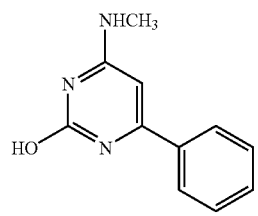
4-methylamino-6-phenylpyrimidin-2-ol;

TABLE 2-continued
Representative compounds in accordance with the present invention.
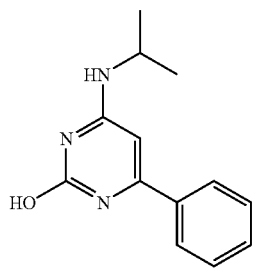
4-Isopropylamino-6-phenyl-pyrimidin-2-ol;
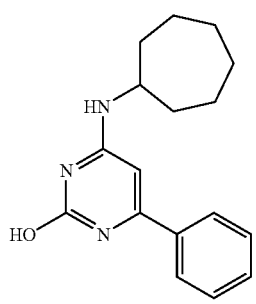
4-Cycloheptylamino-6-phenyl-pyrimidin-2-ol;
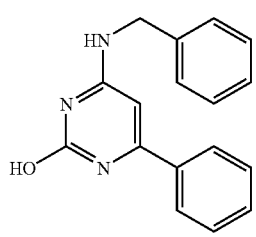
4-Benzylamino-6-phenyl-pyrimidin-2-ol;
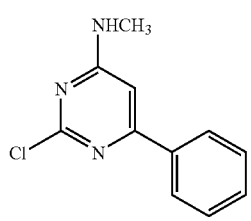
(2-chloro-6-phenylpyrimidin-4-yl) alkylamine;
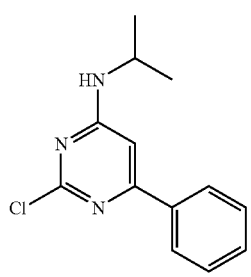
(2-Chloro-6-phenyl-pyrimidin-4-yl)-isopropyl-amine;

TABLE 2-continued
Representative compounds in accordance with the present invention.
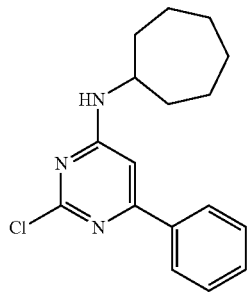
(2-Chloro-6-phenyl-pyrimidin-4-yl)-cycloheptyl-amine;
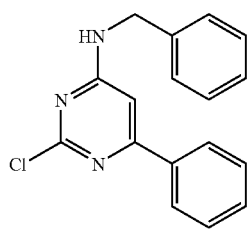
Benzyl-(2-chloro-6-phenyl-pyrimidin-4-yl)-amine;
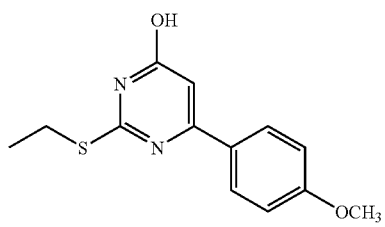
2-ethylsulfanyl-6-(4-methoxy-phenyl)-pyrimidin-4-ol;
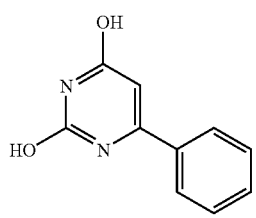
6-phenyl-pyrimidine-2,4-diol;
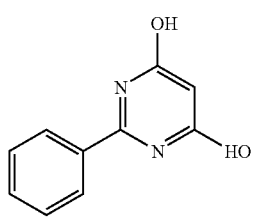
2-phenyl-pyrimidine-4,6-diol;
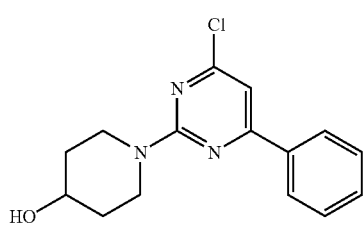
1-(4-chloro-6-phenyl-pyrimidin-2-yl)-piperidin-4-ol;

TABLE 2-continued
Representative compounds in accordance with the present invention.
| | |
|---|---|
| 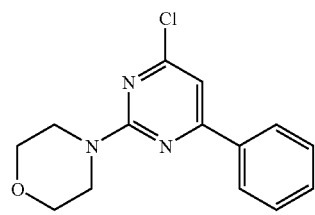 | 4-(4-Chloro-6-phenyl-pyrimidin-2-yl)-morpholine; |
| 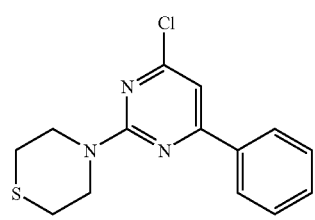 | 4-(4-Chloro-6-phenyl-pyrimidin-2-yl)-thiomorpholine; |
| 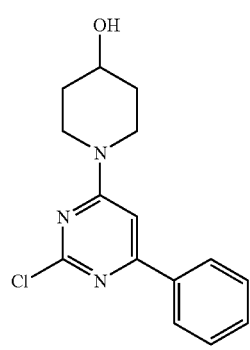 | 1-(2-chloro-6-phenyl-pynmidin-4-yl)-pipendin-4-ol; |
| 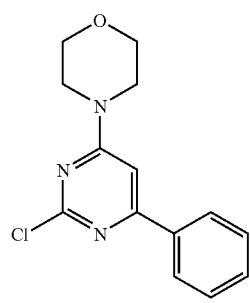 | 4-(2-chloro-6-phenyl-pyrimidin-4-yl)-morpholine; |
| 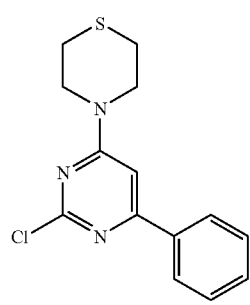 | 4-(2-chloro-6-phenyl-pyrimidin-4-yl)-thiomorpholine; |

TABLE 2-continued
Representative compounds in accordance with the present invention.
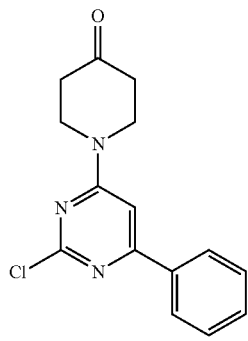
1-(2-Chloro-6-phenyl-pyrimidin-4-yl)-piperidin-4-one;
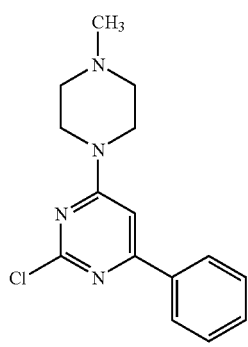
2-Chloro-4-(4-methyl-piperazin-1-yl)-6-phenyl-pyrimidine;
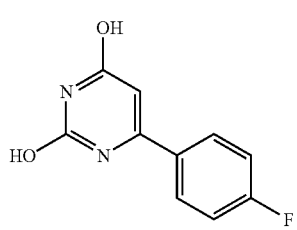
6-(4-Fluoro-phenyl)-pyrimidine-2,4-diol;
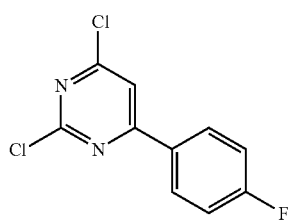
2,4-Dichloro-6-(4-fluoro-phenyl)-pyrimidine;
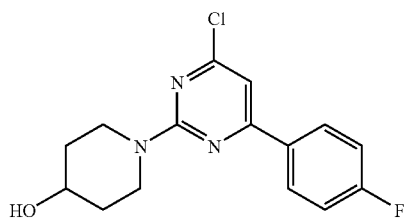
1-[4-Chloro-6-(4-fluoro-phenyl)-pyrimidin-2-yl]-piperidin-4-ol;
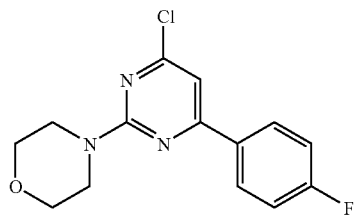
4-[4-Chloro-6-(4-fluoro-phenyl)-pyrimidin-2-yl]-morpholine;

TABLE 2-continued
Representative compounds in accordance with the present invention.
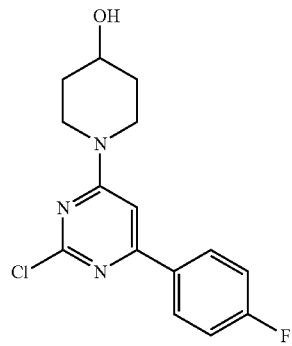
1-[2-Chloro-6-(4-fluoro-phenyl)-pyrimidin-4-yl]-pipendin-4-ol;
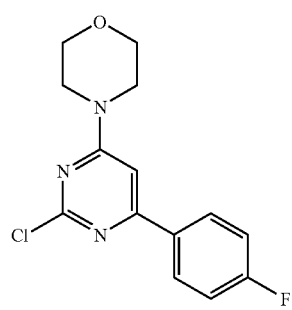
4-[2-Chloro-6-(4-fluoro-phenyl)-pyrimidin-4-yl]-morpholine;
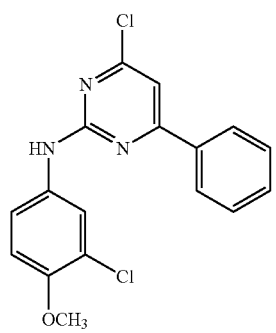
(3-chloro-4-methoxy-phenyl)-(4-chloro-6-phenyl-pyrimidin-2-yl)-amine;
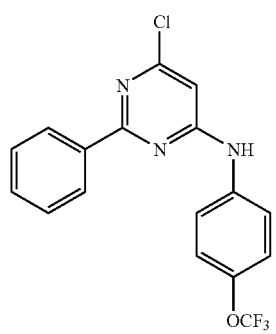
(6-chloro-2-phenyl-pyrimidin-4-yl)-(4-trifluoromethoxy-phenyl)-amine;

TABLE 2-continued

Representative compounds in accordance with the present invention.

(3-Chloro-4-methoxy-phenyl)-(6-chloro-2-phenyl-pyrimidin-4-yl)-amine;

Benzo[1,3]dioxol-5-yl-(6-chloro-2-phenyl-pyrimidin-4-yl)-amine;

(6-Chloro-2-phenyl-pynmidin-4-yl)-(4-trifluoromethoxy-phenyl)-amine;

6-phenyl-pyrimidin-4-ol;

4-chloro-6-phenyl-pyrimidine;

TABLE 2-continued

Representative compounds in accordance with the present invention.

| Structure | Name |
|---|---|
| | (2,6-dichloro-pyrimidin-4-yl)-(4-trifluoromethoxy-phenyl)-amine; |
| | (6-chloro-2-morpholin-4-yl-pyrimidin-4-yl)-(4-trifluoromethoxy-phenyl)-amine; |
| | 1-{3-[4-chloro-6-(4-trifluoromethoxy-phenylamino)-pyrimidin-2-yl]-phenyl}-ethanone; |
| | 2,6-Diphenyl-pyrimidin-4-ol; |
| | 4-Chloro-2,6-diphenyl-pyrimidine; |
| | 4-hydroxy-6-phenyl-pyrimidin-2-ylsulfanyl)-acetic acid ethyl ester; |

TABLE 2-continued

Representative compounds in accordance with the present invention.

| | |
|---|---|
| 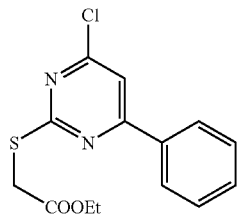 | 4-chloro-6-phenyl-pyrimidin-2-ylsulfanyl)-acetic acid ethyl ester; |
| 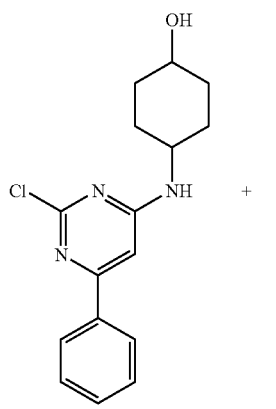 + | 4-(2-chloro-6-phenyl-pyrimidin-4-ylamino)-cyclohexanol; |
| 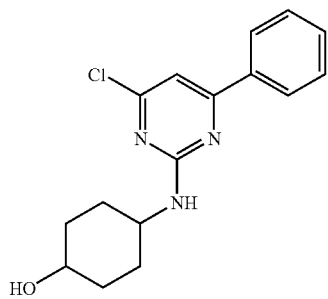 | 4-(4-chloro-6-phenyl-pyrimidin-2-ylamino)-cyclohexanol; |
| 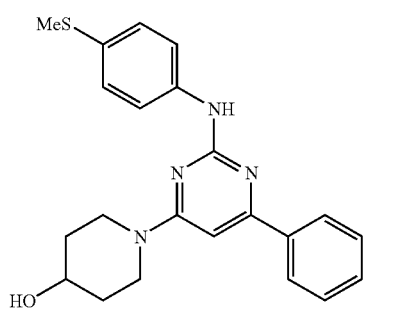 | 1-[2-(4-methylsulfanyl-phenylamino)-6-phenyl-pyrimidin-4-yl]-piperidin-4-ol; |
| 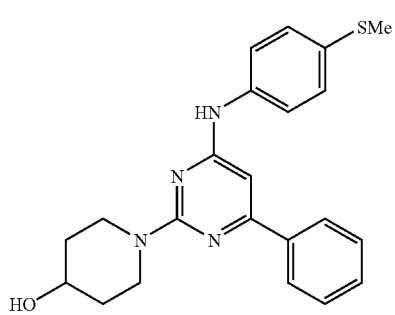 | 1-[4-(4-methylsulfanyl-phenylamino)-6-phenyl-pyrimidin-2-yl]-piperidin-4-ol; |

TABLE 2-continued

Representative compounds in accordance with the present invention.

| Structure | Name |
|---|---|
| | (2,6-diphenyl-pyrimidin-4-yl)-(4-methylsulfanyl-phenyl)-amine; |
| | (6-chloro-2-phenyl-pyrimidin-4-yl)-(4-methylsulfanyl-phenyl)-amine; |
| | (6-chloro-2-phenyl-pyrimidin-4-yl)-(4-methanesulfonyl-phenyl)-amine; |
| | (4,6-dichloro-pyrimidin-2-yl)-(4-trifluoromethoxy-phenyl)-amine; |
| | [4-chloro-6-(3-methanesulfonyl-phenyl)-pyrimidin-2-yl]-(4-trifluoromethoxy-phenyl)-amine; |
| | 2-(4-fluoro-phenyl)-pyrimidine-4,6-diol; |

TABLE 2-continued

Representative compounds in accordance with the present invention.

4,6-dichloro-2-(4-fluoro-phenyl)-pyrimidine;

[6-chloro-2-(4-fluoro-phenyl)-pyrimidin-4-yl]-(4-trifluoromethoxy-phenyl)-amine;

In this aspect of the present invention, compounds provided herein may be chiral or achiral, or they may exist as racemic mixtures, diastereomers, pure enantiomers, a prodrug, a tautomer or any mixture thereof. For chiral compounds, separate enantiomers, separate diastereomers, and any mixture of enantiomers, diastereomers, or both are encompassed herein. Further, the present invention also encompasses any combination of compounds provided herein, including any salts, including pharmaceutically acceptable and non-pharmaceutically acceptable salts, or any mixture thereof.

As used herein, the terms "pharmaceutically acceptable" salt or "pharmacologically acceptable" salt refers generally to a salt or complex of the compound or compounds in which the compound can be either anionic or cationic, and have associated with it a counter cation or anion, respectively, that is generally considered suitable for human or animal consumption. For example, a pharmaceutically acceptable salt can refer to a salt of a compound disclosed herein that forms upon reaction or complexation with an acid whose anion is generally considered suitable for human or animal consumption. In this aspect, pharmacologically acceptable salts include salts with organic acids or inorganic acids. Examples of pharmacologically acceptable salts include, but are not limited to, hydrochloride, hydrobromide, hydroiodide, sulfate, phosphate, propionate, lactate, maleate, malate, succinate, tartarate, and the like.

Salts may also be formed by deprotonating acid moiety of compound, such as a carboxylic acid moiety, OH, or NH, and the like, using a base such as an organic base, an inorganic base, an organometallic base, a Lewis base, a Brønsted base, or any mixture thereof. In cases where compounds carry an acidic moiety, suitable pharmaceutically acceptable salts can include alkali metal salts, alkaline earth metal salts, or salts with organic basis, and the like. In this aspect, examples of alkali metal salts include, but are not limited to, sodium and potassium salts, and examples of salts with organic basis include, but are not limited to, meglumine salts, and the like. The pharmacologically acceptable salts may be prepared by conventional means. Additional examples of pharmaceutically acceptable salts, and methods of preparing such salts, are found, for example, in Berg et.al., J. Pharma. Sci, 66, 1-19 (1977).

In a further aspect, this invention also provides a composition comprising at least one compound as disclosed herein, including a composition comprising a pharmaceutically acceptable carrier and at least one compound as disclosed herein. In this aspect, the at least one compound can be present as a neutral compound, as a salt, or as any combination thereof. This invention also encompasses a composition comprising at least one compound as disclosed herein, and optionally comprising a pharmaceutically acceptable additive selected from a carrier, an auxiliary, a diluent, an excipient, a preservative, a solvate, or any combination thereof.

Further, this invention encompasses a pharmaceutical composition, comprising at least one compound as disclosed herein, and optionally comprising a pharmaceutically acceptable additive selected from a carrier, an auxiliary, a diluent, an excipient, a preservative, a solvate, or any combination thereof, wherein the pharmaceutical composition is in the form of a tablet, a capsule, a syrup, a cachet, a powder, a granule, a solution, a suspension, an emulsion, a bolus, a lozenge, a suppository, a cream, a gel, a paste, a foam, a spray, an aerosol, a microcapsule, a liposome, or a transdermal patch.

In another aspect, this invention encompasses a pharmaceutical composition, comprising at least one compound as disclosed herein, and optionally comprising a pharmaceutically acceptable additive selected from a carrier, an auxiliary, a diluent, an excipient, a preservative, a solvate, or any combination thereof; and further comprising an agent selected from a chemotherapeutic agent, an immunosuppressive agent, a cytokine, a cytotoxic agent, an anti-inflammatory agent, an antirheumatic agent, a cardiovascular agent, or any combination thereof.

Another aspect of this invention is directed to using the compounds and compositions disclosed herein in a method of treating a condition or disease state mediated by the low expression of Perlecan, comprising administering an amount of at least one compound as disclosed herein, effective to induce Perlecan expression.

A further aspect of this invention is directed to using the compounds and compositions disclosed herein in a method of treating atherosclerosis, arthritis, restenosis, diabetic nephropathy, or dyslipidemia, comprising administering an effective amount of at least one compound as disclosed herein.

Preparation of Substituted Pyrimidine Compounds

One more aspect of the present invention provides a process for the preparation of the compounds of the general formula types disclosed herein. Thus, substituted pyrimidine analogs may be prepared generally using standard synthetic methods and employing starting materials that are readily available commercially. As demonstrated by the general reaction schemes and examples disclosed herein, the general synthetic methods provided will ve readily understood by one of ordinary skill in the art, and any variations needed for a particular species are simple and readily understood and appreciated by the skilled artisan. In the following general reaction schemes, variable chemical moieties refer to any chemical group consistent with the description of the compound and substituents on that compound as provided herein. Further, in the schemes that follow, the term "palladium catalyst" refers to a suitable palladium catalyst, typically a complex of Pd(0) or Pd(II), including but not limited to, such compounds as palladium(0) tetrakis(triphenylphosphine), tris(dibenzylideneacetone)dipalladium(0), palladium(II) acetate, that is known to catalyze the reaction shown. In one aspect, the catalytic system may also include monodentate or chelating ligands, examples of which include, but are not limited to, 2,2'-bis(diphenyl phosphino)-1,1-binapthyl, tri-tert-butyl phosphine, and the like, and may also include a base such as sodium carbonate, sodium or potassium tert-butoxide, or potassium phosphate. Transition metal catalyzed reactions may be typically carried out at ambient temperature or at elevated temperatures using various inert solvents, examples of which include, but are not limited to, toluene, dioxane, DMF, n-methyl pyrrolidine, ethylene glycol, dimethyl ether, diglyme, acetonitrile, or any combination thereof. In one aspect, for example, commonly employed reagent and catalyst pairs include, but are not limited to, aryl boronic acids and palladium(0) (Suzuki reaction, Miyaura and Suzuki, *Chem. Rev.* 1995, 95, 2457).

The following general reaction schemes detail the synthetic approaches to the pyrimidine compounds disclosed herein.

Substituted pyrimidine analogs was generally prepared as shown in scheme A and B by using standard synthetic methods and the starting materials are either commercially available or can be synthesized from commercially available precursors using synthetic methods known in the art or variation there in as appreciated by those skilled in the art. Each variable in the following schemes refer to any group consistent with the description of the compound provided herein.

Halogenation was carried out by using reagent chosen from phosphorus oxychloride (POCl$_3$), thionyl chloride (SOCl$_2$) and the like at a temperature in the range of about 80° C. to about 120° C., for about 4 to about 8 hours, followed by pH adjustment of resultant mixture to about 6 to about 7.

Amination was carried out by using amines in presence of a solvent chosen from acetone, acetonitrile, dimethylformamide, dimethylacetamide and the like, with or with out base selected from triethylamine, N,N-diisopropyl ethyl amine, potassium carbonate, sodium carbonate, sodium hydride. The reaction temperature was about 20° C. to about 120° C. The duration of the reaction was in the range of about 4 to about 20 hours.

Arylation was carried out by aryl boronic acids for example in the presence of a palladium catalyst and a base such as sodium carbonate, potassium carbonate, sodium or potassium tert-butoxide, potassium phosphate and the like, at ambient temperature or elevated temperatures using various inert solvent including but not limited to toluene, dioxane, DMF, n-methyl pyrolidine, ethylene glycol, dimethyl ether, diglyne, and acetonitrile. Commonly employed palladium catalysts include [tetrakis-(triphenylphosphine)palladium (0)] [(PPh$_3$)$_4$Pd], tris(dibenzeledine acetone)dipalladium (0) or palladium (II) acetate[Pd(OAc)$_2$], [bis(triphenylphosphine)palladium(II)chloride] [(PPh$_3$)$_2$PdCl$_2$] (Suzuki reaction, Miyaura and Suzuki (1995, Chemical Reviews 95:2457).

Thus one further aspect of the invention relates to the processes of preparing compounds of formulas provided herein. Any compound of any formula disclosed herein may be obtained using procedures provided in the following reaction Schemes, as well as in the schemes provided in the Examples and the Examples themselves, by selecting suitable starting materials and following analogous procedures. Thus, any compound of any formula disclosed above, and exemplified herein, may be obtained by using the appropriate starting materials and appropriate reagents, with the desired substitutions, and following procedures analogous to those described herein.

In one aspect of this invention, compounds of this invention can be prepared as follows.

Scheme A

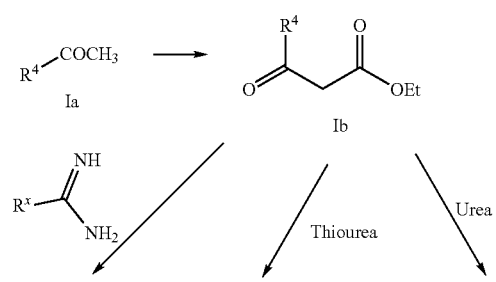

-continued

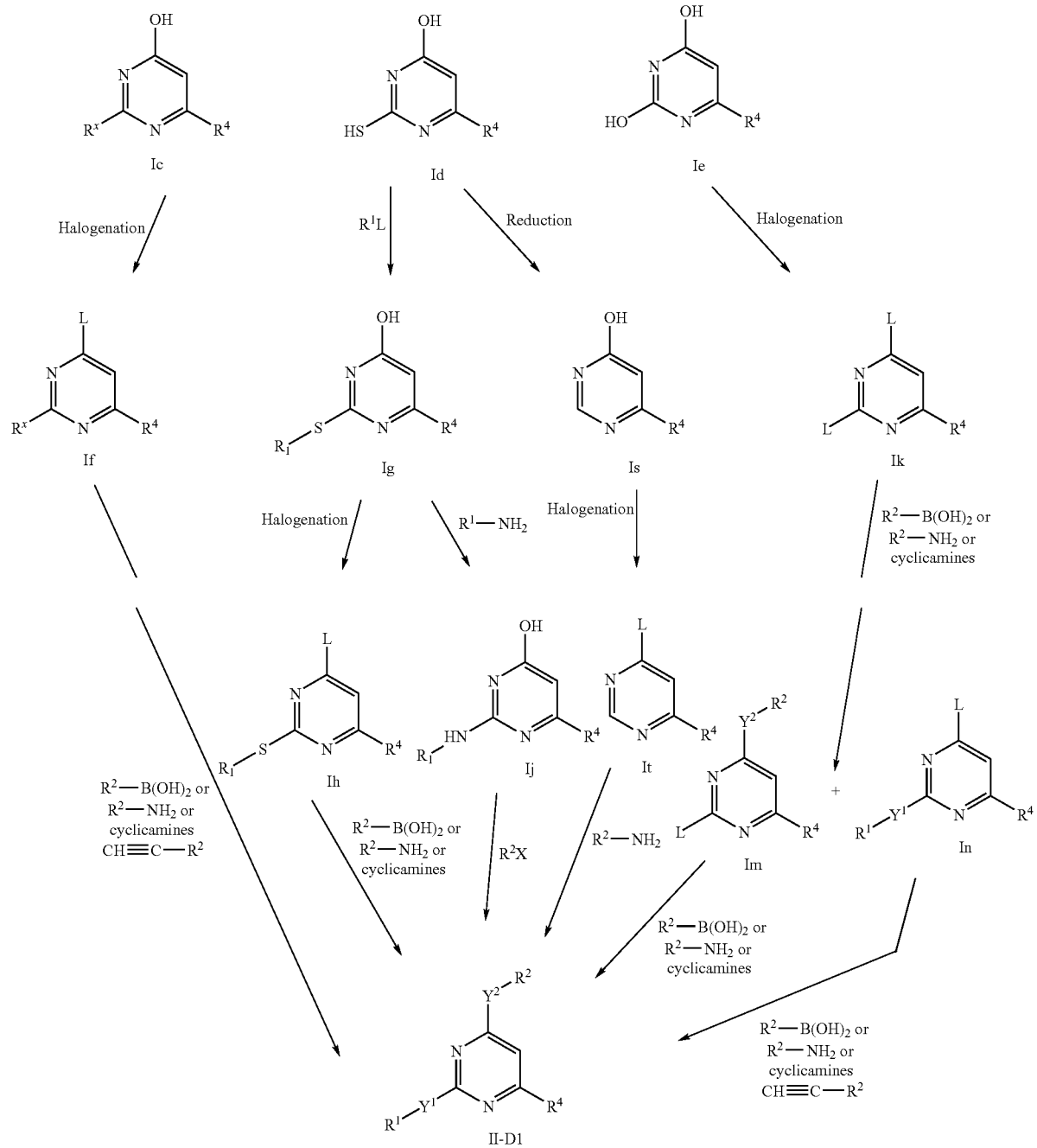

In one aspect, the synthetic transformations illustrated in Scheme A can be carried out using any combination of the following steps, as would be applicable to the desired synthetic transformation. Thus, one of ordinary skill will readily understand that by selecting the proper reagents, including substituents with the appropriate substitution, any compound disclosed herein and any compound related to the compound types disclosed herein, can be prepared using any combination of the following steps:

1) reacting substituted or unsubstituted acetophenones of formula Ia with diethyl carbonate to form a compound of formula Ib;

2) reacting compound of formula Ib with

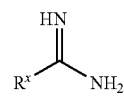

($R^x$ represents aryl or $NH_2$), thiourea or urea to give corresponding compound of formulae Ic, Id or Ie;

2a) halogenation of compounds of formulae Ic, for example with a reagents like $POCl_3$ to give corresponding halogenated compounds of formula If;

2b) reacting the compounds of formula If, with various amines, phenyl boronic acids or thiophenols to obtain compound of formula (II-D) wherein $Y^2$ represents SH, NH or $(CH_2)_n$ where n is zero or $Y^2R^2$ together form cyclicamine, $Y^1R^1$ represents $NH_2$;

2c) compound of formula (II-D1) wherein $Y^2$ represents NH or $(CH_2)_n$ where n is zero or $Y^2R^2$ together form cyclicamine, $Y^1R^1$ represents $NH_2$ can further derivatized by treating with $R^1$-L wherein L represents halogen to get compound of formula (II-D1) wherein $R^1$ is as defined above;

2a(i) alkylation or benzylation of 2-Mercapto-4-hydroxy pyrimidines of formula Id to get compounds of formula Ig;

2a(ii) halogenation of compounds of formula Ig to get 2-sulfanyl-4 halopyrimidines of formula Ih;

2a(iii) reacting the compounds of formula Ih, with various amines or phenyl boronic acids to obtain compound of formula (II-D1) wherein $Y^2$ represents NH or $(CH_2)_n$ where n is zero or $Y^2R^2$ together form cyclicamine, $Y^1$ represents S;

2b(i) substitution of 2-sulfanyl-4-hydroxy pyrimidines of formula Ig with various amines to get 2-amino-4-hydroxy pyrimidines of formula Ij;

2b(ii) alkylation or benzylation of compound of formula Ij to get compound of formula (II-D1) wherein $Y^2$ is oxygen, $Y^1$ is NH and all other symbols are as defined above;

2c(i) reduction of 2-mercapto-4-hydroxy pyrimidines of formula Id to get compounds of formula Is;

2c(ii) halogenation of compounds of formula Is to get 4 halopyrimidines of formula It;

2c(iii) reacting the compounds of formula It, with various amines to obtain compound of formula (II-D1) wherein $Y^2$ represents NH or $(CH_2)_n$ where n is zero or $Y^2R^2$ together form cyclicamine;

2d(i) halogenation of 2,4-dihydroxy pyrimidines of formula Ie to get 2,4-dihalo pyrimidines of formula Ik;

2d(ii) reacting the compounds of formula Ik, with various amines, phenyl boronic acids to get mixture of corresponding 2 and 4 substituted compounds of formulae Im and In wherein $Y^2$ represents NH or $(CH_2)_n$ where n is zero, or $Y^2R^2$ together form cyclicamine (in formula In $Y^1$ is equivalent to $Y^2$ and $R^1$ is equivalent $R^2$), which are separated by column chromatography;

2d(iii) reacting the compounds of formula Im, with various amines or phenyl boronic acids to obtain compound of formula (II-D1) wherein $Y^1$ and $Y^2$ independently represents NH or $(CH_2)_n$ where n is zero, $Y^2R^2$ together form cyclicamine, $Y^1R^1$ together form cyclicamine; or 2d(iv) reacting the compounds of formula In, with various amines or phenyl boronic acids to obtain compound of formula (II-D1) wherein $Y^1$ and $Y^2$ independently represents NH or $(CH_2)_n$ where n is zero, $Y^2R^2$ together form cyclicamine, $Y^1R^1$ together form cyclicamine.

While compound II-D1 is specifically shown in Scheme A, the reaction detailes provided can also be applied to prepare compounds of general formula II-D2.

In one further aspect, the present invention also provides a process of preparing compounds of the present invention, examples of which are also illustrated in Scheme B, by selecting the proper reagents to be used in the syntheses provided therein, and by employing a combination of the following steps.

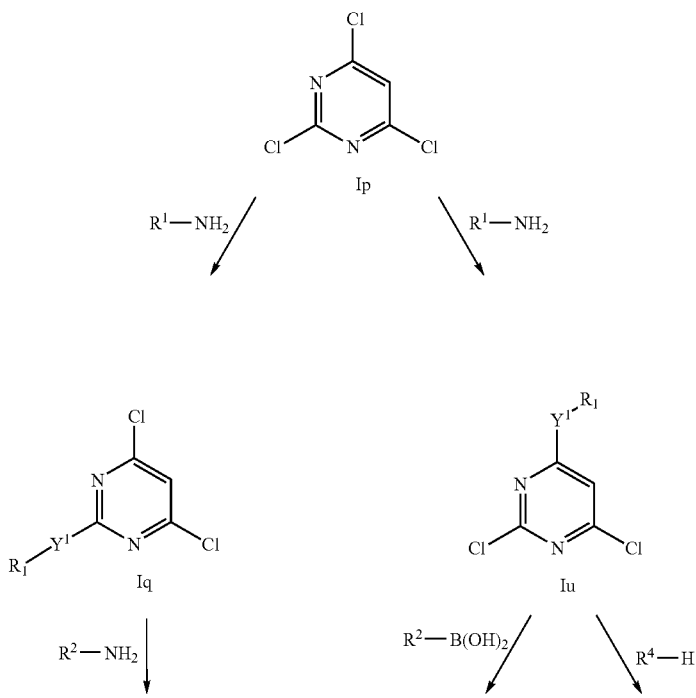

-continued

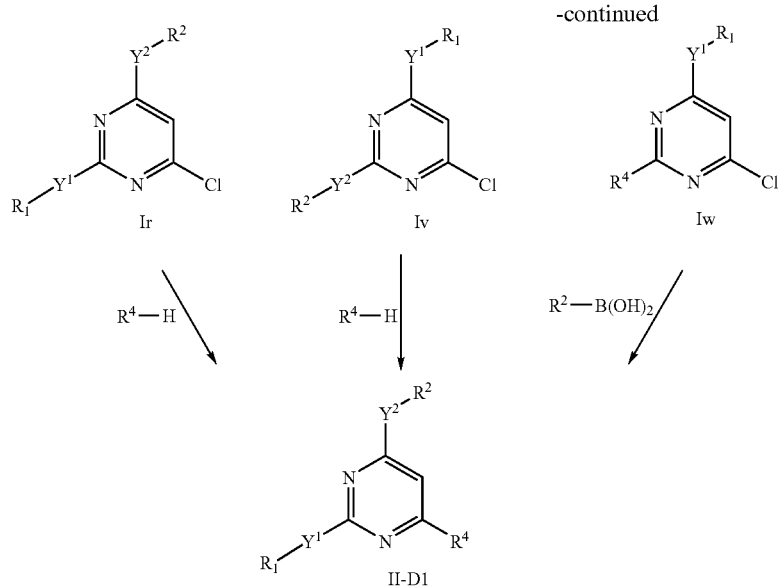

Similarly, the synthetic transformations in Scheme B can be carried out, in one aspect, using any combination of the following steps, as would be applicable to the desired synthetic transformation. Thus, by selecting the proper reagents such as the proper substituted reagents, one of ordinary skill can prepare any of these compound types as follows.

1) 2,4,6-trichloro pyrimidine was reacted with various amines/phenyl boronic acids to get compound of formula Iq wherein $Y^1$ is NH or $(CH_2)_n$ where n is zero or $Y^1$—$R^1$ together form N-containing cyclic ring;

2) Compound of formula Iq is converted to compound of formula Ir wherein $Y^2$ is NH or $(CH_2)_n$ where n is zero or $Y^2$—$R^2$ together form N-containing cyclic ring, by reacting with various anilines/cyclic amines/phenyl boronic acids;

3) Compound of formula Ir is converted to compound of formula II-D wherein $Y^1$ and $Y^2$ represents NH or $(CH_2)_n$ where n is zero or $Y^1$—$R^1$, $Y^2$—$R^2$ together form N-containing cyclic ring, by reacting with various anilines/cyclic amines/phenyl boronic acids;

4) 2,4,6-trichloro pyrimidine was reacted with various amines/phenyl boronic acids to get compound of formula Iu wherein $Y^1$ is NH, $(CH_2)_n$ where n is zero or $Y^1$—$R^1$ is as described in description;

5) reacting compound of formula Iu with various phenyl boronic acids to obtain compound of formula Iv wherein $Y^2$ is NH or $(CH_2)_n$ where n is zero or $Y^2$—$R^2$ is as described in description;

6) Compound of formula Iv is converted to compound of formula II-D wherein $Y^1$ and $Y^2$ represents NH or $(CH_2)_n$ where n is zero or $Y^1$—$R^1$, $Y^2$—$R^2$ together form N-containing cyclic ring, by reacting with various anilines/cyclic amines/phenyl boronic acids or $Y^1$—$R^1$, $Y^2$—$R^2$ is as described in description;

7) Compound of formula Iu is converted to compound of formula Iw wherein $Y^1$ and $Y^2$ represents NH or $(CH_2)_n$ where n is zero or $Y^1$—$R^1$, $Y^2$—$R^2$ together form N-containing cyclic ring, by reacting with various anilines/cyclic amines/phenyl boronic acids or $Y^1$—$R^1$, $Y^2$—$R^2$ is as described in description;

8) Compound of formula Iw is converted to compound of formula II-D1 wherein $Y^1$ and $Y^2$ represents NH or $(CH_2)_n$ where n is zero or $Y^1$—$R^1$, $Y^2$—$R^2$ together form N-containing cyclic ring, by reacting with various anilines/cyclic amines/phenyl boronic acids or $Y^1$—$R^1$, $Y^2$—$R^2$ is as described in description.

In one aspect of Scheme B, $Y^1$ and $Y^2$ can be selected independently from NH or —$(CH_2)$n- wherein n is typically 0, although n can be 1 or 0; $Y^1$—$R^1$ and $Y^2$—$R^2$ can be selected independently from N-containing cyclic amines; and $R^4$ can be selected independently from $Y^1$—$R^1$, wherein $Y^1$, $R^1$, $Y^2$, and $R^2$ are defined herein.

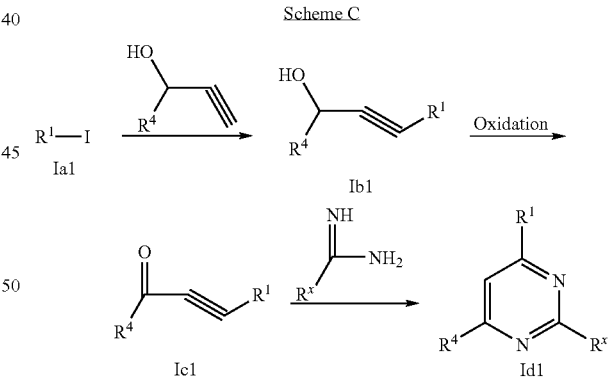

Scheme C

Similarly, the synthetic transformations in Scheme C can be carried out, in one aspect, using any combination of the following steps, as would be applicable to the desired synthetic transformation. Thus, by selecting the proper reagents such as the proper substituted reagents, one of ordinary skill can prepare any of these compound types as follows.

1) Compound of formula Ia1 is converted to compound of formula Ib1 wherein $R^4$ is as described in description;

2) By oxidation reaction compound of formula Ib1 is converted to compound of formula Ic1 wherein $R^4$ is as described in description; 3) reacting compound of formula Ic1 with

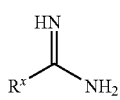

($R^x$ represents aryl or $NH_2$) to give compound of formulae Id1.

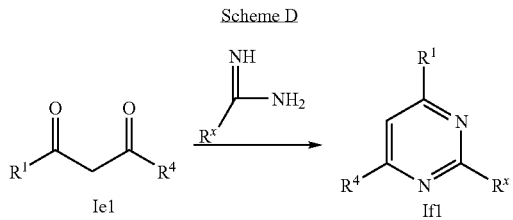

Similarly, the synthetic transformations in Scheme D can be carried out as shown, as would be applicable to the desired synthetic transformation. Thus, by selecting the proper reagents such as the proper substituted reagents, one of ordinary skill can prepare any of the compounds shown as follows.

1) reacting compound of formula Ie1 with

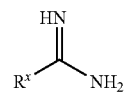

($R^x$ represents aryl or $NH_2$) to give compound of formula If1.

In another aspect, Table 3 provides a listing of exemplary generic pyrimidine compounds types encompassed by the present invention, based upon the general structure shown with substitutents A, B, and C. For every compound type, a synthetic Scheme or Example is provided that details at least one synthetic method that can be used to prepare any compound that is encompassed by that generic compound type. Thus, with the appropriate substitution in the reagents used in the respective Scheme or Example, any compound encompassed by the present invention can be prepared.

TABLE 3

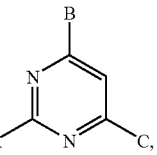

General pyrimidine compound types encompassed by the formula 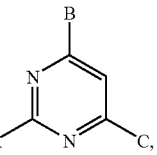, and preparative Schemes (S) or Examples (E) that can be used to prepare them using starting materials with the appropriate substitution.

| Number | A | B | C | Synthesis |
|---|---|---|---|---|
| 1. | $NH_2$ | NHAryl[1] | Aryl[1] (including heteroaryl) | S1 |
| 2. | $NH_2$ | NHAryl[1] | Alkyl | E13 |
| 3. | $NH_2$ | SAryl[1] | Aryl[2] | E23 |
| 4. | $NH_2$ | Aryl[1] (including heteroaryl) | Aryl[2] | E38, E131 |
| 5. | $NH_2$ | hydrocarbyl (including alkynyl) | Aryl[1] | E111 |
| 6. | $NH_2$ | OH | Aryl | S1 |
| 7. | $NH_2$ | Cl | Aryl | S1 |
| 8. | NHAryl | Cl | NHR (R = cycloalkyl) | E15 |
| 9. | NHAryl | N-heterocycle | NHR (R = cycloalkyl) | E15 |
| 10. | NHAryl[1] | NHAryl[2] | Aryl[3] | E16 |
| 11. | NHAryl[1] | NHR (R = alkyl, cycloalkyl, substituted alkyl, benzyl) | Aryl[2] | S3 |
| 12. | NHAryl[1] | OH | Aryl[2] | E30 |
| 13. | NHAryl[1] | OR (R = alkyl, cycloalkyl, benzyl, $CH_2CO_2R$, $CH_2CO_2H$) | Aryl[2] | S4 |
| 14. | NHAryl[1] | N-heterocycle | Aryl[2] | S6 |
| 15. | NHAryl[1] | hydrocarbyl (including alkynyl) | Aryl[2] | E109 |
| 16. | NHAryl[1] | Aryl[2] | Aryl[3] | E144 |
| 17. | NHAryl | Cl | Cl | E15 |
| 18. | NHAryl[1] | Cl | Aryl[2] | E109 |
| 19. | NHX (X = COR, $CH_2CO_2R$) | NHAryl[1] | Aryl[2] | S2 |
| 20. | NHX (X = COR, $CH_2CO_2R$) | Cl | Aryl | S2 |

TABLE 3-continued

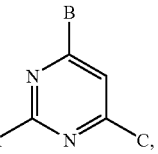

General pyrimidine compound types encompassed by the formula A, and preparative Schemes (S) or Examples (E) that can be used to prepare them using starting materials with the appropriate substitution.

| Number | A | B | C | Synthesis |
|---|---|---|---|---|
| 21. | NHX (X = COR) | OH | Aryl | E22 |
| 22. | SR (R = aryl, $CH_2CO_2R$) | NHAryl$^1$ | Aryl$^2$ | E24 |
| 23. | SR (R = alkyl, $CH_2CO_2R$) | Cl | Aryl | E24 |
| 24. | SR (R = alkyl, $CH_2CO_2R$) | OH | Aryl | E24 |
| 25. | SR (R = alkyl, $CH_2CO_2R$) | NHR (R = alkyl, cycloalkyl, benzyl) | Aryl | S3 |
| 26. | SH | OH | Aryl | E24 |
| 27. | OH | NHAryl$^1$ | Aryl$^2$ | E25 |
| 28. | OH | NHR (R = alkyl, cycloalkyl, benzyl) | Aryl | S3 |
| 29. | OH | OH | Aryl | S5 |
| 30. | NHR (R = alkyl, cycloalkyl) | NHAryl$^1$ | Aryl$^2$ | E133 |
| 31. | NHR (R = alkyl, cycloalkyl) | Cl | Aryl | E132 |
| 32. | N-heterocycle | NRAryl$^1$ (R = H, Me) | Aryl$^2$ | S5 |
| 33. | N-heterocycle | Aryl$^1$ | Aryl$^2$ | S7 |
| 34. | N-heterocycle | Cl | Aryl | S5 |
| 35. | N-heterocycle | Cl | NHAryl | E119 |
| 36. | Aryl$^1$ (including heteroaryl, indolyl, pyrrolyl) | N-heterocycle | Aryl$^2$ | S8, S9 |
| 37. | Aryl$^1$ | NHAryl$^2$ | N-heterocycle | S10 |
| 38. | Aryl$^1$ | NHAryl$^2$ | Aryl$^3$ | E122 |
| 39. | Aryl$^1$ | Cl | Cl | E113 |
| 40. | Aryl$^1$ | N-heterocycle | Cl | S9 |
| 41. | Aryl$^1$ | OH | OH | E113 |
| 42. | Aryl$^1$ | Cl | NHAryl$^2$ | S10 |
| 43. | Aryl$^1$ | OH | Aryl$^2$ | E121 |
| 44. | Aryl$^1$ | Cl | Aryl$^2$ | E121 |
| 45. | H | NHAryl$^1$ | Aryl$^2$ | E118 |
| 46. | H | OH | Aryl | E118 |
| 47. | H | Cl | Aryl | E118 |
| 48. | Cl | Cl | Aryl | S5 |
| 49. | Cl | NHR (R = alkyl, cycloalkyl, benzyl) | Aryl | S3 |
| 50. | Cl | N-heterocycle | Aryl | S5 |
| 51. | Cl | Cl | NHAryl | E119 |

Prodrugs

The compounds alternatively be formulated and administered in a prodrug form. In general, prodrugs comprise functional derivatives of the claimed compounds which are capable of being enzymatically activated or converted into the more active parent form. Thus, in the treatment methods of the present invention, the term "administering" encompasses the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in Wihnan, 14 Biochem. Soc. Trans. 375-82 (1986); Stella et al., Prodrugs: A Chemical Approach to Targeted Drug Delivery in Directed Drug Delivery 247-67 (1985).

The prodrugs of present invention include, but are not limited to derivatives of carboxylic acid, sulfonamide, amine, hydroxyl, and the like, including other functional groups and including any combination thereof.

In another aspect, this invention provides a pharmaceutical composition, comprising one or more compounds of any formula in any combination described above and optionally comprising a pharmaceutically acceptable additive selected from a carrier, an auxiliary, a diluent, an excipient, a preservative, a solvate, or any combination thereof. In a related apect, this invention affords a method of treating a condition or disease state mediated by the low expression of Perlecan, comprising administering at least one compound as disclosed herein, in an amount effective to induce Perlecan expression. In a related aspect, this invention also provides a method of treating atherosclerosis, arthritis, restenosis, diabetic nephropathy, or dyslipidemia, comprising administering an effective amount of at least one compound as disclosed herein.

Antiproliferative Activities

One aspect of the present invention comprises methods and compositions comprising the compounds of the present invention for the treatment and prevention of conditions or diseases that have as an aspect of the disease or condition, unwanted cellular proliferation occurring or are the result of cellular proliferation. For example, many vascular diseases, such as cardiovascular diseases, organ transplant sequellae, vascular occlusive conditions including, but not limited to, neointimal hyperplasia, restenosis, transplant vasculopathy, cardiac allograft vasculopathy, atherosclerosis, and arteriosclerosis, are caused by or have collateral damage due to unwanted cellular proliferation.

One aspect of the present invention relates to methods and compositions for the treatment and prevention of SMC proliferation, preferably comprising compositions and compounds having cellular antiproliferative activity. These compounds as described herein and compositions comprising such compounds are referred to as antiproliferative compounds or compositions. At least one activity of one or more of these compounds is that the compound has the activity of affecting the synthesis of proteoglycans including induction and synthesis of proteoglycans and active fragments of proteoglycans. Thus, one aspect of the activity of one or more of the compounds and compositions of the present invention comprise molecules that induce HSPG production and that regulate SMC proliferation.

Compounds of the present invention that have at least the activity of affecting cellular proliferation are shown in Table 4.

TABLE 4

Compounds of the present invention that have at least the activity of affecting cellular proliferation.

| Entry | Compound name |
|---|---|
| 1. | $N^4$-(3-Chloro-4-methoxy-phenyl)-6-phenyl-pyrimidine-2,4-diamine |
| 2. | $N^4$-(3-Chloro-4-methoxy-phenyl)-6-phenyl-pyrimidine-2,4-diamine.hydrochloride |
| 3. | $N^4$-(3-Chloro-4-methoxy-phenyl)-6-(4-methoxy-phenyl)-pyrimidine-2,4-diamine |
| 4. | $N^4$-(3-Chloro-4-methoxy-phenyl)-6-phenyl-pyrimidine-2,4-diamine |
| 5. | $N^4$-(3-Chloro-4-methoxy-phenyl)-6-(4-methylsulfanyl-phenyl)-pyrimidine-2,4-diamine |
| 6. | $N^4$-(3-Fluoro-4-methoxy-phenyl)-6-(4-methoxy-phenyl)-pyrimidine-2,4-diamine |
| 7. | 4-[2-Amino-6-(4-methoxy-phenyl)-pyrimidin-4-ylamino]-2-chloro-phenol |
| 8. | (3-Chloro-4-methoxy-phenyl)-(2-ethylsulfanyl-6-phenyl-pyrimidin-4-yl)-amine |
| 9. | $N^4$-Benzyl-N2-(3-chloro-4-methoxy-phenyl)-6-phenyl-pyrimidine-2,4-diamine |
| 10. | $N^2$-(3-Chloro-4-methoxy-phenyl)-$N^4$-methyl-6-phenyl-pyrimidine-2,4-diamine |
| 11. | $N^2$-(3-Chloro-4-methoxy-phenyl)-N4-isopropyl-6-phenyl-pyrimidine-2,4-diamine |
| 12. | $N^2$-(3-Chloro-4-methoxy-phenyl)-N4-cycloheptyl-6-phenyl-pyrimidine-2,4-diamine |
| 13. | $N^4$-(3-Chloro-4-methoxy-phenyl)-6-p-tolyl-pyrimidine-2,4-diamine |
| 14. | 2-(3-Chloro-4-methoxy-phenylamino)-6-(4-methoxy-phenyl)-pyrimidin-4-ol |
| 15. | 4-(2-Amino-6-phenyl-pyrimidin-4-ylamino)-2-chloro-phenol |
| 16. | (3-Chloro-4-methoxy-phenyl)-[4-ethoxy-6-(4-methoxy-phenyl)-pyrimidin-2-yl]-amine |
| 17. | N-[4-(3-Chloro-4-methoxy-phenylamino)-6-(4-ethoxy-phenyl)-pyrimidin-2-yl]-acetamide |
| 18. | [4-Benzyloxy-6-(4-methoxy-phenyl)-pyrimidin-2-yl]-(3-chloro-4-methoxy-phenyl)-amine |
| 19. | (3-Chloro-4-methoxy-phenyl)-[4-(4-methoxy-phenyl)-6-(4-methyl-benzyloxy)-pyrimidin-2-yl]-amine |
| 20. | [2-(3-Chloro-4-methoxy-henylamino)-6-(4-methoxy-phenyl)-pyrimidin-4-yloxy]-acetic acid ethyl ester |
| 21. | N-[4-(3-Chloro-4-methoxy-phenylamino)-6-phenyl-pyrimidin-2-yl]-2,2,2-trifluoro-acetamide |
| 22. | 4-(4-Fluoro-phenylsulfanyl)-6-phenyl-pyrimidin-2-ylamine |
| 23. | 6-Chloro-N2-(3-chloro-4-methoxy-phenyl)-N4-cycloheptyl-pyrimidine-2,4-diamine |
| 24. | 2-(3-Chloro-4-methoxy-phenylamino)-6-phenyl-pyrimidin-4-ol |
| 25. | 2-(2-Amino-6-phenyl-pyrimidin-4-ylamino)-benzoic acid ethyl ester |
| 26. | 2-(2-Amino-6-phenyl-pyrimidin-4-ylamino)-benzoic acid |
| 27. | 1-[4-(3-Chloro-4-hydroxy-phenylamino)-6-phenyl-pyrimidin-2-yl]-pyrrolidine-2,5-dione |
| 28. | 2-[2-(3-Chloro-4-methoxy-phenylamino)-6-phenyl-pyrimidin-4-ylamino]-ethanol |
| 29. | 1-[4-(Methyl-phenyl-amino)-6-phenyl-pyrimidin-2-yl]-piperidin-4-ol |
| 30. | 1-[4-(3-Chloro-4-methoxy-phenylamino)-6-phenyl-pyrimidin-2-yl]-piperidin-4-ol |
| 31. | 1-[2-(3-Chloro-4-methoxy-phenylamino)-6-phenyl-pyrimidin-4-yl]-piperidin-4-ol |

TABLE 4-continued

Compounds of the present invention that have at least the activity of affecting cellular proliferation.

| Entry | Compound name |
|---|---|
| 32. | (3-Chloro-4-methoxy-phenyl)-(4-phenyl-6-phenylethynyl-pyrimidin-2-yl)-amine |
| 33. | 4-(3-Chloro-4-methoxy-phenyl)-6-phenyl-pyrimidin-2-ylamine |
| 34. | $N^4$-(4-Chloro-3-methoxy-phenyl)-6-phenyl-pyrimidine-2,4-diamine |
| 35. | 1-[4-(3-Fluoro-4-methoxy-phenylamino)-6-phenyl-pyrimidin-2-yl]-piperidin-4-ol |
| 36. | 1-[2-(3-Chloro-4-hydroxy-phenylamino)-6-phenyl-pyrimidin-4-yl]-piperidin-4-ol |
| 37. | 1-[2-(3-Fluoro-4-methoxy-phenylamino)-6-phenyl-pyrimidin-4-yl]-piperidin-4-ol |
| 38. | (3-Chloro-4-methoxy-phenyl)-(4-morpholin-4-yl-6-phenyl-pyrimidin-2-yl)-amine |
| 39. | Benzo[1,3]dioxol-5-yl-(4-morpholin-4-yl-6-phenyl-pyrimidin-2-yl)-amine |
| 40. | (3-Fluoro-4-methoxy-phenyl)-(4-morpholin-4-yl-6-phenyl-pyrimidin-2-yl)-amine |
| 41. | $N^2$-(3-Chloro-4-methoxy-phenyl)-$N^4$-isopropyl-6-phenyl-pyrimidine-2,4-diamine |
| 42. | 4,6-Bis-(4-fluoro-phenyl)-pyrimidin-2-ylamine |
| 43. | 5-[2-Amino-6-(4-tert-butylsulfanylphenyl)-pyrimidin-4-ylamino]-1-methyl-3-propyl-1H-pyrazole-4-carboxylic acid amide |
| 44. | [4-(3-Chloro-4-methoxy-phenylamino)-6-phenyl-pyrimidin-2-ylamino]-acetic acid ethyl ester |
| 45. | $N^2,N^4$-Bis-(3-chloro-4-methoxy-phenyl)-6-phenyl-pyrimidine-2,4-diamine |
| 46. | 4-Phenyl-6-phenylethynyl-pyrimidin-2-ylamine |
| 47. | [4-(3-Chloro-4-methoxy-phenylamino)-6-phenyl-pyrimidin-2-ylsulfanyl]-acetic acid ethyl ester |
| 48. | 4-(3-Chloro-4-methoxy-phenyl)-6-pyridin-3-yl-pyrimidin-2-ylamine |
| 49. | Succinic acid mono-{1-[2-(3-chloro-4-methoxy-phenylamino)-6-phenyl-pyrimidin-4-yl]-piperidin-4-yl}ester |
| 50. | 1-[6-Phenyl-2-(4-trifluoromethoxy-phenylamino)-pyrimidin-4-yl]-piperidin-4-ol |
| 51. | 4-(2-Benzo[1,3]dioxol-5-yl-6-phenyl-pyrimidin-4-yl)-morpholine |
| 52. | 1-[6-Phenyl-2-(3-trifluoromethyl-phenylamino)-pyrimidin-4-yl]-piperidin-4-ol |
| 53. | 1-[4-Phenyl-6-(3-trifluoromethyl-phenylamino)-pyrimidin-2-yl]-piperidin-4-ol |
| 54. | 1-[4-(4-Chloro-3-trifluoromethyl-phenylamino)-6-phenyl-pyrimidin-2-yl]-piperidin-4-ol |
| 55. | Benzo[1,3]dioxol-5-yl-[4-(4-fluoro-phenyl)-6-morpholin-4-yl-pyrimidin-2-yl]-amine |
| 56. | 1-[4-(Benzo[1,3]dioxol-5-ylamino)-6-phenyl-pyrimidin-2-yl]-piperidin-4-ol |
| 57. | 1-[2-(Benzo[1,3]dioxol-5-ylamino)-6-phenyl-pyrimidin-4-yl]-piperidin-4-ol |
| 58. | [4-(4-Fluoro-phenyl)-6-morpholin-4-yl-pyrimidin-2-yl]-(3-trifluoromethyl-phenyl)-amine |
| 59. | (4-Fluoro-phenyl)-[4-(4-fluoro-phenyl)-6-morpholin-4-yl-pyrimidin-2-yl]-amine |
| 60. | 1-[2-(4-Chloro-3-trifluoromethyl-phenylamino)-6-phenyl-pyrimidin-4-yl]-piperidin-4-ol |
| 61. | 1-(2-Benzo[1,3]dioxol-5-yl-6-phenyl-pyrimidin-4-yl)-piperidin-4-one |
| 62. | 1-[4-Phenyl-6-(4-trifluoromethyl-phenylamino)-pyrimidin-2-yl]-piperidin-4-ol |
| 63. | 1-[6-(3-Chloro-4-methoxy-phenylamino)-2-phenyl-pyrimidin-4-yl]-piperidin-4-ol |
| 64. | Benzo[1,3]dioxol-5-yl-(6-morpholin-4-yl-2-phenyl-pyrimidin-4-yl)-amine |
| 65. | [4-(1,1-Dioxo-1-lambda-6-thiomorpholin-4-yl)-6-phenyl-pyrimidin-2-yl]-(3-fluoro-4-methoxy-phenyl)-amine |
| 66. | Benzo[1,3]dioxol-5-yl-[6-(4-methyl-piperazin-1-yl)-2-phenyl-pyrimidin-4-yl]-amine |
| 67. | 1-[2-(4-Methanesulfonyl-phenylamino)-6-phenyl-pyrimidin-4-yl]-piperidin-4-ol |
| 68. | 1-(6-Benzo[1,3]dioxol-5-yl-2-phenyl-pyrimidin-4-yl)-piperidin-4-ol |
| 69. | 1-[4-(4-Methanesulfonyl-phenylamino)-6-phenyl-pyrimidin-2-yl]-piperidin-4-ol |
| 70. | (2-Morpholin-4-yl-6-phenyl-pyrimidin-4-yl)-(3-trifluoromethyl-phenyl)-amine |
| 71. | (4-Morpholin-4-yl-6-phenyl-pyrimidin-2-yl)-(3-trifluoromethyl-phenyl)-amine |
| 72. | (6-Phenyl-pyrimidin-4-yl)-(4-trifluoromethoxy-phenyl)-amine |
| 73. | (6-Morpholin-4-yl-2-phenyl-pyrimidin-4-yl)-(4-trifluoromethoxy-phenyl)-amine |
| 74. | (4-Morpholin-4-yl-6-phenyl-pyrimidin-2-yl)-(4-trifluoromethoxy-phenyl)-amine |
| 75. | 1-[6-(3-Methanesulfonyl-phenyl)-2-phenyl-pyrimidin-4-yl]-piperidin-4-ol |

TABLE 4-continued

Compounds of the present invention that have at least the activity of affecting cellular proliferation.

| Entry | Compound name |
|---|---|
| 76. | 1-[2-(3-Methanesulfonyl-phenyl)-6-phenyl-pyrimidin-4-yl]-piperidin-4-ol |
| 77. | Phthalic acid mono-[1-(2,6-diphenyl-pyrimidin-4-yl)-piperidin-4-yl] ester |
| 78. | 1-[2-(4-Fluoro-phenyl)-6-phenyl-pyrimidin-4-yl]-piperidin-4-ol |
| 79. | 1-[6-Phenyl-2-(4-trifluoromethoxy-phenyl)-pyrimidin-4-yl]-piperidin-4-ol |
| 80. | 4-(4-Methyl-piperazin-1-yl)-2,6-diphenyl-pyrimidine |
| 81. | 4-(4-Fluoro-phenyl)-6-(4-methyl-piperazin-1-yl)-2-phenyl-pyrimidine |
| 82. | N-{4-[4-(4-Hydroxy-piperidin-1-yl)-6-phenyl-pyrimidin-2-ylamino]-phenyl}-methanesulfonamide |
| 83. | (2-Phenyl-6-piperazin-1-yl-pyrimidin-4-yl)-(4-trifluoromethoxy-phenyl)-amine |
| 84. | (3-Chloro-4-methoxy-phenyl)-[4-(4-methyl-piperazin-1-yl)-6-phenyl-pyrimidin-2-yl]-amine |
| 85. | 1-[4-Phenyl-6-(4-trifluoromethoxy-phenylamino)-pyrimidin-2-yl]-piperidin-4-ol |
| 86. | (3-Chloro-4-methoxy-phenyl)-(4-phenyl-6-piperazin-1-yl-pyrimidin-2-yl)-amine |
| 87. | (3-Chloro-4-methoxy-phenyl)-[4-(4-ethyl-piperazin-1-yl)-6-phenyl-pyrimidin-2-yl]-amine |
| 88. | N-[4-(4-Morpholin-4-yl-6-phenyl-pyrimidin-2-ylamino)-phenyl]-methanesulfonamide. hydrochloride |
| 89. | 1-[6-(4-Methanesulfonyl-phenylamino)-2-phenyl-pyrimidin-4-yl]-piperidin-4-ol |
| 90. | 4-[4-(4-Fluoro-phenyl)-6-(4-hydroxy-piperidin-1-yl)-pyrimidin-2-ylamino]-N,N-dimethyl-benzenesulfonamide |
| 91. | 4-[4-(4-Fluoro-phenyl)-6-(4-hydroxy-piperidin-1-yl)-pyrimidin-2-ylamino]-benzenesulfonamide |
| 92. | 4-[4-(4-Hydroxy-piperidin-1-yl)-6-phenyl-pyrimidin-2-ylamino]-N,N-dimethyl-benzenesulfonamide |
| 93. | 4-[4-(4-Hydroxy-piperidin-1-yl)-6-phenyl-pyrimidin-2-ylamino]-benzenesulfonamide |
| 94. | 4-[4-(4-Hydroxy-piperidin-1-yl)-6-phenyl-pyrimidin-2-ylamino]-N-methyl-benzenesulfonamide |
| 95. | 4-[4-(4-Fluoro-phenyl)-6-(4-hydroxy-piperidin-1-yl)-pyrimidin-2-ylamino]-N-methyl-benzenesulfonamide |
| 96. | (2,6-Diphenyl-pyrimidin-4-yl)-(4-trifluoromethoxy-phenyl)-amine |
| 97. | 4-(4-Ethyl-piperazin-1-yl)-2,6-diphenyl-pyrimidine |
| 98. | 4-(2,6-Diphenyl-pyrimidin-4-yl)-morpholine |
| 99. | (4-Methanesulfonyl-phenyl)-(6-morpholin-4-yl-2-phenyl-pyrimidin-4-yl)-amine |
| 100. | 4-[4-(4-Hydroxy-piperidin-1-yl)-6-phenyl-pyrimidin-2-ylamino]-benzamide |
| 101. | 4-[4-(4-Hydroxy-piperidin-1-yl)-6-phenyl-pyrimidin-2-ylamino]-N-methyl-benzamide |
| 102. | 4-(4-Methyl-piperazin-1-yl)-2,6-diphenyl-pyrimidine |
| 103. | [4,6-Bis-(4-fluoro-phenyl)-pyrimidin-2-yl]-(4-trifluoromethoxy-phenyl)-amine |
| 104. | (2,6-Diphenyl-pyrimidin-4-yl)-(4-methanesulfonyl-phenyl)-amine |
| 105. | [4-(3-Methanesulfonyl-phenyl)-6-morpholin-4-yl-pyrimidin-2-yl]-(4-trifluoromethoxy-phenyl)-amine |
| 106. | 4-(2,6-Diphenyl-pyrimidin-4-ylamino)-N-methyl-benzenesulfonamide |
| 107. | N-Methyl-4-(4-morpholin-4-yl-6-phenyl-pyrimidin-2-ylamino)-benzenesulfonamide |
| 108. | 1-{4-[4-(4-Hydroxy-piperidin-1-yl)-6-phenyl-pyrimidin-2-ylamino]-phenyl}-ethanone. hydro chloride |
| 109. | 3-[4-(4-Hydroxy-piperidin-1-yl)-6-phenyl-pyrimidin-2-ylamino]-benzamide |
| 110. | 1-{3-[4-(4-Hydroxy-piperidin-1-yl)-6-phenyl-pyrimidin-2-ylamino]-phenyl}-ethanone |
| 111. | 3-[4-(4-Hydroxy-piperidin-1-yl)-6-phenyl-pyrimidin-2-ylamino]-N-methyl-benzamide |
| 112. | N-Methyl-3-(4-morpholin-4-yl-6-phenyl-pyrimidin-2-ylamino)-benzamide |
| 113. | 1-[4-(4-Morpholin-4-yl-6-phenyl-pyrimidin-2-ylamino)-phenyl]-ethanone |
| 114. | 3-(4-Morpholin-4-yl-6-phenyl-pyrimidin-2-ylamino)-benzamide |
| 115. | 1-[3-(4-Morpholin-4-yl-6-phenyl-pyrimidin-2-ylamino)-phenyl]-ethanone |
| 116. | 3-[4-(4-Hydroxy-piperidin-1-yl)-6-phenyl-pyrimidin-2-ylamino]-benzenesulfonamide |
| 117. | 3-(4-Morpholin-4-yl-6-phenyl-pyrimidin-2-ylamino)-benzene sulfonamide |
| 118. | [2-(4-Fluoro-phenyl)-6-morpholin-4-yl-pyrimidin-4-yl]-(4-trifluoromethoxy-phenyl)-amine |
| 119. | 1-{3-[2-Morpholin-4-yl-6-(4-trifluoromethoxy-phenylamino)-pyrimidin-4-yl]-phenyl}-ethanone |

TABLE 4-continued

Compounds of the present invention that have at least the activity of affecting cellular proliferation.

| Entry | Compound name |
|---|---|
| 120. | 1-{4-[4-(4-Fluoro-phenyl)-6-morpholin-4-yl-pyrimidin-2-ylamino]-phenyl}-ethanone |
| 121. | 1-{4-[4-(4-Fluoro-phenyl)-6-(4-hydroxy-piperidin-1-yl)-pyrimidin-2-ylamino]-phenyl}-ethanone |

Methods for identifying the activity and screening for one or more of these compounds or molecules that induce synthesis of proteoglycans such as HSPG are taught in U.S. patent application Ser. No. 10/091,357, which is incorporated herein in its entirety. Assays of effects of compounds in vivo are also taught in the incorporated references and are known to those skilled in the art. In general, methods comprise the addition of such compounds to assays and measurement of HSPG synthesis including, but not limited to, the production of syndecans, glypicans and perlecans, for example, syndecans 1, 2 and 4; and glypican-1. Other assays that can be used to determine the activity of the compounds of the present invention include other methods for measuring the induction of perlecan synthesis. For example, in one assay, perlecan is induced in cells by certain inducers, and the response is measured. Compounds of the present invention are then added to a replicate assay and the effect on perlecan induction is determined. Using such methods, compounds are determined that can either inhibit perlecan, elevate induction of perlecan, or that have no effect at all. Those compounds that are effective as therapeutic agents can then be used in animals, humans or patients with cellular proliferation disease aspects, such as vascular-associated diseases or SMC (smooth muscle cell) proliferation pathologies.

Another assay for determining compounds having SMC effects comprises adding a composition suspected of effecting SMC proliferation to smooth muscle cells in growth medium or serum-free medium. The change in cell proliferation can be measured by methods known to those skilled in the art, such as incorporation of labeled nucleotides into dividing cells' DNA, and compared to the proliferation of cells which are not treated with the compound. Other measurements include directly determining levels of HSPG synthesis by measuring the amount or change in amount of HSPG such as with ELISA for HSPGs, and compared to the amount of HSPG synthesis in untreated cells. Other indirect or direct measurements are contemplated by the present invention and are known to those skilled in the art. For example, such methods include, but are not limited to, measurement of RNA levels, RT-PCR, Northern blotting, Western blotting promoter-based assays to identify compounds that affect one or more proteoglycans and assays for proteoglycan biological activity shown by recombinant proteins, partially purified proteins, or lysates from cells expressing proteoglycans in the presence or absence of compounds of interest.

An assay for identifying and determining an activity of one or more of the compounds of the present invention comprises identifying compounds that interact with the promoter regions of a gene, or interact and affect proteins that interact with the promoter region, and are important in the transcriptional regulation of the protein's expression. For example, if perlecan were the protein, in general, the method comprises a vector comprising regulatory sequences of the perlecan gene and an indicator region controlled by the regulatory sequences, such as an enzyme, in a promoter-reporter construct. The protein product of the indicator region is referred to herein as a reporter enzyme or reporter protein. The regulatory region of the sequence of perlecan comprises a range of nucleotides from approximately −4000 to +2000 wherein the transcription initiation site is +1, more preferably, from −2500 to +1200, most preferably, from −1500 to +800 relative to the transcription initiation site.

Cells are transfected with a vector comprising the promoter-reporter construct and then treated with one or more compositions comprising at least one compound of the present invention. For example, the transfected cells are treated with a composition comprising a compound suspected of affecting the transcription of perlecan and the level of activity of the perlecan regulatory sequences are compared to the level of activity in cells that were not treated with the compound. The levels of activity of the perlecan regulatory sequences are determined by measuring the amount of the reporter protein or determining the activity of the reporter enzyme controlled by the regulatory sequences. An increase in the amount of the reporter protein or the reporter enzyme activity shows a stimulatory effect on perlecan, by positively effecting the promoter, whereas a decrease in the amount or the reporter protein or the reporter enzyme activity shows a negative effect on the promoter and thus, on perlecan.

Additionally, the present invention comprises methods and compositions that can be used with gene therapy methods and composition, such as those gene therapy methods comprising administering compositions comprising nucleic acids that affect the synthesis or expression of HSPGs, particularly perlecan. Such methods and compositions are taught in U.S. patent application Ser. No. 10/091,357, incorporated herein by reference.

The present invention comprises methods and compositions for mediating proteoglycan synthesis, expression and for the maintenance of SMC in a quiescent state. Methods and compositions of the present invention comprise treatment and prevention of vascular diseases and pathologies related to cellular proliferation, such as SMC proliferation. Such methods and compositions comprise methods for inhibition of SMC growth and proliferation, and for induction of quiescence in smooth muscle cells. Aspects of the present invention comprise methods and compositions for inducing proteoglycan synthesis, particularly HSPG synthesis and expression including, but not limited to, the induction of HSPGs such as syndecans, glypicans, and perlecans, and preferably perlecan synthesis and gene expression. Perlecan is a major extracellular HSPG in the blood vessel matrix. It interacts with extracellular matrix proteins, growth factors, and receptors. Perlecan is also present in basement membranes other than blood vessels and in other extracellular matrix structures.

The activities of the compounds included in the present invention affect cells or tissues to increase the synthesis of proteoglycans by those cells or tissues or may act directly upon one or more proteoglycans to modulate the biological activity or to increase the biological stability of the proteoglycan itself, for example, of the protein perlecan. Activities also included herein are ones that increase the biosynthesis of one or more proteoglycans by increasing the transcription of the poteoglycan gene, increasing the biological stability, of the proteoglycan mRNA or increasing the translation of proteoglycan mRNA into protein. Further activites include activities of compounds that can block or decrease the effects of agents or proteins that inhibit the activity of proteoglycans.

The present invention comprises methods and compositions for the treatment and prevention of smooth muscle cell proliferation, including vascular occlusive pathologies. Such methods comprise administration of compositions comprising compounds capable of inhibiting SMC proliferation, such as compositions comprising compounds disclosed herein that inhibit SMC proliferation. Administration of such compounds that are effective in inhibiting SMC proliferation are administered to humans and animals suspected of having or who have, for example, vasculopathy or who have undergone angioplasty or other procedures damaging to the endothelium. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities, including, but not limited to, changes in exercise or diet.

Glycosidase Modulation Activity

The present invention also comprises methods and compositions comprising compounds described herein that have an activity associated with modulation of glycosidase enzymes and thus, affecting the substrates for such enzymes. Glycosidase enzymes and their activity with their substrates, such as proteoglycans or glycated proteins, are aspects of a variety of diseases such as vascular conditions, including those conditions discussed supra, proteoglycan-associated diseases, supra, associated diseases with vascular components, including but not limited to, kidney disease, ischemic heart disease, cardiovascular disease, generalized vascular disease, proliferative retinopathy, macroangeopathy, inflammatory diseases and metastatic diseases such as cancer, cellular proliferative conditions, and solid and blood borne tumors or other oncological conditions. Compounds described herein that have an activity that affects the concentrations of substrates of glycosidase enzymes are used in methods of treatment of such vascular, inflammatory, metastatic and systemic diseases.

TABLE 5

Compounds having at least the activity of modulating glycosidase enzyme activity.

Entry Compound name

1. $N^4$-(3-Chloro-4-methoxy-phenyl)-6-phenyl-pyrimidine-2,4-diamine
2. $N^4$-(3-Chloro-4-methoxy-phenyl)-6-(4-methoxy-phenyl)-pyrimidine-2,4-diamine
3. $N^4$-(3-Fluoro-4-methoxy-phenyl)-6-(4-methoxy-phenyl)-pyrimidine-2,4-diamine
4. $N^4$-(3-Chloro-4-methoxy-phenyl)-6-(4-methanesulfonyl-phenyl)-pyrimidine-2,4-diamine
5. 4-[2-Amino-6-(4-methoxy-phenyl)-pyrimidin-4-ylamino]-2-chloro-phenol TABLE 5-continued Compounds having at least the activity of modulating glycosidase enzyme activity.

Entry Compound name 6. (3-Chloro-4-methoxy-phenyl)-(2-ethylsulfanyl-6-phenyl-pyrimidin-4-yl)-amine
7. $N^4$-Benzyl-N2-(3-chloro-4-methoxy-phenyl)-6-phenyl-pyrimidine-2,4-diamine
8. 1-[2-(3-Chloro-4-methoxy-phenylamino)-6-cycloheptylamino-pyrimidin-4-yl]-piperidin-4-ol
9. 1-[2-(3-Chloro-4-methoxy-phenylamino)-6-phenyl-pyrimidin-4-yl]-piperidin-4-ol
10. 1-[4-Phenyl-6-(4-trifluoromethoxy-phenylamino)-pyrimidin-2-yl]-piperidin-4-ol
11. (3-Chloro-4-methoxy-phenyl)-[4-(4-ethyl-piperazin-1-yl)-6-phenyl-pyrimidin-2-yl]-amine
12. 4-[4-(4-Hydroxy-piperidin-1-yl)-6-phenyl-pyrimidin-2-ylamino]-N-methyl-benzenesulfonamide Compounds or compositions comprising such compounds that are effective in modulating glycosidase enzyme activity are useful in treating and/or preventing cancer including, but not limited to, malignant and non-malignant cell growth, and the like. In another aspect of the present invention, the compounds disclosed herein are useful in modulating heparanase activity or the activity of other glycosidases as a means for treating and preventing autoimmune diseases.

Thus, the inhibition of heparanase or the activity of other glycosidases using the compounds of the present invention finds utitlity in treating arthritis and other autoimmune diseases. More specifically, the compounds of the present invention are useful in the treatment or prophylaxis of at least one autoimmune-related disease in a cell, tissue, organ, animal, or patient including, but not limited to, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, autoimmune hemolytic anemia, autoimmune hepatitis, idiopathic pulmonary fibrosis, scleroderma, diabetes mellitus, chronic active hepatitis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, Hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, ankylosing spondylitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia-fibromyositis, Graves' disease, Guillain-Barré, Hashimoto's thyroiditis, idiopathic thrombocytopenia purpura (ITP), IgA nephropathy, insulin dependent diabetes, juvenile arthritis, lichen planus, ménière's disease, multiple sclerosis, pemphigus vulgaris, polyarteritis nodosa, Cogan's syndrome, polychondritis, polyglandular syndromes, polymyalgia rheumatica, polymyositis and dermatomyositis, primary agammaglobulinemia, Raynaud's phenomenon, Reiter's syndrome, rheumatic fever, Sjögren's syndrome, stiffman syndrome, Takayasu arteritis, temporal arteritis/giant cell arteritis, Wegener's granulomatosis; okt3 therapy, anti-cd3 therapy, cytokine therapy, chemotherapy, radiation therapy (e.g., including but not limited toasthenia, anemia, cachexia, and the like), chronic salicylate intoxication, and the like.

Compounds having heparanase activity inhibition, that are effective for example, in treatment of cancer and autoimmune disease, can be determined using assays such as those disclosed in U.S. patent application Ser. No. 09/952,648, which is incorporated herein in its entirety. Such assays, which are used for measurement of cellular and enzymatic activities, both qualitatively and quantitatively, and in methods for diagnosing metastases, metastatic potential and inflammatory states, are performed with and without the addition of at least one of the compounds of the present invention to determine the activity of the compound. Existing heparanase assays are taught in Goshen et al., 2 MOL. HUM. REPROD. 679-84 (1996); Nakajima et al., 31 CANCER LETT. 277-83 (1986); and Vlodasky et al., 12 INVASION METASTASIS 112-27 (1992); Freeman and Parish, 325 BIOCHEM. J. 229-37 (1997); Kahn and Newman, 196 ANAL. BIOCHEM. 373-76 (1991). Solid-phase heparanase assays have also been developed where chemically and biosynthetically radiolabeled heparin and HS chains were attached to a solid support, with release of radiolabel from the solid support being a measure of enzyme activity. Assays using such procedures are taught in U.S. Pat. No. 4,859,581, which is entirely expressly herein incorporated by reference.

The present invention comprises methods and compositions for the treatment and prevention of diseases or conditions that present or result from glycosidase activity. Such methods comprise administration of compositions comprising compounds capable of modulating heparanase activity, such as compositions comprising compounds disclosed herein that inhibit heparanase activity. Administration of such compounds that are effective in modulating heparanase activity are administered to humans and animals suspected of having or who have, for example, inflammatory conditions, autoimmune disease, or diabetic vasculopathy. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents, or in methods comprising steps such as altered patient activities.

Inflammation Modulation

One aspect of the present invention comprises methods and compositions comprising compounds of the present invention for the treatment and prevention of conditions or diseases that have as an aspect of the disease or condition, inflammation. An aspect of the present invention is directed to methods and compositions comprising compounds that are effective in inhibiting inflammation, particularly inflammation associated with the accumulation or presence of glycated proteins or AGE. The activity of modulating inflammation includes, but is not limited to, inhibiting inflammation and/or its associated cell activation by glycated proteins or AGE, blocking the glycation of proteins, blocking AGE interactions with receptors, blocking AGE-induced signaling or signaling-associated inflammatory responses, cytokine induction, synthesis, or release, AGE formation, or AGE cross-linking.

The present invention also provides compositions for and methods of treatment of biological conditions including, but not limited to, vascular complications of type I and type II diabetes and atherosclerosis. Other inflammatory related diseases include, but are not limited to, rheumatoid arthritis, osteoarthritis, intraoccular inflammation, psoriasis, and asthma.

The compounds of the present invention have utility in inhibiting inflammation and/or its associated cell activation by glycated proteins or AGE. Pharmacological inhibition of AGE-induced cell activation provides the basis for therapeutic intervention in many diseases, notably in diabetic complications and Alzheimer's disease. Therapeutic approaches for inhibition of AGE-induced inflammation include, but are not limited to, blocking the glycation of proteins, blocking AGE interactions with receptors, and blocking AGE-induced signaling or signaling-associated inflammatory responses.

Compounds of the present invention that have at least the activity of modulating inflammation activity are shown in Table 6. The compounds shown in this Table have the activity of modulating inflammation activity as measured by the assays taught herein.

TABLE 6

Compounds of the present invention that have at least the activity of modulating inflammation activity.

Entry  Compound name

1. $N^4$-(3-Chloro-4-methoxy-phenyl)-6-phenyl-pyrimidine-2,4-diamine
2. $N^4$-(3-Chloro-4-methoxy-phenyl)-6-phenyl-pyrimidine-2,4-diamine.hydrochloride
3. $N^4$-(3-Chloro-4-methoxy-phenyl)-6-(4-methoxy-phenyl)-pyrimidine-2,4-diamine
4. $N^4$-(3-Chloro-4-methoxy-phenyl)-6-phenyl-pyrimidine-2,4-diamine
5. $N^4$-(3-Chloro-4-methoxy-phenyl)-6-(4-methylsulfanyl-phenyl)-pyrimidine-2,4-diamine
6. $N^4$-(3-Fluoro-4-methoxy-phenyl)-6-(4-methoxy-phenyl)-pyrimidine-2,4-diamine
7. $N^4$-(3-Chloro-4-methoxy-phenyl)-6-(4-methanesulfonyl-phenyl)-pyrimidine-2,4-diamine
8. 4-[2-Amino-6-(4-methoxy-phenyl)-pyrimidin-4-ylamino]-2-chloro-phenol
9. N-[4-(3-Chloro-4-methoxy-phenylamino)-6-(4-methoxy-phenyl)-pyrimidin-2-yl]-acetamide
10. (3-Chloro-4-methoxy-phenyl)-(2-ethylsulfanyl-6-phenyl-pyrimidin-4-yl)-amine
11. $N^4$-Benzyl-N2-(3-chloro-4-methoxy-phenyl)-6-phenyl-pyrimidine-2,4-diamine
12. 4-(2-Amino-6-phenyl-pyrimidin-4-ylamino)-2-chloro-phenol
13. (3-Chloro-4-methoxy-phenyl)-[4-ethoxy-6-(4-methoxy-phenyl)-pyrimidin-2-yl]-amine
14. N-[4-(3-Chloro-4-methoxy-phenylamino)-6-(4-ethoxy-phenyl)-pyrimidin-2-yl]-acetamide
15. (3-Chloro-4-methoxy-phenyl)-[4-isopropoxy-6-(4-methoxy-phenyl)-pyrimidin-2-yl]-amine
16. (3-Chloro-4-methoxy-phenyl)-[4-(4-methoxy-phenyl)-6-(4-methyl-benzyloxy)-pyrimidin-2-yl]-amine
17. [2-(3-Chloro-4-methoxy-phenylamino)-6-(4-methoxy-phenyl)-pyrimidin-4-yloxy]-acetic acid ethyl ester
18. [2-(3-Chloro-4-methoxy-phenylamino)-6-(4-methoxy-phenyl)-pyrimidin-4-yloxy]-acetic acid
19. N-[4-(3-Chloro-4-methoxy-phenylamino)-6-phenyl-pyrimidin-2-yl]-2,2,2-trifluoro-acetamide
20. 4-(4-Fluoro-phenylsulfanyl)-6-phenyl-pyrimidin-2-ylamine
21. 6-Chloro-N2-(3-chloro-4-methoxy-phenyl)-N4-cycloheptyl-pyrimidine-2,4-diamine
22. 2-(3-Chloro-4-methoxy-phenylamino)-6-phenyl-pyrimidin-4-ol
23. 2-(2-Amino-6-phenyl-pyrimidin-4-ylamino)-benzoic acid ethyl ester
24. 1-[2-(3-Chloro-4-methoxy-phenylamino)-6-ycloheptylamino-pyrimidin-4-yl]-piperidin-4-ol
25. 1-[4-(Methyl-phenyl-amino)-6-phenyl-pyrimidin-2-yl]-piperidin-4-ol
26. 1-[4-(3-Chloro-4-methoxy-phenylamino)-6-phenyl-pyrimidin-2-yl]-piperidin-4-ol
27. 1-[2-(3-Chloro-4-methoxy-phenylamino)-6-phenyl-pyrimidin-4-yl]-piperidin-4-ol
28. $N^4$-(4-Chloro-3-methoxy-phenyl)-6-phenyl-pyrimidine-2,4-diamine
29. 1-[4-(3-Fluoro-4-methoxy-phenylamino)-6-phenyl-pyrimidin-2-yl]-piperidin-4-ol
30. 1-[2-(3-Chloro-4-hydroxy-phenylamino)-6-phenyl-pyrimidin-4-yl]-piperidin-4-ol
31. 1-[2-(3-Fluoro-4-methoxy-phenylamino)-6-phenyl-pyrimidin-4-yl]-piperidin-4-ol
32. (3-Chloro-4-methoxy-phenyl)-(4-morpholin-4-yl-6-phenyl-pyrimidin-2-yl)-amine
33. 1-(2,6-Diphenyl-pyrimidin-4-yl)-piperidin-4-ol
34. Benzo[1,3]dioxol-5-yl-(4-morpholin-4-yl-6-phenyl-pyrimidin-2-yl)-amine
35. (3-Fluoro-4-methoxy-phenyl)-(4-morpholin-4-yl-6-phenyl-pyrimidin-2-yl)-amine
36. 4,6-Bis-(4-fluoro-phenyl)-pyrimidin-2-ylamine
37. 5-[2-Amino-6-(4-tert-butylsulfanylphenyl)-pyrimidin-4-ylamino]-1-methyl-3-propyl-1H-pyrazole-4-carboxylic acid amide
38. [4-(3-Chloro-4-methoxy-phenylamino)-6-phenyl-pyrimidin-2-ylamino]-aceticacid ethyl ester
39. $N^2,N^4$-Bis-(3-chloro-4-methoxy-phenyl)-6-phenyl-pyrimidine-2,4-diamine
40. 4-Phenyl-6-phenylethynyl-pyrimidin-2-ylamine
41. [4-(3-Chloro-4-methoxy-phenylamino)-6-phenyl-pyrimidin-2-ylsulfanyl]-acetic acid ethyl ester
42. 4-(3-Chloro-4-methoxy-phenyl)-6-pyridin-3-yl-pyrimidin-2-ylamine
43. Succinic acid mono-{1-[2-(3-chloro-4-methoxy-phenylamino)-6-phenyl-pyrimidin-4-yl]-piperidin-4-yl}ester
44. 1-[6-Phenyl-2-(4-trifluoromethoxy-phenylamino)-pyrimidin-4-yl]-piperidin-4-ol
45. 4-(6-Phenyl-2-pyrrol-1-yl-pyrimidin-4-ylamino)-cyclohexanol TABLE 6-continued Compounds of the present invention that have at least the activity of modulating inflammation activity.

| Entry | Compound name |
|---|---|
| 46. | 1-[6-Phenyl-2-(3-trifluoromethyl-phenylamino)-pyrimidin-4-yl]-piperidin-4-ol |
| 47. | 1-[4-Phenyl-6-(3-trifluoromethyl-phenylamino)-pyrimidin-2-yl]-piperidin-4-ol |
| 48. | 1-[4-(4-Chloro-3-trifluoromethyl-phenylamino)-6-phenyl-pyrimidin-2-yl]-piperidin-4-ol |
| 49. | 1-[4-(Benzo[1,3]dioxol-5-ylamino)-6-phenyl-pyrimidin-2-yl]-piperidin-4-ol |
| 50. | 1-[2-(Benzo[1,3]dioxol-5-ylamino)-6-phenyl-pyrimidin-4-yl]-piperidin-4-ol |
| 51. | [4-(4-Fluoro-phenyl)-6-morpholin-4-yl-pyrimidin-2-yl]-(3-trifluoromethyl-phenyl)-amine |
| 52. | 1-[2-(4-Chloro-3-trifluoromethyl-phenylamino)-6-phenyl-pyrimidin-4-yl]-piperidin-4-ol |
| 53. | 1-[4-Phenyl-6-(4-trifluoromethyl-phenylamino)-pyrimidin-2-yl]-piperidin-4-ol |
| 54. | 1-[6-(3-Chloro-4-methoxy-phenylamino)-2-phenyl-pyrimidin-4-yl]-piperidin-4-ol |
| 55. | Benzo[1,3]dioxol-5-yl-(6-morpholin-4-yl-2-phenyl-pyrimidin-4-yl)-amine |
| 56. | Benzo[1,3]dioxol-5-yl-[6-(4-methyl-piperazin-1-yl)-2-phenyl-pyrimidin-4-yl]-amine |
| 57. | 1-(6-Benzo[1,3]dioxol-5-yl-2-phenyl-pyrimidin-4-yl)-piperidin-4-ol |
| 58. | (2-Morpholin-4-yl-6-phenyl-pyrimidin-4-yl)-(3-trifluoromethyl-phenyl)-amine |
| 59. | (4-Morpholin-4-yl-6-phenyl-pyrimidin-2-yl)-(3-trifluoromethyl-phenyl)-amine |
| 60. | (6-Phenyl-pyrimidin-4-yl)-(4-trifluoromethoxy-phenyl)-amine |
| 61. | (6-Morpholin-4-yl-2-phenyl-pyrimidin-4-yl)-(4-trifluoromethoxy-phenyl)-amine |
| 62. | (4-Morpholin-4-yl-6-phenyl-pyrimidin-2-yl)-(4-trifluoromethoxy-phenyl)-amine |
| 63. | 1-[6-(3-Methanesulfonyl-phenyl)-2-phenyl-pyrimidin-4-yl]-piperidin-4-ol |
| 64. | Phthalic acid mono-[1-(2,6-diphenyl-pyrimidin-4-yl)-piperidin-4-yl] ester |
| 65. | 1-[2-(4-Fluoro-phenyl)-6-phenyl-pyrimidin-4-yl]-piperidin-4-ol |
| 66. | 1-[6-Phenyl-2-(4-trifluoromethoxy-phenyl)-pyrimidin-4-yl]-piperidin-4-ol |
| 67. | 4-(4-Methyl-piperazin-1-yl)-2,6-diphenyl-pyrimidine |
| 68. | 4-(4-Fluoro-phenyl)-6-(4-methyl-piperazin-1-yl)-2-phenyl-pyrimidine |
| 69. | N-{4-[4-(4-Hydroxy-piperidin-1-yl)-6-phenyl-pyrimidin-2-ylamino]-phenyl}-methanesulfonamide |
| 70. | (2-Phenyl-6-piperazin-1-yl-pyrimidin-4-yl)-(4-trifluoromethoxy-phenyl)-amine |
| 71. | (3-Chloro-4-methoxy-phenyl)-[4-(4-methyl-piperazin-1-yl)-6-phenyl-pyrimidin-2-yl]-amine |
| 72. | 1-[4-Phenyl-6-(4-trifluoromethoxy-phenylamino)-pyrimidin-2-yl]-piperidin-4-ol |
| 73. | (3-Chloro-4-methoxy-phenyl)-[4-(4-ethyl-piperazin-1-yl)-6-phenyl-pyrimidin-2-yl]-amine |
| 74. | N-[4-(4-Morpholin-4-yl-6-phenyl-pyrimidin-2-ylamino)-phenyl]-methanesulfonamide |
| 75. | 1-[6-(4-Methanesulfonyl-phenylamino)-2-phenyl-pyrimidin-4-yl]-piperidin-4-ol |
| 76. | 4-[4-(4-Fluoro-phenyl)-6-(4-hydroxy-piperidin-1-yl)-pyrimidin-2-ylamino]-N,N-dimethyl-benzenesulfonamide |
| 77. | 4-[4-(4-Fluoro-phenyl)-6-(4-hydroxy-piperidin-1-yl)-pyrimidin-2-ylamino]-benzenesulfonamide |
| 78. | 4-[4-(4-Hydroxy-piperidin-1-yl)-6-phenyl-pyrimidin-2-ylamino]-N,N-dimethyl-benzenesulfonamide |
| 79. | 4-[4-(4-Hydroxy-piperidin-1-yl)-6-phenyl-pyrimidin-2-ylamino]-benzenesulfonamide |
| 80. | 4-[4-(4-Hydroxy-piperidin-1-yl)-6-phenyl-pyrimidin-2-ylamino]-N-methyl-benzenesulfonamide |
| 81. | 4-[4-(4-Fluoro-phenyl)-6-(4-hydroxy-piperidin-1-yl)-pyrimidin-2-ylamino]-N-methyl-benzenesulfonamide |
| 82. | (2,6-Diphenyl-pyrimidin-4-yl)-(4-trifluoromethoxy-phenyl)-amine |
| 83. | 4-(4-Ethyl-piperazin-1-yl)-2,6-diphenyl-pyrimidine |
| 84. | (4-Methanesulfonyl-phenyl)-(6-morpholin-4-yl-2-phenyl-pyrimidin-4-yl)-amine |
| 85. | 4-[4-(4-Hydroxy-piperidin-1-yl)-6-phenyl-pyrimidin-2-ylamino]-benzamide |
| 86. | [4,6-Bis-(4-fluoro-phenyl)-pyrimidin-2-yl]-(4-trifluoromethoxy-phenyl)-amine |
| 87. | (2,6-Diphenyl-pyrimidin-4-yl)-(4-methanesulfonyl-phenyl)-amine |
| 88. | [4-(3-Methanesulfonyl-phenyl)-6-morpholin-4-yl-pyrimidin-2-yl]-(4-trifluoromethoxy-phenyl)-amine |
| 89. | 4-(2,6-Diphenyl-pyrimidin-4-ylamino)-N-methyl-benzenesulfonamide |

TABLE 6-continued

Compounds of the present invention that have at least the activity of modulating inflammation activity.

Entry  Compound name

90. N-Methyl-4-(4-morpholin-4-yl-6-phenyl-pyrimidin-2-ylamino)-benzenesulfonamide
91. N-Methyl-4-(4-morpholin-4-yl-6-phenyl-pyrimidin-2-ylamino)-benzamide
92. (4-Methanesulfonyl-phenyl)-[2-phenyl-6-(4-trifluoromethoxy-phenyl)-pyrimidin-4-yl]-amine
93. 1-{4-[4-(4-Hydroxy-piperidin-1-yl)-6-phenyl-pyrimidin-2-ylamino]-phenyl}-ethanone.hydro chloride
94. 3-[4-(4-Hydroxy-piperidin-1-yl)-6-phenyl-pyrimidin-2-ylamino]-benzamide
95. 1-{3-[4-(4-Hydroxy-piperidin-1-yl)-6-phenyl-pyrimidin-2-ylamino]-phenyl}-ethanone
96. 1-[4-(4-Morpholin-4-yl-6-phenyl-pyrimidin-2-ylamino)-phenyl]-ethanone
97. 3-(4-Morpholin-4-yl-6-phenyl-pyrimidin-2-ylamino)-benzamide
98. 3-(4-Morpholin-4-yl-6-phenyl-pyrimidin-2-ylamino)-benzenesulfonamide
99. [2-(4-Fluoro-phenyl)-6-morpholin-4-yl-pyrimidin-4-yl]-(4-trifluoromethoxy-phenyl)-amine The inclusion of compounds in the categories of the tables disclosed herein are not to be seen as limiting, in that compounds included in such tables have at least the activity shown for inclusion in the table and may have more or other activities. Nor are the tables to be seen as limiting in that these are the only compounds disclosed herein that have that activity, representative compounds are shown in the tables that have at least that particular activity for inclusion in the table. One or more compounds disclosed herein have at least an activity that has utility in treatment of disease states.

The activity of the compounds of the present invention in inhibiting glycated protein- and AGE-induced inflammation can be determined using the assays described herein and in U.S. patent application Ser. No. 10/026,335, which is incorporated by reference herein in its entirety. Such assays comprise measurement of the specific activity of biological components involved in a known cellular response. The assays provide a measurable response in which the activity of the compounds is determined. One assay comprises measurement of the effects of compounds on an inflammatory response by cells to the presence of a stimulating agent. Yet another assay comprises endothelial cells that are stimulated by the addition of a glycated protein, the stimulating agent. The endothelial cells respond by producing specific cytokines. The amount of cytokines produced are determined by measurement protocols known to those skilled in the art. The compounds of the present invention are then added to the assay and the production of cytokines is measured. From the comparison of the assay without the compound with the assay with the compound, the biological effect of the compound can be determined. The compound may have an inhibitory effect, a stimulatory effect, or no effect at all.

The amount and type of cytokine produced can be determined using immunological methods, such as ELISA assays. The methods of the present invention are not limited by the type of assay used to measure the amount of cytokine produced, and any methods known to those skilled in the art and later developed can be used to measure the amount of cytokines produced in response to the stimulating agent and to the compound having unknown activity.

An aspect of the present invention comprises methods and compositions for the treatment of diseases, preconditions, or pathologies associated with inflammatory cytokines and other inflammation related molecules including, but not limited to IL-6, VCAM-1, or AGE-induced MCP-1 (monocyte chemoattractant protein 1).

Assays for determining the activity of compounds capable of modulating inflammation include those taught in U.S. patent application Ser. Nos. 10/026,335 and 09/969,013, which are both expressly incorporated by reference in their entireties. In general, once the baseline response to the stimulating agent for the production of cytokines by the endothelial cells is established, thus comprising the control levels for the screening assay, the methods comprise addition of compounds of the present invention. The effect of the compound on the baseline response is determined by comparing the amount of cytokine produced in the presence of the stimulating agent and the amount of cytokine produced in the presence of the stimulating agent and the compound of the present invention. In one aspect of the present invention, compounds that have inhibitory effects on the inflammation of the cells in the presence of glycated albumin are then used as therapeutic agents. One or more compounds may be added to the screening assay. Combinations or mixtures of compounds can be added. Different amounts and formulations of the compounds are added to determine the effects on the screening assay. The screening assay may also be used to determine stimulatory compounds or compounds that have no effects in the assay.

The present invention comprises methods and compositions for the treatment and prevention of disease, conditions and pathologies associated with inflammation. Such methods comprise administration of compositions comprising compounds capable of modulating the activity of molecules associated with inflammation such as AGE or cytokines or other cellular factors, including release rates or activity, and include compositions comprising compounds disclosed herein with inflammation modulating activity. Administration of such compounds that are effective in modulating inflammation are administered to humans and animals suspected of having or who have inflammatory diseases, for example, diabetic-induced vasculopathies, autoimmune diseases, renal insufficiency, Alzheimer's syndrome, and inflammation-induced diseases such as atherosclerosis. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities, including, but not limited to, changes in exercise or diet.

Correlation of Physiological Parameters and Assays to Diseases and Conditions

The following Tables 7-10 provide disclosure and references that relate the various physiological parameters and assays disclosed herein to general and specific diseases, disease states, and conditions. Among other things, the references and citations provided in these tables support the specification as fully enabled for treating or modulating all the diseases or conditions encompassed herein, based on the inhibiting activity of the compounds provided in the specification, and the predictive nature of the tests provided of the disclosed uses. In particular, Tables 7-10 provide specific references that link the parameters measured in the key assays disclosed in the application with a specific physiology, pathophysiology, or medical condition.

Table 7 provides scientific references that demonstrate, among other things, the connection between TNF-α and IL-6 in rheumatoid arthritis, vascular inflammation, and atherosclerosis. For example, these references demonstrate the importance of TNF inhibition in preventing rheumatoid arthritis, the therapeutic benefit of IL-6 inhibition in rheumatoid arthritis as well as its importance in preventing rheumatoid arthritis, the role of AGE in different diabetic vascular diseases, and AGE inhibition as a therapeutic strategy for vascular complications.

Further, Table 8 provides scientific references that demonstrate, among other things, the importance of HSPG in the prevention of atherosclerosis and diabetic vascular disease. For example, these references demonstrate that atherosclerotic vessels have reduced HSPG, and that cholesterol deposition is inversely correlated to HSPG content in the vessel.

Table 9 also provides scientific references that demonstrate, among other things, the connection between smooth muscle cell (SMC) proliferation in contributing to restenosis and atherosclerosis. For example, these references demonstrate that: smooth muscle proliferation contributes to unstable angina and restenosis; inhibition of SMC proliferation by LRP is important for atherosclerosis prevention; and the function of the SMC inhibitor, rapamycin, in preventing restenosis and vein graft disease.

Table 10 provides scientific references that demonstrate, among other things, the role of heparanase and TNF-α in promoting tumor angiogenesis and metastasis, as well as the use of inhibitors of heparanase and TNF-α in treating cancer. For example, these references demonstrate the role of heparanase inhibitors in treating tumor angiogenesis and metastasis, the role of TNF-α as a tumor-promoting agent, and the use of TNF-α inhibitors in the treatment of cancer.

The key assays described herein for screening the compounds in the present invention include, but are not limited to: a) the inhibition of smooth muscle cell (SMC) proliferation, that was used to identify, for example, compounds in Table 4; b) the induction of HSPG in smooth muscle cells; c) the induction of heparanase in endothelial cells; d) the inhibition of AGE-induced inflammatory response in endothelial cells as measured by IL-6 or other inflammatory cytokines, that was used to identify, for example, compounds in Table 6; and e) cytotoxicity effects of the disclosed compounds. By using these disclosed assays, the present disclosure is fully enabled for identification of compounds for the treatment of the diseases disclosed generically and specifically.

Accordingly, this evidence along with the references of Tables 7-10 demonstrate that the parameters measured in the key assays above are associated with and predictive of the specific physiology, pathophysiology, or medical conditions disclosed herein. The physiology, pathophysiology, or medical conditions disclosed include generically disclosed conditions and diseases such as, but are not limited to, unwanted cellular proliferation, inflammation mediated diseases, hyperproliferative diseases, and diseases involving a glycosidase. Specifically disclosed diseases include, but are not limited to, restenosis, vascular occlusive diseases, arthritis, cancer, and the like. Therefore, methods of treating diseases, disease states, or conditions disclosed in the specification, or methods of modulating, for example, the production or uptake of a biologically-active chemical, are disclosed in such as way as to allow the skilled artisan to make and use the invention, the tests provided are predictive of the claimed uses, and therefore are fully enabled for all the diseases or conditions encompassed therein.

TABLE 7

The Role of TNF-α, IL-6, and AGE in Rheumatoid Arthritis, Vascular Inflammation, and Atherosclerosis.

| Author | Title of Reference | Reference Citation | Physiological Parameter | Disease | Pages in reference arguing or showing connection | Other comments |
| --- | --- | --- | --- | --- | --- | --- |
| Feldmann M Ref 1 | Discovery of TNF-α as a therapeutic target in rheumatoid arthritis: preclinical and clinical studies | Joint Bone Spine. 2002 Jan; 69(1): 12-8 Review | TNF inhibition | Arthritis | All | Review detailing the importance of TNF-α inhibition in preventing rheumatoid arthritis |
| Choy et al Ref 2 | Therapeutic benefit of blocking interleukin-6 activity with an anti-interleukin-6 receptor monoclonal antibody in rheumatoid arthritis: a randomized, double-blind, placebo-controlled, dose-escalation trial. | Arthritis Rheum. 2002 Dec; 46(12): 3143-50 | IL-6 inhibition | Arthritis | 3144 (abstract), 3146 | Human trial showing the therapeutic benefit of IL-6 inhibition in rheumatoid arthritis |

TABLE 7-continued

The Role of TNF-α, IL-6, and AGE in Rheumatoid Arthritis, Vascular Inflammation, and Atherosclerosis.

| Author | Title of Reference | Reference Citation | Physiological Parameter | Disease | Pages in reference arguing or showing connection | Other comments |
|---|---|---|---|---|---|---|
| Wong et al Ref 3 | The role of the interleukin-6 family of cytokines in inflammatory arthritis and bone turnover | Arthritis Rheum. 2003 May; 48(5): 1177-89. Review | IL-6 inhibition | Arthrits | 1177 para 4 | Review detailing the importance of IL-6 in preventing rheumatoid arthritis |
| Basta et al Ref 4 | Advanced glycation end products and vascular inflammation: implications for accelerated atherosclerosis in diabetes | Cardiovasc Res. 2004 Sep 1; 63(4): 582-92 | AGE-IL6 inhibition | Diabetic vascular diseases | 582, 589 | Highlights the role of AGE in different diabetic vascular diseases and AGE inhibition as a therapeutic strategy for vascular complications |

TABLE 8

The Potential Role of HSPG Induction in the Prevention of Atherosclerosis and Diabetic Vascular Disease.

| Author | Title of Reference | Reference Citation | Physiological Parameter | Disease | Pages in reference arguing or showing connection | Other comments |
|---|---|---|---|---|---|---|
| Engelberg H. Ref 5 | Endogenous heparin activity deficiency: the 'missing link' in atherogenesis? | Atherosclerosis. 2001 Dec; 159(2): 253-60. Review | HSPG induction | Atherosclerosis | All | Review detailing the importance of HSPG in preventing events related to atherosclerosis development |
| Jensen T Ref 6 | Pathogenesis of diabetic vascular disease: evidence for the role of reduced heparan sulfate proteoglycan | Diabetes. 1997 Sep; 46 Suppl 2: S98-100 | HSPG induction | Diabetic vascular disease | All | Review detailing the importance of HSPG in preventing diabetic vascular disease |
| Hollmann J et al, Ref 7 | Relationship of sulfated glycosaminoglycans and cholesterol content in normal and atherosclerotic human aorta | Artherosclerosis. 1989; 9: 154-8 | HSPG | Atherosclerosis | | Data show that atherosclerotic vessels have reduced HSPG and that cholesterol deposition is inversely correlated to HSPG content in the vessel |
| Kruse R et al Ref 8 | Cholesterol-dependent changes of glycosaminoglycan pattern in human aorta | Basic Res Cardiol. 1996 Sep-Oct; 91(5): 344-52 | HSPG | Atherosclerosis | | Data show that atherosclerotic vessels have reduced HSPG and that cholesterol deposition is inversely correlated to HSPG content in the vessel |

TABLE 9

The Role of Smooth Muscle Cell (SMC) Proliferation in Restenosis and Atherosclerosis.

| Author | Title of Reference | Reference Citation | Physiological Parameter | Disease | Pages in reference arguing or showing connection | Other comments |
|---|---|---|---|---|---|---|
| Chen et al Ref 9 | Electron microscopic studies of phenotypic modulation of smooth muscle cells in coronary arteries of patients with unstable angina pectoris and | Circulation. 1997 Mar 4; 95(5): 1169-75 | Smooth muscle cell (SMC) proliferation | Restenosis | 1175 (Conclusion) | Data suggest that smooth muscle proliferation contributes to unstable angina and restenosis |

TABLE 9-continued

The Role of Smooth Muscle Cell (SMC) Proliferation in Restenosis and Atherosclerosis.

| Author | Title of Reference | Reference Citation | Physiological Parameter | Disease | Pages in reference arguing or showing connection | Other comments |
|---|---|---|---|---|---|---|
| Braun-Dullaeus et al Ref 10 | Cell cycle progression: new therapeutic target for vascular proliferative disease | Circulation. 1998 Jul 7; 98(1): 82-9 | Smooth muscle cell (SMC) proliferation | Restenosis | 82 | Review detailing the role of smooth muscle proliferation in restenosis and pharmacological approaches to inhibit cell cycle progression postangioplasty restenosis |
| Boucher et al Ref 11 | LRP: role in vascular wall integrity and protection from atherosclerosis | Science. 2003 Apr 11; 300(5617): 329-32 | Smooth muscle cell (SMC) proliferation | Atherosclerosis | Abstract | Study shows that inhibition of SMC proliferation by LRP (lipoprotein receptor-related protein) is critical for atherosclerosis prevention |
| Marx et al Ref 12 | Bench to bedside: the development of rapamycin and its application to stent restenosis | Circulation. 2001 Aug 21; 104(8): 852-5 | Smooth muscle cell (SMC) proliferation | Restenosis | 852 | Review highlighting the role of smooth muscle cell proliferation in restenosis and the application of smooth muscle cell inhibitor, rapamycin, in preventing restenosis and vein graft disease |

TABLE 10

The Role of Heparanase and TNF-α in Promoting Tumor Angiogenesis and Metastasis and the Use of Heparanase and TNF-α Inhibitors in Treating Cancer.

| Author | Title of Reference | Reference Citation | Physiological Parameter | Disease | Pages in reference arguing or showing connection | Other comments |
|---|---|---|---|---|---|---|
| Vlodavsky I et al Ref 13 | Molecular properties and involvement of heparanase in cancer metastasis and angiogenesis | J Clin Invest. 2001 Aug; 108(3): 341-7. Review | Heparanase inhibition | Cancer | All | Review detailing the role of heparanase in promoting tumor angiogenesis and metastasis |
| Goldshmidt et al Ref 14 | Cell surface expression and secretion of heparanase markedly promote tumor angiogenesis and metastasis | Proc Natl Acad Sci USA. 2002 Jul 23; 99(15): 10031-6 | Heparanase inhibition | Cancer | 10031, 10036 | Study showing that heparanase promotes angiogenesis and tumor metastasis in animal models. |
| Simizu et al Ref 15 | Heparanase as a molecular target of cancer chemotherapy | Cancer Sci. 2004 Jul; 95(7): 553-8 | Heparanase inhibition | Cancer | 553, 557 | Review detailing the role of heparanase inhibitors in tumor angiogenesis and metastasis |
| Szlosarek et al Ref 16 | Tumour necrosis factor α: a potential target for the therapy of solid tumours | The Lancet Oncology 2003 Sept; 4: 565-73 | TNFα inhibition | Cancer | 565 | Review highlighting the role TNFα as a tumor promoting agent and the use of TNF inhibitors in the treatment of cancer |

Compound/Composition-Coated Medical Devices

The compounds of the present invention may be used alone, in various combinations with one another, and/or in combination with other agents along with delivery devices to effectively prevent and treat the diseases described herein, though particular applications are found in vascular disease, and in particular, vascular disease caused by injury and/or by transplantation. Though this example focuses on vascular disease, provision of the compounds of the present invention with medical devices for treatment of the diseases and conditions capable of being treated with the compounds is contemplated by the present invention.

Various medical treatment devices utilized in the treatment of vascular disease may ultimately induce further complications. For example, balloon angioplasty is a procedure utilized to increase blood flow through an artery and is the predominant treatment for coronary vessel stenosis. However, the procedure typically causes a certain degree of damage to the vessel wall, thereby creating new problems or exacerbating the original problem at a point later in time. Although other procedures and diseases may cause similar injury, exemplary aspects of the present invention will be described with respect to the treatment of restenosis and related complications following percutaneous transluminal coronary angioplasty and other similar arterial/venous procedures, including the joining of arteries, veins, and other fluid carrying conduits in other organs or sites of the body, such as the liver, lung, bladder, kidney, brain, prostate, neck, and legs.

The local delivery of a compound of the present invention and, in some aspects, along with other therapeutic agents, from a stent prevents vessel recoil and remodeling through the scaffolding action of the stent. The activity of compound provided, with or without other therapeutic agents, helps determine for which application, to treat which disease, the coated medical device is being administered. For example, compound-coated stents can prevent multiple components of neointimal hyperplasia or restenosis as well as reduce inflammation and thrombosis. Local administration of a compound of the present invention and other therapeutic agents to stented coronary arteries may also have additional therapeutic benefit. For example, higher tissue concentrations of the compounds of the present invention and other therapeutic agents may be achieved utilizing local delivery rather than systemic administration. In addition, reduced systemic toxicity may be achieved utilizing local delivery rather than systemic administration while maintaining higher tissue concentrations. In utilizing local delivery from a stent rather than systemic administration, a single procedure may suffice with better patient compliance. An additional benefit of combination therapeutic agent and/or compound therapy may be to reduce the dose of each of the therapeutic agents, thereby limiting toxicity, while still achieving a reduction in restenosis, inflammation, and thrombosis. Local stent-based therapy is therefore a means of improving the therapeutic ratio (efficacy/toxicity) of anti-restenosis, anti-inflammatory, and anti-thrombotic therapeutic agents.

Although exemplary aspects of the invention will be described with respect to the treatment of restenosis and other related complications, it is important to note that the local delivery of a compound of the present invention, alone or as part of a therapeutic agent combination, may be utilized to treat a wide variety of conditions utilizing any number of medical devices, or to enhance the function and/or life of the device. For example, intraocular lenses, placed to restore vision after cataract surgery, are often compromised by the formation of a secondary cataract. The latter is often a result of cellular overgrowth on the lens surface and can be potentially minimized by combining one or more compounds of the present invention having activity that is effective in preventing unwanted cellular growth with the device. Other medical devices that often fail due to tissue in-growth or accumulation of proteinaceous material in, on and around the device, such as shunts for hydrocephalus, dialysis grafts, colostomy bag attachment devices, ear drainage tubes, leads for pace makers, and implantable defibrillators can also benefit from the combinations of the compounds of the present invention, possibly other pharmaceutical agents, and the devices. Other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this compound-device combination approach. Essentially, any type of medical device may be coated in some fashion with at least one compound of the present invention, alone or as part of a therapeutic agent combination, which enhances treatment over the use of the device or therapeutic agent without combination with the compound.

As disclosed supra, the compounds of the present invention can be administered in combinational therapies with other therapeutic agents, and are not limited to only the other therapeutic agents disclosed herein. Thus, the present invention also contemplates, in addition to various medical devices, the coatings on these devices may be used to deliver a compound of the present invention in combination with other therapeutic agents. This illustrative list of therapeutic agents can be administered through pharmeutical means or in association with medical devices and such therapeutic agents include, but are not limited to, antiproliferative/antimitotic agents including natural products such as vinca alkaloids (e.g., vinblastine, vincristine, and vinorelbine), paclitaxel, epidipodophyllotoxins (e.g., etoposide, teniposide), antibiotics [e.g., dactinomycin (actinomycin D) daunorubicin, doxorubicin, and idarubicin], anthracyclines, mitoxantrone, bleomycins, plicamycin (mithramycin), and mitomycin, enzymes (L-asparaginase which systemically metabolizes L-asparagine and deprives cells which do not have the capacity to synthesize their own asparagine); antiplatelet agents such as G(GP) Ib/IIIa inhibitors and vitronectin receptor antagonists; antiproliferative/antimitotic alkylating agents such as nitrogen mustards (e.g., mechlorethamine, cyclophosphamide and analogs, melphalan, chlorambucil), ethylenimines and methylmelamines (hexaamethylmelamine and thiotepa), alkyl sulfonates-busulfan, nirtosoureas [carmustine (BCNU) and analogs, streptozocin], trazenes-dacarbazinine (DTIC); antiproliferative/antimitotic antimetabolites such as folic acid analogs (methotrexate), pyrimidine analogs (e.g., fluorouracil, floxuridine, and cytarabine), purine analogs and related inhibitors [mercaptopurine, thioguanine, pentostatin, and 2-chlorodeoxyadenosine (cladribine)]; platinum coordination complexes (cisplatin, carboplatin), procarbazine, hydroxyurea, mitotane, aminoglutethimide; hormones (e.g., estrogen); anticoagulants (e.g., heparin, synthetic heparin salts and other inhibitors of thrombin); fibrinolytic agents (such as tissue plasminogen activator, streptokinase, and urokinase), aspirin, dipyridamole, ticlopidine, clopidogrel, abciximab; antimigratory; antisecretory (breveldin); anti-inflammatory agents such as adrenocortical steroids (e.g., cortisol, cortisone, fludrocortisone, prednisone, prednisolone, 6α-methylprednisolone, triamcinolone, betamethasone, and dexamethasone), non-steroidal agents (salicylic acid derivatives, i.e., aspirin; para-aminophenol derivatives, i.e., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives, (Cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor signal transduction kinase inhibitors.

Although any number of stents may be utilized in accordance with the present invention, for simplicity, a limited number of stents will be described in exemplary aspects of the present invention. The skilled artisan will recognize that any number of stents may be utilized in connection with the present invention. In addition, as stated above, other medical devices may be utilized. For example, though stents are described, sleeves outside the vessels are also contemplated, as are other medical devices that can provide a substrate for administration for at least one of the compounds of the present invention.

A stent is commonly used as a tubular structure left inside the lumen of a duct to relieve an obstruction. Typically, stents are inserted into the lumen in a non-expanded form and are then expanded autonomously, or with the aid of a second device in situ. A common method of expansion occurs through the use of a catheter-mounted, angioplasty balloon that is inflated within the stenosed vessel or body passageway in order to shear and disrupt the obstructions associated with the wall components of the vessel and to obtain an enlarged lumen.

A stent may resemble an expandable cylinder and may comprise a fenestrated structure for placement in a blood vessel, duct or lumen to hold the vessel, duct or lumen open, more particularly for protecting a segment of artery from restenosis after angioplasty. The stent may be expanded circumferentially and maintained in an expanded configuration that is circumferentially or radially rigid. The stent may be axially flexible and when flexed at a band, for example, the stent avoids any externally protruding component parts.

The stent may be fabricated utilizing any number of methods. For example, the stent may be fabricated from a hollow or formed stainless steel tube that may be machined using lasers, electric discharge milling, chemical etching or other means. The stent is inserted into the body and placed at the desired site in an unexpanded form. In one aspect, expansion may be effected in a blood vessel by a balloon catheter, where the final diameter of the stent is a function of the diameter of the balloon catheter used. It should be appreciated that a stent in accordance with the present invention may be embodied in a shape-memory material including, for example, an appropriate alloy of nickel and titanium or stainless steel.

Structures formed from stainless steel may be made self-expanding by configuring the stainless steel in a predetermined manner, for example, by twisting it into a braided configuration. In this aspect, after the stent has been formed it may be compressed so as to occupy a space sufficiently small as to permit its insertion in a blood vessel or other tissue by insertion means, wherein the insertion means include a suitable catheter, or flexible rod. Upon emerging from the catheter, the stent may be configured to expand into the desired configuration where the expansion is automatic or triggered by a change in pressure, temperature, or electrical stimulation.

Furthermore, a stent may be modified to comprise one or more reservoirs. Each of the reservoirs may be opened or closed as desired. These reservoirs may be specifically designed to hold the compound or compound/therapeutic agent combination to be delivered. Regardless of the design of the stent, it is preferable to have the compound or compound/therapeutic agent combination dosage applied with enough specificity and a sufficient concentration to provide an effective dosage in the affected area. In this regard, the reservoir size in the bands is preferably sized to adequately apply the compound or compound/therapeutic agent combination dosage at the desired location and in the desired amount.

In an alternative aspect, the entire inner and outer surface of the stent may be coated with the compound or compound/therapeutic agent combination in therapeutic dosage amounts. The coating techniques may vary depending on the compound or compound/therapeutic agent combination. Also, the coating techniques may vary depending on the material comprising the stent or other intraluminal medical device.

One or more compounds of the present invention and, in some instances, other therapeutic agents as a combination, may be incorporated onto or affixed to the stent in a number of ways. In one aspect, the compound is directly incorporated into a polymeric matrix and sprayed onto the outer surface of the stent. The compound elutes from the polymeric matrix over time and enters the surrounding tissue. The compound preferably remains on the stent for at least three days up to approximately six months, and more preferably between seven and thirty days.

Any number of non-erodible polymers may be utilized in conjunction with the compound, and such polymeric compositions are well known in the art. In one aspect, the polymeric matrix comprises two layers. The base layer comprises a solution of poly(ethylene-co-vinylacetate) and polybutylmethacrylate. The compound is incorporated into this base layer. The outer layer comprises only polybutylmethacrylate and acts as a diffusion barrier to prevent the compound from eluting too quickly. The thickness of the outer layer or topcoat determines the rate at which the compound elutes from the matrix. Essentially, the compound elutes from the matrix by diffusion through the polymer matrix. Polymers are permeable, thereby allowing solids, liquids and gases to escape therefrom. The total thickness of the polymeric matrix is in the range from about one micron to about twenty microns or greater. It is important to note that primer layers and metal surface treatments may be utilized before the polymeric matrix is affixed to the medical device. For example, acid cleaning, alkaline (base) cleaning, salinization and parylene deposition may be used as part of the overall process described above.

The poly(ethylene-co-vinylacetate), polybutylmethacrylate, and compound solution may be incorporated into or onto the stent in a number of ways. For example, the solution may be sprayed onto the stent or the stent may be dipped into the solution. Other methods include spin coating and plasma polymerization. In one aspect, the solution is sprayed onto the stent and then allowed to dry. In another aspect, the solution may be electrically charged to one polarity and the stent electrically charged to the opposite polarity. In this manner, the solution and stent will be attracted to one another. In using this type of spraying process, waste may be reduced and more precise control over the thickness of the coat may be achieved.

Drug-coated stents are manufactured by a number of companies including Johnson & Johnson, Inc. (New Brunswick, N.J.), Guidant Corp. (Santa Clara, Calif.), Medtronic, Inc. (Minneapolis, Minn.), Cook Group Incorporated (Bloomington, Ind.), Abbott Labs., Inc. (Abbott Park, Ill.), and Boston Scientific Corp. (Natick, Mass.). See e.g., U.S. Pat. No. 6,273,913; U.S. Patent Application Publication No. 20020051730; WO 02/26271; and WO 02/26139, each expressly entirely incorporated herein by reference.

Pharmaceutical Compositions

In one aspect, the present invention provides a composition comprising at least one compound as disclosed herein.

In another aspect, this invention provides a pharmaceutical composition, comprising:

at least one compound as disclosed herein; and optionally comprising a pharmaceutically acceptable additive selected from a carrier, an auxiliary, a diluent, an excipient, a preservative, a solvate, or any combination thereof.

In yet another aspect, this invention provides a pharmaceutical composition, comprising:

at least one compound as disclosed herein; and optionally comprising a pharmaceutically acceptable additive selected from a carrier, an auxiliary, a diluent, an excipient, a preservative, a solvate, or any combination thereof;

wherein the pharmaceutical composition is in the form of a tablet, a capsule, a syrup, a cachet, a powder, a granule, a solution, a suspension, an emulsion, a bolus, a lozenge, a suppository, a cream, a gel, a paste, a foam, a spray, an aerosol, a microcapsule, a liposome, or a transdermal patch.

In still another aspect, this invention provides a pharmaceutical composition, comprising:

at least one compound as disclosed herein;

optionally comprising a pharmaceutically acceptable additive selected from a carrier, an auxiliary, a diluent, an excipient, a preservative, a solvate, or any combination thereof; and further comprising an agent selected from a chemotherapeutic agent, an immunosuppressive agent, a cytokine, a cytotoxic agent, an anti-inflammatory agent, an antirheumatic agent, a cardiovascular agent, or any combination thereof.

Accordingly, in addition to the compounds disclosed herein, the pharmaceutical compositions of the present invention can further comprise at least one of any suitable auxiliary such as, but not limited to, diluent, binder, stabilizer, buffers, salts, lipophilic solvents, preservative, adjuvant, or the like. In one aspect of the present invention, pharmaceutically acceptable auxiliaries are employed. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

Pharmaceutical Compositions for Oral Administration

For oral administration in the form of a tablet or capsule, a compound can be combined with an oral, non-toxic pharmaceutically acceptable inert carrier such as ethanol, glycerol, water, and the like. Moreover, when desired or necessary, suitable binders, lubricants, disintegrating agents, and coloring agents may also be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes; and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Formulations of the present invention suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, and the like.

Routes of Administration

The invention further relates to the administration of at least one compound disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means.

Dosages

More specifically, the pharmaceutical compositions can be administered in a single daily dose, or the total daily dosage may be administered in divided doses of two, three, or four times daily. In the case of oral administration, the daily dosage of the compositions can be varied over a wide range from about 0.0001 to about 1,000 mg per patient, per day. The range can more particularly be from about 0.001 mg/kg to 10 mg/kg of body weight per day, about 0.1-100 mg, about 1.0-50 mg or about 1.0-20 mg per day for adults (at about 60 kg).

The daily dosage of the pharmaceutical compositions can be varied over a wide range from about 0.01 to about 1000 mg per adult human per day. For oral administration, the pharmaceutical compositions can be provided in the form of tablets containing from about 0.1 mg to about 1000 mg of the compound or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the active compound for the symptomatic adjustment of the dosage to the patient to be treated. An effective amount of the drug is ordinarily supplied at a dosage level of from about 0.1 mg/kg to about 20 mg/kg of body weight per day. In one aspect, the range is from about 0.2 mg/kg to about 10 mg/kg of body weight per day.

In another aspect, the range is from about 0.5 mg/kg to about 10 mg/kg of body weight per day. The compounds can be administered on a regimen of about 1 to about 10 times per day.

In the case of injections, it is usually convenient to give by an intravenous route in an amount of about 0.01-30 mg, about 0.1-20 mg or about 0.1-10 mg per day to adults (at about 60 kg). In the case of other animals, the dose calculated for 60 kg can be administered as well.

In addition, co-administration or sequential administration of the compounds of the present invention and other therapeutic agents can be employed, such as chemotherapeutic agents, immunosuppressive agents, cytokines, cytotoxic agents, nucleolytic compounds, radioactive isotopes, receptors, and pro-drug activating enzymes, which can be naturally occurring or produced by recombinant methods. The combined administration includes co-administration, using separate formulations or a single pharmaceutical formulation, and consecutive administration in either order, wherein preferably there is a time period while both (or all) active therapeutic agents simultaneously exert their biological activities.

It is to be understood that this invention is not limited to the particular methodology, syntheses, formulations, protocols, cell lines, constructs, and reagents described herein and as such can vary. It is also to be understood that the terminology used herein is for the purpose of describing particular aspects only, and is not intended to limit the scope of the present invention.

All publications, patents, and other references mentioned herein are provided for the purpose of describing and disclosing, for example, the constructs and methodologies that are described in these references, which might be used in connection with the presently described invention. The references provided or discussed in the text are provided solely for their disclosure prior to the filing date of the present application. Nothing herein is to be construed as an admission that the inventors are not entitled to antedate such disclosure by virtue of prior invention.

To the extent that any definition or usage provided by any document incorporated herein by reference conflicts with the definition or usage provided herein, the definition or usage provided herein controls.

For any particular compound disclosed herein, any general structure presented also encompasses all conformational isomers, regioisomers, stereoisomers and tantiomers that may arise from a particular set of substituents. The general structure also emcompasses all enantiomers, diastereomers, and other optical isomers whether in enantiomeric or racemic forms, as well as mixtures of stereoisomers, as the context requires. The general structure also encompasses all pharmaceutically acceptable salts and prodrugs thereof.

When Applicants disclose or claim a range of any type, for example a range of temperatures, a range of numbers of atoms, a molar ratio, or the like, Applicants' intent is to disclose or claim individually each possible number that such a range could reasonably encompass, as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that R is selected independently from an alkyl group having up to 20 carbon atoms, or in alternative language a $C_1$ to $C_{20}$ alkyl group, as used herein, refers to an R group that can be selected independently from a hydrocarbyl group having 1, 2, 3, 4, 5, 6, 7, 8, 9, 10, 11, 12, 13, 14, 15, 16, 17, 18, 19, or 20 carbon atoms, as well as any range between these two numbers for example a $C_3$ to $C_8$ alkyl group, and also including any combination of ranges between these two numbers for example a $C_3$ to $C_5$ and $C_7$ to $C_{10}$ hydrocarbyl group. In another example, by the disclosure that the molar ratio typically spans the range from about 0.1 to about 1.1, Applicants intend to recite that the molar ratio can be selected from about 0.1:1, about 0.2:1, about 0.3:1, about 0.4:1, about 0.5:1, about 0.6:1, about 0.7:1, about 0.8:1, about 0.9:1, about 1.0:1, or about 1.1:1.

Applicants reserve the right to proviso out or exclude any individual members of any such group, including any sub-ranges or combinations of sub-ranges within the group, that may be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, compounds, ligands, structures, or groups thereof, or any members of a claimed group, if for any reason Applicants choose to claim less than the full measure of the disclosure, for example, to account for a reference that Applicants may be unaware of at the time of the filing of the application.

The following references discuss certain pyrimidine compounds.

TABLE 11

References disclosing pyrimidine compounds.

| Publication or Patent No. | Title | First Named Author or Inventor |
| --- | --- | --- |
| US 2004/0198728 | Pyridines and Uses Thereof | Hong, Feng |
| US 2004/0204386 | Pyrimidines and Uses Thereof | Bhatt, Rama |
| U.S. Pat. No. 5,728,704 | Substituted Pyrimidines for Control of Diabetic Complications | Mylari, Banavara L. |

TABLE 11-continued

References disclosing pyrimidine compounds.

| Publication or Patent No. | Title | First Named Author or Inventor |
| --- | --- | --- |
| U.S. Pat. No. 5,863,924 | Aryl Pyrimidine Derivatives | Berger, Jacob |
| U.S. Pat. No. 5,977,117 | Substituted Phenyl Compounds and Derivatives Thereof That Modulate the Activity of Endothelin | Chan, Ming Fai |
| WO 97/25321 | Substituted Phenyl Compounds and Derivatives Thereof That Modulate the Activity of Endothelin | Chan, Ming Fai |
| WO 01/62233 | Adenosine Receptor Modulators | Borroni, Edilio |
| WO 02/47690 | Substituted 2-Aryl-4-Arylaminopyrimidines and Analogs as Activators of Caspases and Inducers of Apoptosis and the Use Thereof | Cai, Sui |
| WO 03/030909 | 2- And 4-Aminopyrimidines N-Substituted by a Bicyclic Ring for Use as Kinase Inhibitors in the Treatment of Cancer | Nagarathnam, Dhanapalan |
| WO 03/063794 | 2,4-Pyrimidinediamine Compounds and Their Uses | Singh, Rajinder |
| WO 03/075828 | Compounds Useful in the Treatment of Cancer | Gelvan, Dan |
| WO 2004/000820 | Certain Aromatic Monocycles as Kinase Modulators | Darrow, James W. |
| WO 2004/014382 | Methods of Treating or Preventing Autoimmune Diseases with 2,4-Pyrimidinediamine Compounds | Singh, Rajinder |
| WO 2004/048365 | 2,4,6-Trisubstituted Pyrimidines as Phosphotidylinositol (PI) 3-Kinase Inhibitors and Their Use in the Treatment of Cancer | Nuss, John M. |
| WO 2004/089286 | Novel Compounds and Compositions as Protein Kinase Inhibitors | Ding, Qiang |
| WO 2005/009977 | Substituted Pyrimidin-4-Ylamina Analogues as Vanilloid Receptor Ligands | Blum, Charles A. |
| WO 2005/012262 | 2-Aminophenyl-4-Phenylpyrimidines as Kinase Inhibitors | Wang, Shudong |
| WO 2005/047268 | Substituted Pyrimidine Compositions and Methods of Use | Martin, Richard |
| EP 1 321 169 | Combination of a Serotonin Receptor Antagonist With a Histidine Decarboxylase Inhibitor as a Medicament | Engels, Peter, Dr. |

Applicants reserve the right to proviso out, or to restrict from any claim currently presented, or from any claim that may be presented in this or any further application based upon this disclosure, including claims drawn any genus or subgenus disclosed herein, any compound or group of compounds disclosed in any reference provided herein.

Although methods, syntheses, and materials similar or equivalent to those described herein can be used in the practice or testing of this invention, typical methods, syntheses, and materials are described herein.

Acronyms, Abbreviations, and Reagents

The following abbreviations, acronyms, and reagents are commonly used throughout this disclosure, including the Examples: DMF, dimethylformamide; DMSO, dimethylsulphoxide; NaH, sodium hydride; $CH_2Cl_2$ or DCM, dichloromethane; $CDCl_3$, deuterated chloroform or chloroform-d; $POCl_3$, phosphorus oxychloride; THF, tetrahydrofuran; $AlCl_3$, aluminum chloride; NaOH, sodium hydroxide; $Na_2CO_3$, sodium carbonate; MeOH, methanol; $NH_4OH$, ammonium hydroxide; $K_2CO_3$, potassium carbonate; TFA, trifluoracetic acid; THF, tetrahydrofuran; HCl, hydro chloride or hydrogen chloride; DSC, differential scanning calorimetry; DCE, dichloroethane; $Pd(OAc)_2$, palladium(II) acetate; EtOAc, ethyl acetate; $Na_2SO_4$, sodium sulphate; n-BuOH, n-butanol; KOH, potassium hydroxide; NaOH, sodium hydroxide; DMAP, 4-dimethylamino pyridine; $(PPh_3)_4Pd$ tetrakis(triphenylphosphine)palladium(0); $(PPh_3)_2PdCl_2$, bis(triphenylphosphine) palladium(II) chloride; HPLC, high performance liquid chromatography; TLC, thin layer chromatography; mL, milliliters; M.P. or mp, melting point; RT, room temperature, typically ranging from about 20° C. to about 40° C.; aq, aqueous; min, minutes; h or hr, hours; g, grams; atm, atmosphere; conc., concentrated; MS or Mass Spec, mass spectroscopy/spectrometry; NMR, nuclear magnetic resonance; TMS, tetramethylsilane; $R_f$, TLC retention factor; $R_t$, HPLC retention time; HPFC, high pressure fraction collector; IR, infrared spectroscopy/spectrum; $CH_3CN$, acetonitrile; $N_2$, nitrogen; mg, milligrams; mmol, millimoles; mol, moles; nm, nanometers; HRMS, high resolution mass spectroscopy; and ° C., degrees Centigrade.

Abbreviations especially frequent in the NMR data are as follows: MHz, megahertz; br, broad; apt, apparent; s, singlet; d, doublet; t, triplet; q, quartet; dq, doublet of quartets; dd, doublet of doublets; dt, doublet of triplets; and m, multiplet.

The following precursor compounds obtained as specified in the following listing, Table 12.

TABLE 12

Typical sources of starting materials

| Structure | Name | Source |
|---|---|---|
| 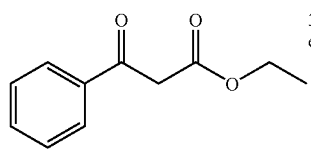 | 3-Oxo-3-phenyl-propionic acid ethyl ester | Lancaster |
| 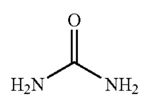 | Urea | Loba |
| 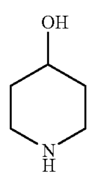 | Piperidin-4-ol | DRL |
| 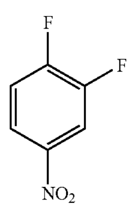 | 1,2-Difluoro-4-nitro-benzene | Lancaster |
| 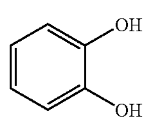 | Benzene-1,2-diol | Loba |
| 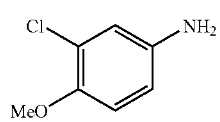 | 3-Chloro-4-methoxy-phenylamine | Loba |
| 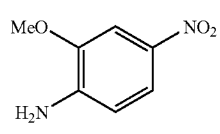 | 2-Methoxy-4-nitro-phenylamine | Lancaster |

TABLE 12-continued

Typical sources of starting materials

| Structure | Name | Source |
|---|---|---|
| 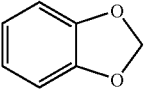 | Benzo[1,3]dioxole | Lancaster |
| 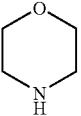 | Morpholine | Loba |
| 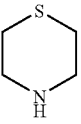 | Thiomorpholine | Loba |
| 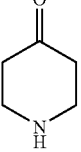 | Piperidin-4-one monohydrate | Lancaster |
| 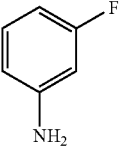 | 3-Fluoro-phenylamine | |
| 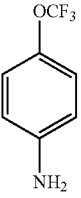 | 4-Trifluoromethoxy-phenylamine | Aldrich |
| 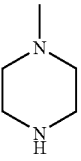 | 1-Methyl-piperazine | Spectrochem |
| 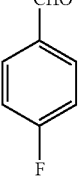 | 4-Fluoro-benzaaldehyde | Lancaster |
| BrCH$_2$CO$_2$Et | Bromo-acetic acid ethyl ester | Lancester |
| 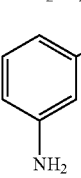 | 3-Trifluoromethyl-phenylamine | Lancester |

TABLE 12-continued

Typical sources of starting materials

| Structure | Name | Source |
|---|---|---|
| 4-(SCH₃)-C₆H₄-NH₂ | 4-Methylsulfanyl-phenylamine | Lancaster |
| 4-(SO₂Cl)-C₆H₄-NO₂ | 4-Nitro-benzenesulfonyl chloride | Lancaster |
| CH₃NH₂ | Methylamine | Spectrochem |
| 4-(NO₂)-C₆H₄-COOH | 4-Nitro-benzoic acid | Loba |
| 3-(NO₂)-C₆H₄-COOH | 3-Nitro-benzoic acid | Loba |
| 4-(CH₃CO)-C₆H₄-NH₂ | 1-(4-Amino-phenyl)-ethanone | Loba |
| 3-(CH₃CO)-C₆H₄-NH₂ | 1-(3-Amino-phenyl)-ethanone | Loba |
| 3-(SO₂Cl)-C₆H₄-NO₂ | 3-Nitro-benzenesulfonyl chloride | Loba |
| C₆H₅-NH₂ | Phenylamine | Spectrochem |

TABLE 12-continued

| Typical sources of starting materials | | |
|---|---|---|
| Structure | Name | Source |
| B(OH)₂-phenyl | Benzene boronic acid | Lancaster |
| 4-Cl, 3-CF₃, 1-NH₂ phenyl | 4-Chloro-3-trifluoromethyl-phenylamine | Lancaster |
| 4-CF₃, 1-NH₂ phenyl | 4-Trifluoromethyl-phenylamine | Lancaster |
| Cyclohexyl-NH₂ | Cyclohexylamine | Lancaster |
| 3-SO₂CH₃, 1-B(OH)₂ phenyl | 3-methanesulfonyl phenyl boronic acid | Lancaster |
| Succinic anhydride | Dihydro-furan-2,5-dione | Loba |
| Phthalic anhydride | Isobenzenefuran-1,3-dione | Loba |
| 4-OCF₃, 1-B(OH)₂ phenyl | 4-trifluoromethoxy phenyl boronic acid | Lancaster |

TABLE 12-continued

Typical sources of starting materials

| Structure | Name | Source |
|---|---|---|
| 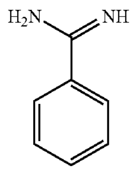 | Benzamidine hydrochloride | Aldrich |
| 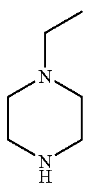 | 1-Ethyl-piperazine | Lancaster |
| 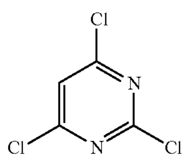 | 2,4,6-Trichloro-pyrimidine | Lancaster |

The following experiments and Examples are merely illustrative, and compounds of the present invention are not limited by the following particular species. The skilled artisan will appreciate how the experiments and Examples may be further implemented as disclosed by variously altering the following examples, substituents, conditions, or reagents.

In the following examples, by the disclosure of any measurements, including temperatures, pressures, times, weights, percentages, concentrations, ranges, chemical shifts, frequencies, molar ratios, and the like, it is to be understood that such measurements are, respectively, "about."

EXAMPLES

Example 1

Synthesis of $N^4$-(3-chloro-4-methoxy-phenyl)-6-(4-methoxy-phenyl)-pyrimidine-2,4-diamine Step (i). Synthesis of 3-(4-methoxy-phenyl)-3-oxo-propionic acid ethyl ester

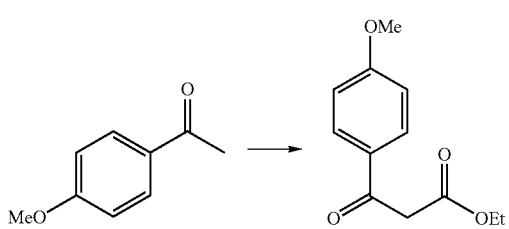

To a solution of 4-methoxyacetophenone (100 g, 0.66 mol) in dry dimethylformamide (400 mL), 60% sodium hydride (34.3 g, 0.85 mol) was added slowly at 10° C. under a nitrogen atmosphere. This mixture was stirred at 25° C. for 30 minutes and again cooled to 10° C. This was added to solution of diethyl carbonate (94.5 g, 0.80 mol) and dissolved in minimum quantity of dry dimethylformamide at the same temperature. The mixture was then stirred at 25° C. for 5 to 6 hours and poured into ice cold water (100 mL) with vigorous stirring. The mixture was then acidified (pH~6-7) using cold 2 N hydrochloric acid and extracted with ethyl acetate. The organic layers were collected, combined, washed with water, dried over anhydrous sodium sulphate, filtered and concentrated under vacuum to afford the desired compound as yellow oil (133 g). Yield: 90%.

$^1$H NMR (200 MHz, CDCl$_3$): δ 7.92 (d, J=8.8 Hz, 2H), 6.94 (d, J=8.6 Hz, 2H), 4.26-4.15 (m, 2H), 3.93 (s, 3H), 1.25 (t, J=7.3, 6.9 Hz, 3H).

IR (Neat, cm$^{-1}$): 1740, 1678, 1602.

MS: m/z (CI) 223 (M$^+$, 100%).

Reference: Parmar, V. S.; Jain, R.; Singh, S. *Bull. Chem. Soc. Jpn.* 1988, 61, 2277-2280.

Step (ii). Synthesis of 2-amino-6-(4-methoxy-phenyl)-pyrimidin-4-ol

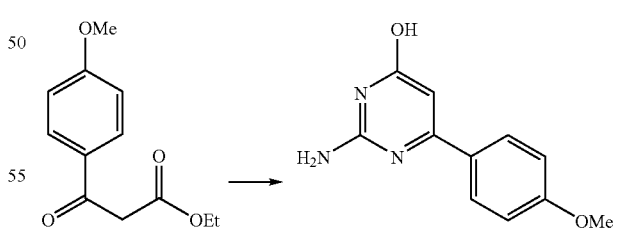

A mixture of compound 3-(4-methoxy-phenyl)-3-oxo-propionic acid ethyl ester (69 g, 0.31 mol), obtained in step (i), guanidine carbonate (61.5 g, 0.34 mol) in ethanol (600 mL) was heated to reflux with vigorous stirring under nitrogen atmosphere for 6 to 12 hours. Ethanol was then removed under vacuum, the mixture was diluted with cold water (20 mL for 1 g of 3-(4-methoxy-phenyl)-3-oxo-propionic acid ethyl ester), and stirred for 10 minutes at temperature in the range of 20-40° C. The white solid separated out was isolated by filtration to afford the desired compound (55 g).

¹H NMR (200 MHz, CDCl₃): δ 10.77 (br s, NH), 7.91 (d, J=8.7 Hz, 2H), 6.97 (d, J=8.7 Hz, 2H), 6.56 (br s, NH), 6.03 (s, 1H), 3.79 (s, 3H, OCH₃).
IR (Neat, cm⁻¹): 1668, 1588.
MS: m/z (CD) 218 (M+1, 100%).

Step (iii). Synthesis of 4-chloro-6-(4-methoxy-phenyl)-pyrimidin-2-ylamine

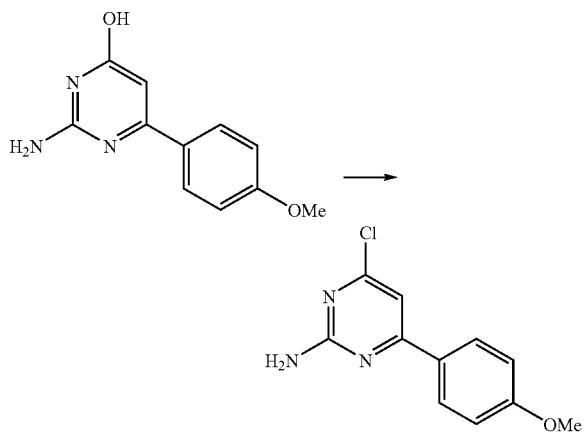

A mixture of compound 2-amino-6-(4-methoxy-phenyl)-pyrimidin-4-ol (18 g, 83 mol) obtained in step (ii) and phosphorus oxychloride (POCl₃) (150 mL) was stirred at 100° C. under anhydrous condition for 5 to 8 hours. The initial turbidity disappeared after completion of the reaction and excess phosphorus oxychloride was then removed by distillation under low vacuum. The residue was diluted with aqueous sodium bicarbonate solution to reach the pH~7-8. The white solid separated was filtered, washed with water, and dried under vacuum to afford the desired product (15 g). Yield: 75%.

¹H NMR (200 MHz, CDCl₃): δ 8.04 (d, J=8.5 Hz, 2H), 7.19 (s, 1H), 7.09 (br s, 1H, NH), 7.05 (d, J=8.5 Hz, 2H), 3.88 (s, 3H, OCH₃).
IR(Neat, cm⁻¹): 1631, 1607, 1583.
MS: m/z (CD) 236 (M+1, 100%).

Step (iv). Synthesis of N⁴-(3-chloro-4-methoxy-phenyl)-6-(4-methoxy-phenyl)-pyrimidine-2,4-diamine

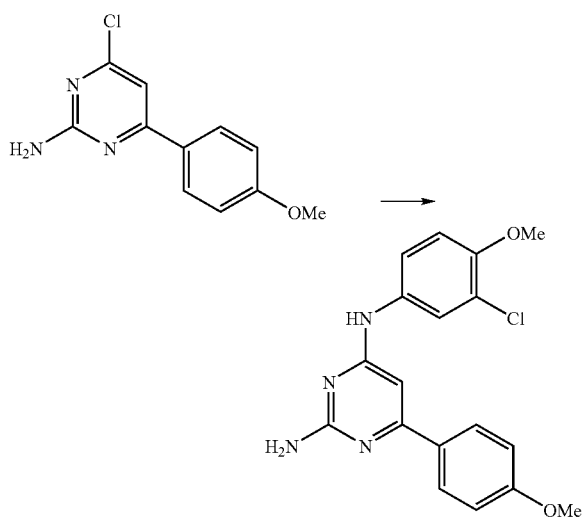

A mixture of compound 4-chloro-6-(4-methoxy-phenyl)-pyrimidin-2-ylamine (1.0 g, 4.2 mmol), obtained in step (iii), 3-chloro-4-methoxyaniline (0.67 g, 4.2 mmol) in dry dimethylformamide (8 mL) was stirred at 80° C. for 12 hours. After completion the reaction mixture was poured into cold water (50 mL) and stirred for 10 to 15 minutes at temperature in the range of 20-40° C. The white solid was filtered, washed with water, and dried under vacuum to afford the desired compound (1 g). Yield: 66%.
M.P.: 165-170° C.
¹H NMR (200 MHz, DMSO-d₆): δ 12.9 (br s, 1H), 10.43 (s, 1H), 7.92-7.85 (m, 3H), 7.64 (d, J=9.2 Hz, 2H), 7.15-7.11 (m, 3H), 6.57 (s, 1H), 3.85 (s, 6H).
IR (Neat, cm⁻¹): 3446, 3386, 2937, 1646, 1604.
MS: m/z (CD) 357 (M⁺, 100%).

Examples 2-12

Synthesis of Substituted Pyrimidine Compounds

Scheme 1

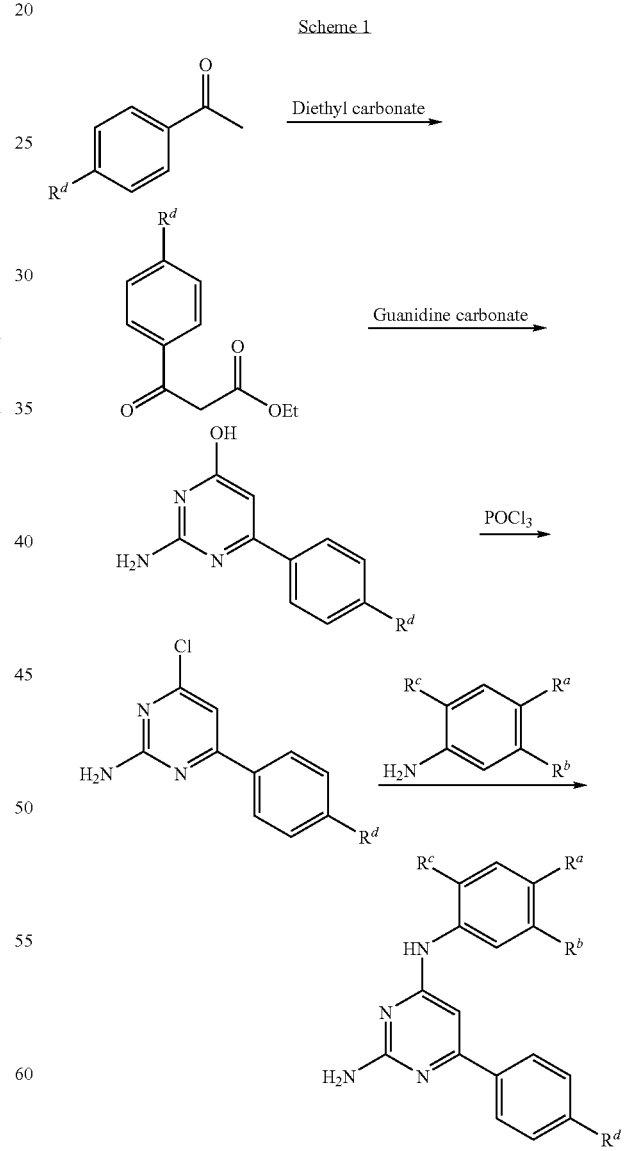

The following compounds presented in Examples 2-12 were prepared in accordance with Scheme 1, by a procedure analogous to that disclosed in Example 1, using starting materials with the appropriate substitution.

| Ex. No. | $R^a$ | $R^b$ | $R^c$ | $R^d$ | Analytical Data |
|---|---|---|---|---|---|
| 2 | OMe | Cl | H | H | M.P.: 262-264° C.<br>$^1$H NMR (200 MHz, DMSO-$d_6$): δ 13.02 (br s, D$_2$O exchange, 1H), 11.01(br s, D$_2$O exchangeable, 1H), 7.96-7.64(m, 9H), 7.19(d, J=8.9 Hz, 1H), 6.72(s, 1H), 3.86(s, 3H).<br>IR (Neat, cm$^-$): 3385, 1646, 1499.<br>MS: m/z (CI) 327 (M$^+$, 100%). |
| 3 | OMe | Cl | H | F | M.P.: 162-164° C.<br>$^1$H NMR (200 MHz, DMSO-$d_6$): δ 10.36(s, D$_2$O exchangeable, 1H), 7.93(m, 3H), 7.64-7.43(m, 5H, 2H exchangeable with D$_2$O), 7.16-7.12(m,1 H), 6.56(s, 1H), 3.86(s, 3H).<br>IR (Neat, cm$^-$): 3440, 1646.<br>MS: m/z (CI) 345 (M$^+$, 100%). |
| 4 | OMe | Cl | H | OEt | M.P.: 184° C.<br>$^1$H NMR (200 MHz, DMSO-$d_6$): δ 9.11(s, 1H, D$_2$O exchangeable), 7.87(d, J=8.5 Hz, 2H), 7.57(d, J=9.0 Hz, 1H), 7.09-6.98(m, 3H), 6.27(s, 3H), 6.36(s, 1H), 4.13-4.03(m, 2H), 3.82(s, 3H), 1.34(t, J=6.8 Hz, 3H).<br>IR (Neat, cm$^{-1}$): 3496, 3296, 1230.<br>MS: m/z (CI) 371 (M$^+$, 100%). |
| 5 | OMe | Cl | H | Me | M.P.: 184° C.<br>$^1$H NMR (200 MHz, DMSO-$d_6$): δ 9.14(s, D$_2$O exchangeable, 1H), 7.90-7.8(m, 2H), 7.58(d, J=8.8 Hz, 1H), 7.27(d, J=7.6 Hz, 2H), 7.07(d, J=8.8 Hz, 2H), 6.40(s, 1H), 6.30(s, 2H), 3.82(s, 3H), 2.35(s, 3H).<br>IR (Neat, cm$^{-1}$): 3491, 3297, 1251.<br>MS: m/z (CI) 341 (M$^+$, 100%). |
| 6 | OMe | Cl | H | SMe | M.P.: 243-246° C.<br>$^1$H NMR (200 MHz, DMSO-$d_6$): δ 13-12.68(s, D$_2$O exchangeable, 1H), 10.18(s, D$_2$O exchangeable, 1H), 7.94-7.64(m, 3H), 7.59-7.45(m, 1H), 7.40-7.25(m, 3H, 1H exchangelable with D$_2$O), 7.16-7.11(m, 1H), 6.56(s, 1H), 3.85(s, 3H), 2.55(s, 3H).<br>I.R: 3480, 3279, 1250.<br>MS: m/z (CI) 373 (M$^+$, 100%). |
| 7 | OMe | F | H | OMe | M.P.: 177-180° C.<br>$^1$H NMR (200 MHz, DMSO-$d_6$): δ 9.33(s, D$_2$O exchangeable, 1H) 7.98-7.86(m, 3H), 7.29-7.28(m, 1H), 7.13-7.01(m, 3H), 6.48(s, D$_2$O exchangeable, 2H), 6.40(s, 1H), 3.81(s, 3H).<br>I.R: 3490, 3295, 1249.<br>MS: m/z (CI) 341 (M$^+$, 100%). |
| 8 | OH | Cl | H | OMe | M.P.: 168-270° C.<br>$^1$H NMR (200 MHz, DMSO-$d_6$): δ 12.79(s, 1H), 10.69(s, 1H), 10.25, 7.88-7.84(m, 3H), 7.45(br s, 2H), 7.19-6.99(m, 3H), 6.57(s, 1H), 3.86(s, 3H).<br>I.R: 3410, 1588. |
| 9 | —O–O— (dioxole) | | H | H | M.P. >260° C.<br>$^1$H NMR (200 MHz, DMSO-$d_6$): δ 12.85(br s, 1H), 10.81(br s, 1H), 7.87-7.65(m, 6H), 7.06-6.93(m, 2H), 6.64(s, 1H), 6.06(s, 2H).<br>IR (Neat, cm$^{-1}$): 3311, 1638, 1488.<br>MS: m/z (CI) 332 (M+1, 100%). |
| 10 | Cl | OMe | H | H | M.P.: 310-312° C.<br>$^1$H NMR (200 MHz, DMSO-$d_6$): δ 12.96(br s, 1H), 10.94(s, 1H), 7.88-7.86(m, 3H), 7.65(m, 4H), 7.44-7.40(m, 2H), 6.69(s, 1H), 3.91(s, 3H).<br>IR (neat, cm$^{-1}$): 1646, 1620, 1572, 1520.<br>MS: m/z (CI) 327 (M+1, 100%). |
| 11 | OH | Cl | H | H | M.P.: 212-214° C.<br>$^1$H NMR (200 MHz, DMSO-$d_6$): δ 2.28(br s, 1H), 10.63(s, 1H), 10.22(s, 1H), 7.78-7.46(m, 8H), 7.04-7.00(m, 1H), 6.59(s, 1H).<br>I.R. (KBr, cm$^{-1}$): 3366, 1645, 1625.<br>MS: m/z (CI) 13 (M$^+$, 100%). |

-continued

| Ex. No. | $R^a$ | $R^b$ | $R^c$ | $R^d$ | Analytical Data |
|---|---|---|---|---|---|
| 12 | H | H | COOEt | H | M.P.: 218-220° C.<br>$^1$H NMR (200 MHz, DMSO-$d_6$): δ 13.06(br s, $D_2O$ exchangeable), 10.87(br s, $D_2O$ exchangeable, 1H), 7.96-7.34(m, 9H), 6.76(s, 1H), 4.25(m, 2H), 1.25(t, J=7.1 Hz, 3H).<br>I.R: 3444, 1721.<br>MS: m/z (CI) 335 (M$^+$, 100%). |

Example 13

Synthesis of N$^4$-(3-chloro-4-methoxy-phenyl)-6-methyl-pyrimidine-2,4-diamine

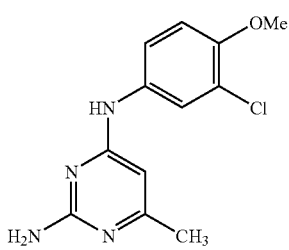

N$^4$-(3-Chloro-4-methoxy-phenyl)-6-methyl-pyrimidine-2,4-diamine was prepared according to the procedure described in Example 1 (steps ii-iv) starting from ethylacetoacetate in place of 3-(4-methoxy-phenyl)-3-oxo-propionic acid ethyl ester.

M.P.: 250° C.

$^1$H NMR (200 MHz, DMSO-$d_6$): δ 12.83 (s, 5H), 10.75 (s, 1H), 7.89 (s, 1H), 7.57 (m, 2H), 7.16-7.12 (d, J=8.9 Hz, 1H), 6.16 (s, 1H), 3.85 (s, 3H), 2.26 (s, 3H).

I.R (cm$^{-1}$): 3481, 3290, 1251.

MS: m/z (CI) 265 (M$^+$, 100%).

Example 14

5-[2-Amino-6-(4-methylsulfanylphenyl)pyrimidin-4-ylamino]-1-methyl-3-propyl-1H-pyrazole-4-carboxylic acid amide

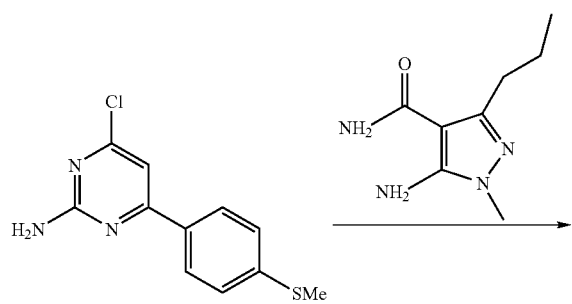

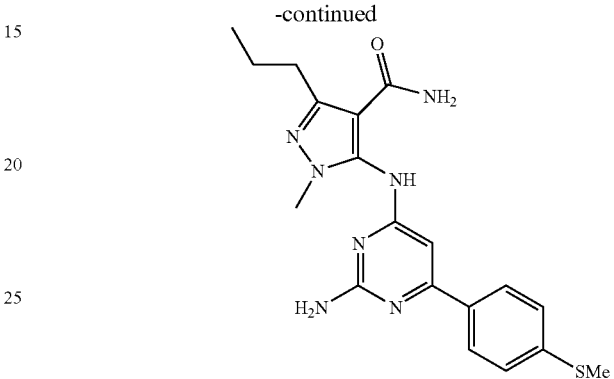

5-[2-Amino-6-(4-methylsulfanylphenyl)pyrimidin-4-ylamino]-1-methyl-3-propyl-1H-pyrazole-4-carboxylic acid amide was prepared by treating 4-chloro-6-(4-methylsulfanylphenyl)pyrimidin-2-ylamine with 5-amino-1-methyl-3-propyl-1H-pyrazole-4-carboxylic acid amide according to the procedure described in step (iv) of Example 1. 4-Chloro-6-(4-methylsulfanylphenyl)pyrimidin-2-ylamine was prepared according to the procedure as described in Example 1 (Steps i-iii) using 4-methylsulfanylacetophenone in place of 4-methoxyacetophenone.

M.P.: 102-104° C.

$^1$H NMR (200 MHz, DMSO-$d_6$): δ 8.22 (br s, $D_2O$ exchangeable, 1H), 7.84-7.72 (m, 3H), 7.42-7.29 (m, 3H), 6.29 (br s, $D_2O$ exchangeable, 2H), 3.93 (s, 3H), 2.51 (s, 3H), 2.37 (t, J=7.5 Hz, 2H), 1.59-1.48 (m, 2H), 0.84 (t, J=7.3 Hz, 3H).

MS: m/z (CI) 298 (M$^+$, 100%).

Reference: For the preparation of 5-amino-1-methyl-3-propyl-1H-pyrazole-4-carboxylic acid amide, see: (a) David J. Dale, Peter J. Dunn, Clare Golightly, Michael L. Hughes, Philip C. Levett, Andrew K. Pearce, Patricia M. Searle, Gordon Ward, and Albert S. Wood *Organic Process Research & Development* 2000, 4, 17-22. (b) Bell, A. S.; Brown, D.; Terrett, N. K. European Patent 0 463 756 A1, 1992.

Example 15

Synthesis of 1-[2-(3-chloro-4-methoxy-phenylamino)-6-cycloheptylamino-pyrimidin-4-yl]-piperidin-4-ol Step (i). Synthesis of (3-chloro-4-methoxy-phenyl)-(4,6-dichloro-pyrimidin-2-yl)-amine

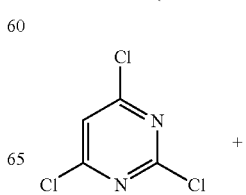 +

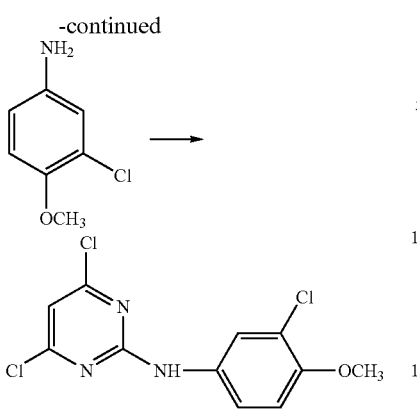

To a solution of 2,4,6-trichloro-pyrimidine (0.29 g, 1.58 mmol) in 1:1 chloroform-hexane (10 mL) was added 3-chloro-p-anisidine (0.5 g, 3.1 mmol) at 25° C. with stirring. To this was added triethylamine (0.22 mL, 1.59 mmol) at 25° C. and the mixture was heated and refluxed for 7 hours under nitrogen atmosphere. The mixture was then concentrated under vacuum, diluted with cold water (30 mL) and extracted with ethyl acetate (2×60 mL). The organic layers were collected, combined, washed with brine (30 mL), dried over anhydrous sodium sulphate, and concentrated under vacuum. The crude product thus obtained was purified by column chromatography using ethyl acetate-petroleum ether to afford the desired compound. Yield: 22%.

$^1$H NMR (200 MHz, CDCl$_3$): δ 7.59 (s, 1H), 7.40 (d, J=6.34 Hz, 1H), 7.20 (br s, D$_2$O exchangeable, 1H), 6.92 (d, J=8.7 Hz, 1H), 6.77 (s, 1H), 3.85 (s, 3H).

I.R: 3428, 1590.

MS: m/z (CI) 306 (M+1, 100%).

Step (ii). Synthesis of 6-chloro-N$^2$-(3-chloro-4-methoxy-phenyl)-N$^4$-cycloheptyl-pyrimidine-2,4-diamine

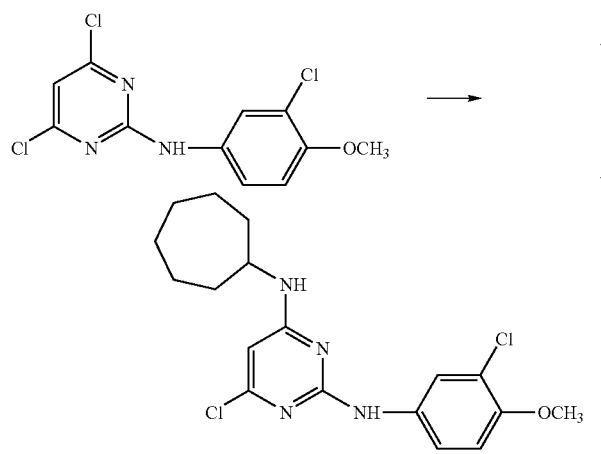

To a solution of compound (3-chloro-4-methoxy-phenyl)-(4,6-dichloro-pyrimidin-2-yl)-amine (0.08 g, 0.26 mmol) in butanol (3 mL) was added to cycloheptylamine (0.03 g, 0.26 mmol) at 25° C. with stirring. To this was added triethylamine (0.14 mL, 1.04 mmol), and the mixture was stirred for 30 minutes at 25° C. and then heated and refluxed for 12 hours under nitrogen atmosphere. The mixture was concentrated under vacuum, diluted with cold water, and extracted with ethyl acetate. The organic layers were collected, combined, washed with brine, dried over anhydrous sodium sulphate, and concentrated under vacuum to give the desired compound. Yield: 60%.

M.P.: 74-76° C.

$^1$H NMR (400 MHz, CDCl$_3$): δ 7.78 (s, 1H), 7.23 (s, 1H), 6.84 (d, J=8.9 Hz, 1H), 6.73 (s, 1H), 5.77 (s, 1H), 3.85 (s, 3H), 2.0-1.40 (m, 12H).

I.R: 3409, 1577.

MS: m/z (CD) 382 (M+1, 100%).

Step (iii). Synthesis of 1-[2-(3-chloro-4-methoxy-phenylamino)-6-cycloheptylamino-pyrimidin-4-yl]-piperidin-4-ol

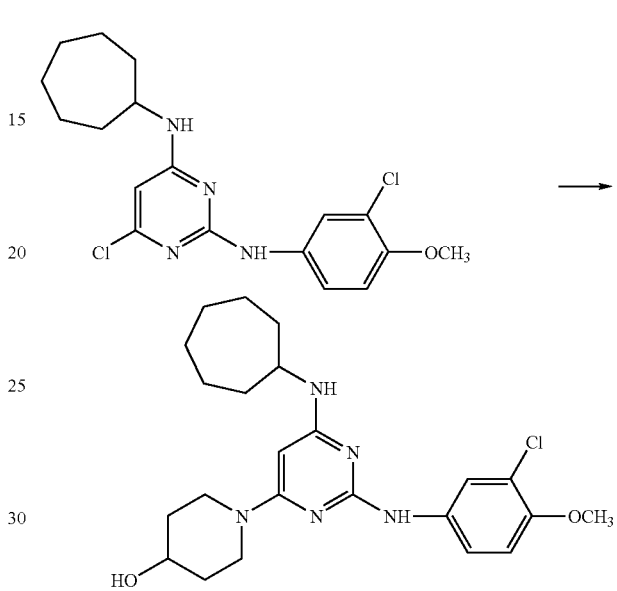

To a solution of compound 6-chloro-N$^2$-(3-chloro-4-methoxy-phenyl)-N$^4$-cycloheptyl-pyrimidine-2,4-diamine (0.15 g, 0.39 mmol) in 1-butanol (5 mL) was added 4-hydroxypiperidine (0.12 g, 1.18 mmol) at 25° C. with stirring. To this triethylamine (0.43 mL, 3.15 mmol) was added dropwise and the mixture was stirred at 25° C. for 30 minutes. This was heated and refluxed for 12 hours under nitrogen atmosphere. The mixture was concentrated under vacuum, diluted with cold water (30 mL) and extracted with ethyl acetate (2×30 mL). The organic layers were collected, combined, washed with brine (30 mL), dried over anhydrous sodium sulphate, and concentrated under vacuum to give the desired compound. Yield: 23%.

M.P.: 84-86° C.

$^1$H NMR (400 MHz, CDCl$_3$): δ 7.88 (s, 1H), 7.23-7.20 (m, 2H), 6.84 (d, J=8.6 Hz, 1H), 5.0 (s, D$_2$O exchange, 1H), 4.69 (br s, D$_2$O exchange, 1H), 4.03-3.67 (m, 7H), 3.17 (t, J=9.9 Hz, 2H), 2.06-1.53 (m, 16H).

I.R: 3408, 1590.

MS: m/z (CI) 446 (M+1, 100%).

Example 16

Synthesis of N$^2$,N$^4$-bis(3-chloro-4-methoxyphenyl)-6-phenylpyrimidine-2,4-diamine

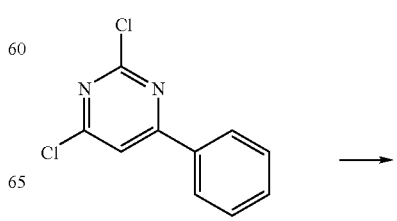

-continued

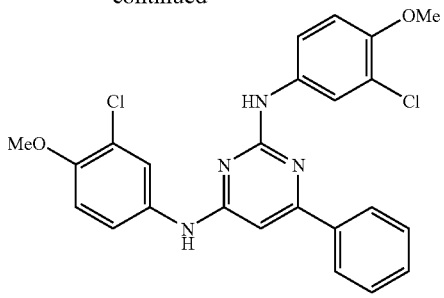

N²,N⁴-Bis(3-chloro-4-methoxyphenyl)-6-phenylpyrimidine-2,4-diamine was prepared by treating 2,4-dichloro-6-phenylpyrimidine with 3-chloro-4-methoxyanisidine (2 equivalent) according to the procedure described in step (iv) of Example 1. Yield: 65%.

M.P.: 250-254° C.

$^1$H NMR (200 MHz, DMSO-$d_6$): δ 10.66 (br s, 1H), 10.33 (br s, 1H), 7.95-7.13 (m, 11 H), 6.74 (s, 1H), 3.85 (s, 6H).

I.R: 3312, 1560.

MS: m/z (CI) 468 (M⁺, 100%).

Example 17

Synthesis of N-[4-(3-chloro-4-methoxy-phenylamino)-6-(4-ethoxy-phenyl)-pyrimidin-2-yl]-acetamide Step (i). Synthesis of N-[4-chloro-6-(4-ethoxy-phenyl)-pyrimidin-2-yl]-formamide

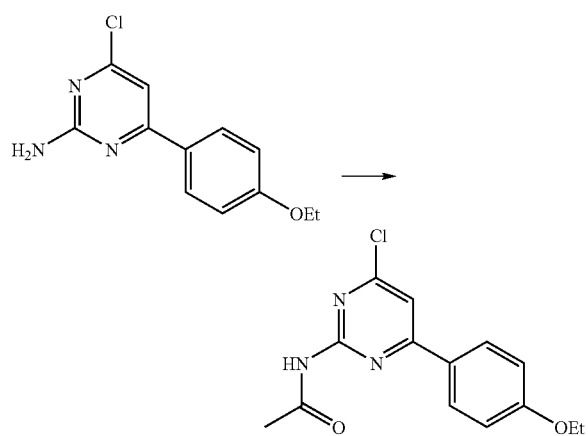

A mixture of compound 4-chloro-6-(4-ethoxy-phenyl)-pyrimidin-2-ylamine (0.4 g, 1.6 mmol) and acetic anhydride (0.98 g, 9.61 mmol) was stirred at 80° C. for 12 hours. After completion the reaction mixture was poured into cold water (50 mL) and stirred for 10 to 15 minutes at temperature in the range of 20-40° C. The mixture was extracted with dichloromethane, washed with water, dried over anhydrous sodium sulphate, and concentrated. The residue thus obtained was purified by column chromatography using ethyl acetate-petroleum ether to afford the desired compound. Yield: 71%.

$^1$H NMR (200 MHz, DMSO-$d_6$): δ 10.20 (br s, 1H), 7.93 (d, J=7.3 Hz, 2H), 7.70 (d, J=7.3 Hz, 2H), 6.75 (s, 1H), 4.14-4.04 (m, 2H), 2.22 (s, 3H), 1.34 (t, J=7.1 Hz, 3H).

IR (Neat, cm⁻¹): 3445, 1660.

MS: m/z (CI) 292 (M+, 100%).

Step (ii). Synthesis of N-[4-(3-chloro-4-methoxy-phenylamino)-6-(4-ethoxy-phenyl)-pyrimidin-2-yl]-acetamide

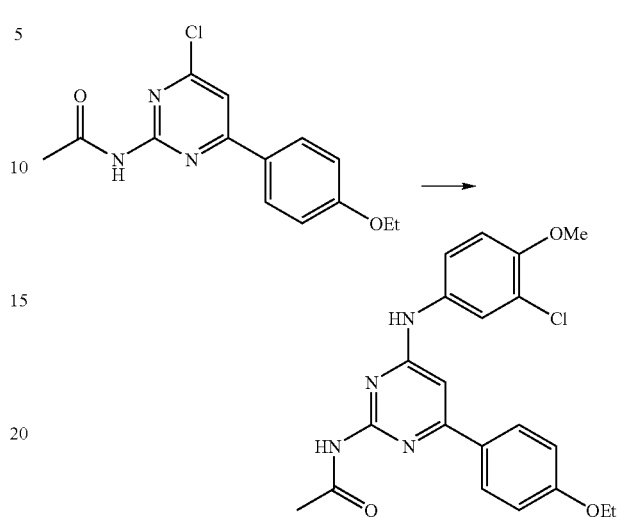

A mixture of compound N-[4-chloro-6-(4-ethoxy-phenyl)-pyrimidin-2-yl]-acetamide (0.4 g, 1.37 mmol), 3-choloro-4-methoxyaniline (0.21 g, 1.37 mmol) in dry dimethylformamide (5 mL) was stirred at 80° C. for 12 hours. After completion the reaction mixture was poured in to cold water and stirred for 10 to 15 minutes at temperature in the range of 20-40° C. The white solid separated was filtered, washed with water, and dried under vacuum to afford the desired compound.

M.P.: 214° C.

$^1$H NMR (200 MHz, DMSO-$d_6$): δ 10.24 (s, 1H), 9.58 (s, 1H), 8.17 (s, 1H), 7.95 (d, J=9.6 Hz, 2H), 7.75 (d, J=7.3 Hz, 2H), 7.09-7.03 (m, 2H), 6.77 (s, 1H), 4.15-4.05 (m, 2H), 3.82 (s, 3H), 2.23 (s, 3H), 1.35 (t, J=7.1 Hz, 3H).

IR (Neat, cm⁻¹): 3448, 3245, 1663.

MS: m/z (CI) 413 (M+, 100%).

Examples 18-20

Synthesis of substituted pyrimidine compounds

Scheme 2

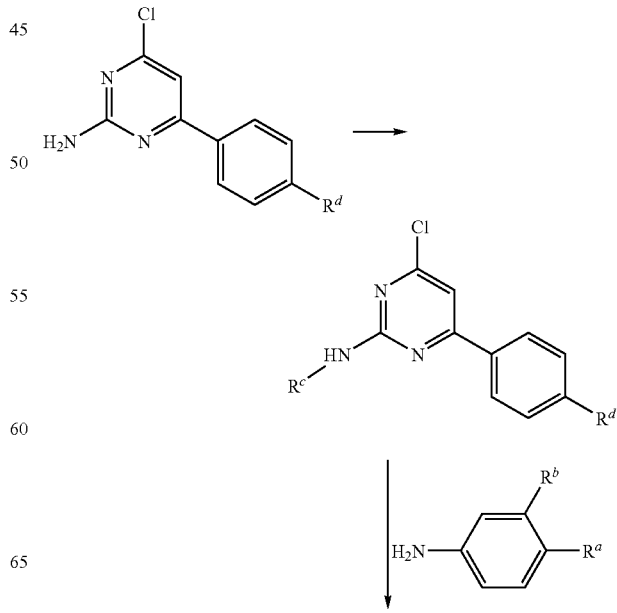

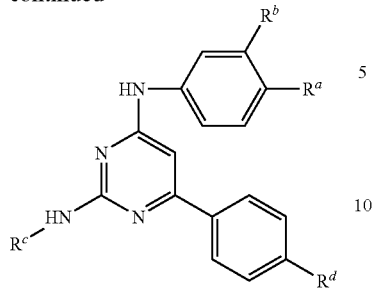

The following compounds presented in Examples 18-20 were prepared in accordance with Scheme 2, by a procedure analogous to that disclosed in Example 17, using starting materials with the appropriate substitution.

| Ex. No. | $R^a$ | $R^b$ | $R^c$ | $R^d$ | Analytical data |
|---|---|---|---|---|---|
| 18 | OMe | Cl | COCH$_3$ | OMe | M.P.: 218-220° C. $^1$H NMR(200MHz, DMSO-d$_6$): δ 8.07(s, 1H), 7.88(d, J=8.9Hz, 2H), 7.72(d, J=8.9Hz, 2H), 7.17-7.11(m, 2H), 6.91(s, 1H), 3.85(s, 6H, 2OCH$_3$), 2.27(s, 3H). MS: m/z(CI) 399(M$^+$, 100%). I.R(KBr, cm$^{-1}$): 3418, 1699. |
| 19 | OMe | Cl | COC$_2$H$_5$ | OMe | M.P.: 206-208° C. $^1$H NMR(200MHz, DMSO-d$_6$): δ 10.99(br s, 1H), 10.36(br s, 1H), 8.03-7.74(m, 4H), 7.16-7.10(m, 3H), 6.94(s, 1H), 3.85(s, 6H), 2.65-2.50(m, 2H), 1.14(t, J=7.4Hz, 3H). MS: m/z(CI) 413(M$^+$, 100%). I.R: (KBr, cm$^{-1}$): 3421, 1695. |
| 20 | OMe | Cl | CH$_2$CO$_2$Et | H | M.P.: 231.41° C. $^1$H NMR(400MHz, DMSO-d$_6$): δ 7.66(d, J=7.3Hz, 1H), 7.49(d, J=8.9Hz, 1H), 7.27-7.10(m, 6H), 6.50(s, 1H), 4.11(q, J=6.9Hz, 2H), 4.21(s, 2H), 3.87(s, 3H), 1.11(t, J=6.9Hz, 3H). MS: m/z(CI) 413(M$^+$, 100%). I.R: 3415, 1729. |

Example 21

Synthesis of N-[4-(3-chloro-4-methoxy-phenylamino)-6-phenyl-pyrimidin-2-yl]-2,2,2-trifluoro-acetamide

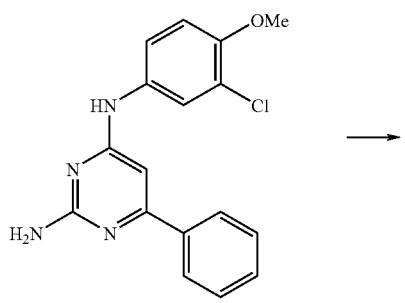

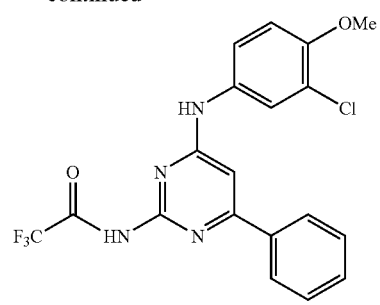

N-[4-(3-Chloro-4-methoxy-phenylamino)-6-phenyl-pyrimidin-2-yl]-2,2,2-trifluoro-acetamide was prepared by refluxing N$^4$-(3-chloro-4-methoxy-phenyl)-6-phenyl-pyrimidine-2,4-diamine (Example 2) in trifluoro acetic anhydride for 72 hours followed by the removal of the trifluoroacetic anhydride under reduced pressure.

DSC: 222.24° C.

$^1$H NMR (200 MHz, DMSO-d$_6$): δ 10.69 (s, 1H, D$_2$O exchangeable), 7.92-7.58 (m, 8H), 7.18 (d, J=8.8 Hz, 1H), 6.54 (s, 1H), 3.87 (s, 3H).

I.R: 3428, 1725.

MS: m/z (CI) 423 (M$^+$, 100%).

Example 22

Synthesis of 2,2,2-Trifluoro-N-(4-hydroxy-6-phenylpyrimidin-2-yl)acetamide

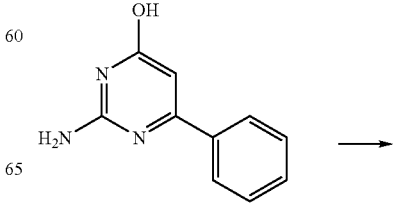

-continued

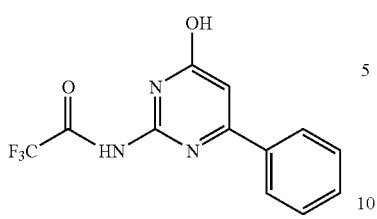

2,2,2-Trifluoro-N-(4-hydroxy-6-phenylpyrimidin-2-yl) acetamide was prepared by treating 2-amino-6-phenylpyrimidin-4-ol with trifluoroacetic anhydride according to the procedure described in Example 21. Yield: 39%.

M.P.: 166-168° C.

$^1$H NMR (200 MHz, DMSO-$d_6$): δ 7.94-7.9 (m, 2H), 7.83-7.43 (m, 3H), 6.73 (s, 1H), 6.60 (s, 1H, $D_2O$ exchangeable), 3.43 (br s, 1H).

I.R: 3421, 1720.

MS: m/z (CD) 284 (M$^+$, 100%).

Example 23

Synthesis of 4-(4-fluoro-phenylsulfanyl)-6-phenyl-pyrimidin-2-ylamine

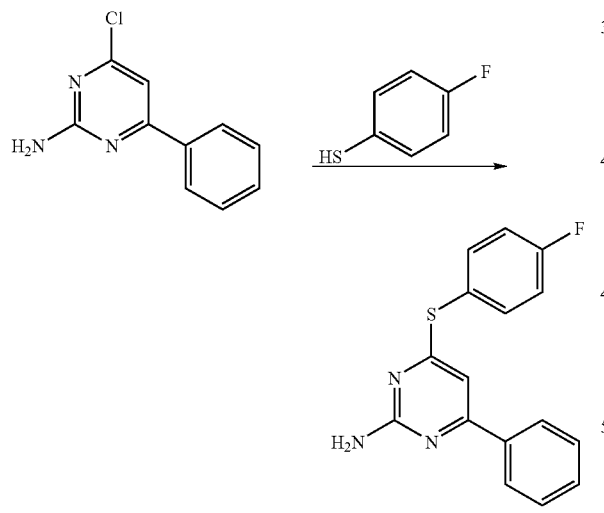

4-(4-Fluoro-phenylsulfanyl)-6-phenyl-pyrimidin-2-ylamine was prepared from 4-Chloro-6-phenyl-pyrimidin-2-ylamine (0.5 g, 2.44 mmol) using 4-fluorothiophenol (0.31 mg, 2.44 mmol) in iso-propanol (15 mL) at 80° C. for 6 hours. Yield: 64%.

M.P.: 218-220° C.

$^1$H NMR (200 MHz, DMSO-$d_6$): δ 7.94 (d, J=6.2 Hz, 2H), 7.76 (d, J=5.4 Hz, 2H), 7.74-7.34 (m, 5H), 6.50 (s, 1H).

I.R: (KBr) 3489, 3246, 1674.

MS: m/z (CD) 298 (M$^+$, 100%).

Example 24

Synthesis of (3-chloro-4-methoxyphenyl)-(2-ethyl-sulfanyl-6-phenylpyrimidin-4-yl)amine Step (i). Synthesis of 2-mercapto-6-arylpyrimidine-4-ol

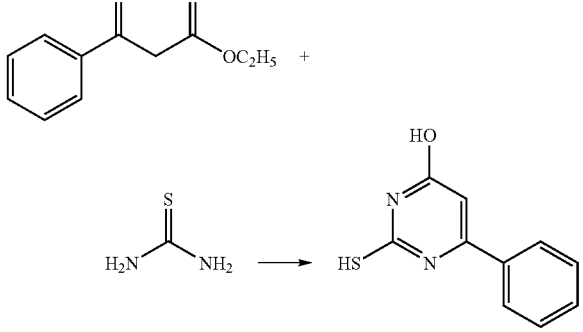

Sodium (3 g, 125 mmol) was added portion wise to ethanol (50 mL) at temperature in the range of 20-40° C. with stirring under nitrogen atmosphere until a clear solution is obtained. To this was added thiourea (7 g, 92 mmol) and the mixture was stirred at the same temperature for 1 to 2 hours. A solution of ethylbenzoylacetate (13 g, 67.7 mmol) in ethanol (60 mL) was added to this mixture and the mixture was heated and refluxed for 16 hours with stirring. Then solvent was removed under reduced pressure; the solid obtained was dissolved in a minimum amount of water and then acidified with 2N hydrochloric acid. The solid appeared was filtered off, dried under vacuum, and was finally triturated with isopropanol to give the title compound as an off white solid.

$^1$H NMR (200 MHz, DMSO-$d_6$): δ 12.13 (s, OH), 7.66-7.42 (m, 5H), 5.98 (s, 1H).

IR (KBr, cm$^{-1}$): 1668.

MS: (CI) m/z 205 (M$^+$).

Step (ii). Synthesis of 2-ethylsulfanyl-6-arylpyrimidin-4-ol

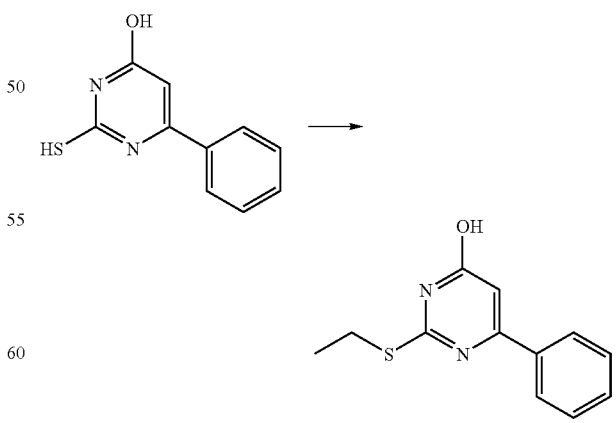

To a suspension of sodium hydride (0.59 g, 14.7 mmol) in dimethylformamide (5 mL) was added to a solution of compound 2-mercapto-6-arylpyrimidine-4-ol (3 g, 14.7 mmol) in dimethylformamide (20 mL) at 0° C. under nitrogen atmosphere and the mixture was stirred for 1 hour at the same temperature. To this was added ethyl bromide (1.1 mL, 14.6 mmol) and the mixture was then stirred at 80° C. for 16 hours. After cooling to temperature in the range of 20-40° C. the mixture was diluted with water (100 mL). The solid appeared was filtered off, dried under vacuum, and was titrated with isopropanol to afford the title compound as an off white solid.

$^1$H NMR (200 MHz, CDCl$_3$): δ 13.13 (s, OH), 8.02-7.97 (m, 2H), 7.49-7.46 (m, 3H), 6.7 (s, 1H), 3.35 (q, J=7.3 Hz, 2H), 1.48 (t, J=7.5 Hz, 3H).

IR (KBr, cm$^{-1}$): 3442, 1667.

MS: (CI) m/z 233 (M$^+$).

Step (iii). Synthesis of 4-chloro-2-ethylsulfanyl-6-phenylpyrimidine

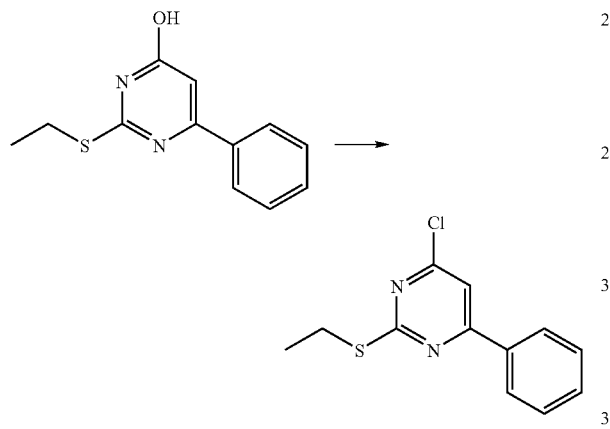

A mixture of compound 2-ethylsulfanyl-6-arylpyrimidin-4-ol (3 g, 13 mmol) and phosphorus oxychloride (25 mL) was stirred at refluxing temperature for 5 to 6 hours and then excess of phosphorus oxychloride was distilled out under low vacuum. The mixture was cooled to temperature in the range of 20-40° C., diluted with water (50 mL), neutralized with sodium bicarbonate solution, and extracted with ethyl acetate (3×20 mL). The organic layers were collected, combined, washed with water, dried over anhydrous sodium sulfate, and concentrated under vacuum to afford the title compound as a pale brown liquid. Yield: 92%.

$^1$H NMR: (CDCl$_3$, 200 MHz): δ 8.73-8.02 (m, 2H), 7.52-7.46 (m, 3H), 7.36 (s, 1H), 3.24 (q, J=7.3 Hz, 2H), 1.45 (t, J=7.3 Hz, 3H).

IR (Neat, cm$^{-1}$): 1547.

MS: (CI) m/z 250 (M$^+$).

Step (iv). Synthesis of (3-chloro-4-methoxyphenyl)-(2-ethylsulfanyl-6-phenylpyrimidin-4-yl)amine

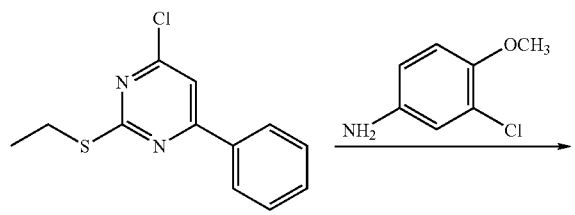

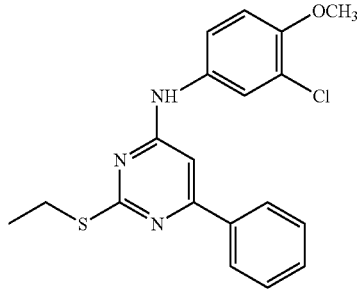

A mixture of compound 4-chloro-2-ethylsulfanyl-6-phenylpyrimidine (0.35 g, 1.4 mmol) and 3-chloro-4-methoxyanisidine (1.88 g, 12 mmol) in isopropanol (5 mL per 1 mmol) was stirred at refluxing temperature for 20 hours under nitrogen atmosphere. The reaction mixture was cooled to temperature in the range of 20-40° C. The solid separated was filtered off and then dried under vacuum to afford the title compound. Yield: 88%.

M.P.: 162-164° C.

$^1$H NMR (200 MHz, CDCl$_3$): δ 7.99-7.94 (m, 3H), 7.47-7.37 (m, 5H), 7.28 (s, 1H), 3.99 (s, 3H), 2.99 (q, J=7.3 Hz, 2H), 1.25 (t, J=7.3 Hz, 3H).

IR (KBr, cm$^{-1}$): 3438, 1552.

MS: m/z (CI) 371 (M$^+$).

Example 25

Synthesis of 4-(3-chloro-4-hydroxyphenylamino)-6-phenylpyrimidin-2-ol

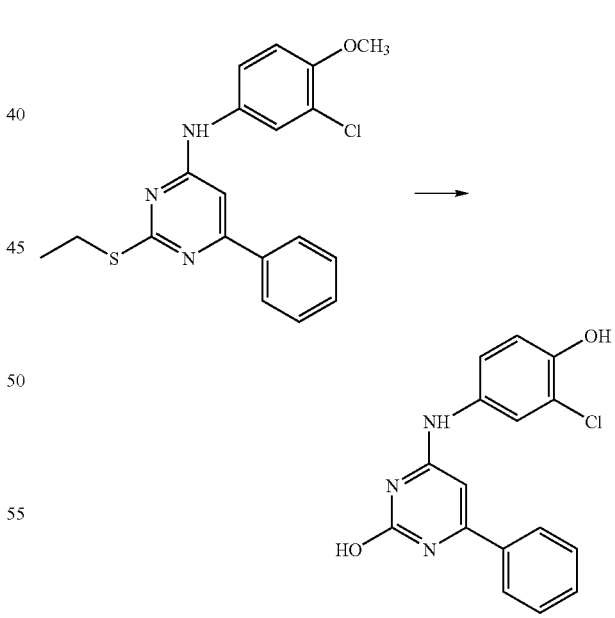

A mixture of compound (3-chloro-4-methoxyphenyl)-(2-ethylsulfanyl-6-phenylpyrimidin-4-yl)amine and 47% hydrobromic acid solution in water (10 mL) was stirred at refluxing temperature for 12 hours. The reaction mixture was cooled to temperature in the range of 20-40° C. and excess of acid was removed under vacuum. The mixture was then neutralized with ammonia solution. The solid thus obtained was filtered off and dried under vacuum to afford the title compound as a pale brown color solid.

M.P.: 280-282° C.

$^1$H NMR (200 MHz, DMSO-d$_6$): δ 11.01(s, 1H), 9.95 (s, 1H), 9.61 (s, 1H), 8.01 (s,1H), 7.72-7.69 (m, 2H), 7.54-7.52 (m, 3H), 7.34 (d, J=8.6 Hz, 1H), 6.93 (d, J=8.6 Hz, 1H), 6.07 (s, 1H).

IR (KBr, cm$^{-1}$): 3396.

MS: m/z (CI) 314 (M+1,100%).

Example 26

Synthesis of N$^2$-(3-chloro-4-methoxyphenyl)-N$^4$-methyl-6-phenylpyrimidine-2,4-diamine Step (i). Synthesis of (2-ethylsulfanyl-6-phenylpyrimidin-4-yl)methylamine

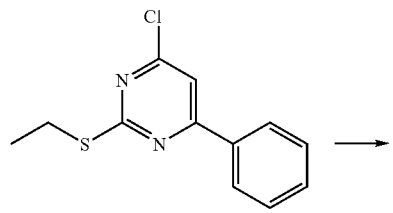

A mixture of compound 4-chloro-2-ethylsulfanyl-6-phenyl-pyrimidine (1 g, 4 mmol) and aqueous methylamine (0.74 g, 24 mmol) in methanol (20 mL) was stirred at refluxing temperature for 16 hours under nitrogen atmosphere. The reaction mixture was then cooled to temperature in the range of 20-40° C. The solid separated was filtered off and dried under reduced pressure. It was finally titrated with petroleum-ether to afford the title compound as an off white solid.

$^1$H NMR (200 MHz, CDCl$_3$): δ 8.02-7.99 (m, 2H), 7.46-7.44 (m, 3H), 6.41 (s, 1H), 5.0 (s, NH), 3.25-3.18 (q, J=7.3 Hz, 2H), 3.0 (d, J=5.1 Hz, 3H), 1.47-1.39 (t, J=7.3 Hz, 3H).

I.R: 3422, 1648.

MS: m/z (CD) 246 (M$^+$,100%).

Step (ii). Synthesis of 4-methylamino-6-phenylpyrimidin-2-ol

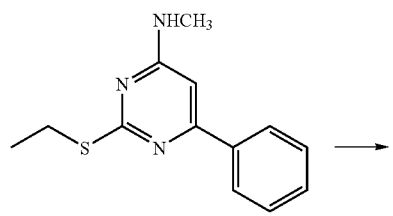

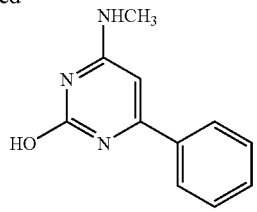

A mixture of compound (2-ethylsulfanyl-6-phenylpyrimidin-4-yl)methylamine (0.85 g, 3.4 mmol) and hydrobromic acid (10-15 mL) was stirred at refluxing temperature for 16 hours. The reaction mixture was cooled to temperature in the range of 20-40° C., concentrated under reduced pressure and neutralized with ammonia solution. The solid separated was filtered off and dried under reduced pressure. It was finally triturated with isopropanol to afford the title compound as an off white solid.

$^1$H NMR (200 MHz, DMSO-d$_6$): δ 10.74 (s, OH), 7.68-7.53 (m, 5H), 5.92 (s, 1H), 2.82 (d, J=3.7 Hz, 3H).

IR (KBr, cm$^{-1}$): 3442.

MS: m/z (CD) 202 (M$^+$).

Step (iii). Synthesis of (2-chloro-6-phenylpyrimidin-4-yl)alkylamine

A mixture of compound 4-methylamino-6-phenylpyrimidin-2-ol (0.55 g, 2.73 mmol) and phosphorus oxychloride (10 mL) was stirred at refluxing temperature for 8 hours. Excess of phosphorus oxychloride was distilled out and the mixture was cooled to temperature in the range of 20-40° C. The mixture was then diluted with water (20 mL), neutralized with sodium bicarbonate solution. The solid separated was filtered off and dried under vacuum to afford the title compound as a white solid.

$^1$H NMR (200 MHz, DMSO-d$_6$): δ 10.68 (s, NH), 7.93 (m, 2H), 7.68-7.49 (m, 3H), 6.90 (s, 1H), 2.84 (d, J=4.9 Hz, 3H).

IR (KBr, cm$^{-1}$): 3458.

MS: m/z (CD) 220 (M$^+$).

Step (iv). Synthesis of N²-(3-chloro-4-methoxyphenyl)-N⁴-methyl-6-phenylpyrimidine-2,4-diamine

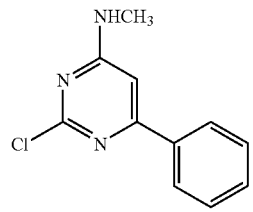

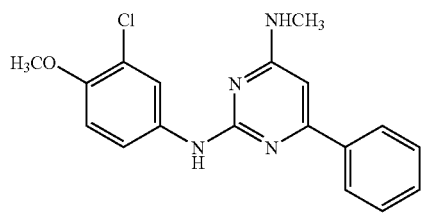

The title compound (0.3 g) was prepared by treating compound (2-chloro-6-phenylpyrimidin-4-yl)methylamine (0.38 g, 1.73 mmol) with 3-chloro-4-methoxyaniline in methanol at refluxing temperature for 20 hours. The solid precipitated was filtered and dried to give the title compound.
M.P.: 280-282° C.
$^1$H NMR (200 MHz, DMSO-d$_6$): δ 10.5 (s, 1H), 8.95 (s, 1H), 7.92 (s, 3H), 7.63-7.51 (m, 3H), 7.18 (d, J=9.0 Hz, 1H), 6.53 (s, 1H), 3.85 (s, 3H), 2.98 (d, J=3.4 Hz, 3H).
IR (KBr, cm$^{-1}$): 3422.
MS: m/z (CI) 341(M+1, 100%).

Examples 27-29

Synthesis of Substituted Pyrimidine Compounds

Scheme 3

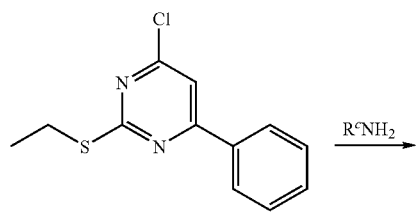

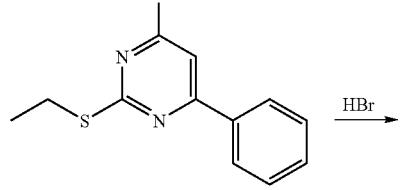

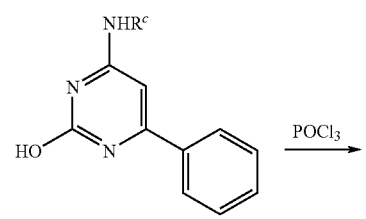

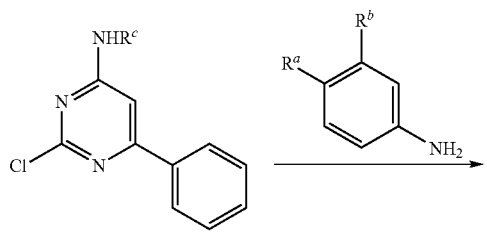

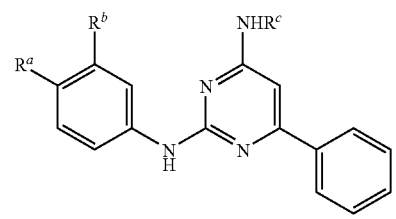

The following compounds presented in Examples 27-29 were prepared in accordance with Scheme 3, by a procedure analogous to that disclosed in Example 26, using starting materials with the appropriate substitution.

| Ex No | R$^a$ | R$^b$ | R$^c$ | Analytical data |
|---|---|---|---|---|
| 27 | OCH$_3$ | Cl | 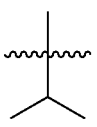 | M.P.: 250-252° C. $^1$H NMR (200 MHz, DMSO-d$_6$): δ 10.72(s, 1H), 9.02(s, 1H), 7.91(s, 3H), 7.64-7.62(m, 3H), 7.44(d, J=8.1 Hz, 1H), 7.19(d, J=9.0 Hz, 1H), 6.50(s, 1H), 4.21-4.11(m, 1H), 3.85(s, 3H), 1.26(d, J=6.4 Hz, 6H). IR (KBr, cm$^{-1}$): 3420. MS: m/z (CI) 369 (M+1, 100%). |

-continued

| Ex No | R$^a$ | R$^b$ | R$^c$ | Analytical data |
|---|---|---|---|---|
| 28 | OCH$_3$ | Cl | ![cycloheptyl] | M.P.: 248-250° C.<br>$^1$H NMR (200 MHz, DMSO-d$_6$): δ 12.7(s, 1H), 10.52(s, 1H), 8.94(s, 1H), 7.99(s, 1H), 7.89(d, J=5.6 Hz, 2H), 7.66(d, J=6.7 Hz, 2H), 7.65(s, 1H), 7.40-7.38(m, 1H), 7.19(d, J=9.1 Hz, 1H), 6.52(s, 1H), 4.07-4.05(m, 1H), 3.87(s, 1H), 2.0-1.96(m, 2H), 1.73-1.46(m, 10H).<br>IR (KBr, cm$^{-1}$): 3423.<br>MS: m/z (CI) 423 (M+1, 100%). |
| 29 | OCH$_3$ | Cl | CH$_2$Ph | M.P.: 264-266° C.<br>$^1$H NMR (200 MHz, DMSO-d$_6$): δ 10.57(s, 1H), 9.47(s, 1H), 7.91-7.81(m, 4H), 7.63-7.61(m, 3H), 7.45-7.27(m, 5H), 7.14(d, J=8.9 Hz, 1H), 6.61(s, 1H), 4.66(d, J=5.4 Hz, 2H), 3.84(s, 3H).<br>I.R: 3441, 1632.<br>MS: m/z (CI) 417 (M$^+$, 100%). |

Example 30

Synthesis of 2-(3-chloro-4-methoxyphenylamino)-6-(4-methoxyphenyl)pyrimidin-4-ol

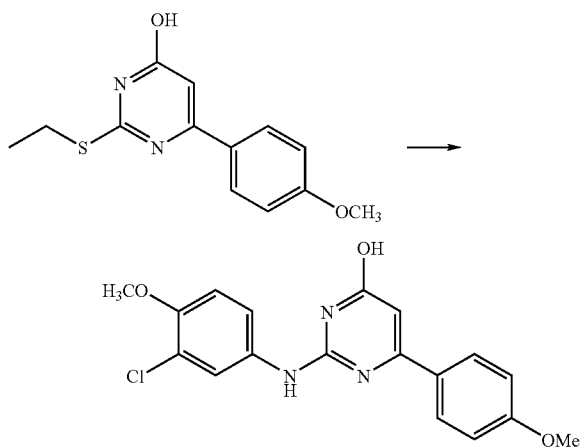

A mixture of compound 2-ethylsulfanyl-6-(4-methoxyphenyl)-pyrimidin-4-ol (2.5 g, 9.5 mmol) and 3-chloroanisidine (1.8 g, 11.4 mmol) in diglyme (30 mL) was stirred at refluxing temperature for 40 hours under nitrogen atmosphere. The reaction mixture was cooled to temperature in the range of 20-40° C., diluted with isopropanol (50 mL) and was stirred for one hour at temperature in the range of 20-40° C. The solid separated was filtered off and dried under vacuum to afford the title compound. Yield: 58%.

M.P.: 292-294° C.

$^1$H NMR (200 MHz, DMSO-d$_6$): δ 10.73 (s, 1H), 8.84 (s,1H), 7.95 (d, J=9.5 Hz, 2H), 7.91 (s, 1H), 7.53 (d, J=9.0 Hz, 1H), 7.13 (d, J=9.0 Hz, 1H), 6.99 (d, J=8.8 Hz, 2H), 6.32 (s, 1H), 3.82 (s, 3H), 3.79 (s, 3H).

IR (KBr, cm$^{-1}$): 3201.

MS: m/z (CI) 358 (M+1, 100%).

Examples 31-36

Synthesis of Substituted Pyrimidine Compounds

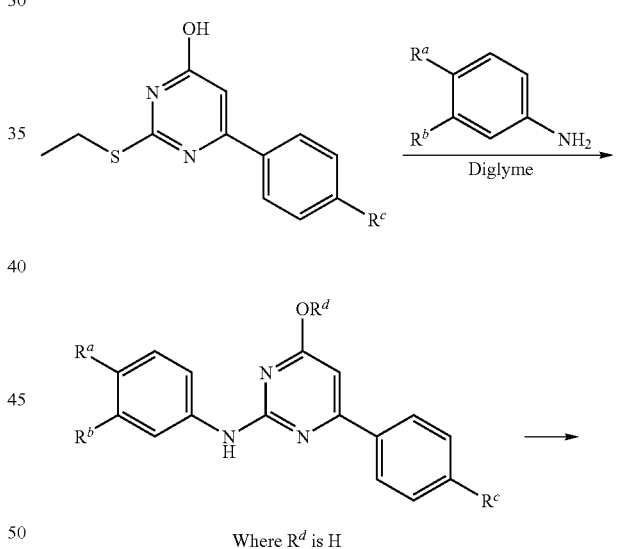

Where R$^d$ is H

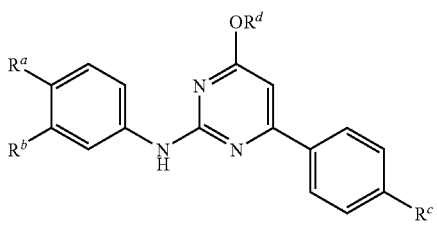

The following compounds presented in Examples 31-36 were prepared in accordance with Scheme 4, by a procedure analogous to that disclosed in Example 30, using starting materials with the appropriate substitution.

| Ex. No. | $R^a$ | $R^b$ | $R^c$ | $R^d$ | Analytical data |
|---|---|---|---|---|---|
| 31 | OCH$_3$ | Cl | H | H | M.P.: 272-274° C.<br>$^1$H NMR (200 MHz, DMSO-d$_6$): δ 10.91(s, 1H), 8.92(s, 1H), 7.99-7.95(m, 3H), 7.58-7.47(m, 4H), 7.15(d, J=8.8 Hz, 1H), 6.42 (s, 1H), 3.84(s, 3H).<br>IR (KBr, cm$^{-1}$): 3451, 1635.<br>MS: m/z (CI) 328 (M+1, 100%). |
| 32 | OCH$_3$ | Cl | OCH$_3$ | CH$_2$CH$_3$ | M.P.: 128-130° C.<br>$^1$H NMR (200 MHz, DMSO-d$_6$): δ 9.48(s, 1H), 8.08(d, J=8.8 Hz, 2H), 8.03(s, 1H), 7.70(d, J=8.8 Hz, 1H), 7.11(d, J=9.3 Hz, 1H), 7.04(d, J=8.8 Hz, 2H), 6.74(s, 1H), 4.41(q, J=6.8 Hz, 2H), 3.82(s, 6H), 1.37(t, J=7.1 Hz, 3H),<br>IR (KBr, cm$^{-1}$): 3352.<br>MS: m/z (CI) 386 (M+1, 100%). |
| 33 | OCH$_3$ | Cl | OCH$_3$ | isopropyl (CH(CH$_3$)$_2$) | M.P.: 138-140° C.<br>$^1$H NMR (200 MHz, DMSO-d$_6$): δ 9.48(s, 1H), 8.11-8.06(d, J=8.8 Hz, 2H), 8.06(s, 1H), 7.67(d, J=8.8 Hz, 1H), 7.12(d, J=9.3 Hz, 1H), 7.05(d, J=8.3 Hz, 2H), 6.70 (s, 1H), 5.38(m, 1H), 3.83(s, 6H), 1.37(t, J=6.3 Hz, 6H).<br>IR (KBr, cm$^{-1}$): 1588.<br>MS: m/z (CI) 400 (M+1, 100%). |
| 34 | OCH$_3$ | Cl | OCH$_3$ | CH$_2$Ph | M.P.: 154-156° C.<br>$^1$H NMR (200 MHz, DMSO-d$_6$): δ 9.55 (s, 1H), 8.11(d, J=7.8 Hz, 2H), 8.01(s, 1H), 7.71(d, J=9.3 Hz, 1H), 7.49-7.38(m, 4H), 7.15-7.08(m, 2H), 7.06(d, J=8.3 Hz, 2H), 6.85(s, 1H), 5.47(s, 2H), 3.84(s, 3H), 3.34(s, 3H).<br>IR (KBr, cm$^{-1}$): 3378, 1601.<br>MS: m/z (CI) 448 (M+1, 100%). |
| 35 | OCH$_3$ | Cl | OCH$_3$ | CH$_2$-(4-methylphenyl) | M.P.: 92-94° C.<br>$^1$H NMR (200 MHz, DMSO-d$_6$): δ 8.07(d, J=8.8 Hz, 2H), 7.99(s, 1H), 7.66(d, J=8.8 Hz, 1H), 7.35(d, J=7.8 Hz, 2H), 7.20-7.13(m, 3H), 7.04(d, J=8.8 Hz, 2H), 6.76 (s, 1H), 5.39(s, 2H), 3.81(s, 6H), 2.28(s, 3H).<br>IR (KBr, cm$^{-1}$): 3392, 1591.<br>MS: m/z (CI) 462 (M+1, 100%). |
| 36 | OCH$_3$ | Cl | OCH$_3$ | CH$_2$COOEt | M.P.: 118-120° C.<br>$^1$H NMR (200 MHz, DMSO-d$_6$): δ 9.52(s, 1H), 8.12(d, J=8.7 Hz, 2H), 7.89(s, 1H), 7.64(d, J=8.8 Hz, 1H), 7.45(m, 1H); 7.11-7.05(m, 2H), 6.88(s, 1H), 5.01(s, 2H), 4.13(q, J=7.3 Hz, 2H), 3.84(s, 3H), 3.80(s, 3H), 1.17(t, J=6.8 Hz, 3H).<br>IR (KBr, cm$^{-1}$): 3402, 1750, 1677.<br>MS: m/z (CI) 444 (M+1, 100%). |

Example 37

Synthesis of [2-(3-chloro-4-methoxyphenylamino)-6-(4-methoxyphenyl)pyrimidin-4-yloxy]acetic acid

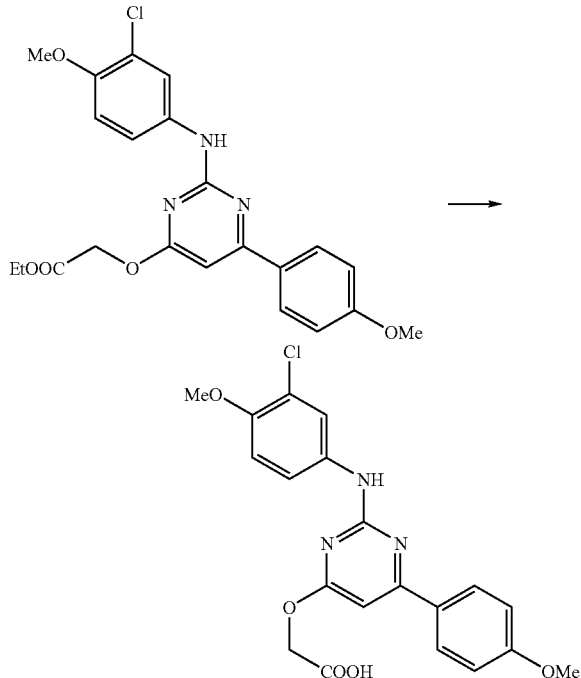

To a solution of [2-(3-chloro-4-methoxyphenylamino)-6-(4-methoxyphenyl)pyrimidin-4-yloxy]acetic acid ethyl ester (0.15 g, 0.33 mmol) in MeOH (5 mL) was added aqueous NaOH (prepared by adding NaOH in 2 mL of water) and the mixture was stirred for 3 hours at refluxing temperature. The mixture was then cooled to temperature in the range of 20-40° C., concentrated under vacuum, diluted with water (5 mL) and washed with ethyl acetate (2 x 2 mL). The aqueous layer was neutralized with 2N HCl. The solid precipitated was filtered off and dried to give the desired compound.

M.P.: 258-260° C.

$^1$H NMR (200 MHz, DMSO-$d_6$): δ 9.45 (s, 1H), 8.09 (d, J=8.5 Hz, 2H), 7.90 (s, 1H), 7.72 (d, J=8.8 Hz, 1H), 7.08-7.03 (m, 3H), 6.79 (s, 1H), 4.82 (s, 2H), 3.83 (s, 3H), 3.80 (s, 3H).

IR (KBr, cm$^{-1}$): 3412, 1701, 1578.

MS: m/z (CI) 416 (M+1, 36%).

Example 38

Synthesis of 4-(3-chloro-4-methoxy-phenyl)-6-phenyl-pyrimidin-2-yl amine

Step (i). Synthesis of 3-(3-chloro-4-methoxy-phenyl)-1-phenyl-prop-2-yn-1-ol

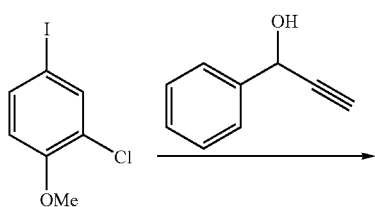

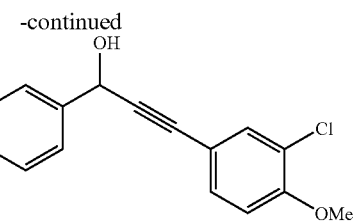

To a stirring mixture of 3-chloro-4-methoxyiodobenzene (0.3 g, 1.1 mmol), (PPh$_3$)$_2$PdCl$_2$ (31 mg, 0.044 mmol), triethylamine (1.2 mL, 8.9 mmol) in dimethylformamide (3 mL) was added to phenylethynylcarbinol (0.29 g, 2.2 mmol) at temperature in the range of 20-40° C. under nitrogen atmosphere. The mixture was then stirred at 80° C. for 12 hours. After cooling the mixture to temperature in the range of 20-40° C. it was diluted with water (15 mL) and extracted with ethyl acetate (3×25 mL). The organic layers were collected, combined, washed with water (2×5 mL), dried over anhydrous sodium sulphate, and concentrated to give the desired compound.

$^1$H NMR (200 MHz, DMSO-$d_6$): δ 7.61-7.31 (m, 7H), 6.85 (d, J=8.7 Hz, 1H), 5.66 (d, J=4.2 Hz, 1H), 3.90 (s, 3H).

IR (KBr, cm$^{-1}$): 3377, 2226, 1598.

MS: m/z (CI) 272 (M$^+$, 100%).

Step (ii). Synthesis of 3-(3-chloro-4-methoxy-phenyl)-1-phenyl-propynone

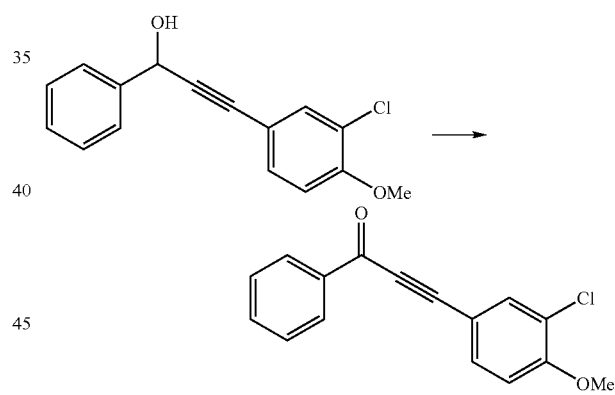

To a solution of compound, 3-(3-chloro-4-methoxy-phenyl)-1-phenyl-prop-2-yn-1-ol, (0.2 g, 0.73 mmol) in acetone (5 mL) was added freshly prepared chromic acid (H$_2$CrO$_4$) drop wise at 20° C. until appearance of precipitate was stopped. The duration of addition was 5 minutes. The mixture was then diluted with water (10 mL) and extracted with ethyl acetate (3×15 mL). The organic layers were collected, combined, washed with water (2×5 mL), dried over anhydrous sodium sulphate, and concentrated to give the desired compound.

$^1$H NMR (200 MHz, DMSO-$d_6$): δ 8 8.19 (d, J=7.0 Hz, 2H), 7.72-7.56 (m, 5H), 6.96 (d, J=8.4 Hz, 1H), 3.96 (s, 3H).

IR (KBr, cm$^{-1}$): 2190, 1632, 1595.

MS: m/z (CI) 272 (M+1, 100%).

Reference: For the synthesis of β-aryl substituted conjugated acetylenic ketones via Pd-catalyzed catalyzed reaction, see: Kundu, N. G.; Pal, M.; Chowdhury, C. *J. Chem. Res., Synop.,* 1995, 4-5.

Step (iii). Synthesis of 4-(3-chloro-4-methoxy-phenyl)-6-phenyl-pyrimidin-2-yl amine

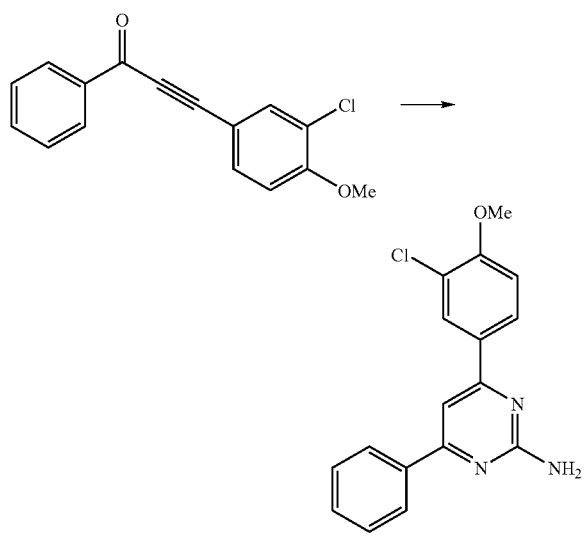

A mixture of compound, 3-(3-chloro-4-methoxy-phenyl)-1-phenyl-propynone (0.15 g, 0.55 mmol) and guanidium carbonate in dimethylformamide (5 mL) was stirred at 80° C. for 12 hours. The mixture was then diluted with water (25 mL) and extracted with ethyl acetate (3×15 mL). The organic layers were collected, combined, washed with water (2×10 mL), dried over anhydrous sodium sulphate, and concentrated. The residue thus obtained was purified by column chromatography using ethyl acetate-petroleum ether to give the desired product.

M.P.: 164-166° C.
$^1$H NMR (400 MHz, DMSO-$d_6$): δ 8.14-8.13 (m, 1H), 8.05-7.95 (m, 3H), 7.50-7.47 (m, 3H), 7.39 (s, 1H), 7.02 (d, J=8.7 Hz, 1H), 5.14 ($D_2O$ exchangeable, 2H), 3.97 (s, 3H).
IR (KBr, cm$^{-1}$): 3487, 1635, 1507.
MS: m/z (CI) 312 (M$^+$, 100).

Example 39

Synthesis of 1-[4-(3-chloro-4-methoxy-phenylamino)-6-phenyl-pyrimidin-2-yl]-piperidin-4-ol

Step (i). Synthesis of 6-phenyl-pyrimidine-2,4-diol

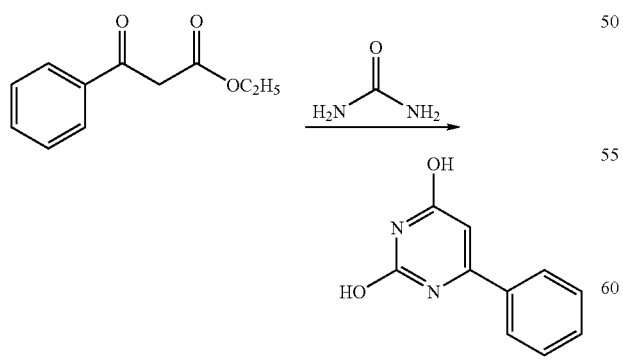

A mixture of 3-oxo-3-phenylpropionic acid ethyl ester (20 g, 104.05 mmol) and urea (6.24 g, 104.05 mmol) was reacted in a microwave irradiation for 3 minutes. The mixture was cooled to temperature in the range of 20-40° C. and diluted with ethyl alcohol (100 mL). The solid precipitated was filtered, washed with hexane (2×20 mL) to afford the desired compound as a yellow solid.

M.P.: 195-200° C.
$^1$H NMR (400 MHz, DMSO-$d_6$): δ 7.98 (br s, 1H), 7.94 (br s, 1H), 7.83 (d, J=8.7 Hz, 2H), 7.56 (d, J=10 Hz, 2H), 7.43 (s, 1H), 5.88 (s, 1H).
IR (KBr, cm$^{-1}$): 3325, 1621.
MS: m/z (CI) 189 (M$^+$, 100).

Step (ii). Synthesis of 2,4-dichloro-6-phenyl-pyrimidine

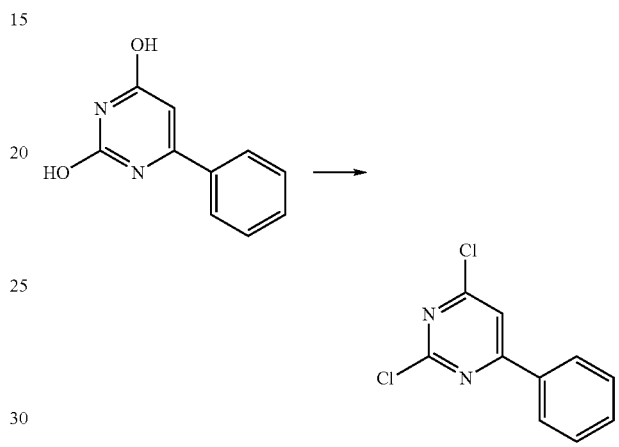

A mixture of compound, 6-phenyl-pyrimidine-2,4-diol (11 g, 58.5 mmol) and phosphorus oxychloride (100 mL) was refluxed for 10 hours under anhydrous condition. Excess of phosphorus oxychloride was removed by distillation and the residue was treated with cold water (100-150 mL). The solid precipitated was filtered, washed with water, and dried under vacuum to give the desired compound (10 g) as a brown solid.

M.P.: 80-85° C.
$^1$H NMR (400 MHz, DMSO-$d_6$): δ 8.07 (d, J=7.9 Hz, 2H), 7.68 (s, 1H), 7.61 (s, 1H), 7.54 (d, J=7.3 Hz, 2H).
IR (KBr, cm$^{-1}$): 3442, 1560.
MS: m/z (CD) 225 (M$^+$, 100).

Step (iii). Synthesis of 1-(4-chloro-6-phenyl-pyrimidin-2-yl)-piperidin-4-ol and 1-(2-chloro-6-phenyl-pyrimidin-4-yl)-piperidin-4-ol

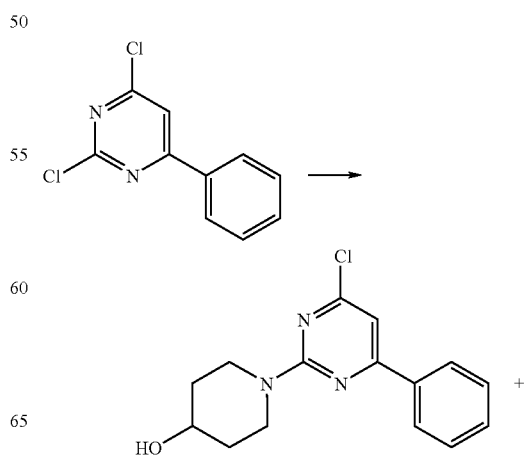

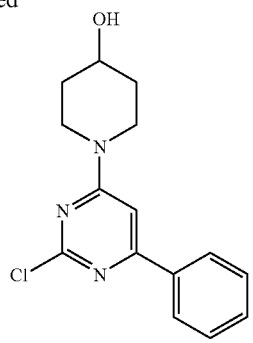

A mixture of compound, 2,4-dichloro-6-phenyl-pyrimidine (13 g, 57.77 mmol), piperidin-4-ol (2.9 g, 28.88 mmol) and triethylamine (32.14 mL, 231.11 mmol) in butanol (110 mL) was stirred at 120° C. for 12 hours under nitrogen atmosphere. The reaction mixture was then poured into water (250 mL) and extracted with ethyl acetate (3×50 mL). The organic layers were collected, combined, washed with water (50 mL), dried over anhydrous sodium sulphate, and concentrated under vacuum. The residue thus obtained was purified by column chromatography using ethyl acetate-petroleum ether to give the two compounds, 1-(4-chloro-6-phenyl-pyrimidin-2-yl)-piperidin-4-ol and 1-(2-chloro-6-phenyl-pyrimidin-4-yl)-piperidin-4-ol in ratio 1:4 (overall yield: 51%).

Spectral data for 1-(4-chloro-6-phenyl-pyrimidin-2-yl)-piperidin-4-ol

M.P.: 105-110° C.
$^1$H NMR (400 MHz, DMSO-$d_6$): δ 8.03-8.0 (m, 2H), 7.56-7.43 (m, 3H), 6.92 (s, 1H), 4.67 (br s, 1H), 4.52-4.0 (m, 2H), 4.02-3.98 (m, 1H), 3.48-3.41 (m, 2H), 2.16-1.96 (m, 2H), 1.59-1.50 (m, 2H).
IR (KBr, cm$^{-1}$): 3327, 1564.
MS: m/z (CD) 290 (M$^+$, 100).

Spectral data for 1-(2-Chloro-6-phenyl-pyrimidin-4-yl)-piperidin-4-ol

M.P.: 120-125° C.
$^1$H NMR (400 MHz, DMSO-$d_6$): δ 7.96-7.92 (m, 2H), 7.48-7.42 (m, 3H), 6.78 (s, 1H), 4.21-4.10 (m, 2H), 4.08-4.0 (m, 1H), 3.49-3.41 (m, 2H), 1.99-1.94 (m, 2H), 1.66-1.57 (m, 2H).
IR (KBr, cm$^{-1}$): 3377, 1591.
MS: m/z (CI) 290 (M$^+$, 100).

Step (iv). Synthesis of 1-[4-(3-chloro-4-methoxy-phenylamino)-6-phenyl-pyrimidin-2-yl]-piperidin-4-ol

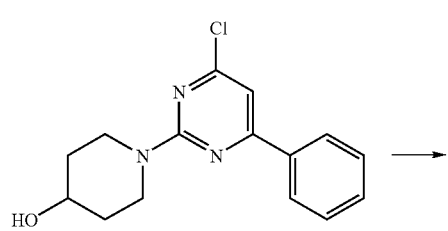

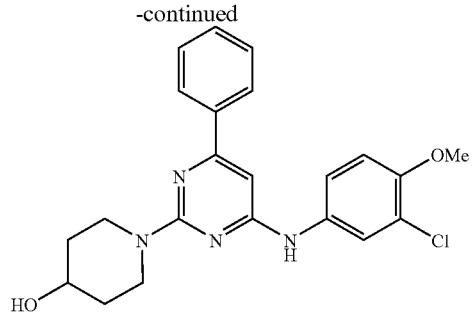

A mixture of compound, 1-(4-chloro-6-phenyl-pyrimidin-2-yl)-piperidin-4-ol (3.97 g, 13.7 mmol), 3-chloro-4-methoxyaniline (2.13 g, 13.7 mmol) in 1-butanol (30 mL) was stirred at 120° C. for 12 hours. The mixture was then cooled to temperature in the range of 20-40° C. The solid precipitated was filtered, collected, stirred in isopropanol (10 mL), filtered, and dried to give the desired compound as a white solid.
M.P.: 188-191° C.
$^1$H NMR (200 MHz, DMSO-$d_6$): δ 9.32 (s, 1H), 7.96 (d, J=2.8 Hz, 3H), 7.49-7.47 (m, 4H), 7.15 (d, J=9.3 Hz, 1H), 6.44 (s, 1H), 4.70 (br s, 1H), 4.39-4.33 (m, 2H), 3.82-3.74 (m, 5H), 1.83-1.80 (m, 2H), 1.39-1.36 (m, 2H).
IR (KBr, cm$^{-1}$): 3549, 3272, 2930, 1605.
MS: m/z (CI) 411 (M+1, 100%).

Examples 40-47

Synthesis of Substituted Pyrimidine Compounds

Scheme 5

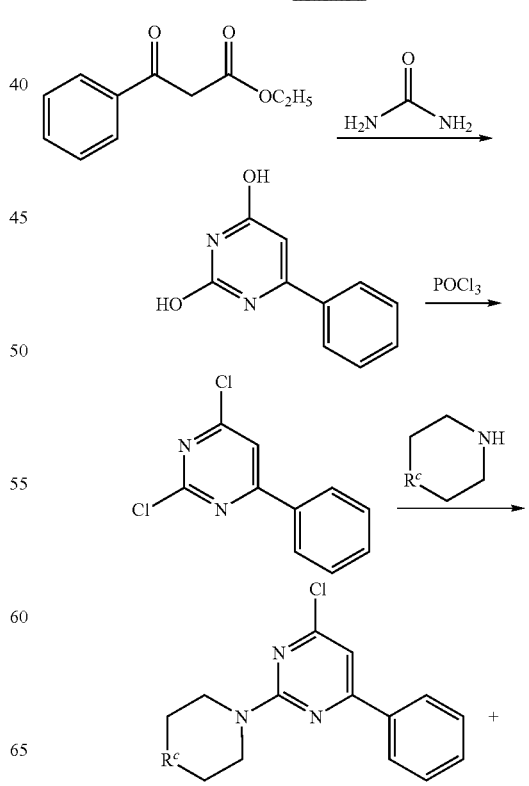

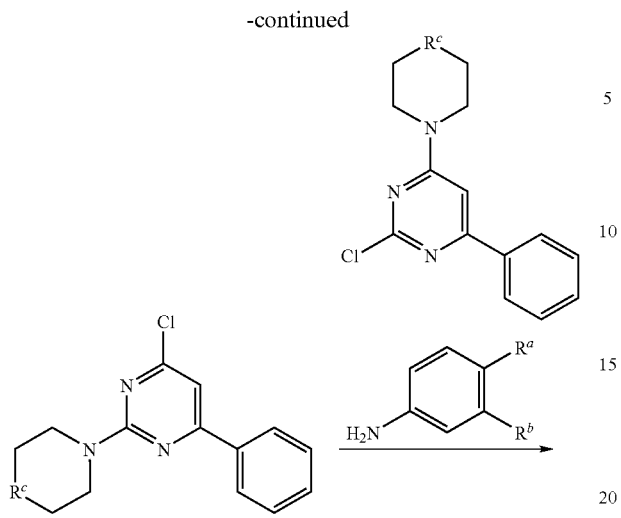

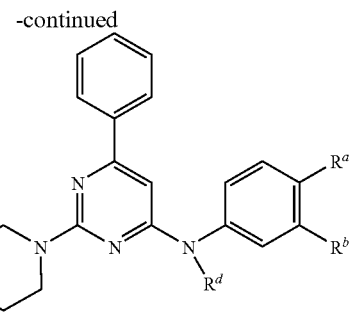

The following compounds presented in Examples 40-47 were prepared in accordance with Scheme 5, by a procedure analogous to that disclosed in Example 39, using starting materials with the appropriate substitution.

| Ex No. | $R^a$ | $R^b$ | $R^c$ | $R^d$ | Analytical data |
|---|---|---|---|---|---|
| 40 | OCH$_3$ | F | C—OH | H | M.P.: 234-236° C.<br>$^1$H NMR (400 MHz, DMSO-d$_6$): δ 10.4(br s, 1H, NH, 7.85(s, 2H), 7.67(d, J=14.0 Hz, 2H), 7.57 (s, 2H), 7.37(d, J=8.6 Hz, 1H), 7.21(t, J=9.1 Hz, 1H), 6.49(s, 1H), 4.18(m, 2H), 3.83-3.76(m, 5H), 3.39-3.36(m, 2H), 1.86-1.84(m, 2H), 1.46-1.44 (m, 2H).<br>IR (KBr, cm$^{-1}$): 3317, 1644, 1608.<br>MS: m/z (CI) 395 (M+1, 100%). |
| 41 | H | H | C—OH | CH$_3$ | DSC: 123.04° C.<br>$^1$H NMR (400 MHz, DMSO-d$_6$): δ 7.82-7.78(m, 2H), 7.50-7.30(m, 8H), 6.08(s, 1H), 4.67(s, 1H, D$_2$O exchangeable), 4.41-4.38(m, 2H), 3.73(q, J= 4.9 Hz, 1H), 3.32(s, 3H), 3.28-3.21(m, 2H), 1.82-1.78(m, 2H), 1.41-1.32(m, 2H).<br>I.R(cm$^{-1}$): 3350, 1630, 1554.<br>MS: m/z (CI) 361 (M$^+$, 100%). |
| 42 | H | CF$_3$ | C—OH | H | M.P.: 256-258° C.<br>$^1$H NMR (400 MHz, DMSO-d$_6$) δ 8.47(s, 1H), 7.89-7.87(t, J=3.8, 2H), 7.76-7.74(d, J=8.1, 1H), 7.62-7.60(d, J=8.0, 1H), 7.57-7.55(m, 3H), 7.42-7.40(d, J=7.5, 1H), 6.63(s, 1H), 4.24-4.20 (m, 2H), 3.82-3.79(m, 1H), 3.55-3.47(m, 2H), 1.87-1.82(m, 2H), 1.49-1.42(m, 2H).<br>I.R (cm$^{-1}$): 3397, 2928, 1641, 1573, 1069.<br>MS: m/z 415 (M$^+$+1, 100%), |
| 43 | Cl | CF$_3$ | C—OH | H | M.P.: 260-262° C.<br>$^1$H NMR (400 MHz, DMSO-d$_6$) δ 8.60(s, 1H), 7.97-7.95(d, J=7.8 Hz, 1H), 7.71-7.69(d, J=7.3 Hz, 2H), 7.58-7.44(m, 4H), 7.16(s, 1H), 4.16-4.04 (m, 2H), 4.02-4.00(m, 1H), 3.75-3.70(m, 2H), 2.00-1.95(m, 2H), 1.76-1.68(m, 2H).<br>I.R (cm$^{-1}$): 3385, 2932, 1639, 1435.<br>MS: m/z 449 (M$^+$+1, 100%), |
| 44 | —O⌐⌐O— (dioxolane) | | C—OH | H | M.P.: 255-260° C.<br>$^1$H NMR (400 MHz, DMSO-d$_6$), δ 10.57(br s, 1H), 7.83(s, 2H), 7.57(s, 3H), 7.37(s, 1H), 7.033(s, 1H), 6.94(s, 1H), 6.47(s, 1H), 6.03(s, 2H), 4.17(s, 2H), 3.79-3.72(m, 1H), 3.39(s, 2H), 1.87-1.82(m, 2H), 1.46-1.44(m, 2H)<br>I.R (cm$^{-1}$): 3349, 1644, 1496<br>MS: m/z 3391 (M$^+$+1, 100%) |

-continued

| Ex No. | $R^a$ | $R^b$ | $R^c$ | $R^d$ | Analytical data |
|---|---|---|---|---|---|
| 45 | CF$_3$ | H | C—OH | H | M.P. >250° C.<br>$^1$H NMR (400 MHz, DMSO-d$_6$) δ 10.31(br s, 1H), 7.92-7.90(d, J=8.6 Hz, 4H), 7.72-7.70(d, J=8.6 Hz, 2H), 7.55-7.54(m, 3H), 6.61(s, 1H), 4.30-4.27 (m, 2H), 3.78-3.75(m, 1H), 3.44-3.39(m, 2H), 1.87-1.85(m, 2H), 1.47-1.43(m, 2H).<br>I.R (cm$^{-1}$): 3414, 2931, 1602, 1325.<br>MS: m/z 415 (M$^+$+1, 100%), |
| 46 | H | CF$_3$ | O | H | M.P.: 262-265° C.<br>$^1$H NMR (400 MHz, DMSO-d$_6$), δ 10.56(br s, 1H), 8.37(s, 1H), 7.93-7.92(t, J=5.0 Hz, 2H), 7.83-7.81(d, J=7.5 Hz, 1H), 7.58-7.52(m, 4H), 7.38-7.37(s, 1H), 6.71(s, 1H), 3.81-3.79(t, J=5.5 Hz, 4H), 3.73-3.71(t, J=4.5 Hz, 4H).<br>I.R (cm$^{-1}$): 3343, 1643, 1576, 1540<br>MS: m/z 4401 (M$^+$+1, 100%) |
| 47 | OCF$_3$ | H | C—OH | H | M.P.: 226-228° C.<br>$^1$H NMR (400 MHz, DMSO-d$_6$) δ 7.89-7.79(m, 4H), 7.56-7.37(m, 5H), 6.56(s, 1H), 4.32-4.22(m, 2H), 3.80-3.78(m, 1H), 3.43-3.39(m, 2H), 1.86-1.84(m, 2H), 1.45-1.43(m, 2H).<br>I.R: 3390, 1642, 1257.<br>MS: m/z 430 (M$^+$+1, 100%). |

Example 48

Synthesis of 1-[2-(3-chloro-4-methoxy-phenylamino)-6-phenyl-pyrimidine-4-yl]-piperidin-4-ol

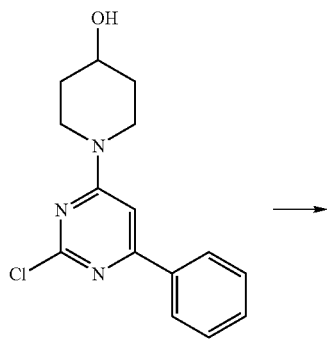

A mixture of compound 1-(2-chloro-6-phenyl-pyrimidin-4-yl)-piperidin-4-ol (3.97 g, 13.7 mmol), 3-chloro-4-methoxyaniline (2.13 g, 13.7 mmol) in butanol (30 mL) was stirred at 120° C. for 12 hours. The mixture was then cooled to temperature in the range of 20-40° C. The solid precipitated was filtered, collected, stirred in isopropanol (10 mL), filtered, and dried to give the desired compound as a white solid. Yield: 48%.

M.P.: 220-240° C.

$^1$H NMR (200 MHz,DMSO-d$_6$): δ 10.42 (s,1H), 8.06 (d, J=2.5 Hz, 2H), 7.80 (d, J=2.5 Hz, 1H), 7.63 (d, J=6.7 Hz, 3H), 7.48 (m,1H), 7.22 (d, J=9 Hz, 1H), 7.02 (s, 1H), 4.12-3.60 (m, 9H), 1.84-1.23 (m, 4H).

IR (KBr, cm$^{-1}$): 3405, 2941, 1634, 1542.

MS: m/z (CI) 411 (M+1, 100%).

Example 49

Synthesis of (4-morpholin-4-yl-6-phenyl-pyrimidin-2-yl)-(4-trifluoromethoxy-phenyl)-amine

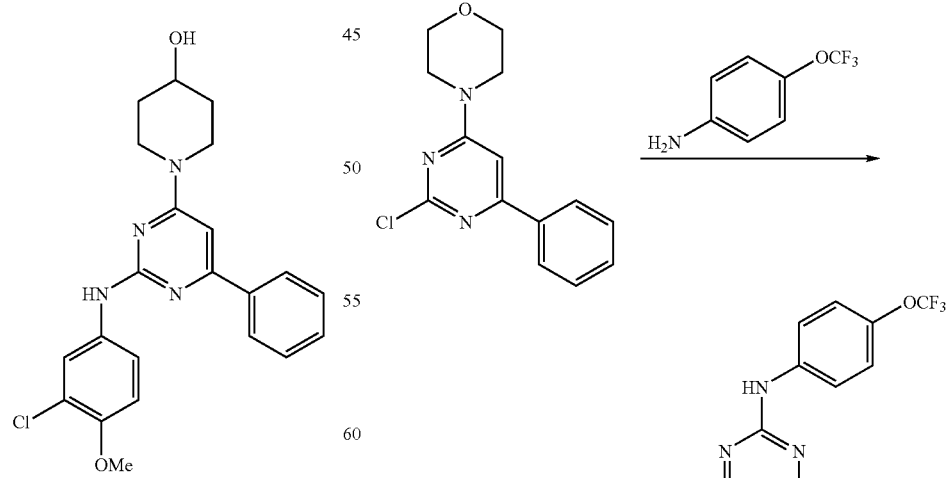

A sample of (4-morpholin-4-yl-6-phenyl-pyrimidin-2-yl)-(4-trifluoromethoxy-phenyl)-amine was prepared from 4-(2-chloro-6-phenyl-pyrimidin-4-yl)-morpholine (0.3 g, 1.04 mmol) and 4-trifluoromethoxy phenylamine (0.14 mL, 1.04 mmol) according to a procedure analogous to that described above in Example 48.

M.P.: 260-262° C.

$^1$H NMR (400 MHz, DMSO-$d_6$): δ 10.76 (br s,1H), 8.35-8.34 (d, J=5 Hz, 1H) 8.13-8.11 (dd, J=1.61, 1.81 Hz, 2H), 7.88-7.86 (d, J=9 Hz, 2H), 7.7-7.64 (m, 2H), 7.63-75.8 (m, 2H), 7.02 (s,1H), 6.99 (s, 1H), 3.90-3.82 (m, 4H), 3.77-3.74 (t, J=5 Hz, 4H).

IR (cm$^{-1}$): 3330, 1615, 1510

MS: m/z 417 (M+,100%)

Example 50

Synthesis of 4-[4-(4-hydroxy-piperidin-1-yl)-6-phenyl-pyrimidin-2-ylamino]-N-methyl-benzene-sulfonamide

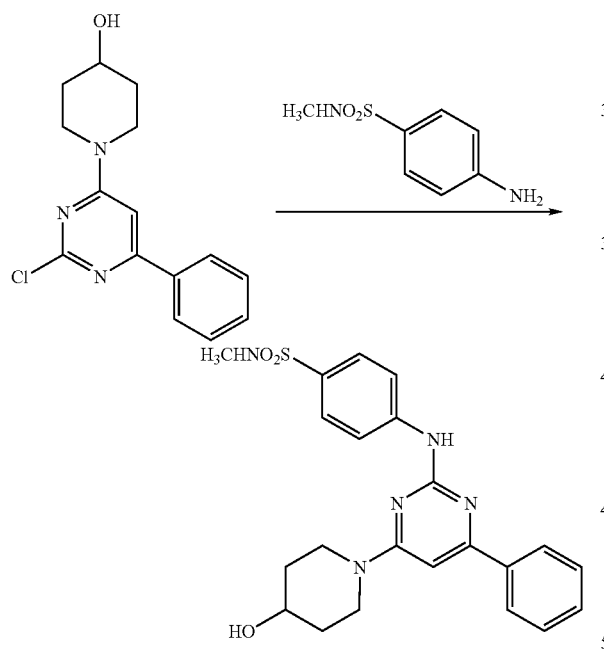

A sample of 4-[4-(4-hydroxy-piperidin-1-yl)-6-phenyl-pyrimidin-2-ylamino]-N-methyl-benzenesulfonamide was prepared from compound 1-(2-chloro-6-phenyl-pyrimidin-4-yl)-piperidin-4-ol (0.5 g, 1.74 mmol) and 4-amino-N-methyl-benzenesulfonamide (0.39 g, 1.74 mmol) according to a procedure analogous to that described above in Example 48.

M.P.: 280-285° C.

$^1$H NMR (400 MHz, DMSO-$d_6$): δ 10.97 (br s, 1H), 8.14-8.09 (m, 2H) 7.86-7.66 (m, 4H), 7.65-7.58 (m, 3H), 7.07 (s, 1H), 4.20-4.16 (t, J=5.0 Hz, 2H), 3.89-3.84 (m, 1H), 3.65-3.38 (m, 2H), 2.47 (s, 3H), 1.91-1.86 (m, 2H), 1.55-1.46 (m, 2H).

IR (cm$^{-1}$): 3324, 1635, 1589, 1546.

MS: m/z 441 (M$^+$+1,100%)

Example 51

Synthesis of 1-{4-[4-(4-hydroxy-piperidin-1-yl)-6-phenyl-pyrimidin-2-ylamino]-phenyl}-ethanone hydrochloride

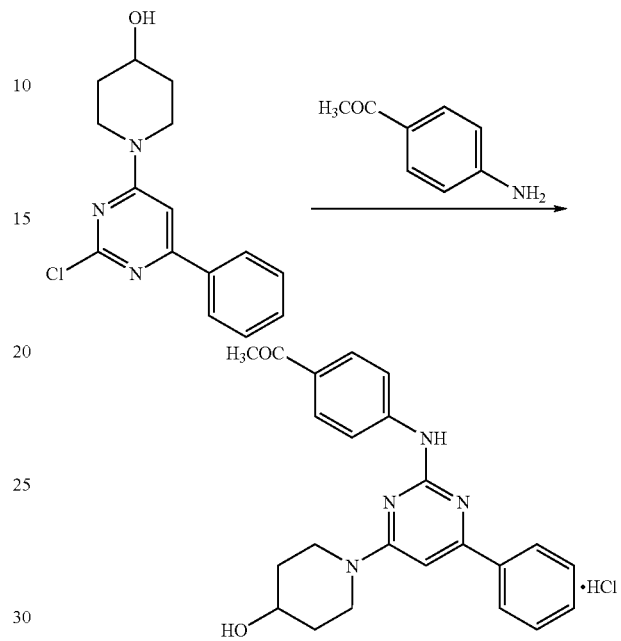

A sample of 1-{4-[4-(4-hydroxy-piperidin-1-yl)-6-phenyl-pyrimidin-2-ylamino]-phenyl}-ethanone hydrochloride was prepared from compound 1-(2-chloro-6-phenyl-pyrimidin-4-yl)-piperidin-4-ol (0.3 g, 1.04 mmol) and 1-(4-amino-phenyl)-ethanone (0.14 g, 1.04 mmol) according to a procedure analogous to that described above in Example 48.

M.P.: 292-294° C.

$^1$H NMR (400 MHz, DMSO-$d_6$): δ 10.7 (br s, 1H), 8.13-8.10 (dd, J=1.9, 1.7 Hz, 2H), 8.02-7.99 (d, J=8 Hz, 2H), 7.81-7.79 (d, J=9 Hz, 2H), 7.61-7.58 (m, 3H), 7.07 (s,1H), 4.20-4.17 (t, J=5.0 Hz, 2H), 3.88-3.84 (m, 1H), 3.63-3.58 (m, 2H), 2.53 (s, 3H), 1.90-1.87 (m, 2H), 1.54-1.46 (m, 2H).

IR: 3376, 1634, 1591

MS: m/z 389 (M$^+$+1, 100%)

Examples 52-92

Synthesis of Substituted Pyrimidine Compounds

Scheme 6

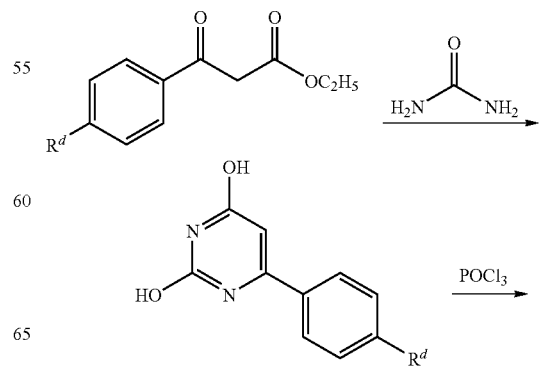

-continued

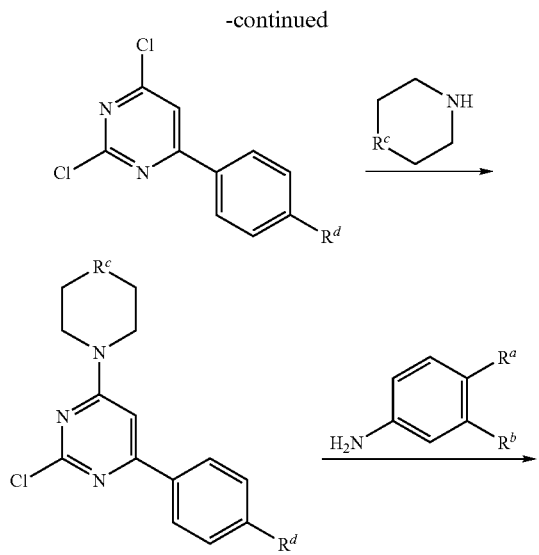

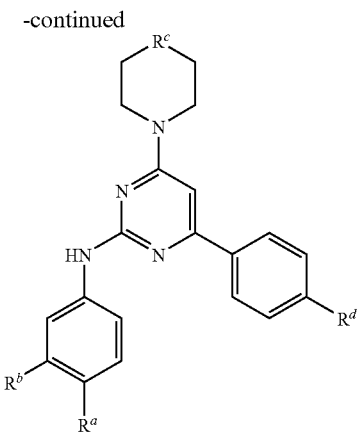

The following compounds presented in Examples 52-92 were prepared in accordance with Scheme 6, by a procedure analogous to that disclosed in Examples 39 and 48, using starting materials with the appropriate substitution.

| Ex. No. | $R^a$ | $R^b$ | $R^c$ | $R^d$ | Analytical data |
|---|---|---|---|---|---|
| 52 | OH | Cl | C—OH | H | M.P.: 265-267° C.<br>$^1$H NMR (400 MHz, DMSO-$d_6$): δ 10.06(br s, 2H), 8.02(t, J=4.2 Hz, 2H), 7.72(s, 1H), 7.64-7.58(m, 3H), 7.28-7.25(m, 1H), 6.98 (d, J=9 Hz, 2H), 4.14-4.11(m, 3H), 3.86-3.82(m, 1H), 3.56(t, J=10 Hz, 2H), 1.87-1.83(m, 2H), 1.49-1.23(m, 2H).<br>IR (KBr, cm$^{-1}$): 3422, 3226, 1635, 1545.<br>MS: m/z (CI) 397 (M+1, 100%). |
| 53 | OCH$_3$ | F | C—OH | H | M.P.: 260-262° C.<br>$^1$H NMR (400 MHz, DMSO-$d_6$): δ 10.08(br s, 1H, NH), 8.05-8.03(m, 2H), 7.61-7.58 (m, 4H), 7.31(d, 1H), 7.21-7.17(t, J=8.2 Hz, 1H), 6.99(s, 1H), 4.15-4.02(m, 3H), 3.86-3.83(s, 4H), 3.56(t, J=10 Hz, 2H), 1.87-1.84(m, 2H), 1.47-1.43(m, 2H).<br>IR (KBr, cm$^{-1}$): 3388, 1628, 1579.<br>MS: m/z (CI) 395 (M+1, 100%). |
| 54 | H | H | C—OH | H | M.P.: 288-290° C.<br>$^1$H NMR (400 MHz, DMSO-$d_6$): δ 10.65 (NH, D$_2$O exchang), 8.10(t, J=8.1 Hz, 2H), 7.67-7.59(m, 5H), 7.41(t, J=7.8 Hz, 2H), 7.14(t, J=7.3 Hz, 1H), 7.04(s, 1H), 4.16(t, J=7.5 Hz, 2H), 3.88-3.84(m, 1H), 3.65(t, J=5.6 Hz, 2H), 1.89-1.84(m, 2H), 1.52-1.56(m, 2H).<br>IR (KBr, cm$^{-1}$): 3362, 1636, 1544.<br>MS: m/z (CI) 347 (M+1, 100%). |
| 55 | OCH$_3$ | Cl | S | H | M.P.: 282-284° C.<br>$^1$H NMR (400 MHz, DMSO-$d_6$): δ 10.2 (br s, 1H), 8.09-8.06(m, 2H), 7.79(s, 1H), 7.64-7.57(m, 3H), 7.48-7.45(m, 1H), 7.17 (d, J=9.0 Hz, 1H), 7.0(s, 1H), 4.14-4.11 (m, 4H), 3.85(s, 3H), 2.76-3.74(m, 4H).<br>IR (KBr, cm$^{-1}$): 3445, 2919, 1638.<br>MS: m/z (CI) 413 (M+1, 100%). |
| 56 | | ↘O⌐⌐O↗ | S | H | M.P.: 276-277° C.<br>$^1$H NMR (400 MHz, DMSO-$d_6$): δ 10.2(br s, 1H), 8.06(d, J=7.0 Hz, 2H), 7.63-7.58 (m, 4H), 7.27(s, 1H), 6.99-6.91(m, 2H), 6.03(s, 2H), 4.14-4.11(m, 4H), 2.75-3.73 (m, 4H).<br>IR (KBr, cm$^{-1}$): 3450, 2884, 1635.<br>MS: m/z (CI) 393 (M+1, 100%). |

-continued

| Ex. No. | R$^a$ | R$^b$ | R$^c$ | R$^d$ | Analytical data |
|---|---|---|---|---|---|
| 57 | OCH$_3$ | F | S | H | M.P.: 261-262° C.<br>$^1$H NMR (400 MHz, DMSO-d$_6$): δ 9.98(br s, 1H), 8.06(dd, J=2.0, 2.4 Hz, 2H), 7.60-7.58(d, J=7.0 Hz, 4H), 7.34-7.32(d, J=9.0 Hz, 1H), 7.14-7.12(t, J=9.0 Hz, 1H), 6.97(s, 1H), 4.12-4.10(t, J=5.0 Hz, 4H), 3.83(s, 3H), 2.74-2.73(d, J=5.0 Hz, 4H).<br>IR (KBr, cm$^{-1}$): 3434, 2933, 1633.<br>MS: m/z (CI) 399 (M+1, 100%). |
| 58 | OH | Cl | S | H | M.P.: 265-268° C.<br>$^1$H NMR (400 MHz, DMSO-d$_6$): δ 10.2(br s, 1H), 10.1(br s, 1H), 8.07(dd, J=2.0, 1.65 Hz, 2H), 7.66-7.58(m, 4H), 7.28-7.25(m, 1H), 6.99(d, J=8.0 Hz, 2H), 4.14-4.12(m, 4H), 2.76-2.73(m, 4H).<br>IR (KBr, cm$^{-1}$): 3443, 2924, 1636.<br>MS: m/z (CI) 399 (M+1, 100%). |
| 59 | OCH$_3$ | Cl | O | H | M.P.: 278-280° C.<br>$^1$H NMR (400 MHz, DMSO-d$_6$) δ 10.06(br s, 1H), 8.04(dd, J=3.0, 2.6 Hz, 2H), 7.79 (s, 1H), 7.61-7.57(m, 3H), 7.56-7.54(m, 1H), 7.19-7.16(br s, 1H), 6.98(s, 1H), 3.85 (s, 3H), 3.85-3.81(m, 4H), 3.73(t, J=4 Hz, 4H).<br>IR (KBr, cm$^{-1}$): 3440, 1590, 1496.<br>MS: m/z (CI) 397 (M+1, 100%). |
| 60 |  | | O | H | M.P.: 275-276° C.<br>$^1$H NMR (400 MHz, DMSO-d$_6$): δ 10.0(br s, 1H), 8.04(t, J=5.0 Hz, 2H), 7.61-7.51(m, 3H), 7.31(s, 1H), 7.0(d, J=7.0 Hz, 1H), 6.93(t, J=9.0 Hz, 2H), 6.02(s, 2H), 3.81 (s, 4H), 3.72(t, J=5.0 Hz, 4H).<br>IR (KBr, cm$^{-1}$): 2958, 1631, 1537.<br>MS: m/z (CI) 377 (M+1, 100%). |
| 61 | OCH$_3$ | F | O | H | M.P.: 265-266° C.<br>$^1$H NMR (400 MHz, DMSO-d$_6$) δ 10.28(br s, 1H), 8.09-8.07(m, 2H), 7.64-7.54(m, 4H), 7.32(d, J=8.0 Hz, 1H), 7.19(t, J=9.0 Hz, 1H), 6.98(s, 1H), 3.83(s, 3H), 3.83 (s, 4H), 3.73(t, J=5.0 Hz, 4H).<br>IR (KBr, cm$^{-1}$): 2964, 1627, 1518.<br>MS: m/z (CI) 381 (M+1, 100%). |
| 62 | OH | Cl | O | H | M.P.: 280-285° C.<br>s, 2H), 8.06-8.04(m, 2H), 7.61(s, 1H), 7.59 (d, J=5.0 Hz, 3H), 7.32(dd, J=2.5, 2.4 Hz, 1H), 6.97(t, J=7.0 Hz, 2H0, 3.82(d, J=4.0 Hz, 4H), 3.72(t, J=5.0 Hz, 4H).<br>IR (KBr, cm$^{-1}$): 3070, 2962, 1633.<br>MS: m/z (CI) 383 (M+1, 100%). |
| 63 | H | CF$_3$ | C—OH | H | M.P.: 278-280° C.<br>$^1$H NMR (400 MHz, DMSO-d$_6$) δ 10.65(br s, 1H), 8.34(s, 1H), 8.11-8.10(m, 3H), 7.70-7.57(m, 5H), 7.45-7.43(d, J=7.79, 1H), 7.06(s, 1H), 4.17-4.13(t, J=9.13, 2H), 3.89-3.84(m, 1H), 3.62-3.57(t, J=9.40, 2H), 1.87-1.84(m, 2H), 1.53-1.50(m, 2H).<br>IR: 3356, 2928, 1638, 1548.<br>MS: m/z 415 (M$^+$+1, 100%). |
| 64 |  | | O | F | M.P.: 264-266° C.<br>$^1$H NMR (400 MHz, DMSO-d$_6$) 9.91(br s, 1H), 8.15-8.11(m, 2H), 7.46-7.42(m, 2H), 7.31(s, 1H), 7.02-7.00(m, 1H), 6.92-6.81(m, 2H), 6.01(s, 2H), 3.80-3.68(m, 8H).<br>IR: 3424, 1836, 1543<br>MS: m/z 395 (M$^+$+1, 100%) |

| Ex. No. | $R^a$ | $R^b$ | $R^c$ | $R^d$ | Analytical data |
|---|---|---|---|---|---|
| 65 |  | | C—OH | H | M.P.: 230-250° C.<br>$^1$H NMR (400 MHz, DMSO-$d_6$), δ 10.2(br s, 1H), 7.83(s, 2H), 7.57-7.56(d, J=7 Hz, 3H), 7.37(s, 1H), 7.03-7.01(d, J=7 Hz, 1H0, 6.94-6.92(d, J=8.0 Hz, 1H), 6.46(s, 1H), 6.03(s, 2H), 4.16(m, 2H), 3.80-3.50 (m, 1H), 3.38(m, 2H), 1.85-1.82(t, J=6 Hz, 2H), 1.46-1.44(d, J=8 Hz, 2H)<br>IR: 3369, 1634, 1488<br>MS: m/z 391 (M$^+$+1, 100%) |
| 66 | H | $CF_3$ | O | F | M.P.: 254-256° C.<br>$^1$H NMR (400 MHz, DMSO-$d_6$) δ 10.1(br s, 1H), 8.36(s, 1H), 8.21-8.17(m, 2H), 7.82-7.80(m, 1H), 7.55-7.52(m, 1H), 7.41-7.37(m, 2H), 7.34-7.30(m, 1H), 6.97(s, 1H), 3.78-3.71(m, 8H).<br>IR: 3445, 2971, 1642<br>MS: m/z 419 (M$^+$+1, 100%) |
| 67 | F | H | O | F | M.P.: 196-200° C.<br>$^1$H NMR (400 MHz, DMSO-$d_6$) δ 9.9 (br s, $D_2O$ exch, 1H), 8.15-8.12(m, 2H), 7.82-7.80(m, 2H), 7.64-7.63(m, 2H), 7.44(t, J=8.6 Hz, 2H), 6.94(s, 1H), 3.79-3.66(m, 8H)<br>IR: 3432, 2964, 1639<br>MS: m/z 369 (M$^+$, 100%) |
| 68 | Cl | $CF_3$ | C—OH | H | M.P.: 292-294° C.<br>$^1$H NMR (400 MMHz, DMSO-$d_6$) δ 10.96(br s, 1H), 8.47(s, 1H), 8.12-8.10(dd, J=1.3, 1.9 Hz, 2H), 7.73-7.57(m, 5H), 7.01(s, 1H), 4.16-4.12(m, 2H), 3.90-3.84(m 1H), 3.63-3.58(m, 2H), 1.88-1.83(m, 2H), 1.53-1.45(m, 2H).<br>IR: 3412, 2942, 1687, 1544.<br>MS: m/z 449 (M$^+$+1, 100%) |
| 69 | H | $CF_3$ | O | H | $^1$H NMR (400 MHz, DMSO-$d_6$), δ 10.25(br s, 1H), 8.27(s, 2H), 8.08-8.06(d, J=7.5 Hz, 2H), 7.79-7.77(d, J=8 Hz, 2H), 7.61-7.58 (m, 3H), 7.43-7.41(d, J=7.5 Hz, 1H), 7.02 (s, 1H), 3.86-3.81(m, 4H), 3.77-3.75(m, 4H).<br>IR: 3340, 1630, 1530<br>MS: m/z 401 (M$^+$+1, 100%) |
| 70 | $NHSO_2Me$ | H | C—OH | H | $^1$H NMR (400 MHz, DMSO-$d_6$) δ 10.15(br s, 1H), 9.64(br s, 1H), 8.06-8.04(dd, J=1.3, 1.9 Hz, 2H), 7.62-7.57(m, 5H), 7.25-7.23(m, 2H), 7.00(s, 1H), 4.13(m, 2H), 3.86-3.82(m, 1H), 3.57-3.43(m, 2H), 2.97 (s, 3H), 1.88-1.84(m, 2H), 1.50-1.44(m, 2H).<br>IR: 3102, 1632, 1580, 1510, 1155<br>MS: m/z 440 (M$^{+1}$, 100%). |
| 71 | $NHSO_2Me$ | H | O | H | M.P.: 261-263° C.<br>$^1$H NMR (400 MHz, DMSO-$d_6$), δ 10.56(br s, 1H), 9.7(br s, 1H), 8.15-8.13(dd, J=1.6, 1.6 Hz, 2H), 7.71-7.56(m, 3H), 7.41-7.09 (m, 2H), 7.30-7.28(d, J=9.0 Hz, 2H), 7.05 (s, 1H), 3.92-4.90(t, J=4 Hz, 4H), 3.79-3.77(t, J=3.0 Hz, 4H), 2.97(s, 3H).<br>IR: 3404, 1632, 1546<br>MS: m/z (1358, 100%) |
| 72 | $SO_2NMe_2$ | H | C—OH | F | $^1$H NMR (400 MHz, DMSO-$d_6$) δ 8.22-8.19 (m, 2H), 7.95(d, J=8.9 Hz, 2H), 7.74(d, J=8.6 Hz, 2H), 7.42(t, J=8.8 Hz, 2H), 7.03 (s, 1H), 4.19-4.05(m, 2H), 3.86-3.82(m, 1H), 3.55-3.50(m, 2H), 2.60(s, 6H), 1.88-1.85(m, 2H), 1.49-1.46(m, 2H)<br>IR: 3449.9, 1634.2<br>MS: m/z 472 (M$^+$+1, 100%). |

-continued

| Ex. No. | $R^a$ | $R^b$ | $R^c$ | $R^d$ | Analytical data |
|---|---|---|---|---|---|
| 73 | SO$_2$NH$_2$ | H | C—OH | F | $^1$H NMR (400 MHz, DMSO-d$_6$) 10.55(br s, —NH), 8.19(t, J=7.3 Hz, 2H), 7.84-7.82 (m, 4H), 7.44(t, J=8.3 Hz, 2H), 7.24(br s, —NH$_2$), 7.04(s, 1H), 4.18-4.05(m, 2H), 3.85-3.82(m, 1H), 3.56-3.52(m, 2H), 1.86-182(m, 2H), 1.49-1.46(m, 2H) IR: 3450.6, 1636.6 MS: m/z 443 (M$^+$+1, 100%) |
| 74 | SO$_2$NMe$_2$ | H | C—OH | H | M.P.: 280-285° C. $^1$H NMR (400 MHz, DMSO-d$_6$) δ 10.97 (NH, 1H), 8.14-8.09(m, 2H), 7.86-7.66(m, 4H), 7.65-7.58(m, 3H), 7.09(s, 1H), 4.20-4.16(t, J=5.0 Hz, 2H), 3.89-3.84(m, 1H), 3.65-3.38(m, 2H), 2.47(s, 6H), 1.91-1.86 (m, 2H), 1.55-1.46(m, 2H). IR: 3324, 1635.4, 1546 MS: m/z 440 (M$^+$+1, 100%) |
| 75 | SO$_2$NH$_2$ | H | C—OH | H | M.P.: 320° C. $^1$H NMR (400 MHz, DMSO-d$_6$) δ 10.67(br s, 1H), 8.11-8.10(d, J=7.5 Hz, 2H), 7.89-7.82(m, 3H), 7.61-7.59(d, J= 6.5 Hz, 2H), 7.24(m, 2H), 7.05(s, 1H), 4.16-4.02(m, 2H), 3.96-3.85(m, 1H), 3.69-3.60(m, 2H), 1.96-1.86(m, 2H), 1.49-1.45 (m, 2H) IR: 3330, 1635, 1548 MS: m/z 425 (M$^+$+1, 100%) |
| 76 | SO$_2$NHCH$_3$ | H | C—OH | F | M.P.: 280-285° C. $^1$H NMR (400 MHz, DMSO-d$_6$), δ 10.4(br s, 1H), 8.22-8.18(m, 2H), 7.89-7.87(d, J= 8.5 Hz, 2H), 7.78-7.75(d, J=9.0 Hz, 2H), 7.45-7.41(t, J=5.6 Hz, 2H), 7.03(s, 1H), 4.17(d, J=5.6 Hz, 2H), 7.03(s, 1H), 3.57-3.52(t, J=6 Hz, 2H), 2.47(s, 3H), 1.89-1.84(m, 2H), 1.50-1.46(m, 2H). IR: 3433, 1637, 1548 MS: m/z 458 (M$^+$+1, 100%) |
| 77 | CONH$_2$ | H | C—OH | H | $^{12}$H NMR (400 MHz, DMSO-d6), 10.71(br s, 1H), 8.12-8.09(dd, J=2.1, 2.0 Hz, 2H), 7.93-7.89(d, J=9 Hz, 2H), 7.70-7.68(d, J=8 Hz, 2H), 7.66-7.58(m, 2H), 7.24(s, 1H), 7.07(s, 1H), 4.19-4.16(m, 2H), 388-3.84(m, 1H), 3.64-3.60(m, 2H), 1.90-1.85(m, 2H), 1.54-1.46(m, 2H) IR: 3361, 1640, 1596 MS: m/z 390 (M$^+$+1, 100%) |
| 78 | CONHCH$_3$ | H | C—OH | H | M.P.: 285-290° C. $^1$H NMR (400 MHz, DMSO-d$_6$), δ 10.70(br s, 1H), 8.39-8.36(m, 1H), 8.12-8.09(m, 2H), 7.94-7.81(m, 2H), 7.11-7.66(m, 2H), 7.64-7.60(m, 2H), 7.06(s, 1H), 4.19-4.16(d, J= 8.7 Hz, 2H), 3.88-3.84(m, 1H), 3.64-3.44 (m, 2H), 2.78-2.77(d, J=8.2 Hz, 3H), 1.90-1.85(m, 2H), 1.54-1.50(m, 2H) IR: 3374, 1636, 1539 MS: m/z 404 (M$^+$+1, 100%) |
| 79 | SO$_2$NHCH$_3$ | H | O | H | $^1$H NMR (400 MHz, DMSO-d$_6$) δ 9.76(br s, —NH), 8.08-8.06(m, 2H), 7.93(d, J=8.8 Hz, 2H), 7.58-7.56(m, 3H), 7.24(m, 2H), 6.98(s, 1H), 4.37(br s, —NH), 3.80-3.73(m, 8H), 2.51(s, 3H) IR: 3282.4, 1626 MS: m/z 426 (M$^+$+1, 100%) |
| 80 | CONNHCH$_3$ | H | O | H | $^1$H NMR (400 MHz, DMSO-d$_6$) δ 10.83(br s, 1H), 8.36-7.35(d, J=5 Hz, 1H), 8.14-8.12(dd, J=1.6, 1.8 Hz, 2H), 7.89-7.87(d, J=9.0 Hz, 2H), 7.7-7.64(m, 2H), 7.63-7.58 (m, 2H), 7.01(s, 1H), 3.90-3.82(m, 4H), 3.76-3.74(t, J=5.0 Hz, 4H), 2.78-2.77(d, J= 4.0 Hz, 3H) IR: 3317, 1640, 1600, 1541 MS: m/z 389 (M$^+$+1, 100%) |

-continued

| Ex. No. | $R^a$ | $R^b$ | $R^c$ | $R^d$ | Analytical data |
|---|---|---|---|---|---|
| 81 | H | CONH$_2$ | C—OH | H | M.P.: 280-285° C.<br>$^1$H NMR (400 MHz, DMSO-d6) δ 13.10 (NH, br s, 1H), 10.87(br s, 1H), 8.32(s, 1H), 8.13-8.11(dd, J=1.6, 1.6 Hz, 2H), 7.98(s, 1H), 7.67-7.59(m, 3H), 7.49-7.45(t, J=8 Hz, 1H), 7.37(s, 1H), 7.07(s, 1H), 4.17(m, 2H), 3.99-3.85(m, 1H), 3.68-2.50(m, 2H), 1.89-1.85(m, 2H), 1.55-1.47(m, 2H)<br>IR: 3416, 1641, 1594<br>MS: m/z 390 (M$^+$+1, 100%) |
| 82 | H | COCH$_3$ | C—OH | H | M.P.: 242-244° C.<br>$^1$H NMR (400 MHz, DMSO-d6) δ 10.78(br s, 1H), 8.45(s, 1H), 8.29-8.09(dd, J=1.8, 1.6 Hz, 2H), 7.75-7.73(d, J=5.0 Hz, 1H), 7.67-7.59(m, 4H), 7.56-7.53(t, J=8.0 Hz, 1H), 7.07(s, 1H), 4.18(s, 2H), 3.90-3.87 (m, 1H), 3.70-3.37(m, 2H), 2.50(s, 3H), 1.91-1.86(m, 2H), 1.56-1.52(m, 2H)<br>IR: 3405, 1689, 1629, 1590<br>MS: m/z 388 (M$^+$+1, 100%) |
| 83 | H | CONHCH$_3$ | C—OH | H | M.P.: 280-282° C.<br>$^1$H NMR (400 MHz, DMSO-d6), δ 10.58(br s, 1H), 8.42-8.41(d, J=8.5, 1H), 8.29-8.26 (d, J=8.8, 1H), 8.10-8.08(dd, J=1.9, 1.7 Hz, 2H), 7.66-7.57(m, 4H), 7.47-7.43(t, J= 8.0, 1H), 7.05(s, 1H), 4.17(m, 2H), 3.99-3.86(m, 1H), 3.78-3.16(m, 2H), 2.83(d, J= 7.0, 3H), 1.91-186(m, 2H), 1.58-1.50(m, 2H).<br>IR: 3271, 1632, 1592, 1539<br>MS: m/z 403 (M$^+$+1, 100%) |
| 84 | H | CONHCH$_3$ | O | H | M.P.: 290-292° C.<br>$^1$H NMR (400 MHz, DMSO-d6) δ 10.40(br s, 1H), 8.14-8.12(dd, J=1.6, 1.6 Hz, 2H), 7.98-7.96(d, J=9.0 Hz, 2H), 7.85-7.83(d, J=9.0 Hz, 2H), 7.59-7.58(t, J=4.0 Hz, 3H), 7.02(s, 1H), 3.84-3.88(d, J=5.0 Hz, 4H), 3.76-7.74(t, J=5.0 Hz, 4H), 2.50(s, 3H).<br>IR: 3446, 1640, 1593, 1540.<br>MS: m/z 375 (M$^+$+1, 100%) |
| 85 | COCH$_3$ | H | O | H | M.P.: 282-284° C.<br>$^1$H NMR (400 MHz, DMSO-d6), δ 10.79(br s, 1H), 8.46-8.45(d, J=6.0 Hz, 1H), 8.25 (s, 1H), 8.14-8.12(dd, J=1.9, 1.6 Hz, 2H), 7.68-7.56(m, 4H), 7.48-7.49(t, J=6.5 Hz, 1H), 7.05(s, 1H), 3.92-3.81(m, 4H), 3.76-3.73(t, J=5.0 Hz, 4H), 2.80(s, 3H)<br>IR: 3429, 1635, 1542<br>MS: m/z 390 (M$^+$+1, 100%) |
| 86 | H | CONH$_2$ | O | H | M.P.: 288-290° C.<br>$^1$H NMR (400 MHz, DMSO-d6) δ 13.5(br s, 2H), 10.79(br s, 1H), 8.31(s, 1H) 8.15-8.12(m, 2H), 7.67-7.38(m, 6H) 7.05(s, 1H), 4.08-3.90(m, 4H), 3.81-3.73 (m, 4H)<br>IR: 3370, 2958, 1642, 1543, 1493<br>MS: m/z 376 (M$^+$, 100%) |
| 87 | H | COCH$_3$ | O | H | M.P.: 260-264° C.<br>$^1$H NMR (400 MHz, DMSO-d6) δ 10.65(br s, 1H), 8.44(s, 1H), 8.15-8.12 (m, 2H), 7.76-7.52(m, 6H), 7.04(s, 1H), 4.03-3.83(m, 4H), 3.77-3.74(m, 4H), 2.59 (s, 3H)<br>IR: 3452, 2956, 1680, 1637, 1592, 1547<br>MS: m/z 375 (M$^+$, 100%) |
| 88 | H | SO$_2$NH$_2$ | C—OH | H | M.P.: 290-292° C.<br>$^1$H NMR (400 MHz, DMSO-d$_6$), δ 12.5(br s, 1H), 10.87(br s, 1H), 8.45(s, 1H), 8.13 (d, J=6.7 Hz, 2H), 7.62-7.61(d, J=7.0 Hz, 2H), 7.59-7.57(m, 2H), 7.37(s, 1H), 7.08(s, 1H), 4.17(br s, 2H), 3.86(br s, 1H), 3.66-3.61(t, J=7.0 Hz, 2H), 1.84(br s, 2H), 1.58(br s, 2H)<br>IR: 3496, 1636, 1544<br>MS: m/z 425 (M$^+$+1, 100%) |

-continued

| Ex. No. | $R^a$ | $R^b$ | $R^c$ | $R^d$ | Analytical data |
|---|---|---|---|---|---|
| 89 | H | SO$_2$NH$_2$ | O | H | M.P.: 292-294° C.<br>$^1$H NMR (400 MMHz, DMSO-d6), δ 10.99 (br s, 1H), 8.44(s, 1H), 8.16-8.13(dd, J=1.4, 1.4 Hz, 2H), 7.66-7.62(m, 2H), 7.60-7.58(m, 2H), 7.58-7.48(m, 1H), 7.38 (s, 1H), 7.06(s, 1H), 3.91-3.88(t, J=4.1 Hz, 4H), 3.75-3.73(t, J=6.2 Hz, 4H).<br>IR: 3399, 3050, 1630, 1535<br>MS: m/z 412 (M$^+$+1, 100%) |
| 90 | COCH$_3$ | H | O | F | M.P.: 266-270° C.<br>$^1$H NMR (400 MHz, DMSO-d$_6$), δ 10.12(br s, 1H), 8.23-8.20(m, 2H), 7.96-7.94(d, J=8 Hz, 2H), 7.87-7.85(d, J=8 Hz, 2H), 7.43-7.38(t, J=7 Hz, 2H), 6.98(s, 1H), 3.80-3.79(m, 4H), 3.75-4.74(m, 4H)<br>IR: 3399, 1640, 1542<br>MS: m/z 393 (M$^+$+1, 100%) |
| 91 | COCH$_3$ | H | C—OH | F | M.P.: 245-250° C.<br>$^1$H NMR (400 MHz, DMSO-d$_6$), δ 10.4 (br s, 1H), 8.21-8.18(m, 2H), 7.98-7.96(d, J=9 Hz, 2H), 7.83-7.81(d, J=9 Hz, 2H), 7.47-7.40(t, J=7 Hz, 2H), 7.02(s, 1H), 4.20-4.16(m, 2H), 3.86-3.82(m, 1H), 3.56-3.51(t, J=7.0 Hz, 2H), 2.50(s, 3H), 1.88-1.85(m, 2H), 1.48-1.42(m, 2H)<br>IR: 3361, 1635, 1541<br>MS: m/z 407 (M$^+$+1, 100%) |
| 92 | OCF$_3$ | H | C—OH | H | M.P.: 250-252° C.<br>$^1$H NMR (400 MHz, DMSO-d$_6$), δ 10.87(br s, 1H), 8.12-8.10(dd, J=1.31, 1.9 Hz, 2H), 7.73-7.71(dd, J=1.9, 1.9 Hz, 2H), 7.70-7.61(m, 3H), 7.59-7.41(m, 2H), 7.06(s, 1H), 4.17-4.12(m, 2H), 3.89-3.83(m, 1H), 3.65-3.60(m, 2H), 1.90-1.85(m, 2H), 1.54-1.46(m, 2H).<br>IR: 3331, 2928, 1638, 1549<br>MS: m/z 430 (M$^+$+1, 100%) |

Example 93

Synthesis of 1-(4-indol-1-yl-6-phenyl-pyrimidin-2-yl)-piperidin-4-ol

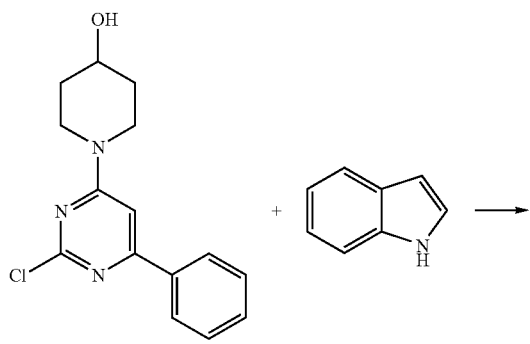

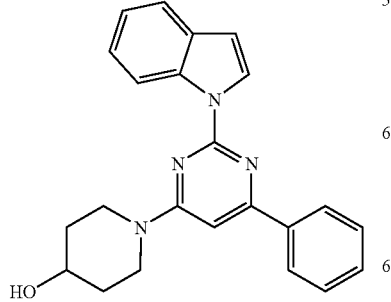

To a mixture of indole (0.13 g, 1.08 mmol) and 60% NaH [64 mg (38 mg, 1.61 mmol)] in DMF (2 mL) was added a solution of compound 1-(2-chloro-6-phenyl-pyrimidin-4-yl)-piperidin-4-ol (0.31 g, 1.08 mmol) in DMF (2 mL) dropwise at 0° C. under a nitrogen atmosphere. The mixture was then stirred at 80° C. for 24 hours. The mixture was poured in to ice (3 g) and stirred for 30 minutes. The solid was filtered, dried and purified by column chromatography over silica gel using 20% ethyl acetate-petroleum ether.

M.P.: 168-170° C.

$^1$H NMR (400 MHz, DMSO-d$_6$): δ 8.85 (d, J=8.6 Hz, 1H), 8.37-8.36 (m, 1H), 8.12-8.09 (m, 2H), 7.63-7.61 (m, 2H), 7.52-7.50 (m, 2H), 7.33-7.31 (m, 1H), 7.22-7.21 (m, 1H), 6.76 (s, 1H), 6.66-6.65 (m, 1H), 4.30-4.24 (m, 2H), 4.1 (br s, 1H), 3.51-3.36 (m, 2H), 2.05-2.04 (m, 2H), 1.68-1.66 (m, 2H).

IR (KBr, cm$^{-1}$): 3439, 2926.

MS: m/z (CI) 371 (M+1, 100%).

Example 94

Synthesis of 1-(6-phenyl-2-pyrrol-1-yl-pyrimidin-4-yl)-piperidin-4-ol

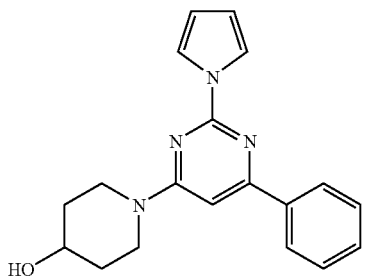

The title compound was prepared from pyrrole (0.072 g, 1.07 mmol) and compound 1-(2-chloro-6-phenyl-pyrimidin-4-yl)-piperidin-4-ol (0.31 g, 1.07 mmol) in the presence of 60% NaH (0.039 g, 1.6 mmol) in DMF by a procedure analogous to that disclosed in Example 93.

M.P.: 150-152° C.
$^1$H NMR (400 MHz, CDCl$_3$) δ 8.08-8.03 (m, 2H), 7.86-7.85 (m, 2H), 7.50-7.44 (m, 3H), 6.73 (s, 1H), 6.30-6.29 (m, 2H), 4.23-4.18 (m, 2H), 4.05-3.99 (m, 1H), 3.47-3.41 (m, 2H), 2.04-1.98 (m, 2H), 1.67-1.58 (m, 2H)
IR: 3427.6, 1898, 1530
MS: m/z 321(M$^+$+1, 100%).

Example 95

Synthesis of 1-(4-benzo[1,3]dioxol-5-yl-6-phenyl-pyrimidin-2-yl)-piperidin-4-ol

Step (i). Synthesis of 5-bromo-benzo[1,3]dioxole

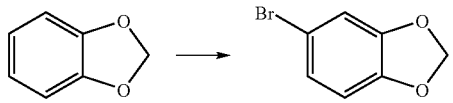

A mixture of ceric ammonium nitrate (9.88 g, 18.0 mmol) and lithium bromide (1.5 g, 18.0 mmol) in acetonitrile (20 mL) was stirred for 30 minutes at 25° C. under nitrogen atmosphere. A solution of benzo[1,3]dioxol (2 g, 16 mmol) in acetonitrile (20 mL) was added slowly to it and the mixture was stirred for 4 hours at 25° C. The mixture was then diluted with water (50 mL) and extracted with ethyl acetate (3×50 mL). The organic layers were collected, combined, washed with water (50 mL), dried over anhydrous sodium sulphate, and concentrated under vacuum to give the desired product.

$^1$H NMR (200 MHz, DMSO-d$_6$): δ 6.95 (s, 1H), 6.84 (d, J=5.3 Hz, 1H), 6.71 (d, J=5.3 Hz, 1H), 5.96 (s, 2H).
IR (KBr, cm$^{-1}$): 1594, 1474.
MS: m/z (CD) 203 (M+2, 50%).
Reference: Roy, S. C.; Guin, C.; Rana, K. K.; Maiti, G. *Tetrahedron Lett.* 2001, 42, 6941-6942.

Step (ii). Synthesis of benzo[1,3]dioxo-5-yl boronic acid

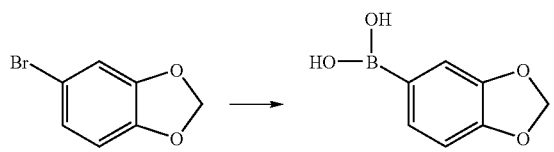

To a solution of compound, 5-bromo-benzo[1,3]dioxole (3.0 g, 14.9 mmol) in tetrahydrofuran (25 mL) was added butyl lithium (0.95 g, 14.9 mmol) slowly and drop wise at −75° C. under nitrogen atmosphere. The mixture was then stirred for 2.5 hours at −75° C. and triisopropylborate (2.88 g, 14.9 mmol) was added drop wise at −75° C. The mixture was stirred at the same temperature for 1 hour and then at 25° C. for 12 hours. The mixture was acidified (pH~5-6) with diluted hydrochloric acid and extracted with ethyl acetate (3×50 mL). The organic layers were collected, combined, washed with water (50 mL), dried over anhydrous sodium sulphate, and concentrated under vacuum. The residue was triturated with petroleum ether and diethyl ether. The solid was filtered and dried to give the desired product.

$^1$H NMR (200 MHz, DMSO-d$_6$): δ 7.48 (s, 1H), 7.41-7.33 (m, 1H), 6.86-6.78 (m, 1H), 5.94 (s, 2H).
IR (KBr, cm$^{-1}$): 3379, 1572.
MS: m/z (CI) 166 (M+1, 10%).
Reference: For a similar preparation of boronic acid from aryl bromide, see: Meltzer, P. C.; McPhee, M.; Madras, B. K. *Bioorg. Med. Chem. Lett.* 2003, 13, 4133-4138.

Step (iii). Synthesis of 1-(4-benzo[1,3]dioxol-5-yl-6-phenyl-pyrimidin-2-yl)-piperidin-4-ol

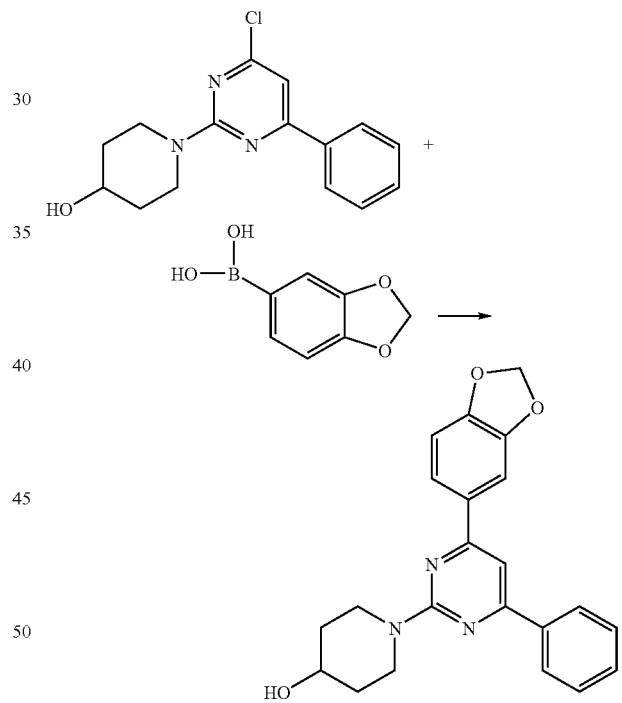

A mixture of compound benzo[1,3]dioxo-5-yl boronic acid (0.14 g, 83 mmol), and compound 1-(4-chloro-6-phenyl-pyrimidin-2-yl)-piperidin-4-ol (90.2 g, 69 mmol), (PPh$_3$)$_4$Pd (31 mg, 0.03 mmol) and sodium carbonate (0.73 g, 69 mmol) in dimethylformamide (5 mL) was stirred for 1 hour at 25° C. and then for 12 hours at 80° C. under nitrogen atmosphere. The mixture was cooled to temperature in the range of 20-40° C., diluted with water (10 mL) and extracted with ethyl acetate (3×10 mL). The organic layers were collected, combined, washed with water (10 mL), dried over anhydrous sodium sulphate, and concentrated under vacuum. The residue thus obtained was purified by column chromatography using ethyl acetate-petroleum ether to give the desired compound.

M.P.: 120-122° C.

$^1$H NMR (400 MHz, DMSO-d$_6$): δ 8.10-8.08 (m, 2H), 7.67-7.64 (m, 2H), 7.49-7.45 (m, 3H), 7.28 (s, 1H), 6.90 (d, J=8.6 Hz, 1H), 6.03 (s, 2H), 4.71-4.65 (m, 2H), 3.98-3.97 (m, 1H), 3.46-3.40 (m, 2H), 2.04-2.00 (m, 2H), 1.63-1.58 (m, 2H).

IR (KBr, cm$^{-1}$): 3396, 1565, 1548.

MS: m/z (CI) 376 (M+1, 100%).

Example 96

Synthesis of Substituted Pyrimidine Compounds

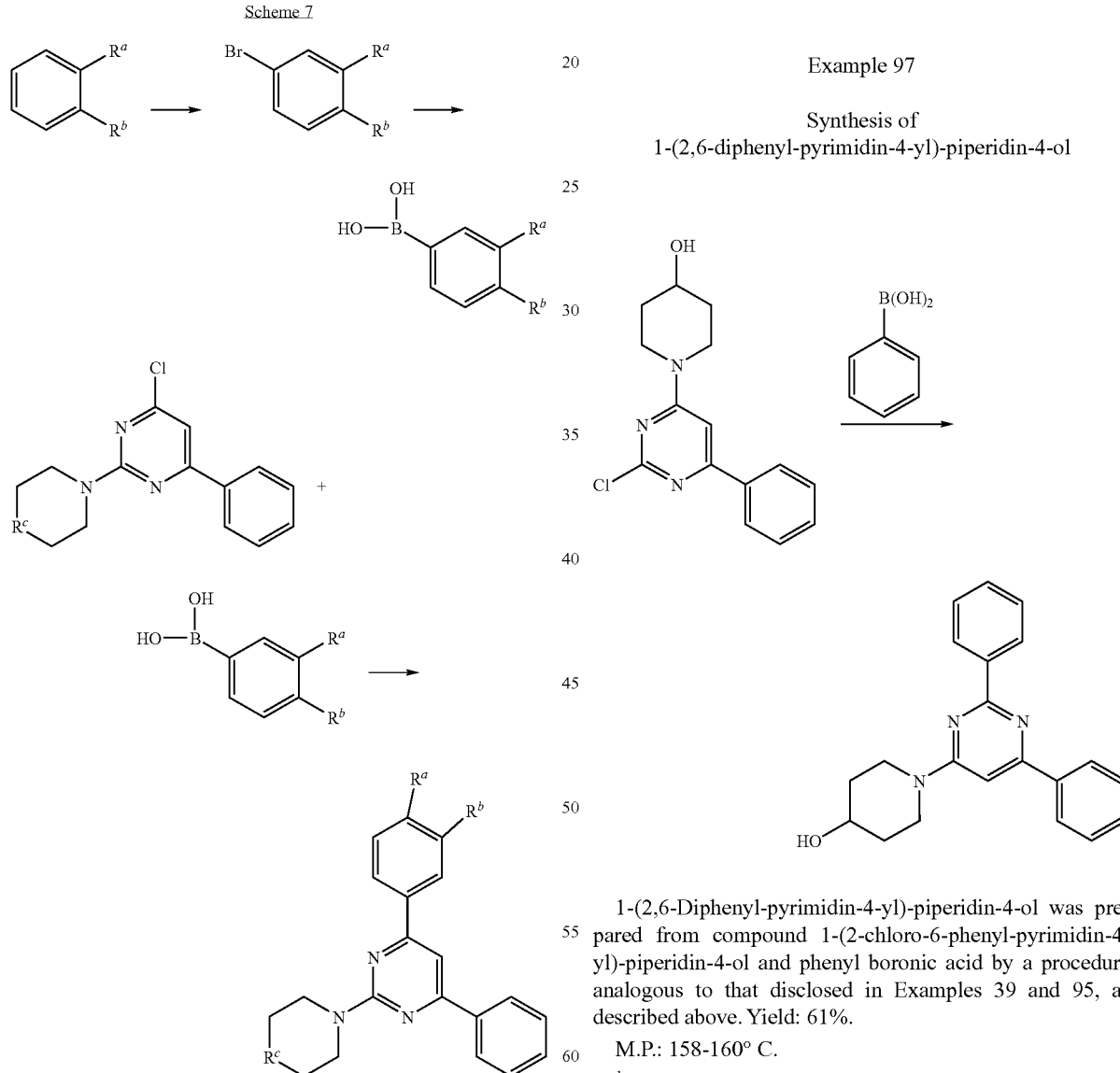

The following compounds presented in Example 96 was prepared in accordance with Scheme 7, by a procedure analogous to that disclosed in Examples 39 and 95, using starting materials with the appropriate substitution.

| Ex. No. | R$^a$ | R$^b$ | R$^c$ | Analytical data |
|---|---|---|---|---|
| 96 | H | H | C—OH | M.P.: 158-160° C. <br> $^1$H NMR(400MHz, DMSO-d$_6$): δ 8.56-8.51(m, 2H), 8.15-8.11(m, 2H), 7.49-7.44(m, 6H), 6.86(s, 1H), 4.34-4.28(m, 2H), 4.06-4.00(m, 1H), 3.50-3.37(m, 2H), 2.20-2.01(m, 2H), 1.72-1.57(m, 2H). <br> IR(KBr, cm$^{-1}$): 3289, 1594, 1574. <br> MS: m/z(CI) 332(M+1, 100%). |

Example 97

Synthesis of 1-(2,6-diphenyl-pyrimidin-4-yl)-piperidin-4-ol 1-(2,6-Diphenyl-pyrimidin-4-yl)-piperidin-4-ol was prepared from compound 1-(2-chloro-6-phenyl-pyrimidin-4-yl)-piperidin-4-ol and phenyl boronic acid by a procedure analogous to that disclosed in Examples 39 and 95, as described above. Yield: 61%.

M.P.: 158-160° C.

$^1$H NMR (400 MHz, DMSO-d$_6$): δ 8.56-8.51 (m, 2H), 8.15-8.11 (m, 2H), 7.49-7.44 (m, 6H), 6.86 (s, 1H), 4.34-4.28 (m, 2H), 4.06-4.00 (m, 1H), 3.50-3.37 (m, 2H), 2.20-2.01 (m, 2H), 1.72-1.57 (m, 2H).

IR (KBr, cm$^{-1}$): 3289, 1594, 1574.

MS: m/z (CI) 332 (M+1, 100%).

Examples 98-103

Synthesis of Substituted Pyrimidine Compounds

Scheme 8

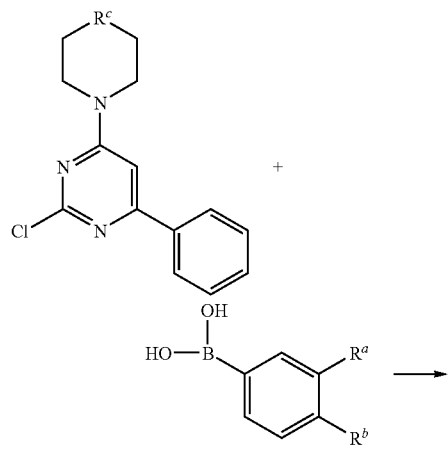

+

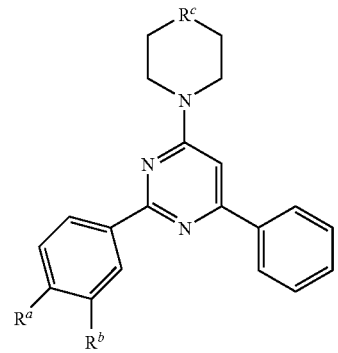

-continued

The following compounds presented in Examples 98-103 were prepared in accordance with Scheme 8, by a procedure analogous to that disclosed in Examples 39 and 95, using starting materials with the appropriate substitution.

| Ex. No. | $R^a$ | $R^b$ | $R^c$ | Analytical data |
|---|---|---|---|---|
| 98 | —O-CH2-O— (dioxole) | | C—OH | M.P.: 158-160° C.<br>$^1$H NMR (400 MHz, DMSO-$d_6$) δ 8.16(dd, J=1.9, 1.61 Hz, 2H), 8.10(dd, J=1.6, 1.6 Hz, 1H), 8.04(d, J=1.6 Hz, 1H), 7.50-7.43(m, 3H), 6.90(d, J=8.1 Hz, 1H), m6.82(s, 1H), 6.02(s, 2H), 4.31-4.28(m, 2H), 4.04-4.00(m, 1H), 3.46-3.40(m, 2H), 2.05-2.00(m, 2H), 1.67-1.58(m, 2H).<br>IR (KBr, cm$^{-1}$): 3347, 1588, 1573.<br>MS: m/z (CI) 376 (M+1, 100%). |
| 99 | —O-CH2-O— (dioxole) | | O | M.P.: 210-212° C.<br>$^1$H NMR (400 MHz, CDCl$_3$) δ 8.15(dd, J=1.6, 1.6 Hz, 2H), 8.10(dd, J=2.1, 1.5 Hz, 1H), 8.03(s, 1H), 7.49-7.46(m, 3H), 6.89(d, J=8.1 Hz, 1H), 6.78(s, 1H), 6.02(s, 2H), 3.86-3.84(m, 4H), 3.79-3.77(m, 4H).<br>IR: 3425.3<br>MS: m/z 362(M$^+$+1, 100%) |
| 100 | F | H | C—OH | M.P.: 186-188° C.<br>$^1$H NMR (400 MHz, DMSO-$d_6$) δ 8.57-8.51(m, 2H), 8.12-8.11(dd, J=2.0, 1.9 Hz, 2H), 7.51-7.46(m, 3H), 7.25-7.10(m, 2H), 6.86(s, 1H), 4.32-4.26(m, 2H), 4.05-4.01(m, 1H), 3.49-3.42(m, 2H), 2.06-2.01(m, 2H), 1.68-1.60(m, 2H).<br>IR: 3383, 2935, 1573, 1375, 1212.<br>MS: m/z 349 (M$^+$+1, 100%), |
| 101 | OCF$_3$ | H | C—OH | M.P.: 128-130° C.<br>$^1$H NMR (400 MHz, DMSO-$d_6$) δ 8.59-8.56(m, 2H), 8.12-8.09(m, 2H), 7.52-7.46(m, 2H), 7.30-7.28(d, J=8.0 Hz, 2H), 6.88(s, 1H), 4.31-4.26(m, 2H), 4.04-4.03 (m, 1H), 3.50-3.43(m, 2H), 2.06-2.01(m, 2H), 1.69-1.62(m, 2H).<br>IR: 3484, 2926, 1573, 1262.<br>MS: m/z 415 (M$^+$+1, 100%), |
| 102 | —O-CH2-O— (dioxole) | | C=O | M.P.: 184-186° C.<br>$^1$H NMR (400 MHz, DMSO-$d_6$) δ 8.18-8.11(m, 3H), 8.07-8.05(t, J=1.9 Hz, 1H), 7.53-7.47(m, 3H), 6.90 (s, 1H), 6.89(s, 1H), 6.03(s, 2H), 4.15-4.12(t, J=6.2 Hz, 4H), 2.63-2.60(t, J=6.2 Hz, 4H).<br>IR: 1720, 1576, 1232, 1037, 765.<br>MS: m/z 374 (M$^+$+1, 100%) |
| 103 | H | SO$_2$CH$_3$ | C—OH | M.P.: 150-152° C.<br>$^1$H NMR (400 MHz, DMSO-$d_6$) δ 9.08-9.08(d, J=1.9 Hz, 1H), 8.86-8.84(d, J=8.0 Hz, 1H), 8.13-8.11(m, |

| Ex. No. | $R^a$ | $R^b$ | $R^c$ | Analytical data |
|---|---|---|---|---|
| | | | | 3H), 7.69-7.49(m, 4H), 6.92(s, 1H), 4.39-4.26(m, 2H), 4.12-4.02(m, 1H), 3.52-3.49(m, 2H), 3.12(s, 3H), 2.04-2.03(m, 2H), 1.67-1.54(m, 2H). IR: 3385, 2932, 1650, 1495. MS: m/z 409 (M⁺+1, 100%) |

Examples 104-107

Synthesis of Substituted Pyrimidine Compounds

Preparation of 1-(6-chloro-2-phenyl pyrimidin-4-yl)-piperidin-4-ol

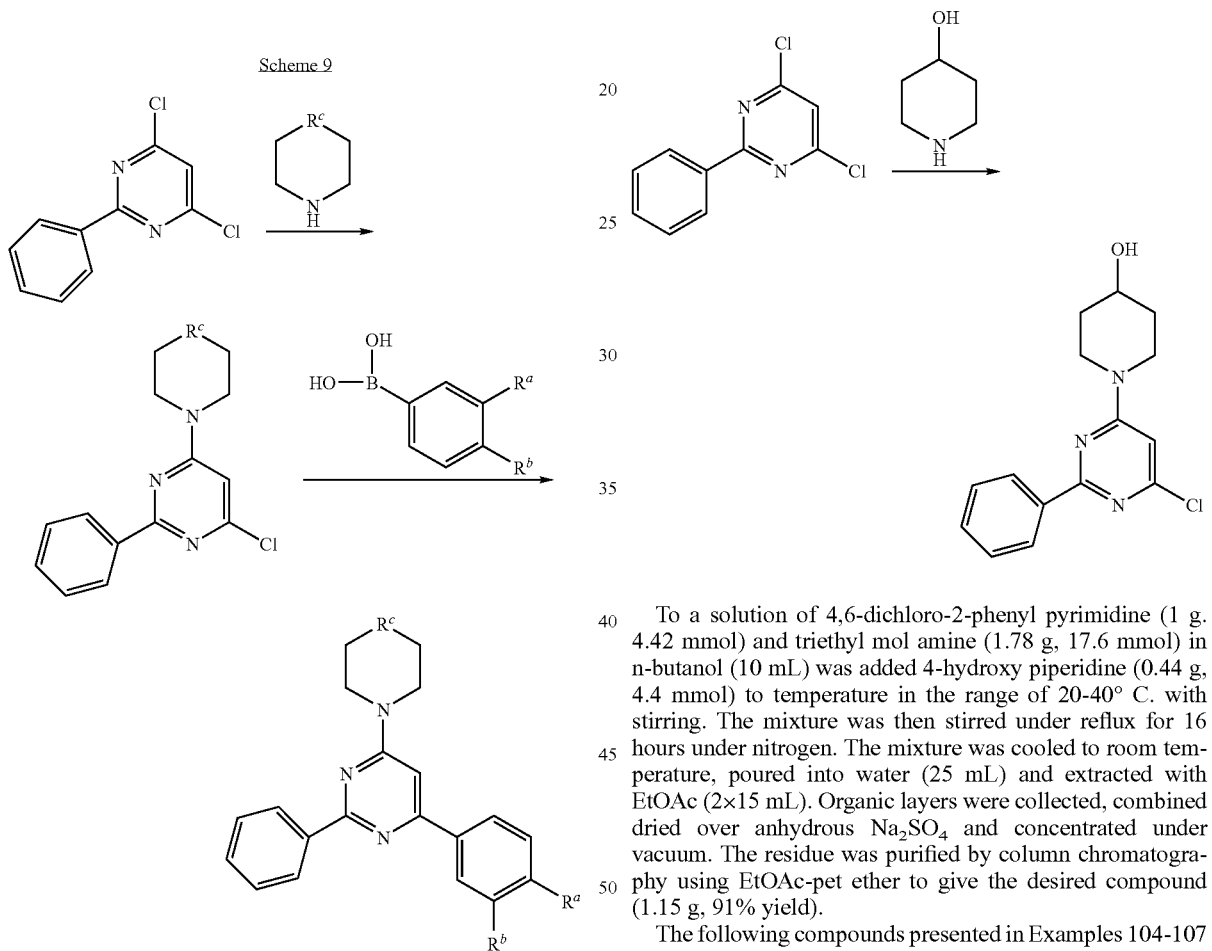

To a solution of 4,6-dichloro-2-phenyl pyrimidine (1 g, 4.42 mmol) and triethyl mol amine (1.78 g, 17.6 mmol) in n-butanol (10 mL) was added 4-hydroxy piperidine (0.44 g, 4.4 mmol) to temperature in the range of 20-40° C. with stirring. The mixture was then stirred under reflux for 16 hours under nitrogen. The mixture was cooled to room temperature, poured into water (25 mL) and extracted with EtOAc (2×15 mL). Organic layers were collected, combined dried over anhydrous Na₂SO₄ and concentrated under vacuum. The residue was purified by column chromatography using EtOAc-pet ether to give the desired compound (1.15 g, 91% yield).

The following compounds presented in Examples 104-107 were prepared in accordance with Scheme 9, by a procedure analogous to that disclosed in Examples 39 and 95, using starting materials with the appropriate substitution.

| Ex. No. | $R^a$ $R^b$ | $R^c$ | Analytical data |
|---|---|---|---|
| 104 | (methylenedioxy) | C—OH | M.P.: 152-154° C.<br>¹H NMR (400 MHz, CDCl₃) δ 8.53-8.51(m, 2H), 7.67-7.45(m, 5H), 7.45(d, J=5.6 Hz, 1H), 6.76(s, 1H), 6.03(s, 2H), 4.31-4.27(m, 3H), 3.45-3.40(m, 2H), 2.04-2.00(m, 2H), 1.65-1.61(m, 2H)<br>IR: 3418.2<br>MS: m/z 376(M⁺, 100%) |

-continued

| Ex. No. | $R^a$ | $R^b$ | $R^c$ | Analytical data |
|---|---|---|---|---|
| 105 | H | SO$_2$CH$_3$ | C—OH | M.P.: 178-180° C.<br>$^1$H NMR (400 MHz, CDCl$_3$) δ 8.62(s, 1H) 8.54-8.48(m, 4H), 8.05-8.02(m, 1H), 7.71(t, J=7.9 Hz, 1H), 7.51-7.46(m, 3H), 6.90(s, 1H), 4.33-4.29(m, 2H), 4.08-4.03(m, 1H), 3.54-3.46(m, 2H), 3.12(s, 3H), 2.08-2.02(m, 2H), 1.70-1.62(m, 2H)<br>IR: 3421.7<br>MS: m/z 409(M$^+$, 100%) |
| 106 | F | H | N—CH$_3$ | M.P.: 136-139° C.<br>$^1$H NMR (400 MHz, DMSO-d$_6$)<br>δ 8.53-8.51(m, 2H), 8.15-8.11(m, 2H), 7.49-7.45 (m, 3H), 7.19-7.14(m, 2H), 6.78(s, 1H), 3.86-3.84 (t, J=4.8 Hz, 4H), 2.57-2.54(t, J=5.1 Hz, 4H), 2.38(s, 3H).<br>IR: 3448, 2927, 1573, 1514<br>MS: m/z 349 (M$^+$, 100%). |
| 107 | H | H | N—CH$_3$ | M.P.: 147-149° C.<br>$^1$H NMR (400 MHz, DMSO-d$_6$)<br>δ 8.47-8.45(m, 2H), 8.32-8.28(m, 2H), 7.52-7.51 (m, 5H), 7.3(s, 1H), 7.03(s, 1H), 3.83-3.8(m, 4H), 2.50-2.45(m, 4H), 2.25(s, 3H).<br>IR: 3419, 2934, 1593, 1526<br>MS: m/z 331(M$^+$, 30%), (260, 100%) |

Example 108

Synthesis of 4,6-bis-(4-fluoro-phenyl)-pyrimidin-2-ylamine

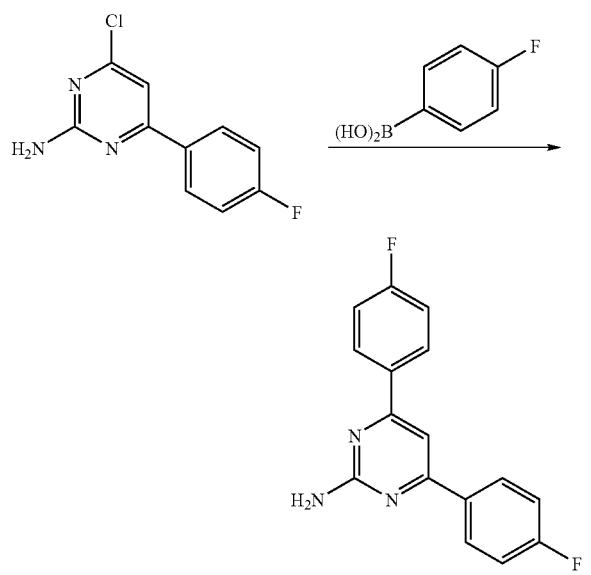

A mixture of compound 4-fluoro phenyl boronic acid, compound 4-chloro-6-(4-fluoro-phenyl)-pyrimidin-2-ylamine, (PPh$_3$)$_4$Pd and sodium carbonate in dimethylformamide was stirred for 1 hour at 25 ° C. and then for 12 hours at 80 ° C. under nitrogen atmosphere followed by purification to yield the desired compound.

M.P.: 207-210° C.

$^1$H NMR (200 MHz, DMSO-d$_6$): δ 8.34-8.27 (m, 4H), 7.74 (s, 1H), 7.40-7.32 (m, 4H), 6.79 (s, D$_2$O exchangeable, 2H).

MS: m/z 284 (M$^+$, 100%).

Example 109

Synthesis of (3-chloro-4-methoxy-phenyl)-(4-phenyl-6-phenylethynyl-pyrimidin-2-yl)-amine

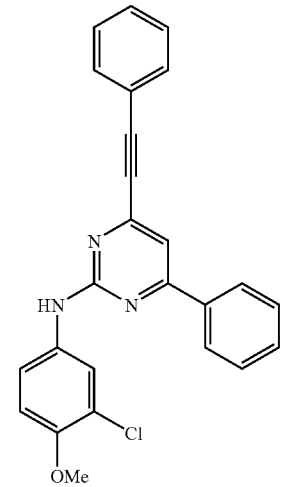

Step (i). Synthesis of (3-chloro-4-methoxy-phenyl)-(4-chloro-6-phenyl-pyrimidin-2-yl)-amine

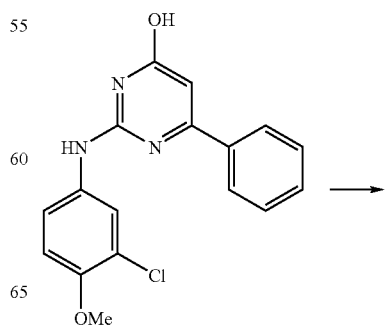

-continued

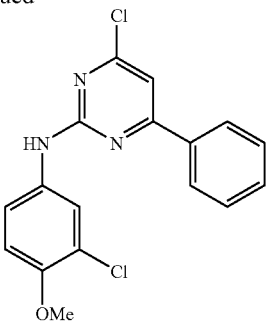

The compound 2-(3-chloro-4-methoxy-phenylamino)-6-phenyl-pyrimidin-4-ol (0.78 mg, 2.4 mmol) was chlorinated by refluxing (80 to 90° C.) in phosphorus oxychloride (15 mL) for 4 to 5 hours. The reaction mixture was cooled to temperature in the range of 20-40° C.; excess of phosphorus oxychloride was distilled out and then diluted with water (100 mL). The mixture was neutralized with sodium bicarbonate solution. The solid precipitated was filtered off and dried to give compound.

$^1$H NMR (200 MHz, CDCl$_3$): δ 8.05-8.02 (m, 2H), 7.82 (m, 1H), 7.54-7.44 (m, 5H), 7.17 (s, 1H), 6.94 (d, J=8.8 Hz, 1H), 3.91 (s, 3H).

IR (KBr, cm$^{-1}$): 3405, 1594.

MS: m/z (CI) 346 (M+1, 100%).

Step (ii). Synthesis of (3-chloro-4-methoxy-phenyl)-(4-phenyl-6-phenylethynyl-pyrimidin-2-yl)-amine

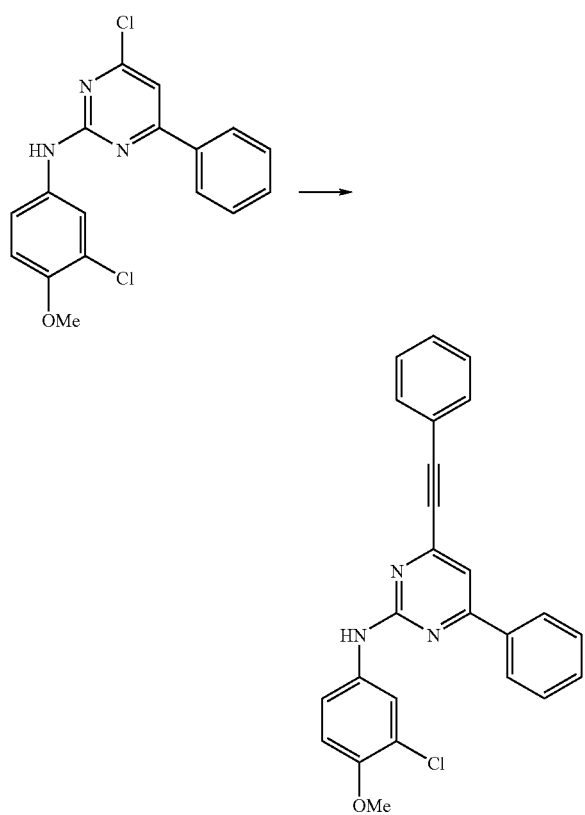

A mixture of compound (3-chloro-4-methoxy-phenyl)-(4-chloro-6-phenyl-pyrimidin-2-yl)-amine (0.4 g, 1.15 mmol), (PPh$_3$)$_4$Pd (53 mg, 0.05 mmol), copper iodide (11 mg, 0.06 mmol) and triethylamine (0.93 g, 9.23 mmol) in dimethylformamide (10 mL) was stirred at 80° C. for 0.5 hour under nitrogen atmosphere. The mixture was cooled to temperature in the range of 20-40° C. and phenylacetylene (0.24 g, 2.30 mmol) was added to it. The mixture was stirred at 80° C. for 12 hours under nitrogen atmosphere. The mixture was cooled to temperature in the range of 20-40° C., diluted with water (20 mL) and extracted with ethyl acetate (3×15 mL). The organic layers were collected, combined, washed with water (10 mL), dried over anhydrous sodium sulphate and concentrated under vacuum. The residue was purified by column chromatography using ethyl acetate-petroleum ether to give the desired product.

M.P.: 200-202° C.

$^1$H NMR (400 MHz, DMSO-d$_6$): δ 9.89 (s, 1H), 8.23-8.20 (m, 1H), 7.98 (s, 1H), 7.75-7.49 (m, 11H), 7.16 (d, J=8.9 Hz, 1H), 3.84 (s, 3H).

IR (KBr, cm$^{-1}$): 3345, 2210, 1253.

MS: m/z (CI) 412 (M$^+$, 100%).

Reference: Pal, M.; Kundu, N. G. *J. Chem. Soc., Perkin Trans.* 1, 1996, 449-451.

Example 110

Synthesis of 2-[2-(3-chloro-4-methoxy-phenylamino)-6-phenyl-6-pyrimidin-4-yl-amino)-ethanol

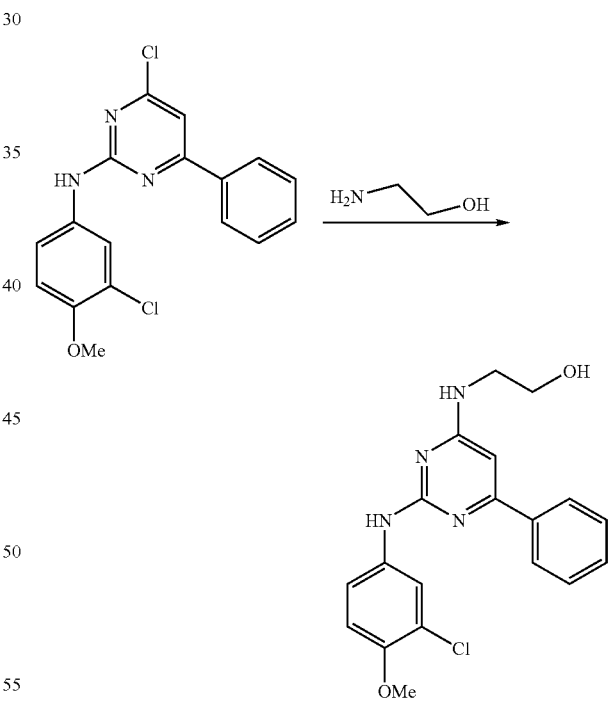

A mixture of the compound (3-chloro-4-methoxy-phenyl)-(4-chloro-6-phenyl-pyrimidin-2-yl)-amine (0.2 g, 0.577 mmol), 2-aminoethanol (0.035 mL, 0.577 mmol) in diglyme (2 mL) was stirred at 166-170° C. for 16 hours. The mixture was cooled and the excess of diglyme was removed by column chromatography. The crude product thus obtained was titrated in diethyl ether to give the desired compound.

M.P.: 152-154° C.

$^1$H NMR (400 MHz, DMSO-d$_6$): δ 7.95 (s, 3H), 7.44-7.47 (m, 3H), 7.36 (d, J=6.5 Hz, 1H), 6.89 (d, J=8.9 Hz, 2H), 6.30

(s, 1H), 5.19 (br s, 2H), 3.85-3.89 (m, 3H), 3.61-3.65 (m, 2H), 3.47-3.48 (m, 2H), 1.25 (br s, 1H).

IR (KBr, cm$^{-1}$): 3389, 1253, 1061.

MS: m/z (CI) 371 (M$^+$, 100%).

Example 111

Synthesis of 4-phenyl-6-phenylethynylpyrimidin-2-ylamine

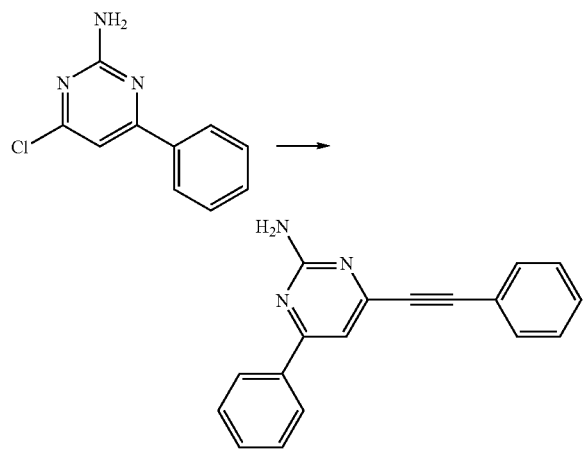

A mixture of 4-chloro-6-phenylpyrimidin-2-ylamine (2.0 g, 9.7 mmol), (PPh$_3$)$_2$PdCl$_2$ (204 mg, 0.29 mmol), triethylamine (4.9 g, 48.5 mmol) in DMF (10 mL) was stirred at 25° C. for 0.5 hour under a nitrogen atmosphere. Then phenylacetylene (1.29 g, 12.70 mmol) was added to it and the mixture was stirred at 100° C. for 4 hours under a nitrogen atmosphere. The mixture was cooled to temperature in the range of 20-40° C., diluted with water (20 mL) and extracted with EtOAc (3×25 mL). The organic layers were collected, combined, washed with water (30 mL), dried over anhydrous Na$_2$SO$_4$, and concentrated under vacuum. The residue was purified by column chromatography using EtOAc-petroleum ether to give the desired product.

M.P.: 136-138° C.

$^1$H NMR (200 MHz, CDCl$_3$): δ 8.05-8.00 (m, 2H), 7.65-7.38 (m, 8H), 7.27 (s, 1H), 5.26 (s, 2H).

I.R: (neat) 3315, 2215, 1562.

MS: m/z (CI) 272 (M$^+$, 100%).

Example 112

Synthesis of (3-chloro-4-methoxy-phenyl)-(4-phenyl-6-piperazin-1-yl-pyrimidin-2-yl)-amine Step (i). Synthesis of 2-(3-chloro-4-methoxy-phenylamino)-6-phenyl-pyrimidin-4-ol

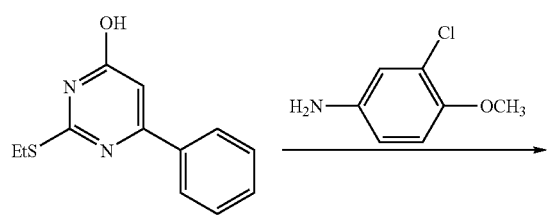

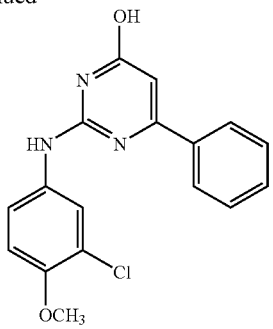

2-Ethylsulfanyl-6-phenyl-pyrimidin-4-ol (3.0 g, 12.8 mmol) was treated with 3-chloro-4-methoxy-phenylamine (2.0 g, 12.8 mmol) in diphenyl ether at 180° C. for 16 hours to give 2-(3-chloro-4-methoxy-phenylamino)-6-phenyl-pyrimidin-4-ol.

Step (ii). Synthesis of (3-chloro-4-methoxy-phenyl)-(4-chloro-6-phenyl-pyrimidin-2-yl)-amine

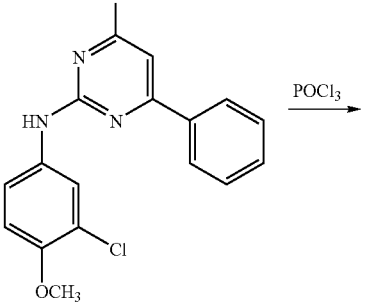

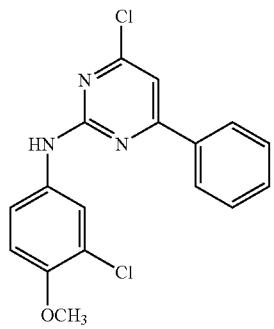

Chlorination of 2-(3-chloro-4-methoxy-phenylamino)-6-phenyl-pyrimidin-4-ol (1.5 g, 4.1 mmol) with POCl$_3$ (10 mL) as explained above, afforded (3-chloro-4-methoxy-phenyl)-(4-chloro-6-phenyl-pyrimidin-2-yl)-amine.

Step (iii). Synthesis of (3-chloro-4-methoxy-phenyl)-(4-phenyl-6-piperazin-1-yl-pyrimidin-2-yl)-amine

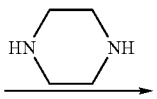

-continued

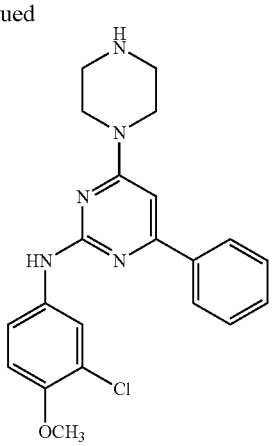

(3-Chloro-4-methoxy-phenyl)-(4-chloro-6-phenyl-pyrimidin-2-yl)-amine compound (1 g, 2.8 mmol) on treatment with piperazine (0.24 g, 2.8 mmol), as described above yielded the desired compound.

$^1$H NMR (400 MHz, DMSO-d$_6$): δ 9.19-9.15(br s, 1H), 8.16-8.05 (m, 2H), 7.97 (s, 1H), 7.70-7.49 (m, 4H), 7.11-7.08 (d, J=8.9 Hz 1H), 6.90 (s, 1H), 3.96-3.82 (m, 4H), 3.81 (s, 3H), 3.30-3.16 (m, 4H).

IR: 3312, 2495, 1574, 1397.

MS: m/z 396 (M$^+$+1, 100%).

Example 113

Synthesis of (6-morpholin-4-yl-2-phenyl-pyrimidin-4-yl)-(4-trifluoromethoxy-phenyl)-amine Step (i). Synthesis of 2-phenyl-pyrimidine-4,6-diol

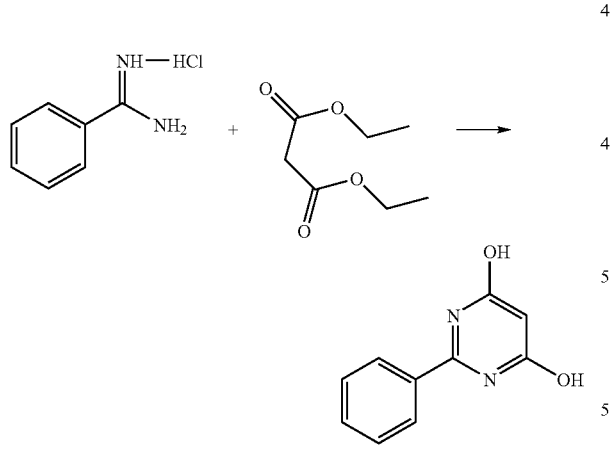

Sodium ethoxide was generated in-situ by adding sodium (18.4 g, 801 mmol) to absolute ethanol (500 mL) and then benazamidine hydrochloride (50 g, 320 mmol) was added followed by diethylmalonate (48.8 mL, 320 mmol), This reaction mixture was allowed to stir at refluxing temperature for 16 hours, under nitrogen atmosphere. Then the mixture was cooled to room temperature and concentrated under reduced pressure. The crude white solid was dissolved in water, acidified with 2N HCl. White solid obtained was filtered off, washed with i-propanol and dried to afford the compound 2-phenyl-pyrimidine-4,6-diol (34 g, 56%) as off white solid.

Step (ii). Synthesis of 4,6-dichloro-2-phenyl-pyrimidine

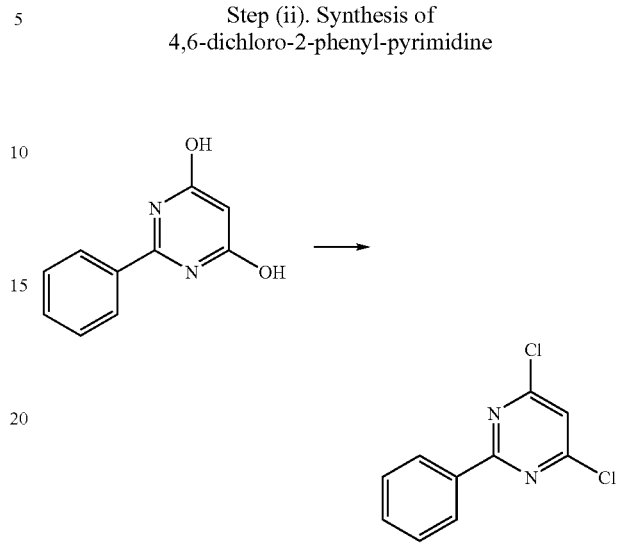

A mixture of compound 2-phenyl-pyrimidine-4,6-diol (33 g, 175.5 mmol) and POCl$_3$ (300 ml) was refluxed for 12-16 hours, excess of POCl$_3$ was distilled out and the crude was neutralized by saturated sodiumbicarbonte solution. The solid obtained was filtered and dried under vacuum to afford the compound 4,6-dichloro-2-phenyl-pyrimidine (28 g, 71%) as off white solid.

Step (iii). Synthesis of (6-chloro-2-phenyl-pyrimidin-4-yl)-(4-trifluoromethoxy-phenyl)-amine

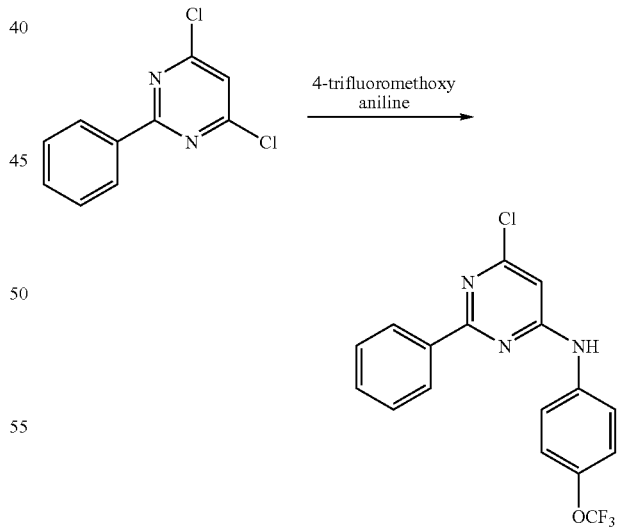

A mixture of compound 4,6-dichloro-2-phenyl-pyrimidine (27 g, 112 mmol), 4-trifluoromethoxy aniline (21 g, 119 mmol) and triethylamine (33 mL, 225 mmol) in n-butanol (300 mL) was refluxed for 20 hours under nitrogen atmosphere. The reaction mixture was then cooled to room temperature and concentrated under vacuum. The crude compound was passed through the silica gel by using 5-6% ethylacetate in petroleum ether to afford the compound (6-chloro-2-phenyl-pyrimidin-4-yl)-(4-trifluoromethoxy-phenyl)-amine (20 g, 46%) as off-white solid.

Step (iv). Synthesis of (6-morpholin-4-yl-2-phenyl-pyrimidin-4-yl)-(4-trifluoromethoxy-phenyl)-amine

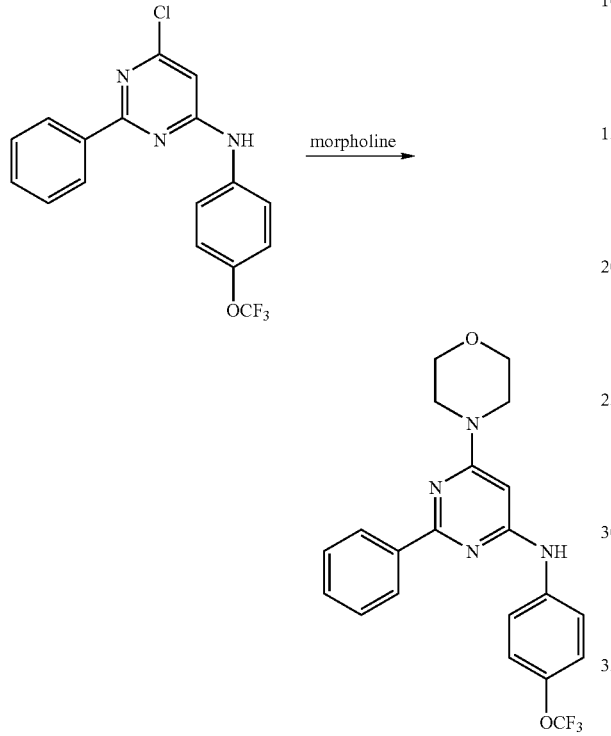

A mixture of compound (6-chloro-2-phenyl-pyrimidin-4-yl)-(4-trifluoromethoxy-phenyl)-amine (39 g, 106 mmol) and morpholine (28 mL, 319 mmol) in n-butanol (400 mL) was refluxed for 24 hours under nitrogen atmosphere. Then the reaction mixture was cooled to room temperature and evaporated under reduced pressure. The crude compound was passed through the silica gel by using 20% ethylacetate in petroleum ether to afford the compound (6-morpholin-4-yl-2-phenyl-pyrimidin-4-yl)-(4-trifluoromethoxy-phenyl)-amine (35.5 g, 80%) as off-white solid.

M.P.: 144-146° C.

$^1$H NMR (400 MHz, DMSO-$d_6$): δ 9.37 (br s, NH), 8.34-8.32 (m, 2H), 7.84-7.82 (d, J=9.1 Hz, 2H), 7.49-7.47 (m, 3H), 7.34-7.32 (d, J=8.6 Hz, 2H), 5.94 (s, 1H), 3.73 (t, J=4.8 Hz, 4H), 3.58 (t, J=4.8 Hz, 4H).

IR: 3299, 2968, 1559, 1286

MS: m/z 417 (M$^+$, 100%)

Examples 114-117

Synthesis of Substituted Pyrimidine Compounds

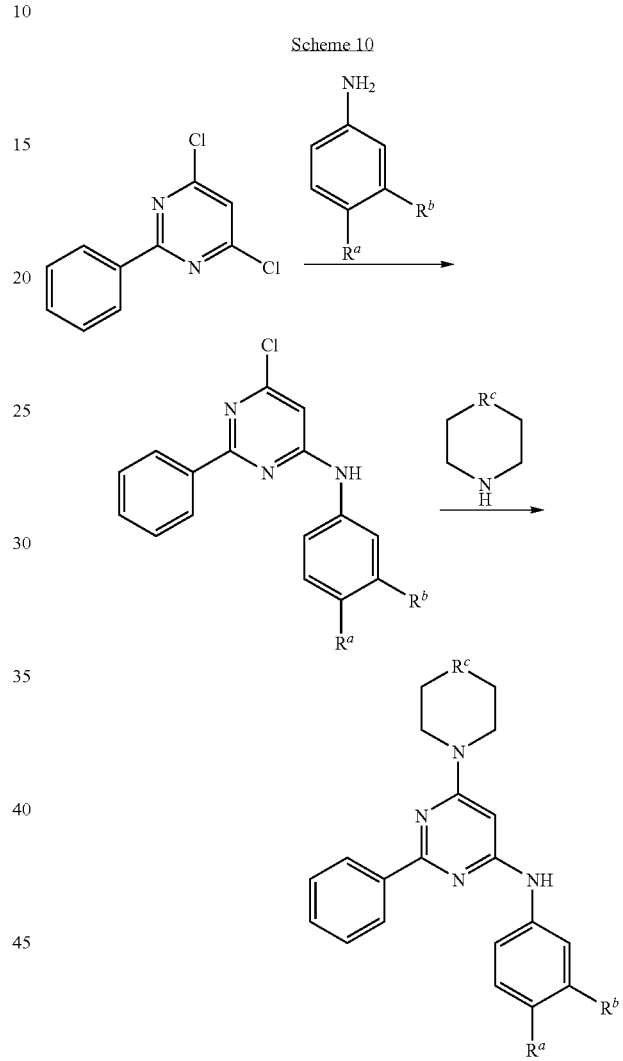

The following compounds presented in Examples 114-117 were prepared in accordance with Scheme 10, by a procedure analogous to that disclosed in Example 113, using starting materials with the appropriate substitution.

| Ex. No. | R$^a$ | R$^b$ | R$^c$ | Analytical data |
|---|---|---|---|---|
| 114 | OCH$_3$ | Cl | C—OH | M.P.: 190-192° C.<br>$^1$H NMR (400 MHz, DMSO-$d_6$) δ 9.09(s, 1H), 8.31-8.28 (m, 2H), 7.95(s, 1H), 7.56-7.53(m, 1H), 7.49-7.45(m, 4H), 7.13(d, J=8.8 Hz, 1H), 4.07-4.06(m, 2H), 3.83(s, 3H), 3.77-3.70(m, 1H), 3.41-3.10(m, 2H), 2.85-2.80(m, 1H), 1.84-1.80(m, 2H), 1.54-1.40(m, 2H).<br>IR (KBr): 3392, 2938, 1571, 1495.<br>MS: m/z 411 (M$^+$, 100%) |

-continued

| Ex. No. | R$^a$ | R$^b$ | R$^c$ | Analytical data |
|---|---|---|---|---|
| 115 | (dioxolane) | | O | M.P.: 132-135° C.<br>$^1$H NMR (400 MHz, DMSO-d$_6$) δ 9.01(br s, NH), 8.31-8.28(m, 2H), 7.47-7.43(m, 4H), 6.98-6.96(s, 1H), 6.89-6.86(m, 1H), 5.99(s, 2H), 5.83(s, 1H), 3.72-3.70(t, J= 4.5 Hz, 4H), 3.56-3.53(t, J=4.5 Hz, 4H)<br>IR: 3310, 2854, 1571, 1442<br>MS: m/z 377 (M$^+$, 100%) |
| 116 | (dioxolane) | | N—CH$_3$ | M.P.: 136-138° C.<br>$^1$H NMR (400 MHz, DMSO-d$_6$)<br>9.03(br s, NH), 8.30-8.28(m, 2H), 7.49-7.43(m, 4H), 6.98-6.86(m, 2H), 5.99(s, 2H), 5.83(s, 1H), 3.78-3.75 (m, 4H), 2.42-2.39(m, 4H), 2.22(s, 3HH)<br>IR: 3416.5, 2928.8, 1592, 1504<br>MS: m/z 232 (M$^+$+1, 100%) |
| 117 | OCF$_3$ | H | NH | M.P.: 195-198° C.<br>$^1$H NMR (400 MHz, DMSO-d$_6$)<br>δ 8.38-8.35(m, 2H), 7.72-7.69(d, J=8.8 Hz, 2H), 7.53-7.42(m, 3H), 7.19-7.17(d, J=8.6 Hz, 2H), 5.87(s, 1H), 3.68-3.66(t, J=4.8 Hz, 4H), 3.09-2.98(t, J=4.8 Hz, 4H)<br>IR: 3258.7, 2926.4, 1563.7, 1257.5<br>MS: m/z 415 (M$^+$, 100%) |

Example 118

Synthesis of (6-phenyl-pyrimidin-4-yl)-(4-trifluoromethoxy-phenyl)-amine

Step (i). Synthesis of 6-phenyl-pyrimidin-4-ol

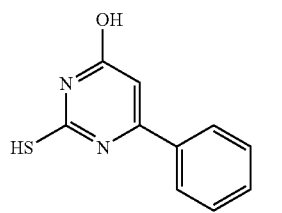 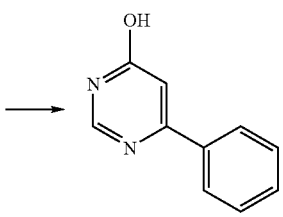

6-Phenyl-pyrimidin-4-ol was prepared by reducing 2-mercapto-6-phenyl-pyrimidin-4-ol (1.5 g, 7.3 mmol) in the presence of raney nickel (5 equivalents) in aqueous ammonia (30 mL) at room temperature followed by refluxing for 3 hours. The mixture was filtered through Celite™ and extracted with ethyl acetate (3×20 mL). Combined organic layers were dried over anhydrous Na$_2$SO$_4$, concentrated under vacuum and the residue purified by column chromatography to give the desired compound (0.5 g, 40% yield) as a off white solid.

Step (ii). Synthesis of 4-chloro-6-phenyl-pyrimidine

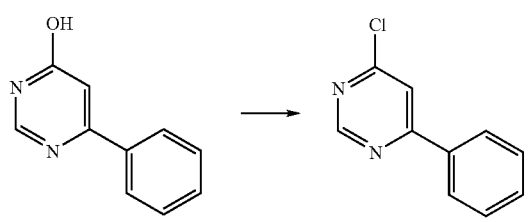

Chlorination of 6-phenyl-3H-pyrimidin-4-one (0.5 g, 2.9 mmol) was carried out according to the procedure described in the literature, see: Burdeska, K.; Fuhrer, H.; Kabas, G.; Siegrist, A. E. *Helv. Chim. Acta* 1981, 64, 113-152.

Step (iii). Synthesis of (6-phenyl-pyrimidin-4-yl)-(4-trifluoromethoxy-phenyl)-amine

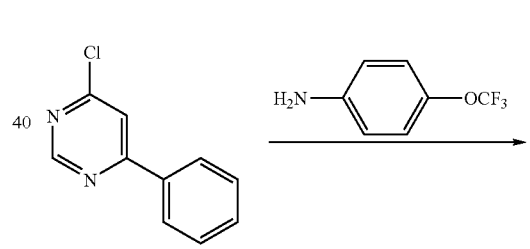

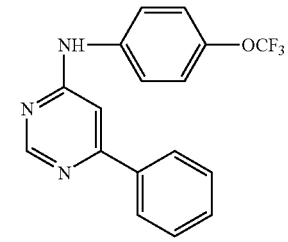

The resulting chloro compound (0.25 g, 1.31 mmol) was treated with 4-trifluoromethoxy phenylamine according to the procedure as described above to give the desired compound.

M.P.: 245-247° C.

$^1$H NMR (400 MHz, DMSO-d$_6$): δ 10.87 (br s, 1H), 8.86 (s, 1H), 7.99-7.97 (m, 2H), 7.87-7.83 (m, 2H), 7.63-7.59 (m, 3H), 7.42-7.37(m, 2H), 7.37 (s, 1H)

IR: 3422, 2869, 1645, 1516

MS: m/z 332 (M$^+$, 100%)

Example 119

Synthesis of 1-{3-[2-morpholin-4-yl-6-(4-trifluoromethoxy-phenylamino)-pyrimidin-4-yl]-phenyl}-ethanone Step (i). Synthesis of (2,6-dichloro-pyrimidin-4-yl)-(4-trifluoromethoxy-phenyl)-amine

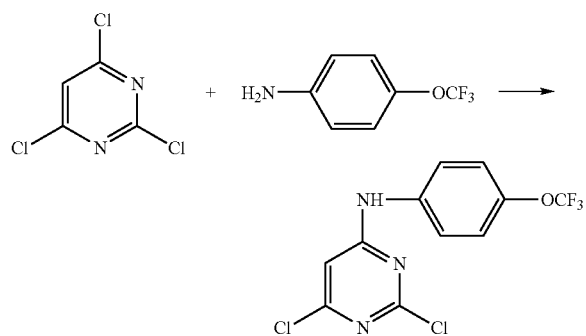

A mixture of compound 2,4,6-trichloro-pyrimidine (1 g, 5.63 mmol), 4-trifluromethoxy aniline (1.99 g, 11.24 mmol) and $K_2CO_3$ (0.7 g, 6.60 mmol) in 20 mL of ethanol was stirred at room temperature for 15 hours under nitrogen atmosphere. Ethanol was then removed under reduced pressure and water was added. The solid obtained was filtered and dried under vacuum to afford the compound (2,6-dichloro-pyrimidin-4-yl)-(4-trifluoromethoxy-phenyl)-amine (1.7 g, 96%) as a white solid.

Step (ii). Synthesis of (6-chloro-2-morpholin-4-yl-pyrimidin-4-yl)-(4-trifluoromethoxy-phenyl)-amine

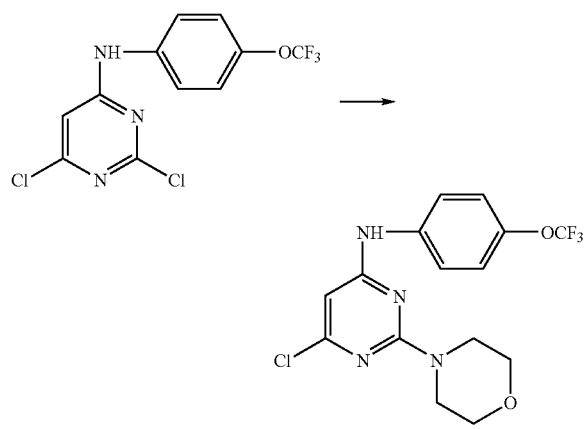

A mixture of compound (2,6-dichloro-pyrimidin-4-yl)-(4-trifluoromethoxy-phenyl)-amine (0.4 g, 1.23 mmol), morpholine (0.1 g, 1.16 mmol) and triethyl amine (0.5 ml, 3.66 mmol) in solvent ethanol (10 mL) was refluxed for 12 hours under nitrogen atmosphere. The reaction mixture was cooled to temperature in the range of 20-40° C. and concentrated under vacuum. The crude compound was passed through the silica gel by using 8-10% ethylacetate in pet-ether to afford the compound (6-chloro-2-morpholin-4-yl-pyrimidin-4-yl)-(4-trifluoromethoxy-phenyl)-amine (0.32 g, 69%) as white solid.

Step (iii). Synthesis of 1-{3-[2-morpholin-4-yl-6-(4-trifluoromethoxy-phenylamino)-pyrimidin-4-yl]-phenyl}-ethanone

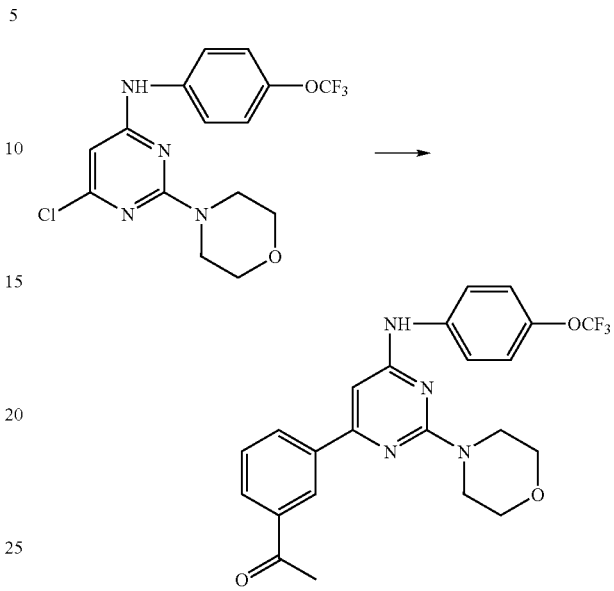

To a mixture of compound (6-chloro-2-morpholin-4-yl-pyrimidin-4-yl)-(4-trifluoromethoxy-phenyl)-amine (0.3 g, 0.8 mmol) and 3-acetyl benzene boronic acid (0.13 g, 0.79 mmol) in DMF (10 mL) was added palladium tetrakis triphenyl phosphine (0.027 g, 0.023 mmol) and 2M $Na_2CO_3$ soln (0.67 g, 6.32 mmol) at room temperature. The reaction mixture was then heated for 12 hours under nitrogen atmosphere. The reaction mixture was cooled to temperature in the range of 20-40° C., diluted with water, extracted with ethyl acetate (3×10 mL). Combined organic layers were concentrated and the residue was purified by column chromatography using 15% ethylacetate in pet-ether to afford the desired compound (0.18 g, 49%) as a brown solid.

M.P.: 194-196° C.

$^1$H NMR (400 MHz, $CDCl_3$): 8.17-8.15 (m, 2H), 8.00-7.78 (m, 2H), 7.54 (t, J=7.8 Hz, 1H), 7.48 (d, J=5.0 Hz, 1H), 7.25-7.21 (m, 2H), 6.45 (s, 1H), 3.90-3.79 (m, 8H), 2.65 (s, 3H)

IR: 3329.8, 1678.1

MS: m/z 459($M^+$+1, 100%)

Example 120

Synthesis of 1-{3-[4-morpholin-4-yl-6-(4-trifluoromethoxy-phenylamino)-pyrimidin-2-yl]-phenyl}-ethanone Step (i). Synthesis of 1-{3-[4-chloro-6-(4-trifluoromethoxy-phenylamino)-pyrimidin-2-yl]-phenyl}-ethanone

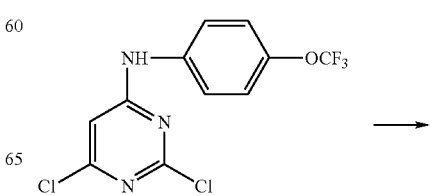

-continued

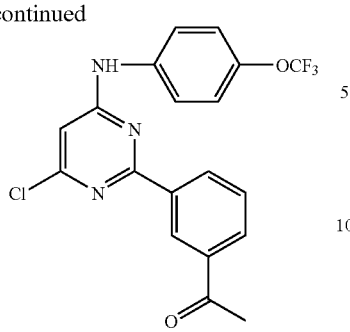

To a mixture of compound (6-chloro-2-morpholin-4-yl-pyrimidin-4-yl)-(4-trifluoromethoxy-phenyl)-amine (0.5 g, 1.54 mmol) and 3-acetyl benzene boronic acid (0.125 g, 0.31 mmol) in DMF (10 mL) was added palladium tetrakis triphenyl phosphine (0.053 g, 0.046 mmol) and 2M Na$_2$CO$_3$ solution (1.3 g, 12.34 mmol) at temperature in the range of 20-40° C. The reaction mixture was heated for 12 hours under nitrogen atmosphere. After cooling to room temperature the mixture was diluted with water and extracted with ethyl acetate (3×10 mL). Combined the organic layers were concentrated and the residue was purified by column chromatography using 15% ethylacetate in petroleum ether to afford the desired compound (0.125 g, 20%) as a white solid.

Step (ii). Synthesis of 1-{3-[4-morpholin-4-yl-6-(4-trifluoromethoxy-phenylamino)-pyrimidin-2-yl]-phenyl}-ethanone

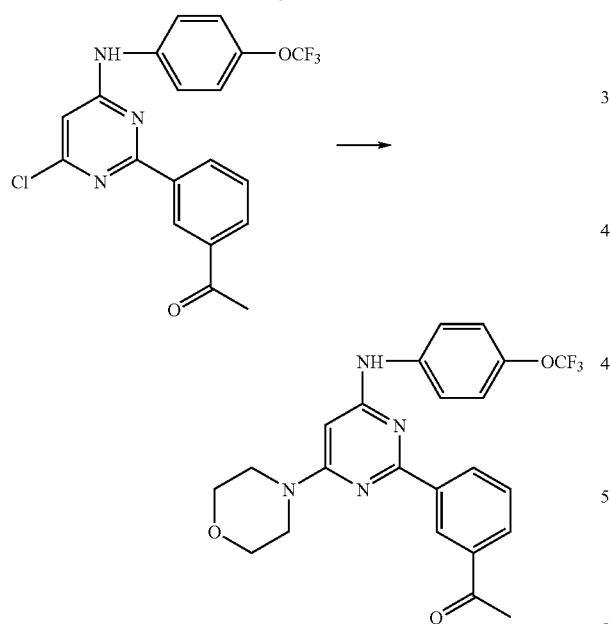

A mixture of compound 1-{3-[4-chloro-6-(4-trifluoromethoxy-phenylamino)-pyrimidin-2-yl]-phenyl}-ethanone (0.13 g, 0.32 mmol) and morpholine (0.22 g, 2.55 mmol) in n-butanol (10 mL) was refluxed for 24 hours under nitrogen atmosphere. The mixture was cooled to temperature in the range of 20-40° C. and concentrated under vacuum. The crude compound was purified by column chromatography using 18-20% ethylacetate in petroleum ether to afford the desired compound (0.11 g, 75%) as a white solid.

M.P.: 218-220° C.

$^1$H NMR (400 MHz, CDCl$_3$): δ 8.95 (s, 1H), 8.57 (d, J=7.6 Hz, 1H), 8.04 (d, J=8.4 Hz, 1H), 7.54 (t, J=7.8 Hz, 1H), 7.42 (d, J=8.1 Hz, 2H), 7.25-7.23 (m, 2H), 5.80 (br s, 1H), 3.83-3.81 (m, 4H), 3.66-3.64 (m, 4H), 2.68 (s, 3H).

IR: 3365.3, 1668.9

MS: m/z 459(M$^+$+1, 100%).

Example 121

Synthesis of (2,6-diphenyl-pyrimidin-4-yl)-(4-trifluoromethoxy-phenyl)-amine

Step (i). Synthesis of 2,6-diphenyl-pyrimidin-4-ol

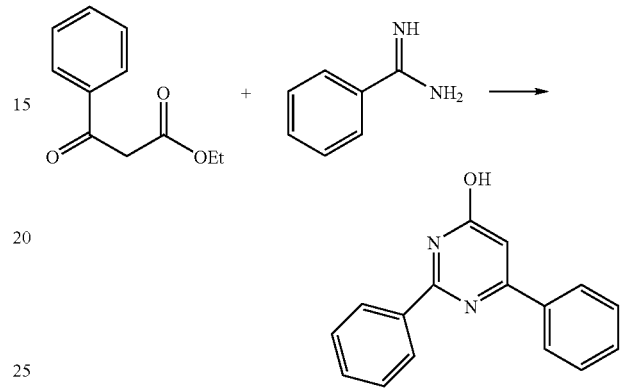

Ethyl benzoyl acetate (60 g, 312 mmol), benzamidine hydrochloride (65 g, 375 mmol) and potassium carbonate (172 g, 1250 mmol) were dissolved in 1,4-dioxane (1.2 liter) the reaction mixture was refluxed for 12 hours under nitrogen atmosphere. Reaction mixture was diluted with water, neutralized with cold 2N HCl, solid was filtered, washed with water and dried to yield the desired compound.

Step (ii). Synthesis of 4-chloro-2,6-diphenyl-pyrimidine

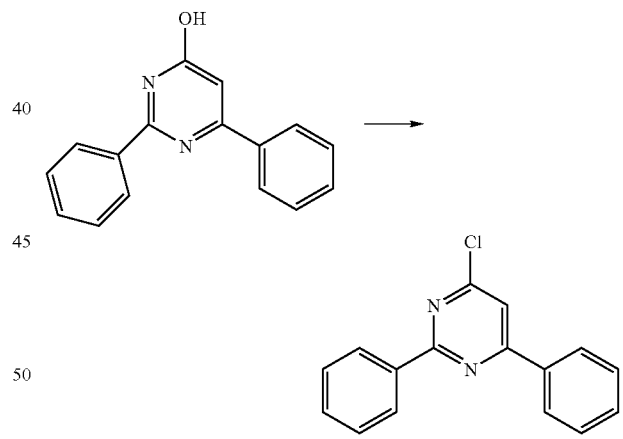

2,6-diphenyl-pyrimidin-4-ol converted to 4-chloro-2,6-diphenyl-pyrimidine by refluxing it in POCl$_3$ for 10 hours according to the procedure described in Example 39, step ii.

Step (iii). Synthesis of (2,6-diphenyl-pyrimidin-4-yl)-(4-trifluoromethoxy-phenyl)-amine

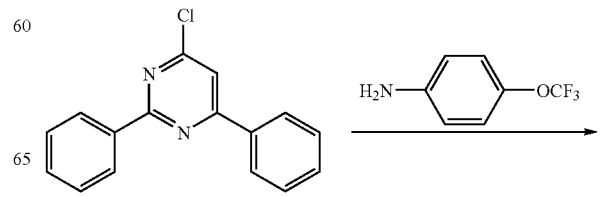

-continued

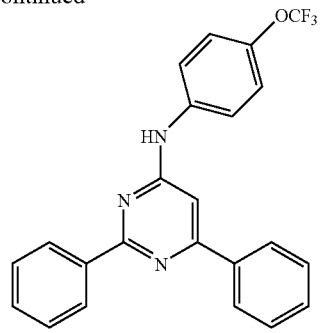

The title compound was prepared from 4-chloro-2,6-diphenyl-pyrimidine (0.25 g, 0.93 mmol) and 4-trifluoromethoxy aniline (0.16 g, 0.93 mmol) according to the procedure as described above.

M.P.: 220-222° C.
$^1$H NMR (400 MHz, DMSO-$d_6$): δ 10.07 (br s, 1H), 8.50-8.47 (dd, J=3.9, 1.9 Hz, 2H), 8.18-8.16 (dd, J=1.7, 1.4 Hz, 2H), 7.98-7.96 (d, J=9.3 Hz, 2H), 7.61-7.32 (m, 8H), 7.25 (s, 1H).
IR: 2924,1643,1507,1278.
MS: m/z 408 (M$^+$+1 100%).

Example 122

Synthesis of 4-(2,6-diphenyl-pyrimidin-4-ylamino)-N-methyl-benzenesulfonamide

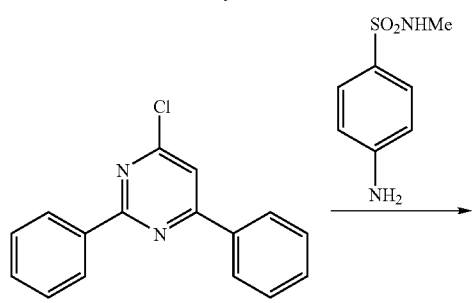

-continued

To a solution of 4-chloro-2,6-diphenyl-pyrimidine (0.2 g, 0.75 mmol) in n-BuOH (7 mL) was added 4-amino-N-methyl-benzenesulfonamide (0.146 g, 0.78 mmol) and the mixture was stirred at reflux temperature for 72 hours under nitrogen. The mixture was then cooled to temperature in the range of 20-40° C., the solid precipitated was filtered off and dried to give the title compound (0.13 g, 43% yield).

Examples 123-125

Synthesis of Substituted Pyrimidine Compounds

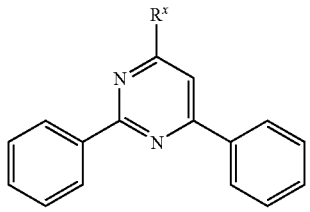

The following compounds presented in Examples 123-125 were prepared by a procedure analogous to that disclosed in Example 121, using starting materials with the appropriate substitution.

| Ex. No. | R$^x$ | Analytical data |
|---|---|---|
| 123 | ethyl-piperazinyl | M.P.: 124-126° C.<br>$^1$H NMR (400 MHz, DMSO-$d_6$) δ 8.49-8.44 (m, 2H), 8.30-8.27 (m, 2H), 7.55-7.48 (m, 6H), 7.28 (s, 1H), 3.83-3.82 (m, 4H), 3.29-3.28 (m, 4H), 2.49-2.39 (m, 2H), 1.07-1.03 (t, J = 7.0 Hz, 3H).<br>IR: 2939, 1594, 1571, 1375.<br>MS: m/z 346 (M$^+$ + 1 100%). |
| 124 | morpholinyl | M.P.: 196-198° C.<br>$^1$H NMR (400 MHz, DMSO-$d_6$) δ 8.49-8.46 (m, 2H), 8.31-8.29 (m, 2H), 7.56-7.49 (m, 6H), 7.29 (s, 1H), 3.78-3.74 (m, 8H).<br>IR: 3422, 1572, 1523, 1375.<br>MS: m/z 318 (M$^+$ + 1 100%). |

-continued

| Ex. No. | R$^x$ | Analytical data |
|---|---|---|
| 125 | 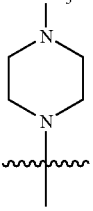 | 148-150° C.<br>$^1$H NMR (400 MHz, DMSO-d$_6$), δ 8.55-8.52 (m, 2H), 8.14-8.11 (dd, J = 1.9, 1.6 Hz, 2H), 7.49-7.45 (m, 6H), 6.84 (s, 1H), 3.88-3.85 (m, 4H), 2.58-2.57 (m, 4H), 2.38 (s, 3H).<br>IR: 3444, 2937, 1594, 1527.<br>MS: m/z 331 (M$^+$ + 1, 100%). |

Example 126

Synthesis of N$^4$-(3-chloro-4-methoxy-phenyl)-6-(4-methanesulfonyl-phenyl)-pyrimidine-2,4-diamine

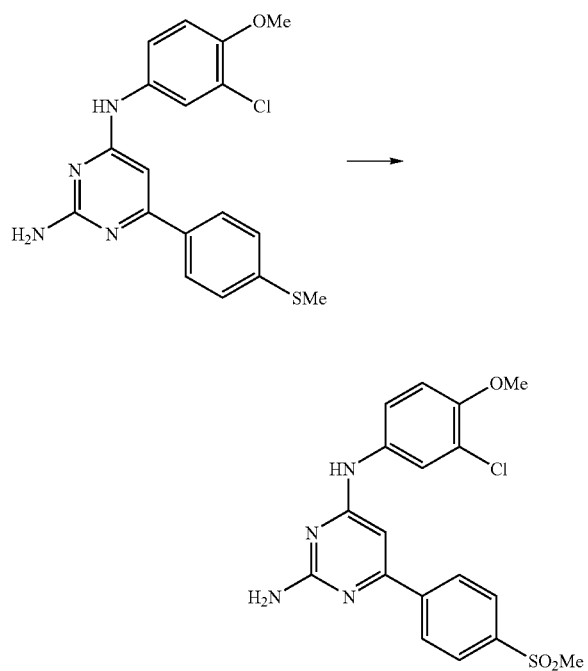

N$^4$-(3-Chloro-4-methoxy-phenyl)-6-(4-methanesulfonyl-phenyl)-pyrimidine-2,4-diamine was prepared from compound N$^4$-(3-chloro-4-methoxy-phenyl)-6-(4-methylsulfanyl-phenyl)-pyrimidine-2,4-diamine, in aqueous acetone (3:1) using oxone (2KHSO$_5$.KHSO$_4$.K$_2$SO$_4$) as an oxidizing agent.

M.P.: 241-244° C.

$^1$H NMR (200 MHz, DMSO-d$_6$): δ 9.3 (s, D$_2$O exchangeable, 1H), 8.18-8.01 (m, 3H), 7.92 (s, 1H), 7.62-7.58 (m, 1H), 7.11-7.07 (m, 1H), 6.51-6.49 (m, 2H), 3.83 (s, 3H), 3.26 (s, 3H).

I.R: 3490, 3287, 1253.

MS: m/z (CI) 405 (M$^+$, 100%).

Example 127

Synthesis of 1-[4-(3-chloro-4-hydroxy-phenylamino)-6-phenyl-pyrimidin-2-yl]-pyrrolidine-2,5-dione

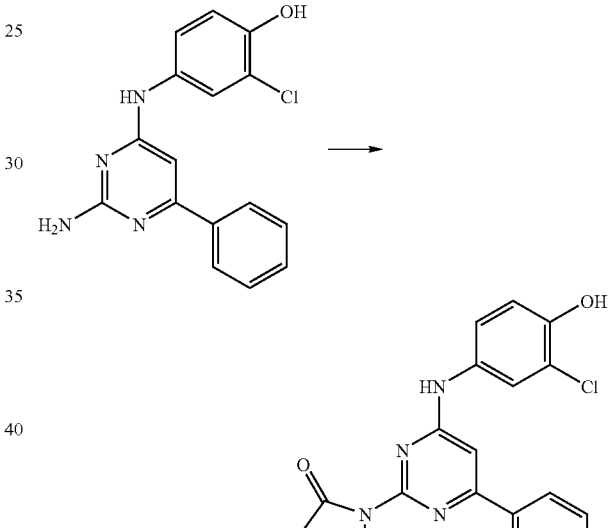

To a solution of compound 4-(2-amino-6-phenyl-pyrimidin-4-ylamino)-2-chloro-phenol (0.5 g, 1.6 mmol) in dry dimethylformamide (10 mL) was added 4-(N,N-dimethylamino)pyridine (0.39 g, 3.2 mmol) at 0° C. with stirring under nitrogen atmosphere. To this was added freshly prepared succinyl chloride (0.62 g, 4 mmol). The mixture was then stirred at 80° C. for 20 hours. After completion of the reaction the mixture was diluted with water (75 mL), the solid separated was filtered off, washed with cold water (200 mL) and dried. The solid was purified further by column chromatography using petroleum ether-ethyl acetate to give the desired product as a light brown solid.

M.P.: 274-276° C.

$^1$H NMR (200 MHz, DMSO-d$_6$): δ 10.01 (s, 1H), 9.88 (s, 1H), 7.96 (s, 2H); 7.60-7.33 (m, 5H), 7.14 (s, 1H), 6.94 (d, J=8.8 Hz, 1H), 2.89 (s, 4H).

IR (KBr, cm$^{-1}$): 3345.0, 1784.9, 1696.3, 1618.7, 1498.4, 1183.3.

MS: m/z (CI) 395 (M+1, 100%).

Example 128

Synthesis of 2-(2-amino-6-phenyl-pyrimidin-4-ylamino)-benzoic acid

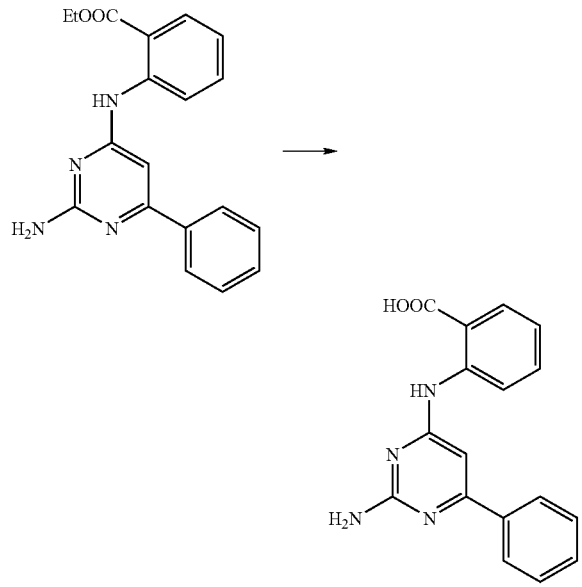

2-(2-Amino-6-phenyl-pyrimidin-4-ylamino)-benzoic acid was prepared by hydrolyzing 2-(2-amino-6-phenyl-pyrimidin-4-ylamino)-benzoic acid ethyl ester (0.2 g, 0.59 mmol) in methanol (5 mL) using aqueous solution of potassium hydroxide (6 N KOH). The mixture was concentrated under vacuum, diluted with water (5 mL), neutralized with cold 2N HCl. The solid precipitated was filtered and dried to give the desired product.

M.P.: 260-262° C.
$^1$H NMR (200 MHz, CDCl$_3$+CF$_3$COOD): δ 5 (d, J=7.8 Hz, 2H), 7.87-7.50 (m, 7H), 6.65 (s, 1H).
I.R: 3335, 1667, 1588.
MS: m/z (CI) 307 (M$^+$, 100%).

Example 129

Synthesis of succinic acid mono-{1-[2-(3-chloro-4-methoxy-phenylamino)-6-phenyl-pyrimidin-4-yl]-piperidin-4-yl}ester

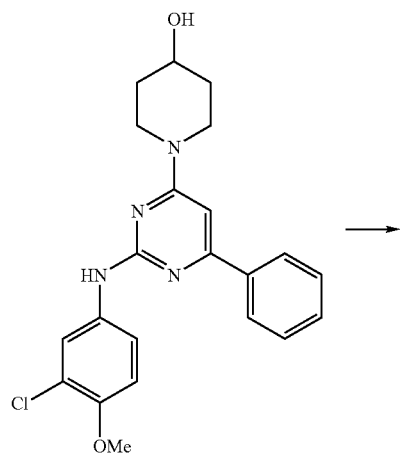

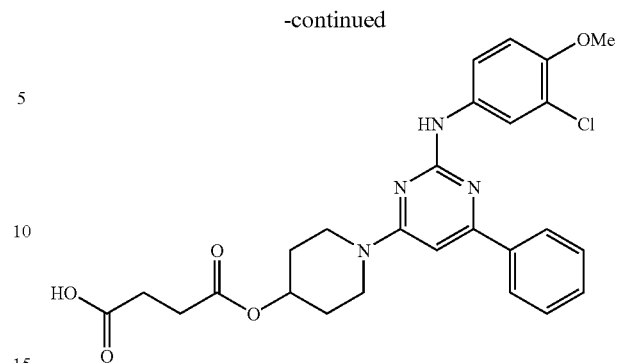

A mixture of compound 1-[2-(3-chloro-4-methoxy-phenylamino)-6-phenyl-pyrimidin-4-yl]-piperidin-4-ol (1.0 g, 2.4 mmol), 4-(N,N-dimethyl)aminopyridine (0.45 g, 3.66 mmol) and succinic anhydride (0.73 g, 7.33 mmol) in dichloroethane (20 mL) was stirred at refluxing temperature for 48 hours. The mixture was cooled to temperature in the range of 20-40° C. and solvent was removed under reduced pressure. The residue was treated with water (20 mL) and the solid precipitated was filtered and washed with isopropanol to give the desired product.

M.P.: 218-220° C.
Spectral data: $^1$H NMR (400 MHz, DMSO-d$_6$) δ 10.59 (br s, 1H), 8.11 (d, J=6.8 Hz, 2H), 7.78 (d, J=2.1 Hz, 1H), 7.66-7.58 (m, 2H), 7.47 (d, J=8.9 Hz, 1 H), 7.20 (d, J=8.9 Hz, 1H), 7.05 (s, 1H), 5.05-5.01 (m, 1H), 4.03-3.98 (m, 1H), 3.89-3.79 (m, 3H), 2.57-2.49 (m, 8H), 1.99-1.94 (m, 2H), 1.72-1.68 (m, 2H).
MS: m/z (CI) 511 (M$^+$, 100).

Example 130

Synthesis of [4-(3-chloro-4-methoxyphenylamino)-6-phenylpyrimidine-2-ylsulfanyl]-acetic acid ethyl ester

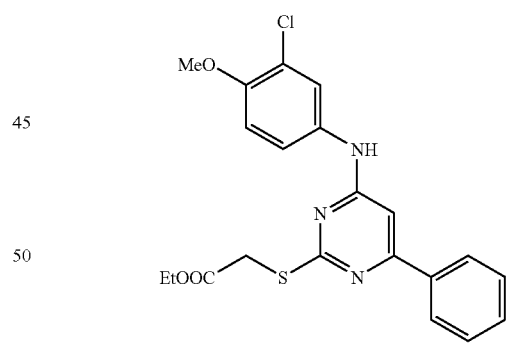

Step (i). Synthesis of 4-hydroxy-6-phenyl-pyrimidin-2-ylsulfanyl)-acetic acid ethyl ester

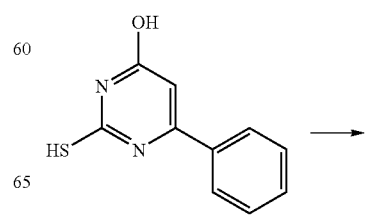

-continued

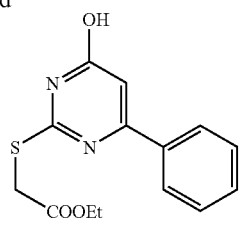

To a suspension of 60% sodium hydride (1.96 g, 4.90 mmol) in dimethylformamide (15 mL) was added to a solution of compound 2-mercapto-6-phenyl-pyrimidin-4-ol (1 g, 4.90 mmol) in dimethylformamide (10 mL) at 0° C. under nitrogen atmosphere and the mixture was stirred for 1 hour at the same temperature. To this was added ethyl bromoacetate (0.54 mL, 4.89 mmol) and the mixture was then stirred at 80° C. for 16 hours. After cooling to temperature in the range of 20-40° C. the mixture was diluted with water (70 mL). The solid was filtered off, dried under vacuum and was triturated with isopropanol to afford the title compound as an off white solid.

$^1$H NMR (200 MHz, DMSO-d$_6$): δ 8.06-8.04 (m, 2H), 7.49-7.47 (m, 3H), 6.74 (br s, 1H), 4.15-4.04 (m, 4H), 1.17 (t, J=7.3 Hz, 3H).

IR (KBr, cm$^{-1}$): 3445, 1748, 1655.

MS: (CI) m/z 245 (M$^+$–29, 100).

Step (ii). Synthesis of 4-chloro-6-phenyl-pyrimidin-2-ylsulfanyl)-acetic acid ethyl ester

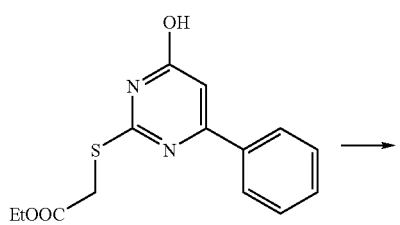

A mixture of compound 4-hydroxy-6-phenyl-pyrimidin-2-ylsulfanyl)-acetic acid ethyl ester (1.0 g, 3.44 mmol) and phosphorus oxychloride (15 mL) was stirred at 80-90° C. for 4 to 5 hours and then excess of phosphorus oxychloride was distilled out under low vacuum. The mixture was cooled to temperature in the range of 20-40° C., diluted with water (30 mL) and neutralized with sodium bicarbonate solution. The solid was filtered off, washed with hexane (10 mL), and dried to afford the title compound.

$^1$H NMR: (CDCl$_3$, 200 MHz): δ 8.06-8.03 (m, 2H), 7.52-7.41 (m, 4H), 4.27-4.16 (m, 4H), 1.27 (t, J=7.3 Hz, 3H).

IR (Neat, cm$^{-1}$): 3429, 1730, 1648.

MS: (CI) m/z 309 (M$^{+1}$, 100%).

Step (iii). Synthesis of [4-(3-chloro-4-methoxyphenylamino)-6-phenylpyrimidine-2-ylsulfanyl]-acetic acid ethyl ester

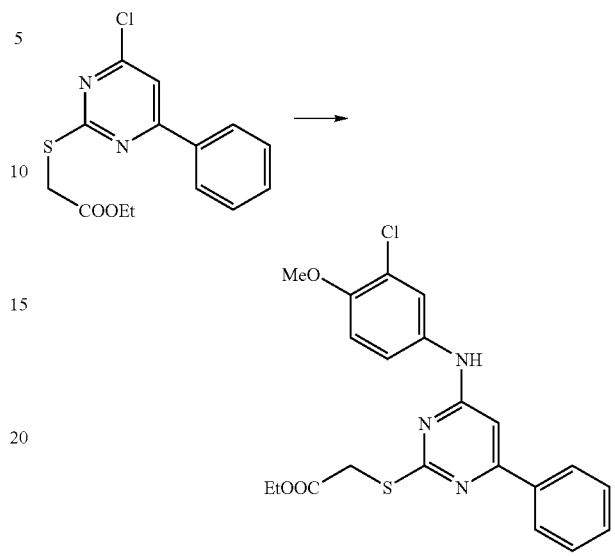

A mixture of compound 4-chloro-6-phenyl-pyrimidin-2-ylsulfanyl)-acetic acid ethyl ester (0.30 g, 0.97 mmol) and 3-chloro-4-methoxyaniline (0.17 g, 1.07 mmol) in isopropanol (8 mL) was stirred at refluxing temperature for 20 hours under a nitrogen atmosphere. The reaction mixture was cooled to temperature in the range of 20-40° C. The solid separated was filtered off and then dried under vacuum to afford the title compound.

M.P.: 154.86° C.

$^1$H NMR (200 MHz, DMSO-d$_6$): δ 9.8 (s, 1H), 8.05-8.03 (m, 2H), 7.81-7.79 (m, 1H), 7.53-7.49 (m, 4H), 7.48 (d, J=9.1 Hz, 1H), 6.9 (s, 1H), 4.13-4.0 (m, 5H), 3.86-3.80 (m, 2H), 1.15 (t, J=6.9 Hz, 3H).

IR (KBr, cm$^{-1}$): 3352, 1720, 1616.

MS: m/z (CI) 430 (M$^+$, 100%).

Example 131

Synthesis of 4-(3-chloro-4-methoxy-phenyl)-6-pyridin-3-yl-pyrimidin-2-ylamine

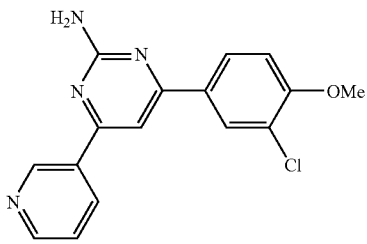

Step (i). Synthesis of 1-(3-chloro-4-methoxy-phenyl)-3-pyridin-3-yl-propane-1,3-dione

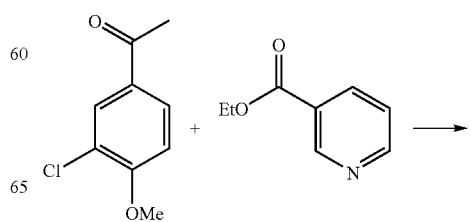

-continued

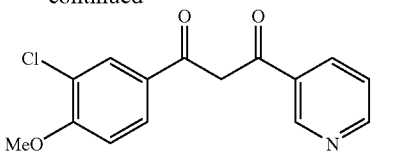

To a solution of 3-chloro-4-methoxy acetophenone (3.0 g, 16.30 mmol) in DMF (15 mL) was added 60% NaH [0.717 g (0.430 g, 17.93 mmol)] at 0° C. under a nitrogen atmosphere. The mixture was stirred for 30 min and a solution of nicotinic acid ethyl ester (2.95 g, 19.56 mmol) in DMF (10 mL) was added slowly to it. The mixture was stirred at temperature in the range of 20-40° C. for 12 hour. It was then poured into ice-cold water (100 mL) and stirred for 15 minutes. The solid was filtered and dried to give the desired compound.

$^1$H NMR (400 MHz, CDCl$_3$): δ 16.7 (br s, 1H), 9.20 (s, 1H), 8.8 (s, 1H), 8.15 (s, 1H), 8.0-7.8 (m, 2H), 7.47-7.44 (m, 1H), 7.04-7.02 (m, 2H), 6.76 (s, 1H), 4.0 (s, 3H).

IR (KBr, cm$^{-1}$): 3429, 1600, 1594.

MS: m/z (CI) 290 (M+1, 100%).

Reference: 3-chloro-4-methoxy acetophenone was prepared according to the procedure described in Watanabe, N.; Kabasawa, Y.; Takase, Y.; Matsukura, M.; Miyazaki, K. Ishihara, H.; Kodama, K.; Adachi, H. *J. Med. Chem.* 1998, 41, 3367-3372.

Step (ii). Synthesis of 4-(3-chloro-4-methoxy-phenyl)-6-pyridin-3-yl-pyrimidin-2-ylamine

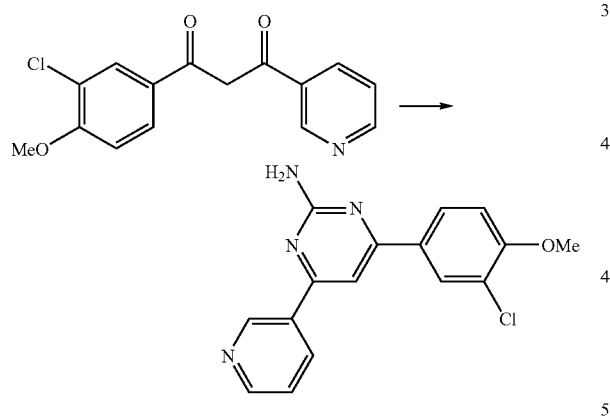

4-(3-Chloro-4-methoxy-phenyl)-6-pyridin-3-yl-pyrimidin-2-yl amine was prepared by treateing 1-(3-chloro-4-methoxy-phenyl)-3-pyridin-3-yl-propane-1,3-dione (0.3 g, 1.0 mmol) with guanidine carbonate (0.21 g, 1.1 mmol) in dowtherm (7 mL) at 180° C. for 30 minutes. The mixture was cooled to temperature in the range of 20-40° C. and diluted with petroleum ether (25 mL). The mixture was stirred for 1 hour. The solid was filtered and dried to give the desired product.

M.P.: 194-196 ° C.

$^1$H NMR (400 MHz, DMSO-d$_6$): δ 8.7-8.69 (m, 1H), 8.56 (d, J=7.8 Hz, 1H), 8.37 (s, 1H), 8.25 (d, J=8.4 Hz, 1H), 7.83 (s, 1H), 7.58-7.52 (m, 1H), 7.30 (d, J=8.9 Hz, 1H), 6.84 (D$_2$O exchangeable), 3.95 (s, 3H).

IR (KBr, cm$^{-1}$): 3313, 1635, 1536.

MS: m/z (CI) 313 (M+1, 100%).

Example 132

Synthesis of 4-[2-(3-chloro-4-methoxy-phenylamino)-6-phenyl-pyrimidin-4-yaminol]-cyclohexanol

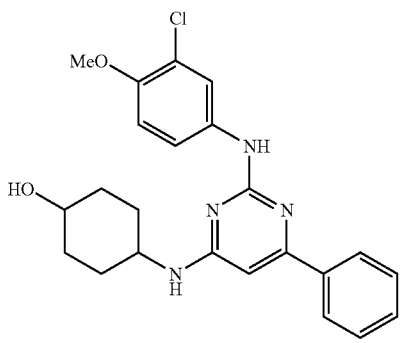

Step (i). Synthesis of 4-(2-chloro-6-phenyl-pyrimidin-4-ylamino)-cyclohexanol and 4-(4-chloro-6-phenyl-pyrimidin-2-ylamino)-cyclohexanol

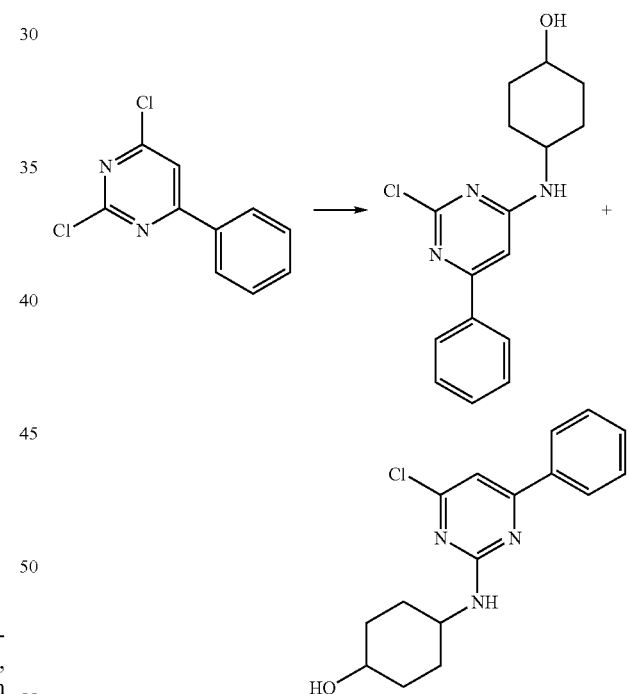

A mixture of compound 2,4-dichloro-6-phenyl-pyrimidine (0.5 g, 2.22 mmol), 4-aminocyclohexanol hydrochloride (0.12 g, 1.11 mmol), triethylamine (0.67 g, 6.62 mmol) in n-butanol (10 mL) was stirred at 120° C. for 12 hours under a nitrogen atmosphere. The reaction mixture was then concentrated under vacuum, diluted with water (25 mL) and extracted with ethyl acetate (3×20 mL). The organic layers were collected, combined, washed with water (20 mL), dried over anhydrous sodium sulphate, and concentrated under vacuum. The residue thus obtained was purified by column chromatography using ethyl acetate-petroleum ether to give the two compounds 4-(2-chloro-6-phenyl-pyrimidin-4-ylamino)-cyclohexanol and 4-(4-chloro-6-phenyl-pyrimidin-2-ylamino)-cyclohexanol in ratio 1:2 (overall yield: 63%).

Spectral Data for 4-(2-chloro-6-phenyl-pyrimidin-4-ylamino)-cyclohexanol $^1$H NMR (200 MHz, DMSO-d$_6$): δ 10.71 (br s, 1H), 7.64-7.50 (m, 5H), 6.49 (s, 1H), 3.85-3.64 (m, 2H), 1.96-1.90 (m, 4H), 1.32-1.19 (m, 4H)
IR (KBr, cm$^{-1}$): 3325, 1554.
MS: m/z (CI) 304 (M$^+$, 100).

Spectral Data for 4-(4-chloro-6-phenyl-pyrimidin-2-ylamino)-cyclohexanol $^1$H NMR (200 MHz, DMSO-d$_6$): δ 10.89 (br s, 1H), 8.20-8.11 (m, 2H), 7.60-7.52 (m, 3H), 6.55 (s, 1H), 3.86-3.70 (m, 2H), 2.02-1.88 (m, 4H), 1.34-1.21 (m, 4H).
IR (KBr, cm$^{-1}$): 3327, 1551.
MS: m/z (CI) 304 (M$^+$, 100).

Step (ii). Synthesis of 1-[4-(3-chloro-4-methoxy-phenylamino)-6-phenyl-pyrimidin-2-yl]-piperidin-4-ol

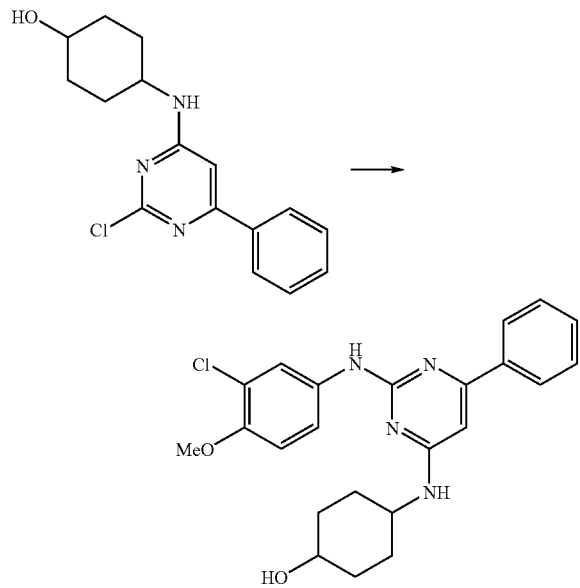

A mixture of compound 4-(2-chloro-6-phenyl-pyrimidin-4-ylamino)-cyclohexanol (0.28 g, 0.91 mmol), 3-chloro-4-methoxyaniline (0.158 g, 1.0 mmol) in 1-butanol (5 mL) was stirred at 120° C. for 6 hours. The mixture was then cooled to temperature in the range of 20-40° C. The solid was filtered, collected, washed with 1-butanol (1 mL), filtered and dried to give the desired compound as a white solid.
M.P.: 289-292° C.
$^1$H NMR (200 MHz, DMSO-d$_6$): δ 12.9 (br s, 1H), 10.71 (s, 1H), 9.01 (s, 1H), 8.02 (s, 1H), 7.89 (d, J=3.9 Hz, 2H), 7.64-7.61 (m, 3H), 7.35-7.31 (m, 1H), 7.20 (d, J=9.0 Hz, 1H), 6.49 (s, 1H), 3.86-3.45 (m, 5H), 1.97-1.91 (m, 4H), 1.33-1.20 (m, 4H)
IR (KBr, cm$^{-1}$): 3476, 1587.
MS: m/z (CI) 425 (M+1, 100%).

Example 133

Synthesis of 4-[4-(3-chloro-4-methoxy-phenylamino)-6-phenyl-pyrimidin-2-ylamino]-cyclohexanol

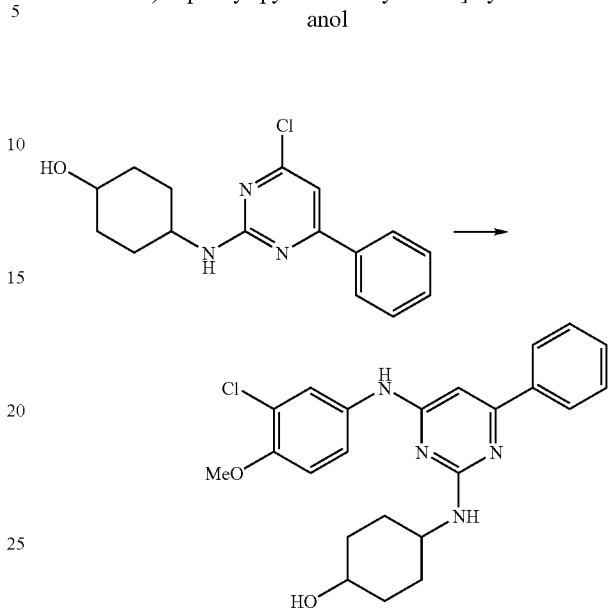

4-[4-(3-Chloro-4-methoxy-phenylamino)-6-phenyl-pyrimidin-2-ylamino]-cyclohexanol was prepared by reacting compound 4-(4-chloro-6-phenyl-pyrimidin-2-ylamino)-cyclohexanol (0.15 g, 0.49 mmol) with 3-chloro-4-methoxyaniline (85 mg, 0.54 mmol) in 1-butanol according to the procedure described above. Yield: 53%.
M.P.: 293-295° C.
$^1$H NMR (200 MHz, DMSO-d$_6$): δ 12.6 (br s, 1H), 10.89 (br s, 1H), 8.23-8.16 (m, 2H), 7.86 (d, J=7.9 Hz, 2H), 7.65 (s, 3H), 7.46 (d, J=7.8 Hz, 1H), 7.22 (d, J=9.0 Hz, 1H), 6.59 (s, 1H), 3.87-3.72 (m, 5H), 2.01-1.89 (m, 4H), 1.36-1.23 (m, 4H).
IR (KBr, cm$^{-1}$): 3512, 3249, 1495.
MS: m/z (CI) 425 (M+1, 100%).

Example 134

Synthesis of (3-chloro-4-methoxy-phenyl)-[4-(4-ethyl-piperazin-1-yl)-6-phenyl-pyrimidin-2-yl]-amine

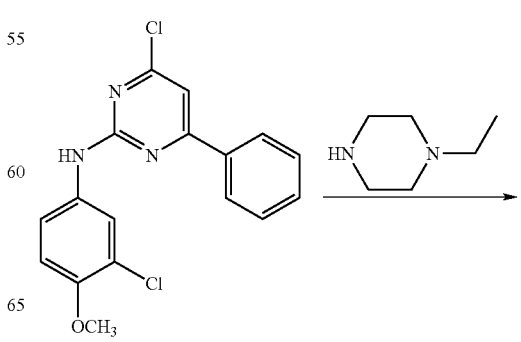

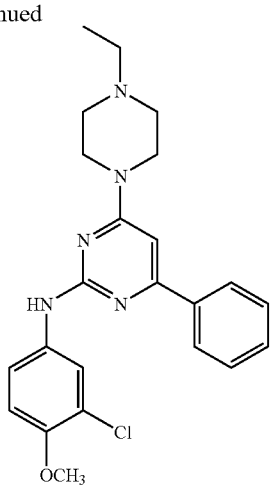

The title compound was prepared by treating (3-chloro-4-methoxy-phenyl)-(4-chloro-6-phenyl-pyrimidin-2-yl)-amine (0.5 g, 1.4 mmol) with N-ethyl piperazine (0.16 g, 1.4 mmol) in n-butanol at refluxing temperature.

M.P.: 248-250° C.

$^1$H NMR (400 MHz, DMSO-d$_6$): δ 9.21 (br s, 1H), 8.15-8.12 (dd, J=4.3, 1.9 Hz, 2H), 7.99-7.98 (d, J=2.1 Hz, 1H), 7.64-7.61 (dd, J=2.7, 2.4 Hz, 1H), 7.52-7.49 (m, 3H), 7.11-7.08 (d, J=9.1 Hz, 1H), 6.93 (s, 1H), 3.81 (s, 3H), 3.80-3.79 (m, 8H), 3.09 (m, 2H), 1.28-1.25 (t, J=6.9 Hz, 3H).

IR: 3425, 1499, 1061.

MS: m/z 424 (M$^+$+1, 100%).

Example 135

Synthesis of (3-chloro-4-methoxy-phenyl)-[4-(4-ethyl-piperazin-1-yl)-6-phenyl-pyrimidin-2-yl]-amine

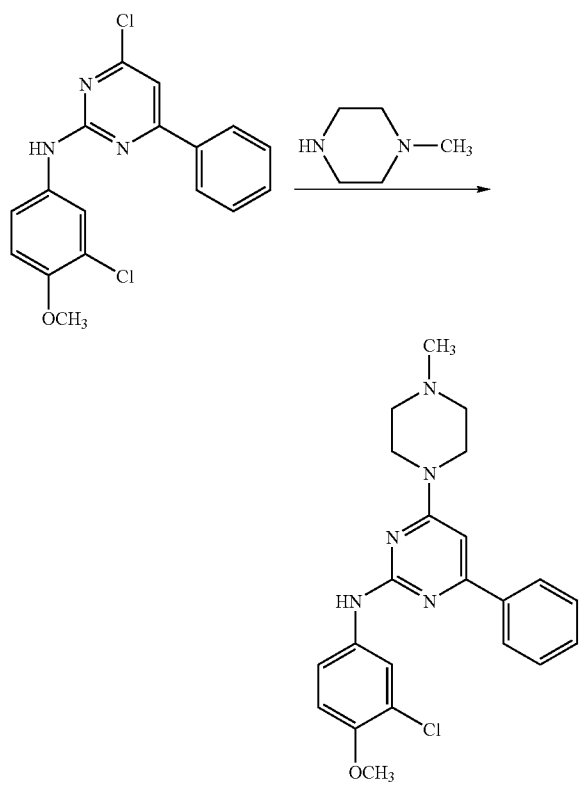

The title compound was prepared by treating (3-chloro-4-methoxy-phenyl)-(4-chloro-6-phenyl-pyrimidin-2-yl)-amine (0.5 g, 1.4 mmol) with N-methyl piperazine in n-butanol at refluxing temperature.

$^1$H NMR (400 MHz, DMSO-d$_6$): δ 9.21 (br s, 1H), 8.14-8.12 (m, 2H), 7.99-7.98 (d, J=2.2 Hz, 1H), 7.65-7.62 (d, J=2.7, 2.4 Hz, 1H), 7.52-7.49 (m, 3H), 7.11-7.08 (d, J=8.9 Hz, 1H), 6.93 (s, 1H), 4.61-4.57 (m, 4H), 3.81 (s, 3H), 3.30-3.11 (m, 4H), 2.77 (s, 3H).

IR: 3424, 1574, 1499, 1060.

MS: m/z 409 (M$^+$+1, 100%).

Example 136

Synthesis of [4-(1,1-dioxo-1-lambda6-thiomorpholin-4-yl)-6-phenyl-pyrimidin-2-yl]-(3-fluoro-4-methoxy-phenyl)-amine

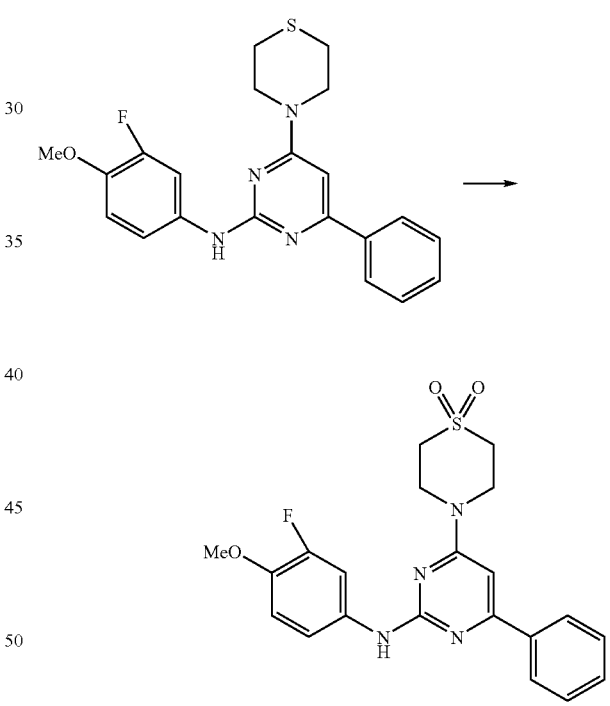

The title compound was prepared by treating (3-fluoro-4-methoxy-phenyl)-(4-phenyl-6-thiomorpholin-4-yl-pyrimidin-2-yl)-amine (0.3 g, 0.76 mmol) with oxone (1.39 g, 2.27 mmol) in acetone-water (3:1) at room temperature for 1 hour.

$^1$H NMR (400 MHz, DMSO-d$_6$): δ 9.2 (br s,1H), 8.30 (s,1H), 8.15-8.13 (dd, J=1.9, 1.9 Hz, 1H), 7.51-7.50 (d, J=8 Hz, 2H), 7.48-7.49 (m, 4H), 6.99 (s, 1H), 4.2 (s, 4H), 3.80 (s, 3H), 3.29 (s, 4H)

IR: 3330, 1645, 1430

MS: m/z 429 (M$^+$+1,100%)

Example 137

Synthesis of 1-[2-(4-methanesulfonyl-phenylamino)-6-phenyl-pyrimidin-4-yl]-piperidin-4-ol Step (i). Synthesis of 1-[2-(4-methylsulfanyl-phenylamino)-6-phenyl-pyrimidin-4-yl]-piperidin-4-ol

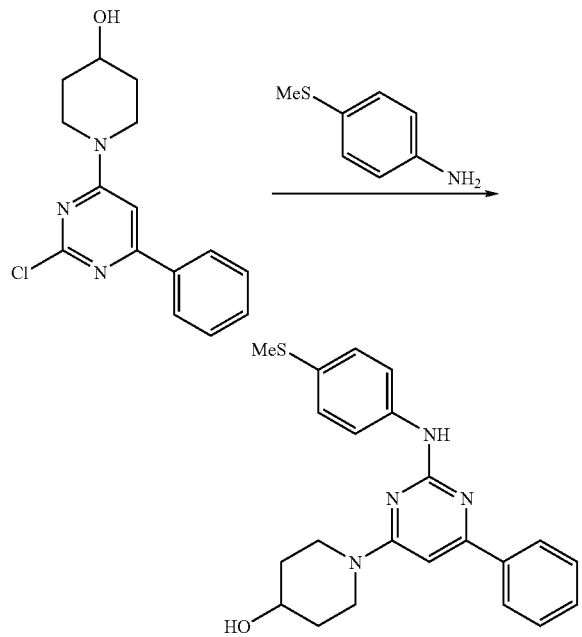

The title compound was prepared by treating 1-(2-chloro-6-phenyl-pyrimidin-4-yl)-piperidin-4-ol (0.3 g, 1.04 mmol) with 4-methylsulfanyl-phenylamine (0.15 g, 1.04 mmol) according to the procedure as described above.

Step (ii). Synthesis of 1-[2-(4-methanesulfonyl-phenylamino)-6-phenyl-pyrimidin-4-yl]-piperidin-4-ol

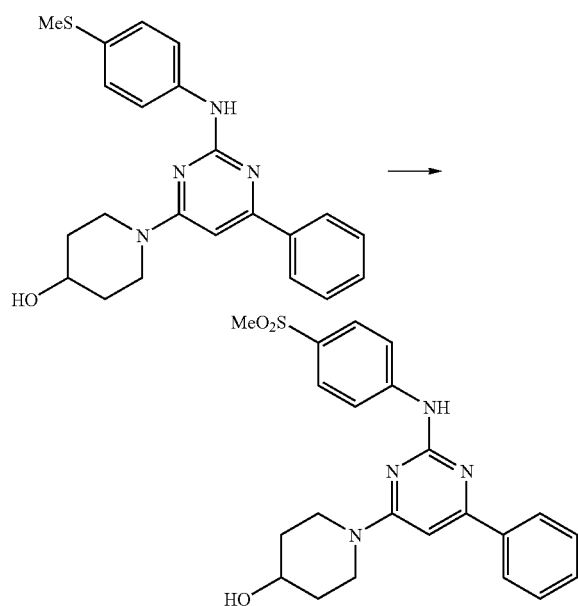

1-[2-(4-Methylsulfanyl-phenylamino)-6-phenyl-pyrimidin-4-yl]-piperidin-4-ol was oxidized (0.26 g, 0.66 mmol) with oxone (1.55 g, 2.64 mmol) in acetone-water (3:1) at room temperature for 1 hour.

M.P.: 235-240° C.

$^1$H NMR (400 MHz, DMSO-$d_6$): 9.72 (br s, 1H), 8.09-8.08 (d, J=4.0 Hz, 2H), 8.01-7.99 (d, J=8.0 Hz, 2H), 7.86-7.84 (d, J=8.5 Hz, 2H), 7.55-7.44 (m, 3H), 6.98 (s, 1H), 4.19-4.12 (m, 2H), 3.83-3.81 (m, 1H), 3.46-3.36 (m, 2H), 3.16 (s, 3H), 1.86-1.84 (d, J=8 Hz, 2H), 1.45-1.42 (m, 2H).

IR: 3340, 1610, 1520

MS: m/z 424(M$^+$, 100%)

Example 138

Synthesis of 1-[4-(4-methanesulonyl-phenylamino)-6-phenyl-pyrimidin-2-yl]-piperidin-4-ol Step (i). Synthesis of 1-[4-(4-methylsulfanyl-phenylamino)-6-phenyl-pyrimidin-2-yl]-piperidin-4-ol

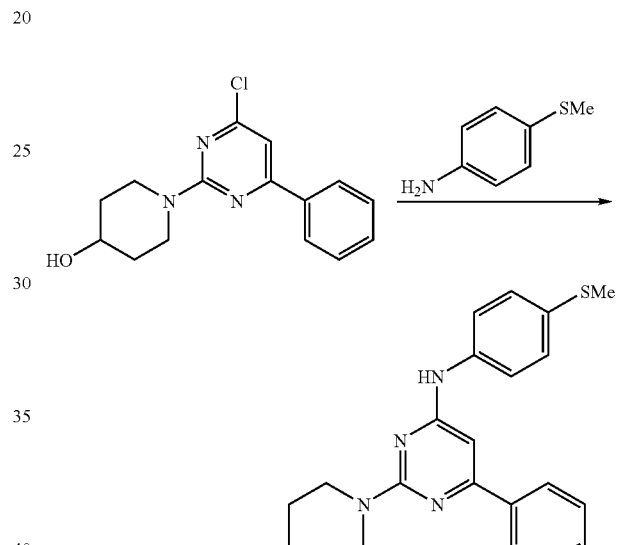

The title compound was prepared by treating 1-(4-chloro-6-phenyl-pyrimidin-2-yl)-piperidin-4-ol (0.3 g, 1.04 mmol) with 4-methylsulfanyl-phenylamine (0.14 g, 1.04 mmol) according to the procedure described above.

Step (ii). Synthesis of 1-[4-(4-methanesulfonyl-phenylamino)-6-phenyl-pyrimidin-2-yl]-piperidin-4-ol

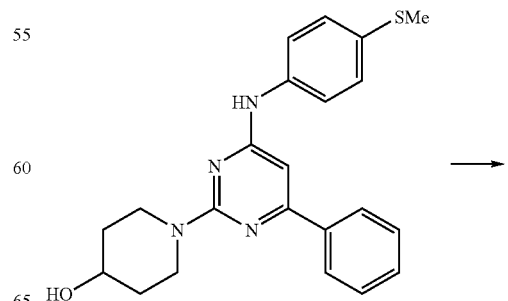

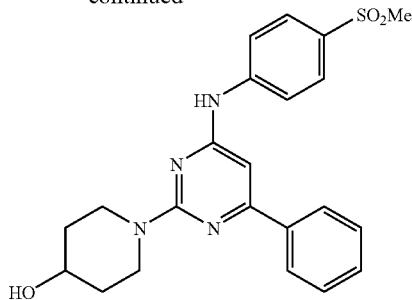

1-[4-(4-Methylsulfanyl-phenylamino)-6-phenyl-pyrimidin-2-yl]-piperidin-4-ol was oxidized (0.27 g, 0.69 mmol) with oxone (1.6 g, 2.76 mmol) in acetone-water (3:1) at room temperature for 1 hour.

M.P.: 245-250° C.

$^{1}$H NMR (400 MHz, DMSO-$d_6$): 10.20 (br s, 1H), 8.10-8.08 (d, J=4 Hz, 2H), 8.01-7.95 (d, J=8 Hz, 2H), 7.84-7.82 (d, J=8.5 Hz, 2H), 7.52-7.43 (m, 3H), 6.48 (s, 1H), 4.20-4.14 (m, 2H), 3.82-3.75 (m, 1H), 3.43-3.36 (m, 2H), 3.18 (s, 3H), 1.87-1.85 (d, J=8 Hz, 2H), 1.44-1.38 (m, 2H).

IR: 3330, 1615, 1510

MS: m/z 424 (M$^+$, 100%)

Example 139

Synthesis of (2,6-diphenyl-pyrimidin-4-yl)-(4-methanesulfonyl-phenyl)-amine

Step (i). Synthesis of (2,6-diphenyl-pyrimidin-4-yl)-(4-methylsulfanyl-phenyl)-amine

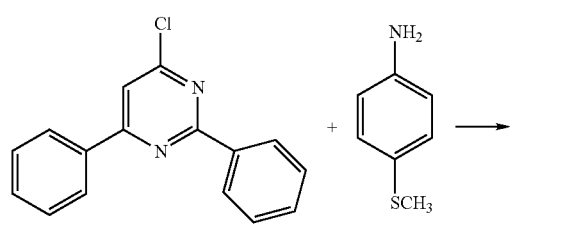

4-Chloro-2,6-diphenyl-pyrimidine (0.4 g, 1.5 mmol) was reacted with 4-methylsulfanyl-phenylamine (0.22 g, 1.6 mmol) in a solvent n-butanol (10 mL) at reflux temperature for 12 hours to yield (2,6-diphenyl-pyrimidin-4-yl)-(4-methylsulfanyl-phenyl)-amine.

Step (ii). Synthesis of (2,6-diphenyl-pyrimidin-4-yl)-(4-methanesulfonyl-phenyl)-amine

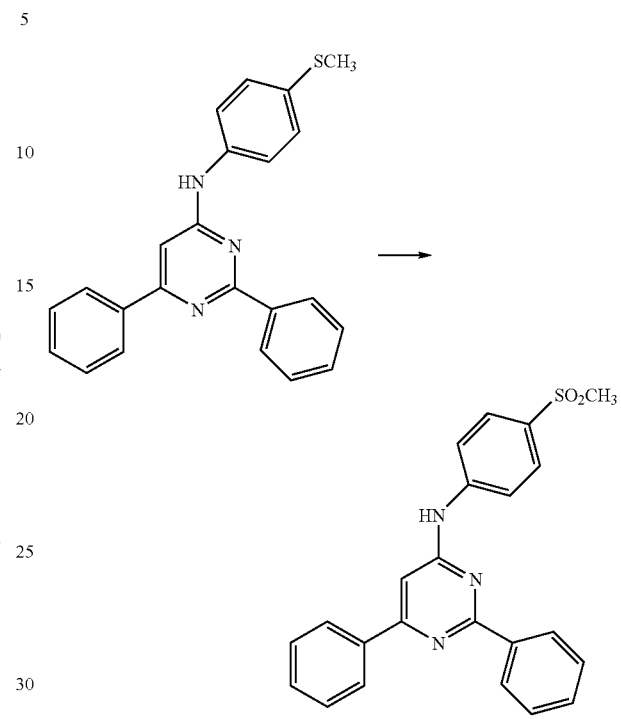

(2,6-Diphenyl-pyrimidin-4-yl)-(4-methylsulfanyl-phenyl)-amine (0.17 g, 0.46 mmol) was oxidized with oxone (0.84 g, 1.3 mmol) in acetone-water (2:1, 9 mL) at room temperature for 5 minutes. Solid was filtered and dried.

$^{1}$H NMR (400 MHz, DMSO-$d_6$): δ 10.26 (br s, 1H), 8.53-8.51 (dd, J=2.7, 1.9 Hz, 2H), 8.21-8.19 (dd, J=1.9, 1.3 Hz, 2H), 8.13-8.11 (d, J=8.9 Hz, 2H), 7.97-7.95 (d, J=8.9 Hz, 2H), 7.62-7.57 (m, 6H), 7.30 (s, 1H), 3.20 (s, 3H).

IR: 3443, 1589, 1509, 1300, 1144.

MS: m/z 402 (M$^+$+1, 100%).

Example 140

Synthesis of 1-[6-(4-methanesulfonyl-phenylamino)-2-phenyl-pyrimidin-4-yl]-piperidin-4-ol Step (i). Synthesis of (6-chloro-2-phenyl-pyrimidin-4-yl)-(4-methylsulfanyl-phenyl)-amine

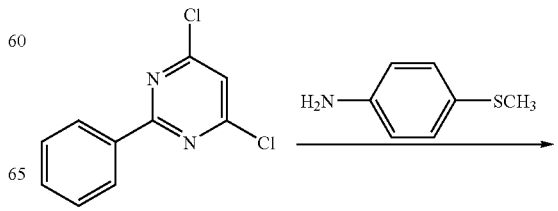

-continued

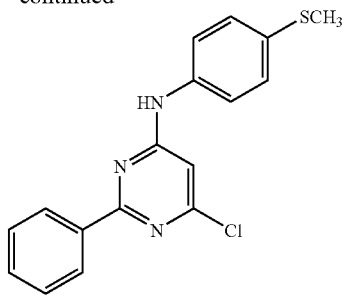

The title compound was prepared from 4,6-dichloro-2-phenyl-pyrimidine (1 g, 4.42 mmol) and 4-thiomethyl aniline (0.61 g, 4.42 mmol) in the presence of triethyl amine in n-butanol at refluxing temperature for 12 hours.

Step (ii). Synthesis of (6-chloro-2-phenyl-pyrimidin-4-yl)-(4-methanesulfonyl-phenyl)-amine

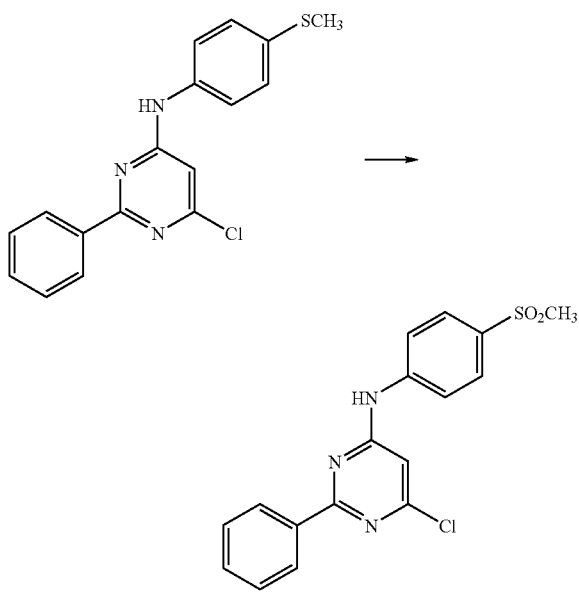

(6-Chloro-2-phenyl-pyrimidin-4-yl)-(4-methylsulfanyl-phenyl)-amine (1 g, 3.03 mmol) was treated with oxone in acetone-water at temperature in the range of 20-40° C. for 1 hour to yield the desired compound.

Step (iii). Synthesis of 1-[6-(4-methanesulfonyl-phenylamino)-2-phenyl-pyrimidin-4-yl]-piperidin-4-ol

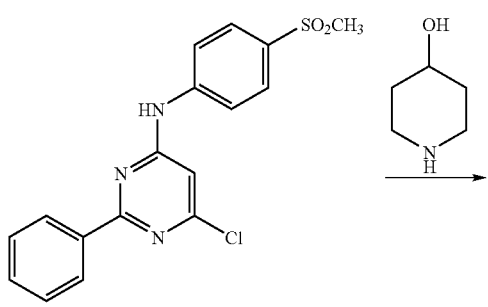

-continued

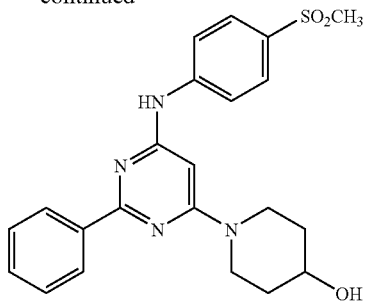

The (6-chloro-2-phenyl-pyrimidin-4-yl)-(4-methanesulfonyl-phenyl)-amine (0.18 g, 0.48 mmol) was treated with 4-hydroxy piperidine (0.097 g, 0.97 mmol) in n-butanol at refluxing temperature for 12 hour to give the desired product.

$^1$H NMR (400 MHz, DMSO-$d_6$): δ 9.64 (s,NH), 8.35-8.33 (m, 2H), 8.0-7.9 (d, J=8.86, 2H), 7.86-7.84 (d, J=8.9 Hz, 2H), 7.51-7.45 (m, 3H), 6.05 (s,1H), 4.09-4.02 (m, 2H), 3.90-3.81 (m,1H), 3.29-3.21 (m, 2H), 3.15 (s, 3H), 1.90-1.83 (m, 2H), 1.45-1.40 (m, 2H).

IR: 3353, 2930, 1623, 1566

MS: m/z 425 (M$^+$, 425).

Example 141

Synthesis of (4-methanesulfonyl-phenyl)-(6-morpholin-4-yl-2-phenyl-pyrimidin-4-yl)-amine

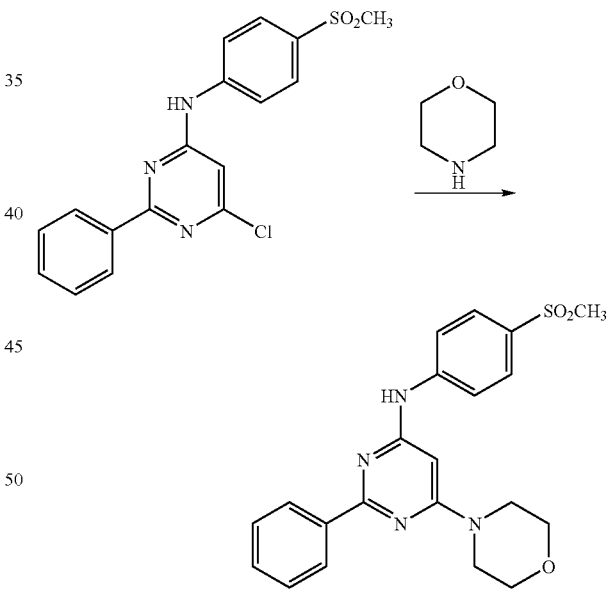

A sample of (6-chloro-2-phenyl-pyrimidin-4-yl)-(4-methanesulfonyl-phenyl)-amine (0.18 g, 0.48 mmol) was treated with morpholine (0.08 g, 0.97 mmol) in n-butanol at refluxing temperature for 12 hour to give the desired product.

M.P.: 238-240° C.

$^1$H NMR (400 MHz, DMSO-$d_6$):δ 9.73 (br s,1H), 8.36-8.34 (m, 2H), 8.04-8.02 (d, J=8.9 Hz, 2H), 7.97-7.95 (d, J=9.9 Hz, 2H), 7.57-7.48 (m, 3H), 6.03 (s, 1H), 3.75-3.72 (t, J=5.1 Hz, 4H), 3.62-3.59 (t, J=5.1 Hz, 4H), 3.16 (s, 3H).

IR: 3359, 1589,1505, 1143

MS: m/z 411 (M$^+$+,100%).

Example 142

Synthesis of (4-methanesulfonyl-phenyl)-[2-phenyl-6-(4-trifluoromethoxy-phenyl)-pyrimidin-4-yl]-amine

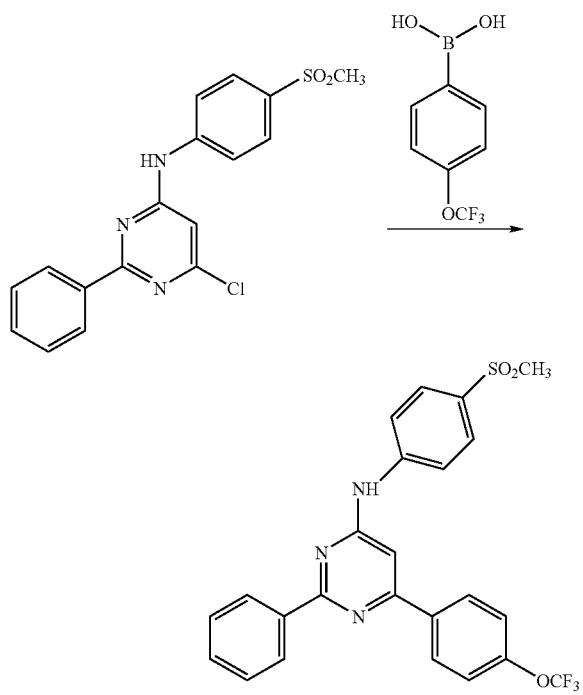

The title compound was prepared by reacting (6-chloro-2-phenyl-pyrimidin-4-yl)-(4-methanesulfonyl-phenyl)-amine (0.15 g, 0.41 mmol) with 4-trifluoromethoxy-phenyl boronic acid (0.09 g, 4.3 mmol) in presence of (PPh$_3$)$_4$Pd (0.02 g, 0.017 mmol) and 2 M sodium carbonate (0.35 g in 1.5 mL H$_2$O) in DMF at 80° C. for 12 hours. Followed by work up and column purification to yield the desired compound.

M.P.: 272-274° C.

$^1$H NMR (400 MHz, DMSO-d$_6$): δ 10.31 (br s, —NH), 8.53-8.50 (m, 2H), 8.32 (d, J=8.9 Hz, 2H), 8.12 (d, J=8.9 Hz, 2H), 7.96 (d, J=8.8 Hz, 2H), 7.59-7.57 (m, 5H), 7.31 (s, 1H), 3.30 (s, 3H).

IR: 3347, 1645, 1545

MS: m/z 486(M$^+$+1, 100%)

Example 143

Synthesis of phthalic acid mono-[1-(2,6-diphenyl-pyrimidin-4-yl)-piperidin-4-yl]ester

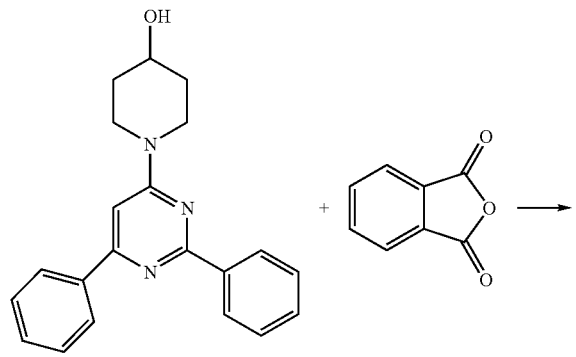

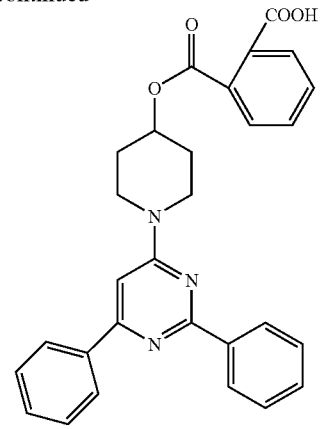

The title compound was prepared by reacting 1-(2,6-diphenyl-pyrimidin-4-yl)-piperidin-4-ol (0.25 g, 0.75 mmol) with pthalic anhydride (0.335 g, 2.0 mmol) in presence of DMAP (0.13 g, 10 mmol) in solvent DCE (10 mL) at refluxing temperature for 2 hours, followed by column purification.

M.P.: 96-98° C.

$^1$H NMR (400 MHz, DMSO-d$_6$): δ 8.53-8.50 (m, 2H), 8.11-8.09 (m, 2H), 7.89-7.87 (m, 1H), 7.74-7.72 (dd, J=2.0, 1.9 Hz 1H), 7.61-7.42 (m, 8H), 6.85 (s, 1H), 5.36-5.35 (m, 1H), 4.14-4.08 (m, 2H), 3.77-3.71 (m, 2H), 2.16-2.09 (m, 2H), 1.97-1.90 (m, 2H).

IR: 3439, 1723, 1636, 1571, 1287, 985.

MS: m/z 480 (M$^+$+1, 100%).

Example 144

Synthesis of [4,6-bis-(4-fluoro-phenyl)-pyrimidin-2-yl]-(4-trifluoromethoxy-phenyl)-amine Step (i). Synthesis of (4,6-dichloro-pyrimidin-2-yl)-(4-trifluoromethoxy-phenyl)-amine

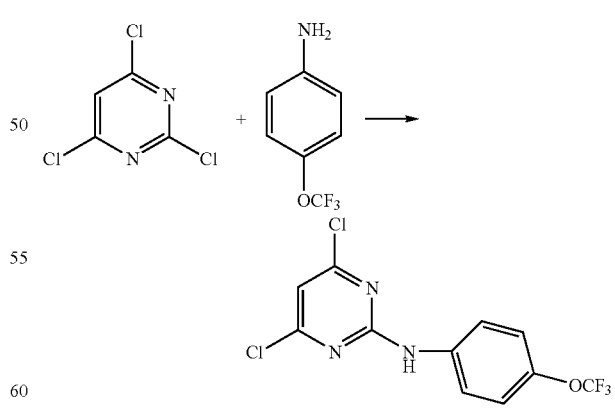

The title compound was prepared by reacting 2,4,6-trichloro pyrimidine (2 g, 10 mmol) with 4-trifluoromethoxy aniline (1.94 g, 10 mmol) in presence of triethylamine (5.5 g, 50 mmol) in a solvent chloroform: hexane (1:1, 20 mL) at reflux temperature for 7 hours.

Step (ii). Synthesis of [4,6-bis-(4-fluoro-phenyl)-pyrimidin-2-yl]-(4-trifluoromethoxy-phenyl)-amine

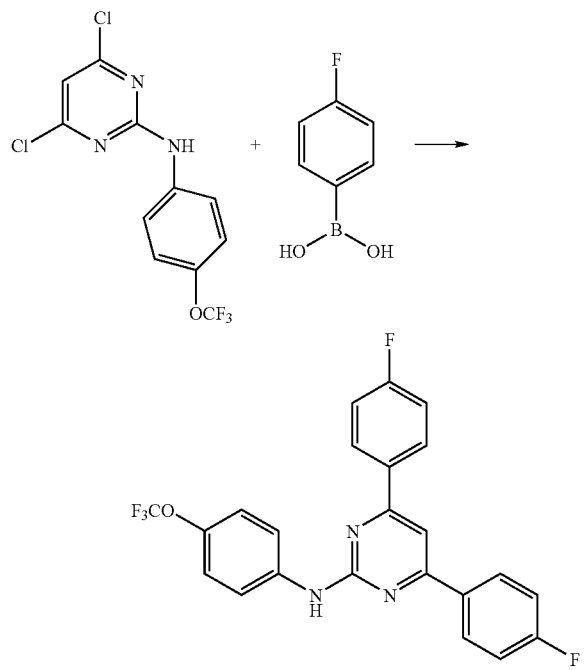

(4,6-Dichloro-pyrimidin-2-yl)-(4-trifluoromethoxy-phenyl)-amine (0.3 g, 0.92 mmol) was reacted with 4-fluoro-phenyl boronic acid (0.25 g, 1.8 mmol) in presence of a catalyst Pd(OAc)$_2$ (7 mg, 0.02 mmol) and sodium carbonate (0.78 g, 7.4 mmol) in a solvent DMF (10 mL) at 80° C. for 12 hours. Followed by work up and column purification to yield [4,6-bis-(4-fluoro-phenyl)-pyrimidin-2-yl]-(4-trifluoromethoxy-phenyl)-amine.

M.P.: 148-150° C.

$^1$H NMR (400 MHz, CDCl$_3$) δ 8.55-8.51 (m, 2H), 8.13-8.09 (m, 2H), 7.55-7.51 (m, 2H), 7.30-7.15 (m, 6H), 6.91 (s, 1H).

IR: 3438,1580,1505,1290.

MS: m/z 444 (M$^+$+1,100%).

Example 145

Synthesis of [4-(3-methanesulfonyl-phenyl)-6-morpholin-4-yl-pyrimidin-2-yl]-(4-trifluoromethoxy-phenyl)-amine Step (i). Synthesis of [4-chloro-6-(3-methanesulfonyl-phenyl)-pyrimidin-2-yl]-(4-trifluoromethoxy-phenyl)-amine

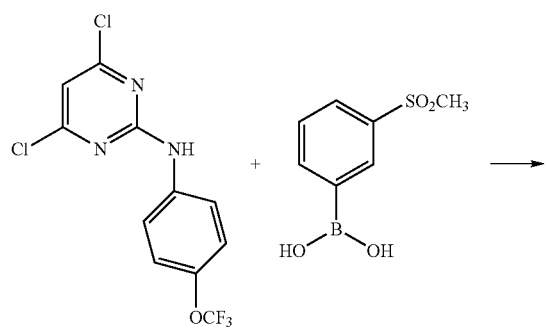

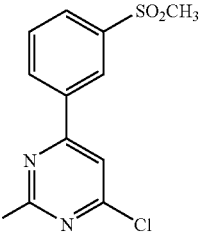

The title compound was prepared by reacting (4,6-dichloro-pyrimidin-2-yl)-(4-trifluoromethoxy-phenyl)-amine (0.3 g, 0.92 mmol) with 3-methanesulfonyl-phenyl boronic acid (0.37 g, 1.85 mmol) in presence of Pd(OAc)$_2$ (7 mg, 0.02 mmol) and sodium carbonate (0.78 g, 7.4 mmol) in a solvent DMF (10 mL) at 80° C. for 12 hours, followed by work up and column purification.

MS: m/z 444 (M$^+$,100%).

Step (ii). Synthesis of [4-(3-methanesulfonyl-phenyl)-6-morpholin-4-yl-pyrimidin-2-yl]-(4-trifluoromethoxy-phenyl)-amine

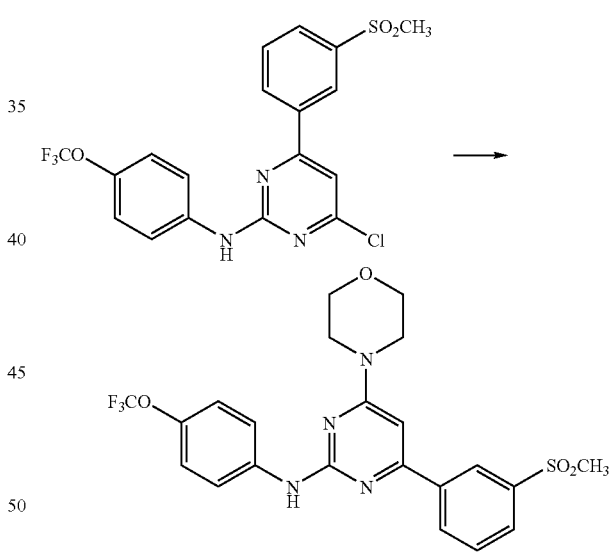

[4-Chloro-6-(3-methanesulfonyl-phenyl)-pyrimidin-2-yl]-(4-trifluoromethoxy-phenyl)-amine (0.14 g, 0.3 mmol) was reacted with morpholine (0.09 mL) in a solvent n-butanol (7 mL) at reflux temperature for 12 hours. Solid was filtered and dried to afford the desired compound.

$^1$H NMR (400 MHz, DMSO-d$_6$), δ 9.68 (br s, 1H), 8.46 (s, 1H), 8.35 (d, J=7.8 Hz 1H), 8.04 (d, J=8.1 Hz 1H), 7.81-7.77 (m, 3H), 7.33 (d, J=8.6 Hz, 2H), 6.70 (s, 1H), 3.78-3.70 (m, 8H), 3.29 (s, 3H).

IR: 3370,1577,1507,1280.

MS: m/z 495 (M$^+$+1,100%).

Example 146

Synthesis of [2-(4-Fluoro-phenyl)-6-morpholin-4-yl-pyrimidin-4-yl]-(4-trifluoromethoxy-phenyl)-amine

Step (i). Synthesis of 4-fluoro-benzonitrile

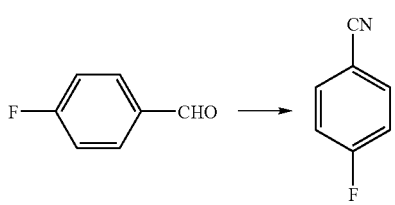

To a solution of 4-fluoro benzaldehyde (8 g, 64 mmol) in acetonitrile (100 mL) was added NH$_2$OH.HCl (5.78 g, 83 mmol) and NaI (4.8 g, 32 mmol) with stirring. The mixture was then stirred for 7 hours at refluxing temperature, cooled at the temperature in the range of 20-40° C., poured into water (200 mL) and extracted with EtOAc (2×250 mL). The organic layers were collected, combined, washed with brine solution, dried over anhydrous Na$_2$SO$_4$ and concentrated under vacuum to give the 4-fluoro-benzonitrile (6.0 g, 76% yield).

$^1$H NMR (200 MHz, CDCl$_3$): δ 8.11-7.52 (m, 2H), 7.22-7.03 (m, 2H).

IR: 3313, 2233, 1603.

MS: m/z 121 (M$^+$,100%).

Reference: Chakraborti, A. K.; Kaur, G.; Roy, S. *Indian J. Chem. Sect. B;* 2001, 40, 1000-1006.

Step (ii). Synthesis of 4-fluoro-benzamidine

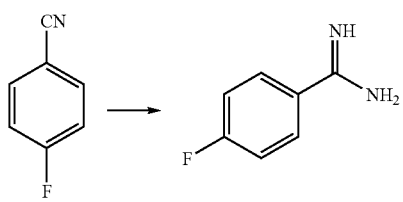

A solution of lithium hexamethyldisilazane was prepared by adding 15% n-BuLi in n-hexane (40 mL) to a solution of HMDS (13.3 g, 82 mmol) in Et$_2$O (80 mL) at 0° C. 4-fluoro benzonitrile (5 g, 41 mmol) was then added to it and the mixture was kept at room temperature for 12 hours under a nitrogen atmosphere. The mixture was then cooled to 0° C. and methanol (80 mL) was added carefully. The mixture was stirred for 30 minutes, diluted with water (200 mL) and extracted with EtOAc (2×250 mL). Organic layers collected, combined, dried over anhydrous Na$_2$SO$_4$ and concentrated under vacuum to give the desired product (2.3 g, 43% yield).

$^1$H NMR (200 MHz, DMSO-d$_6$): δ 10.34 (br s, NH), 7.90-7.83 (m, 2H), 7.47-7.38 (m, 2H).

IR: 3218, 3051, 1616.

MS: m/z 138 (M$^+$,100%).

Reference: Thurkauf, A.; Hutchison, A.; Peterson, J.; Cornfield, L.; Meade, R.; et al.; *J. Med. Chem.* 1995, 38, 2251-2255.

Step (iii). Synthesis of 2-(4-fluoro-phenyl)-pyrimidine-4,6-diol

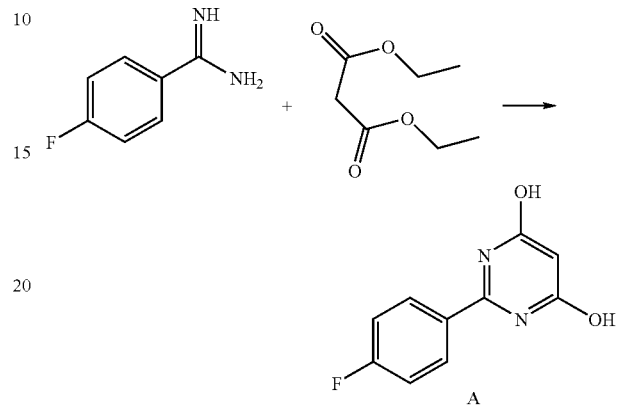

Sodium ethoxide was generated in-situ by adding sodium (0.86 g, 37 mmol) to absolute ethanol (20 mL) and then 4-fluoro benazamidine (2 g, 14.4 mmol) was added followed by diethylmalonate (2.3 g, 14.4 mmol), This reaction mixture was stirred at refluxing temperature for 16 hours under nitrogen. Reaction mixture was then cooled to temperature in the range of 20-40° C. and concentrated under reduced pressure. The white solid residue was dissolved in water and acidified with 2N HCl. The white solid precipitated was filtered off, washed with iso-propanol and dried under vacuum to afford the title compound (2.49 g, 89%) as an off white solid.

$^1$H NMR (200 MHz, DMSO-d$_6$): δ 11.68 (br s, OH), 8.23-8.16 (m, 2H), 7.20-7.11 (m, 2H), 5.52 (s, 1H).

IR: 3240, 2560, 1625.

MS: m/z 206 (M$^+$,100%).

Step (iv). Synthesis of 4,6-dichloro-2-(4-fluoro-phenyl)-pyrimidine

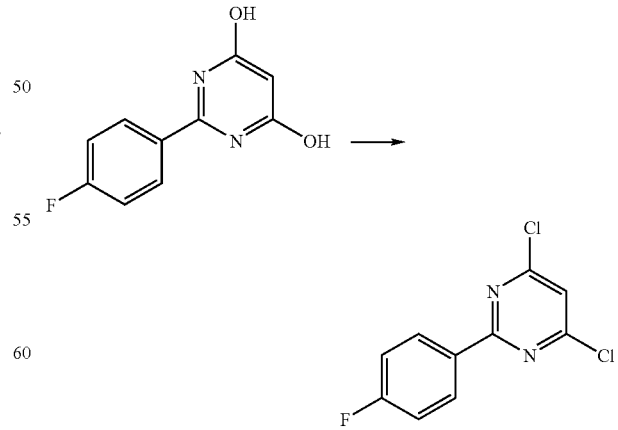

To a mixture of compound 2-(4-fluoro-phenyl)-pyrimidine-4,6-diol (2.46 g, 11.0 mmol) and POCl$_3$ (20 mL) was added 0.7 mL of N,N-diethylaniline and the mixture was refluxed for 12-16 hours. The excess of POCl₃ was distilled out and the residue was neutralized by saturated sodium bicarbonate solution. The solid precipitated was filtered and dried under vacuum to afford the compound 4,6-dichloro-2-(4-fluoro-phenyl)-pyrimidine (1.67 g, 58%) as an off white solid.

¹H NMR (200 MHz, CDCl₃): δ 8.49-8.41 (m, 2H), 7.26 (s, 1H), 7.20-7.11 (m, 2H).

IR: 3093, 2925, 1606.

MS: m/z 242 (M⁺, 100%).

Step (v). Synthesis of [6-chloro-2-(4-fluoro-phenyl)-pyrimidin-4-yl]-(4-trifluoromethoxy-phenyl)-amine

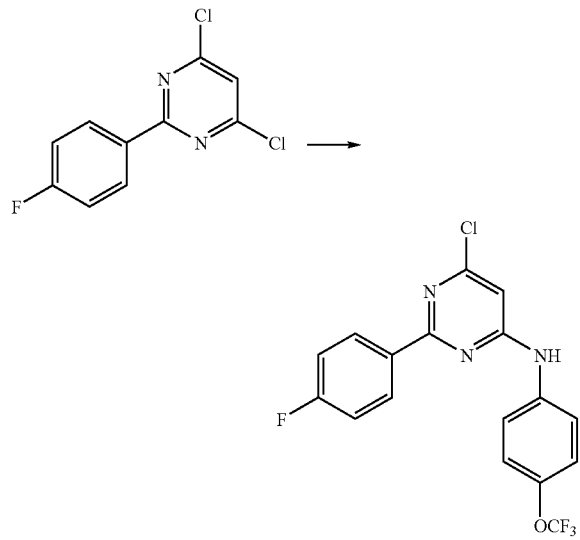

A mixture of compound 4,6-dichloro-2-(4-fluoro-phenyl)-pyrimidine (1 g, 4.10 mmol), 4-trifluoromethoxy aniline (0.8 g, 4.5 mmol) and triethyl amine (0.83 g, 8.20 mmol) in n-butanol (10 mL) was refluxed for 12 hours under nitrogen. The reaction mixture was then cooled to room temperature and concentrated under vacuum, the crude compound was passed through the silicagel by using 5-6% ethylacetate—petroleum ether to afford the compound [6-chloro-2-(4-fluoro-phenyl)-pyrimidin-4-yl]-(4-trifluoromethoxy-phenyl)-amine (0.75 g, 50%) as light brown solid.

¹H NMR (200 MHz, CDCl₃): δ 8.42-8.35 (m, 2H), 7.47-7.09 (m, 6H), 6.87 (br s, NH), 6.56 (s, 1H).

IR: 3370, 1577, 1507, 1280.

MS: m/z 384 (M⁺+1, 100%).

Step (vi). Synthesis of [2-(4-fluoro-phenyl)-6-morpholin-4-yl-pyrimidin-4-yl]-(4-trifluoromethoxy-phenyl)-amine

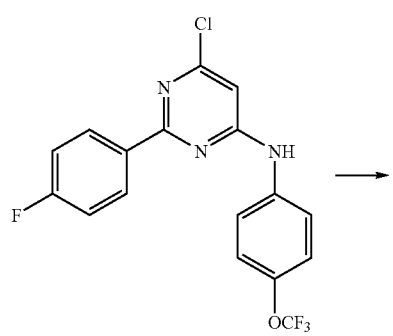

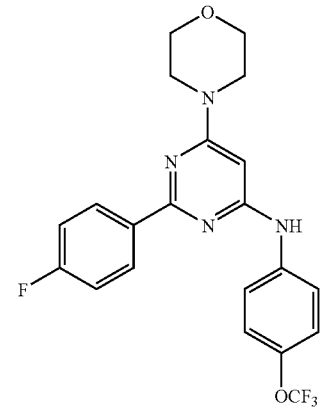

A mixture of compound [6-chloro-2-(4-fluoro-phenyl)-pyrimidin-4-yl]-(4-trifluoromethoxy-phenyl)-amine (0.25 g, 0.65 mmol) and morpholine (0.113 g, 8.20 mmol) in n-butanol (10 mL) was refluxed for 12 hours under nitrogen. The mixture was then cooled to temperature in the range of 20-40° C. and evaporated under reduced pressure. The crude compound was passed through the silicagel by using 20% ethylacetate—petroleum ether to afford the compound [2-(4-fluoro-phenyl)-6-morpholin-4-yl-pyrimidin-4-yl]-(4-trifluoromethoxy-phenyl)-amine (0.157 g, 56%) as off white solid.

¹H NMR (400 MHz, CDCl₃): δ 8.38-8.34 (m, 2H), 7.42-7.40 (dd, J=2.1, 2.4 Hz, 2H), 7.25-7.22 (m, 2H), 7.13-7.08 (m, 2H), 5.76 (s, 1H), 6.57 (br s, NH), 3.82-3.79 (t, J=5.10 Hz, 4H), 3.64-3.62 (t, J=5.1 Hz, 4H).

IR: 2854, 1604, 1576, 1272.

MS: m/z 435 (M⁺+1, 100%).

Example 147

Synthesis of 2-amino-6-phenyl-pyrimidin-4-ol

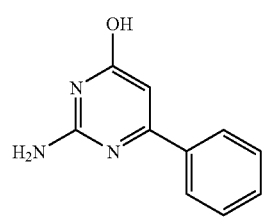

This compound was prepared by a procedure analogous to that disclosed in Example 1, using starting materials with the appropriate substitution.

¹H NMR (200 MHz, DMSO-d₆): δ 10.84 (br s, 1H), 7.96-7.91 (m, 2H), 7.52-7.41 (m, 3H), 6.10 (s, 1H).

IR: 3349, 1654, 1504.

MS: m/z 188 (M⁺+1, 100%).

Example 148

Synthesis of
2-amino-6-(4-fluoro-phenyl)-pyrimidin-4-ol

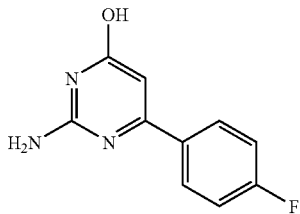

This compound was prepared by a procedure analogous to that disclosed in Example 1, using starting materials with the appropriate substitution.

Example 149

Synthesis of
2-amino-6-(4-ethoxy-phenyl)-pyrimidin-4-ol

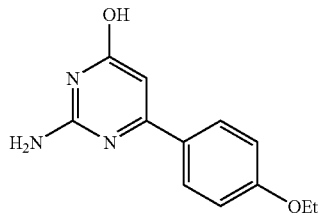

This compound was prepared by a procedure analogous to that disclosed in Example 1, using starting materials with the appropriate substitution.

Example 150

Synthesis of 2-amino-6-p-tolyl-pyrimidin-4-ol

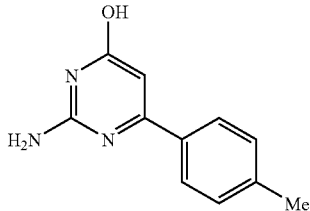

This compound was prepared by a procedure analogous to that disclosed in Example 1, using starting materials with the appropriate substitution.

Example 151

Synthesis of
2-amino-6-(4-methylsulfanyl-phenyl)-pyrimidin-4-ol

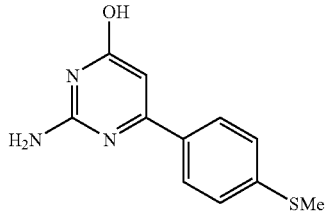

This compound was prepared by a procedure analogous to that disclosed in Example 1, using starting materials with the appropriate substitution.

Example 152

Synthesis of 4-chloro-6-phenyl-pyrimidin-2-ylamine

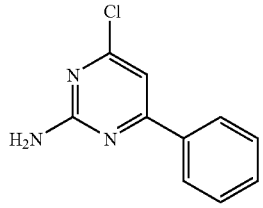

This compound was prepared by a procedure analogous to that disclosed in Example 1, using starting materials with the appropriate substitution.

$^1$H NMR (200 MHz, DMSO-d6): δ 8.11-8.08 (m, 2H), 7.52-7.49 (m, 3H), 7.25 (s, 1H), 7.19 (br s, 1H).
IR: 3319, 1643, 1560.
MS: m/z 206 (M$^+$+1,100%).

Example 153

Synthesis of
4-chloro-6-(4-fluoro-phenyl)-pyrimidin-2-ylamine

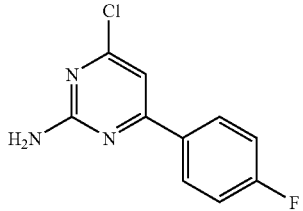

This compound was prepared by a procedure analogous to that disclosed in Example 1, using starting materials with the appropriate substitution.

Example 154

Synthesis of
4-chloro-6-(4-ethoxy-phenyl)-pyrimidin-2-ylamine

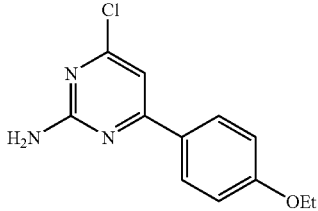

This compound was prepared by a procedure analogous to that disclosed in Example 1, using starting materials with the appropriate substitution.

Example 155

Synthesis of 4-chloro-6-p-tolyl-pyrimidin-2-ylamine

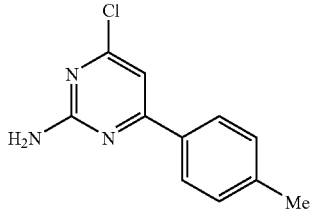

Example 156

Synthesis of 4-chloro-6-(4-methylsulfanylphenyl)pyrimidin-2-ylamine

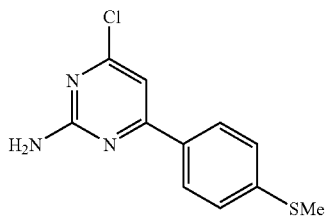

This compound was prepared by a procedure analogous to that disclosed in Example 1, using starting materials with the appropriate substitution.

Example 157

Synthesis of 2,4-dichloro-6-(4-methoxy-phenyl)-pyrimidine

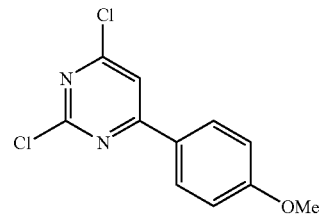

This compound was prepared by a procedure analogous to that disclosed in Example 39, using starting materials with the appropriate substitution.

Example 158

Synthesis of 2,4-dichloro-6-(4-ethoxy-phenyl)-pyrimidine

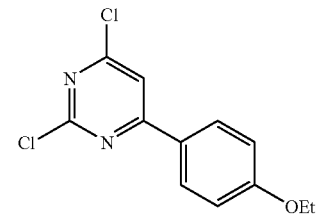

This compound was prepared by a procedure analogous to that disclosed in Example 39, using starting materials with the appropriate substitution.

Example 159

Synthesis of 2,4-dichloro-6-p-tolyl-pyrimidine

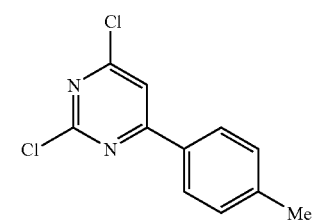

This compound was prepared by a procedure analogous to that disclosed in Example 1, using starting materials with the appropriate substitution.

Example 160

Synthesis of 2,4-dichloro-6-(4-methylsulfanyl-phenyl)-pyrimidine

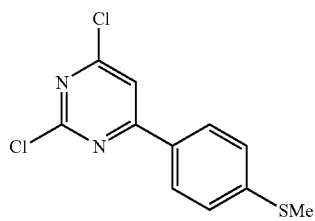

This compound was prepared by a procedure analogous to that disclosed in Example 39, using starting materials with the appropriate substitution.

Example 161

Synthesis of N-[4-chloro-6-(4-methoxy-phenyl)-pyrimidin-2-yl]-acetamide

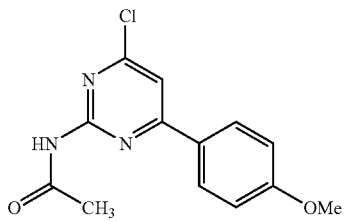

This compound was prepared by a procedure analogous to that disclosed in Example 17, using starting materials with the appropriate substitution.

Example 162

Synthesis of N-[4-chloro-6-(4-methoxy-phenyl)-pyrimidin-2-yl]-propionamide

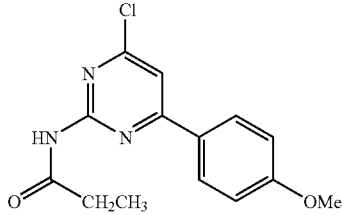

This compound was prepared by a procedure analogous to that disclosed in Example 17, using starting materials with the appropriate substitution.

Example 163

Synthesis of (4-chloro-6-phenyl-pyrimidin-2-ylamino)-acetic acid ethyl ester

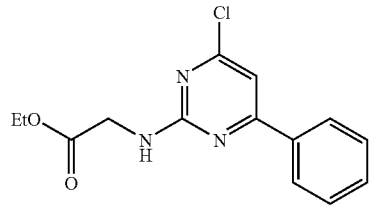

This compound was prepared by a procedure analogous to that disclosed in Example 17, using starting materials with the appropriate substitution.

Example 164

Synthesis of (2-ethylsutfanyl-6-phenyl-pyrimidin-4-yl)-isopropyl-amine

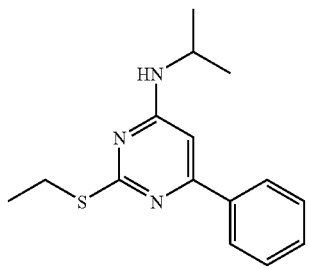

This compound was prepared by a procedure analogous to that disclosed in Example 26, using starting materials with the appropriate substitution.

Example 165

Synthesis of cycloheptyl-(2-ethylsulfanyl-6-phenyl-pyrimidin-4-yl)-amine

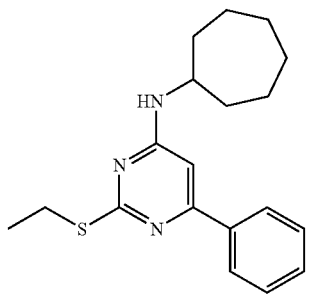

This compound was prepared by a procedure analogous to that disclosed in Example 26, using starting materials with the appropriate substitution.

Example 166

Synthesis of benzyl-(2-ethylsulfanyl-6-phenyl-pyrimidin-4-yl)-amine

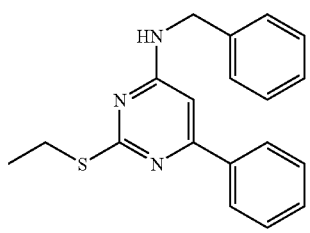

This compound was prepared by a procedure analogous to that disclosed in Example 26, using starting materials with the appropriate substitution.

Example 167

Synthesis of 4-isopropylamino-6-phenyl-pyrimidin-2-ol

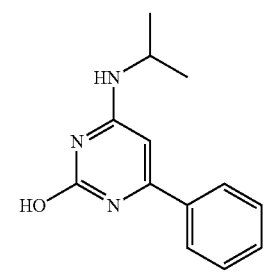

This compound was prepared by a procedure analogous to that disclosed in Example 26, using starting materials with the appropriate substitution.

Example 168

Synthesis of 4-cycloheptylamino-6-phenyl-pyrimidin-2-ol

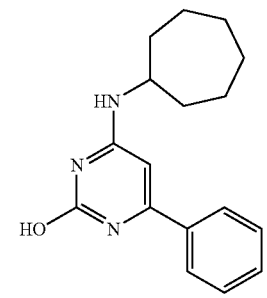

This compound was prepared by a procedure analogous to that disclosed in Example 26, using starting materials with the appropriate substitution.

Example 169

Synthesis of 4-benzylamino-6-phenyl-pyrimidin-2-ol

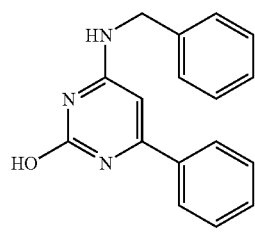

This compound was prepared by a procedure analogous to that disclosed in Example 26, using starting materials with the appropriate substitution.

Example 170

Synthesis of (2-chloro-6-phenyl-pyrimidin-4-yl)-isopropyl-amine

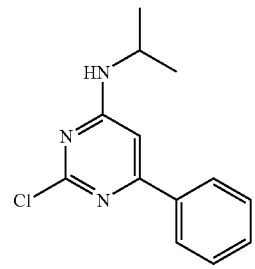

This compound was prepared by a procedure analogous to that disclosed in Example 26, using starting materials with the appropriate substitution.

Example 171

Synthesis of (2-chloro-6-phenyl-pyrimidin-4-yl)-cycloheptyl-amine

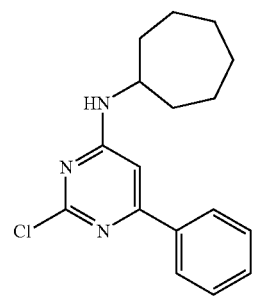

This compound was prepared by a procedure analogous to that disclosed in Example 26, using starting materials with the appropriate substitution.

Example 172

Synthesis of benzyl-(2-chloro-6-phenyl-pyrimidin-4-yl)-amine

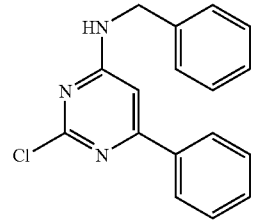

This compound was prepared by a procedure analogous to that disclosed in Example 26, using starting materials with the appropriate substitution.

Example 173

Synthesis of 2-ethylsulfanyl-6-(4-methoxy-phenyl)-pyrimidin-4-ol

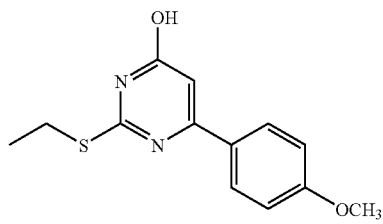

This compound was prepared by a procedure analogous to that disclosed in Example 24, using starting materials with the appropriate substitution.

Example 174

Synthesis of 2-phenyl-pyrimidine-4,6-diol

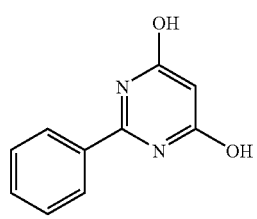

This compound was prepared by a procedure analogous to that disclosed in Example 113 (step i), using starting materials with the appropriate substitution.

Example 175

Synthesis of 4-(4-chloro-6-phenyl-pyrimidin-2-yl)-morpholine

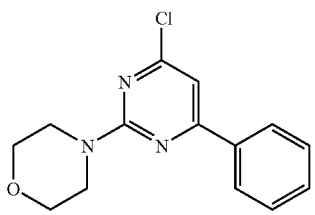

This compound was prepared by a procedure analogous to that disclosed in Example 39, using starting materials with the appropriate substitution.

$^1$H NMR (400 MHz, CDCl$_3$): δ 7.96-7.92 (m, 2H), 7.47-7.45 (m, 3H), 6.75 (s, 1H), 3.81-3.78 (m, 4H), 3.73-3.71 (m, 4H).

IR: 3437, 1638, 1247.

MS: m/z 276 (M$^+$+1,100%).

Example 176

Synthesis of 4-(4-chloro-6-phenyl-pyrimidin-2-yl)-thiomorpholine

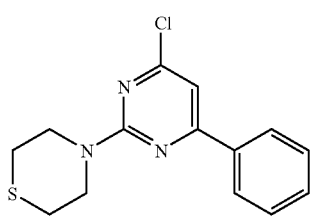

This compound was prepared by a procedure analogous to that disclosed in Example 39, using starting materials with the appropriate substitution.

This material was used directly in the next step without further characterization.

Example 177

Synthesis of 1-(2-chloro-6-phenyl-pyrimidin-4-yl)-piperidin-4-ol

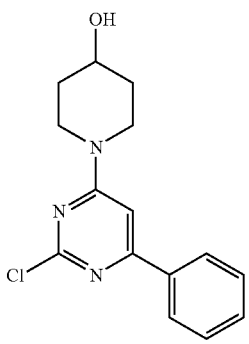

This compound was prepared by a procedure analogous to that disclosed in Example 39, using starting materials with the appropriate substitution.

$^1$H NMR (400 MHz, CDCl$_3$): δ 7.95-7.93 (m, 2H), 7.47-7.43 (m, 3H), 6.78 (s, 1H), 4.11-4.00 (m, 3H), 3.47-3.41 (m, 2H), 2.0-1.94 (m, 2H), 1.66-1.60 (m, 2H).

IR: 3312, 1563.

MS: m/z 290 (M$^+$+1,100%).

Example 178

Synthesis of 1-(2-chloro-6-phenyl-pyrimidin-4-yl)-piperidin-4-one

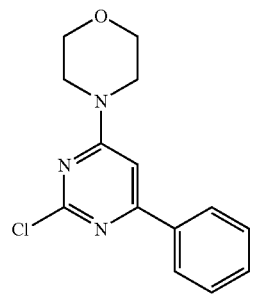

This compound was prepared by a procedure analogous to that disclosed in Example 39, using starting materials with the appropriate substitution.

$^1$H NMR (400 MHz, CDCl$_3$): δ 8.01-7.99 (m, 2H), 7.20-7.02 (m, 3H), 6.68 (s, 1H), 3.91-3.86 (m, 4H), 3.78-3.77 (m, 4H).

IR: 3313, 1563, 1312.

MS: m/z 276 (M$^+$+1,100%).

Example 179

Synthesis of 4-(2-chloro-6-phenyl-pyrimidin-4-yl)-thiomorpholine

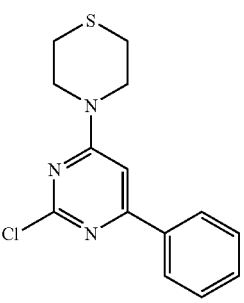

This compound was prepared by a procedure analogous to that disclosed in Example 39, using starting materials with the appropriate substitution.

$^1$H NMR (400 MHz, CDCl$_3$): δ 8.01-7.96 (m, 2H), 7.49-7.46 (m, 3H), 6.94 (s, 1H), 4.42-4.24 (m, 4H), 2.72-2.67 (m, 4H).

IR: 3445, 1591, 1497.

MS: m/z 292 (M$^+$+1,100%).

Example 180

Synthesis of 1-(2-chloro-6-phenyl-pyrimidin-4-yl)-piperidin-4-one

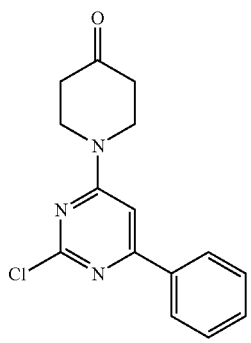

This compound was prepared by a procedure analogous to that disclosed in Example 39, using starting materials with the appropriate substitution.

$^1$H NMR (400 MHz, CDCl$_3$): δ 7.99-7.96 (m, 2H), 7.48-7.47 (m, 3H), 6.85 (s, 1H), 4.06-4.03 (m, 4H), 2.63-2.60 (m, 4H).

IR: 3409, 1718, 1204.

MS: m/z 288 (M$^+$+1,100%).

Example 181

Synthesis of 2-chloro-4-(4-methyl-piperazin-1-yl)-6-phenyl-pyrimidine

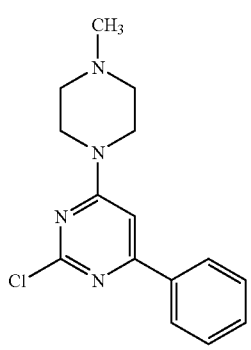

This compound was prepared by a procedure analogous to that disclosed in Example 39, using starting materials with the appropriate substitution.

$^1$H NMR (400 MHz, CDCl$_3$): δ 7.95-7.93 (m, 2H), 7.46-7.43 (m, 3H), 6.76 (s, 1H), 4.67-3.75 (m, 4H), 2.65-2.50 (m, 4H), 2.35 (s, 3H).

IR: 2852, 1575, 1318.

MS: m/z 289 (M$^+$+1,100%).

Example 182

Synthesis of 6-(4-fluoro-phenyl)-pyrimidine-2,4-diol

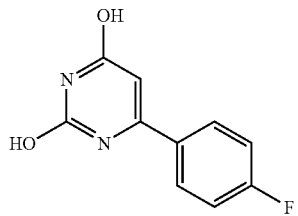

This compound was prepared by a procedure analogous to that disclosed in Example 39, using starting materials with the appropriate substitution.

$^1$H NMR (200 MHz, CDCl$_3$): δ 7.82-7.75 (m, 2H), 7.38-7.29 (m, 2H), 5.81 (s, 1H).

IR: 3008, 1711, 1667.

MS: m/z 207 (M$^+$+1,100%).

Example 183

Synthesis of 2,4-dichloro-6-(4-fluoro-phenyl)-pyrimidine

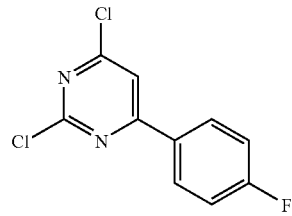

This compound was prepared by a procedure analogous to that disclosed in Example 39, using starting materials with the appropriate substitution.

$^1$H NMR (400 MHz, CDCl$_3$): δ 8.41-8.32 (m, 2H), 7.79-7.38 (m, 2H), 5.80 (s, 1H).

IR: 2925, 1558.

MS: m/z 243 (M$^+$+1,100%).

Example 184

Synthesis of 1-[4-chloro-6-(4-fluoro-phenyl)-pyrimidin-2-yl]-piperidin-4-ol

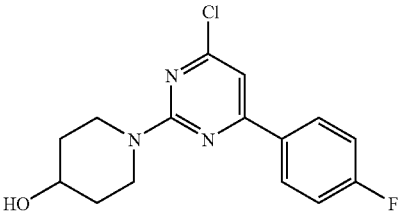

This compound was prepared by a procedure analogous to that disclosed in Example 39, using starting materials with the appropriate substitution.

¹H NMR (400 MHz, CDCl₃): δ 7.98-7.93 (m, 2H), 7.21-7.10 (m, 2H), 6.73 (s, 1H), 4.11-4.01 (m, 3H), 3.48-3.42 (m, 2H), 2.08-2.00 (m, 2H), 1.99-1.95 (m, 2H).

IR: 3377, 1591, 1223.

MS: m/z 307 (M⁺+1,100%).

Example 185

Synthesis of 4-[4-chloro-6-(4-fluoro-phenyl)-pyrimidin-2-yl]-morpholine

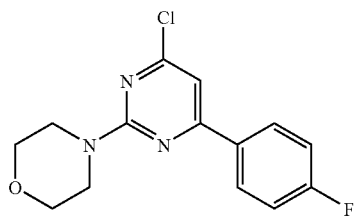

This compound was prepared by a procedure analogous to that disclosed in Example 39, using starting materials with the appropriate substitution.

This material was used directly in the next step without further characterization.

Example 186

Synthesis of 1-[2-chloro-6-(4-fluoro-phenyl)-pyrimidin-4-yl]-piperidin-4-ol

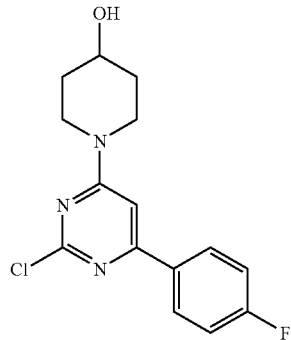

This compound was prepared by a procedure analogous to that disclosed in Example 39, using starting materials with the appropriate substitution.

¹H NMR (400 MHz, CDCl₃): δ 7.97-7.94 (m, 2H), 7.14-7.11 (m, 2H), 6.73 (s, 1H), 4.07-4.02 (m, 3H), 3.49-3.42 (m, 2H), 2.0-1.96 (m, 2H), 1.66-1.54 (m, 2H).

IR: 3307, 1590.

MS: m/z 307 (M⁺+1,100%).

Example 187

Synthesis of 4-[2-chloro-6-(4-fluoro-phenyl)-pyrimidin-4-yl]-morpholine

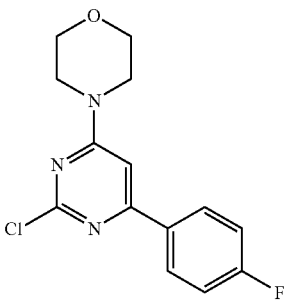

This compound was prepared by a procedure analogous to that disclosed in Example 39, using starting materials with the appropriate substitution.

¹H NMR (400 MHz, CDCl₃): δ 8.02-7.98 (m, 2H), 7.05-7.20 (m, 2H), 6.67 (s, 1H), 3.90-3.81 (m, 4H), 3.80-3.78 (m, 4H).

IR: 3437, 1630.

MS: m/z 292 (M⁺+1,100%).

Example 188

Synthesis of (3-chloro-4-methoxy-phenyl)-(6-chloro-2-phenyl-pyrimidin-4-yl)-amine

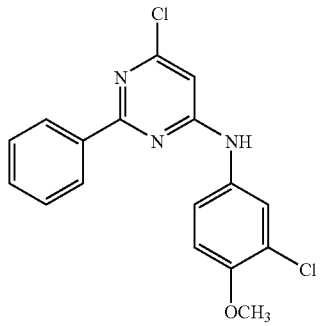

This compound was prepared by a procedure analogous to that disclosed in Example 113, using starting materials with the appropriate substitution.

¹H NMR (400 MHz, CDCl₃): δ 9.9 (s, NH), 8.27 (d, J=9.7 Hz, 2H), 7.90 (s, 1H), 7.59-7.51 (m, 4H), 7.21 (d, J=8.9 Hz, 1H), 6.67 (s, 1H), 3.87 (s, 3H).

IR: 1615.

MS: m/z 347 (M⁺,100%).

Example 189

Synthesis of benzo[1,3]dioxol-5-yl-(6-chloro-2-phenyl-pyrimidin-4-yl)-amine

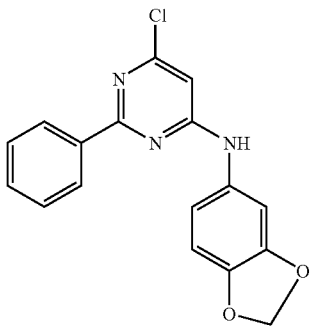

This compound was prepared by a procedure analogous to that disclosed in Example 113, using starting materials with the appropriate substitution.

$^1$H NMR (400 MHz, CDCl$_3$): δ 9.8 (s, NH), 8.26 (d, J=9.7 Hz, 2H), 7.55-7.49 (m, 2H), 7.39 (s, 1H), 7.02 (d, J=8.3 Hz, 1H), 6.95 (d, J=8.3 Hz, 1H), 6.63 (s, 1H).

IR: 1617.

MS: m/z 326 (M$^+$,100%).

Example 190

Synthesis of (6-chloro-2-phenyl-pyrimidin-4-yl)-(4-trifluoromethoxy-phenyl)-amine

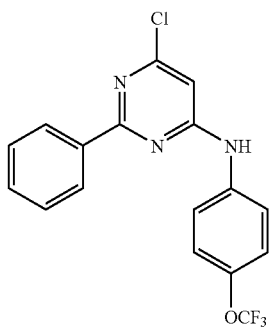

This compound was prepared by a procedure analogous to that disclosed in Example 113, using starting materials with the appropriate substitution.

$^1$H NMR (400 MHz, CDCl$_3$): δ 10.08 (s, NH), 8.31-8.25 (m, 2H), 7.87-7.83 (m, 2H), 7.55-7.421 (m, 5H), 6.77 (s, 1H).

IR: 1620.

MS: m/z 366 (M$^+$,100%).

In another aspect of the present invention, this invention encompasses salts of the compounds disclosed herein, including pharmaceutically acceptable and non-pharmaceutically acceptable salts. It is envisioned that the compounds, compositions, and all the salts disclosed therein, including the non-pharmaceutically acceptable salts, can have uses and applications beyond pharmaceutical applications. For example, the pyrimidine compounds and compositions comprising pryimidine compounds of this invention can be used in a variety of agricultural uses or applications such as herbicides and pesticides, hardness stabilizers in rubber processing, ultraviolet light absorbers, and other uses.

The foregoing description has been presented for purposes of illustration and description. It is not intended to be exhaustive or to limit the invention to the precise examples or embodiments disclosed. Obvious modifications or variations are possible in light of the above teachings. The embodiment or embodiments discussed were chosen and described to provide the best illustration of the principles of the invention and its practical application to enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

We claim:

1. A compound having the formula:

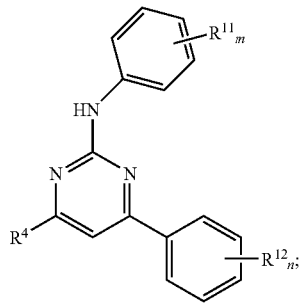

or a salt thereof;

wherein:

$R^4$ is selected from a substituted or an unsubstituted heterocyclyl comprising at least one heteroatom or heterogroup selected from —O—, —NH—, —S—, or, any of which having up to 10 carbon atoms;

n and m are independently an integer from 0 to 3, inclusive;

$R^{11}$ and $R^{12}$, in each occurrence, are selected independently from: 1) an alkyl, an alkoxy, a haloalkyl, a haloalkoxy, —COR$^9$, —CONR$^8_2$, —CO$_2$R$^8$, —SO$_2$R$^9$, —SR$^8$, —NHSO$_2$R$^9$, or —SO$_2$NR$^8_2$, any of which having up to 10 carbon atoms; or 2) halogen, hydroxyl, or —OCH$_2$O—; and $R^4$ is optionally substituted with at least one group independently selected from: 1) an alkyl, —COR$^9$, —CO$_2$R$^8$, —CONR$^8_2$, —SO$_2$R$^9$, or —SO$_2$NR$^{10}_2$, any of which having up to 10 carbon atoms; or 2) hydroxyl;

$R^8$, in each occurrence, is selected independently from: 1) an alkyl, a haloalkyl, or an aryl having up to 6 carbon atoms; or 2) hydrogen;

$R^9$, in each occurrence, is selected independently from an alkyl, a haloalkyl, an aryl, or a heterocyclyl or a heteroaryl comprising at least one heteroatom selected from —O— or —N—, any of which having up to 10 carbon atoms; and $R^{10}$, in each occurrence, is selected independently from: 1) an alkyl, an aryl, or a heterocyclyl comprising at least one heteroatom selected from —O— or —N—, any of which having up to 10 carbon atoms; or 2) hydrogen.

2. A compound according to claim 1, wherein:

$R^4$ is selected from

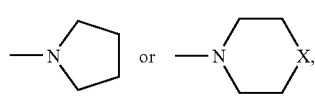

wherein X is selected from CH$_2$, O, NH, NMe, NEt, S, SO$_2$, or CH(OH); and $R^{11}$ and $R^{12}$, in each occurrence, are selected independently from $OCF_3$, OMe, Cl, F, $SO_2Me$, $CF_3$, Me, COMe, SMe, CONHMe, $NHSO_2Me$, $SO_2NH_2$, $SO_2NHMe$, $SO_2NMe_2$, $CONH_2$, $CONMe_2$, $CO_2Me$, $CO_2H$, —$OCH_2O$—, or OH.

3. A compound according to claim 1 selected from:

1-[2-(3-Chloro-4-methoxy-phenylamino)-6-phenyl-pyrimidin-4-yl]-piperidin-4-ol;
(4-Morpholin-4-yl-6-phenyl-pyrimidin-2-yl)-(4-trifluoromethoxy-phenyl)-amine;
4-[4-(4-Hydroxy-piperid in-1-yl)-6-phenyl-pyrimid in-2-ylamino]-N-methylbenzenesulfonamide;
1-{4-[4-(4-Hydroxy-piperid in-1-yl)-6-phenyl-pyrimid in-2-ylamino]-phenyl}-ethanone hydro chloride;
1-[2-(3-Chloro-4-hydroxy-phenylamino)-6-phenyl-pyrimidin-4-yl]-piperidin-4-ol;
1-[2-(3-Fluoro-4-methoxy-phenylamino)-6-phenyl-pyrimidin-4-yl]-piperidin-4-ol;
1-(6-Phenyl-2-phenylamino-pyrimidin-4-yl)-piperidin-4-ol;
(3-Chloro-4-methoxy-phenyl)-(4-phenyl-6-thiomorpholin-4-yl-pyrimidin-2-yl)-amine;
Benzo[1,3]dioxol-5-yl-(4-phenyl-6-thiomorpholin-4-yl-pyrimidin-2-yl)-amine;
(3-Fluoro-4-methoxy-phenyl)-(4-phenyl-6-thiomorpholin-4-yl-pyrimidin-2-yl)-amine;
2-Chloro-4-(4-phenyl-6-thiomorpholin-4-yl-pyrimidin-2-ylamino)-phenol;
(3-Chloro-4-methoxy-phenyl)-(4-morpholin-4-yl-6-phenyl-pyrimidin-2-yl)-amine;
Benzo[1,3]dioxol-5-yl-(4-morpholin-4-yl-6-phenyl-pyrimidin-2-yl)-amine;
(3-Fluoro-4-methoxy-phenyl)-(4-morpholin-4-yl-6-phenyl-pyrimidin-2-yl)-amine;
2-Chloro-4-(4-morpholin-4-yl-6-phenyl-pyrimidin-2-ylamino)-phenol;
1-[6-Phenyl-2-(3-trifluoromethyl-phenylamino)-pyrimidin-4-yl]-piperidin-4-ol;
Benzo[1,3]dioxol-5-yl-[4-(4-fluoro-phenyl)-6-morpholin-4-yl-pyrimidin-2-yl]-amine;
1-[2-Benzo[1,3]dioxol-5-ylamino)-6-phenyl-pyrimid in-4-yl]-piperdin-4-ol;
[4-(4-Fluoro-phenyl)-6-morpholin-4-yl-pyrimidin-2-yl]-(3-trifluoromethyl-phenyl)-amine
(4-Fluoro-phenyl)-[4-(4-fluoro-phenyl)-6-morpholin-4-yl-pyrimidin-2-yl]amine;
1-[2-(4-Chloro-3-trifluoromethyl-phenylamino)-6-phenyl-pyrimidin-4-yl]-piperidin-4-ol;
(4-Morpholin-4-yl-6-phenyl-pyrimidin-2-yl)-(3-trifluoromethyl-phenyl)-amine;
N-{4-[4-(4-Hydroxy-piperidin-1-yl)-6-phenyl-pyrimid in-2-ylamino]-phenyl}-methanesulfonamide;
N-[4-(4-Morpholin-4-yl-6-phenyl-pyrimidin-2-ylamino)-phenyl]-methanesulfonamide hydrochloride;
4-[4-(4-Fluoro-phenyl)-6-(4-hydroxy-piperid in-1-yl)-pyrimidin-2-ylamino]-N, N-dimethyl-benzenesulfonamide;
4-[4-(4-Fluoro-phenyl)-6-(4-hydroxy-piperidin-1-yl)-pyrimidin-2-ylamino]-benzenesulfonamide;
4-[4-(4-Hydroxy-piperidin-1-yl)-6-phenyl-pyrimidin-2-ylamino]-N, N-dimethyl-benzenesulfonamide;
4-[4-(4-Hydroxy-piperidin-1-yl)-6-phenyl-pyrimid in-2-ylamino]-benzenesulfonamide;
4-[4-(4-Fluoro-phenyl)-6-(4-hydroxy-piperidin-1-yl)-pyrimidin-2-ylamino]-N-methyl-benzenesulfonamide;
4-[4-(4-Hydroxy-piperidin-1-yl)-6-phenyl-pyrimidin-2-ylamino]-benzamide;
4-[4-(4-Hydroxy-piperidin-1-yl)-6-phenyl-pyrimid in-2-ylamino]-N-methyl-benzamide;
N-Methyl-4-(4-morpholin-4-yl-6-phenyl-pyrimid in-2-ylamino)-benzenesulfonamide;
N-Methyl-4-(4-morpholin-4-yl-6-phenyl-pyrimidin-2-ylamino)-benzamide;
3-[4-(4-Hydroxy-piperidin-1-yl)-6-phenyl-pyrimidin-2-ylamino]-benzamide;
1-{3-[4-(4-Hydroxy-piperid in-1-yl)-6-phenyl-pyrimid in-2-ylamino]-phenyl}-ethanone;
3-[4-(4-Hydroxy-piperidin-1-yl)-6-phenyl-pyrimidin-2-ylamino]-N-methyl-benzamide;
N-Methyl-3-(4-morpholin-4-yl-6-phenyl-pyrimid in-2-ylamino)-benzamide;
1-[4-(4-Morpholin-4-yl-6-phenyl-pyrimid in-2-ylamino)-phenyl]-ethanone;
3-(4-Morpholin-4-yl-6-phenyl-pyrimid in-2-ylamino)-benzamide;
1-[3-(4-Morpholin-4-yl-6-phenyl-pyrimidin-2-ylamino)-phenyl]-ethanone;
3-[4-(4-Hydroxy-piperidin-1-yl)-6-phenyl-pyrimidin-2-ylamina]-benzenesulfonamide;
3-(4-Morpholin-4-yl-6-phenyl-pyrimid in-2-ylamino)-benzenesulfonamide;
1-{4-[4-(4-Fluoro-phenyl)-6-morpholin-4-yl-pyrimid in-2-ylamino]-phenyl}-ethanone;
1-{4-[4-(4-Fluoro-phenyl)-6-(4-hydroxy-piperidin-1-yl)-pyrimidin-2-ylamino]-phenyl}-ethanone;
1-[6-Phenyl-2-(4-trifluoromethoxy-phenylamino)-pyrimidin-4-yl]-piperid in-4-ol;
(3-Chloro-4-methoxy-phenyl)-(4-phenyl-6-piperazin-1-yl-pyrimidin-2-yl)-amine;
Succinic acid mono-{1-[2-(3-chloro-4-methoxy-phenylamino)-6-phenyl-pyrimidin-4-yl]-piperidin-4-yl}ester;
(3-Chloro-4-methoxy-phenyl)-[4-(4-ethyl-piperazin-1-yl)-6-phenyl-pyrimid in-2-yl]-amine;
(3-Chloro-4-methoxy-phenyl)-[4-(4-methyl-piperazin-1-yl)-6-phenyl-pyrimidin-2-yl]-amine;
[4-(1,1-Dioxo-1-lambda-6-thiomorpholin-4-yl)-6-phenyl-pyrimidin-2-yl]-(3-fluoro-4-methoxy-phenyl)-amine;
1-[2-(4-Methanesulfonyl-phenylamino)-6-phenyl-pyrimidin-4-yl]-piperidin-4-ol;
[4,6-Bis-(4fluoro-phenyl)-pyrimidin-2-yl]-(4-trifluoromethoxy-phenyl)-amine;
[4-(3-Methanesulfonyl-phenyl)-6-morpholin-4-yl-pyrimidin-2-yl]-(4-trifluoromethoxyphenyl)-amine;
1-{4-[4-(4-Hydroxy-piperid in-1-yl)-6-phenyl-pyrimid in-2-ylamino]-phenyl}-ethanone;
1-[2-(4-methylsulfanyl-phenylamino)-6-phenyl-pyrimidin-4-yl]-piperidin-4-ol; or any combination thereof;
or a salt thereof.

4. A pharmaceutical composition comprising a pharmaceutically acceptable carrier and a compound selected from:

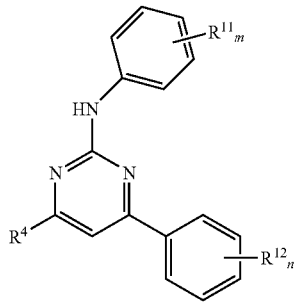

wherein:
R⁴ is selected from a substituted or an unsubstituted heterocyclyl comprising at least one heteroatom or heterogroup selected from —O—, —NH—, —S—, or, any of which having up to 10 carbon atoms;
n and m are independently an integer from 0 to 3, inclusive;
R⁴ is optionally substituted with at least one group independently selected from: 1) an alkyl, —COR⁹, —CO₂R⁸, —CONR⁸₂, —SO₂R⁹, or, —SO₂NR¹⁰₂ any of which having up to 10 carbon atoms; or 2) hydroxyl;
R⁸, in each occurrence, is selected independently from: 1) an alkyl, a haloalkyl, or an aryl having up to 6 carbon atoms; or 2) hydrogen;
R⁹, in each occurrence, is selected independently from an alkyl, a haloalkyl, an aryl, or a heterocyclyl or a heteroaryl comprising at least one heteroatom selected from —O— or —N—, any of which having up to 10 carbon atoms; and
R¹⁰, in each occurrence, is selected independently from: 1) an alkyl, an aryl, or a heterocyclyl comprising at least one heteroatom selected from —O— or —N—, any of which having up to 10 carbon atoms; or 2) hydrogen;
R¹¹ and R¹², in each occurrence, are selected independently from: 1) an alkyl, an alkoxy, a haloalkyl, a haloalkoxy, —COR⁹, —CONR⁸₂, —CO²R₈, SO₂R⁹, SR⁸, NHSO₂R⁹, or —SO²NR⁸₂, any of which having up to 10 carbon atoms; or 2) halogen, hydroxyl, or —OCH₂O—;
or a pharmaceutically acceptable salt thereof.

5. The composition as claimed in claim 4, wherein the composition is in the form of a tablet, a capsule, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash.

6. A pharmaceutical composition according to claim 4 comprising pharmaceutically acceptable carrier and a compound selected from:
1-[2-(3-Chloro-4-methoxy-phenylamino)-6-phenyl-pyrimidin-4-yl]-piperidin-4-ol;
(4-Morpholin-4-yl-6-phenyl-pyrimidin-2-yl)-(4-trifluoromethoxy-phenyl)-amine;
4-[4-(4-Hydroxy-piperidin-1-yl)-6-phenyl-pyrimid in-2-ylamino]-N-methylbenzenesulfonamide;
1-{4-[4-(4-Hydroxy-piperidin-1-yl)-6-phenyl-pyrimidin-2-ylamino]-phenyl}-ethanone hydro chloride;
1-[2-(3-Chloro-4-hydroxy-phenylamino)-6-phenyl-pyrimidin-4-yl]-piperidin-4-ol;
1-[2-(3-Fluoro-4-methoxy-phenylamino)-6-phenyl-pyrimidin-4-yl]-piperidin-4-ol;
1-(6-Phenyl-2-phenylamino-pyrimidin-4-yl)-piperidin-4-ol;
(3-Chloro-4-methoxy-phenyl)-(4-phenyl-6-thiomorpholin-4-yl-pyrimidin-2-yl)-amine;
Benzo[1,3]dioxol-5-yl-(4-phenyl-6-thiomorpholin-4-yl-pyrimidin-2-yl)-amine;
(3-Fluoro-4-methoxy-phenyl)-(4-phenyl-6-thiomorpholin-4-yl-pyrimidin-2-yl)-amine;
2-Chloro-4-(4-phenyl-6-thiomorpholin-4-yl-pyrimidin-2-ylamino)-phenol;
(3-Chloro-4-methoxy-phenyl)-(4-morpholin-4-yl-6-phenyl-pyrimidin-2-yl)-amine;
Benzo[1,3]dioxol-5-yl-(4-morpholin-4-yl-6-phenyl-pyrimidin-2-yl)-amine;
(3-Fluoro-4-methoxy-phenyl)-(4-morpholin-4-yl-6-phenyl-pyrimidin-2-yl)-amine;
2-Chloro-4-(4-morpholin-4-yl-6-phenyl-pyrimid in-2-ylamino)-phenol;
1-[6-Phenyl-2-(3-trifluoromethyl-phenylamino)-pyrimidin-4-yl]-piperidin-4-ol;
Benzo[1,3]dioxol-5-yl-[4-(4-fluoro-phenyl)-6-morpholin-4-yl-pyrimidin-2-yl]-amine;
1-[2-(Benzo[1,3]dioxol-5-ylamino)-6-phenyl-pyrimidin-4-yl]-piperidin-4-ol;
[4-(4-Fluoro-phenyl)-6-morpholin-4-yl-pyrimidin-2-yl]-(3-trifluoromethyl-phenyl)-amine;
(4-Fluoro-phenyl)-[4-(4-fluoro-phenyl)-6-morpholin-4-yl-pyrimidin-2-yl]-amine;
1-[2-(4-Chloro-3-trifluoromethyl-phenylamino)-6-phenyl-pyrimidin-4-yl]-piperidin-4-ol;
(4-Morpholin-4-yl-6-phenyl-pyrimidin-2-yl)-(3-trifluoromethyl-phenyl)-amine;
N-{4-[4-(4-Hydroxy-piperidin-1-yl)-6-phenyl-pyrimid in-2-ylamino]-phenyl}-methanesulfonamide;
N-[4-(4-Morpholin-4-yl-6-phenyl-pyrimidin-2-ylamino)-phenyl]-methanesulfonamide hydrochloride;
4-[4-(4-Fluoro-phenyl)-6-(4-hydroxy-piperidin-1-yl)-pyrimidin-2-ylamino]-N,N-dimethyl-benzenesulfonamide;
4-[4-(4-Fluoro-phenyl)-6-(4-hydroxy-piperid in-1-yl)-pyrimidin-2-ylamino]-benzenesulfonamide;
4-[4-(4-Hydroxy-piperid in-1-yl)-6-phenyl-pyrimidin-2-ylamino]-N, N-dimethyl-benzenesulfonamide;
4-[4-(4-Hydroxy-piperidin-1-yl)-6-phenyl-pyrimidin-2-ylamino]-benzenesulfonamide;
4-[4-(4-Fluoro-phenyl)-6-(4-hydroxy-piperidin-1-yl)-pyrimidin-2-ylamino]-N-methyl-benzenesulfonamide;
4-[4-(4-Hydroxy-piperidin-1-yl)-6-phenyl-pyrimidin-2-ylamino]-benzamide;
4-[4-(4-Hydroxy-piperidin-1-yl)-6-phenyl-pyrimidin-2-ylamino]-N-methyl-benzamide;
N-Methyl-4-(4-morpholin-4-yl-6-phenyl-pyrimidin-2-ylamino)-benzenesulfonamide;
N-Methyl-4-(4-morpholin-4-yl-6-phenyl-pyrimidin-2-ylamino)-benzamide;
3-[4-(4-Hydroxy-piperidin-1-yl)-6-phenyl-pyrimidin-2-ylamino]-benzamide;
1-{3-[4-(4-Hydroxy-piperidin-1-yl)-6-phenyl-pyrimidin-2-ylamino]-phenyl}-ethanone;
3-[4-(4-Hydroxy-piperidin-1-yl)-6-phenyl-pyrimid in-2-ylamino]-N-methyl-benzamide;
N-Methyl-3-(4-morpholin-4-yl-6-phenyl-pyrimidin-2-ylamino)-benzamide;
1-[4-(4-Morpholin-4-yl-6-phenyl-pyrimid in-2-ylamino)-phenyl]-ethanone;

3-(4-Morpholin-4-yl-6-phenyl-pyrimidin-2-ylamino)-benzamide;
1-[3-(4-Morpholin-4-yl-6-phenyl-pyrimidin-2-ylamino)-phenyl]-ethanone;
3-[4-(4-Hydroxy-piperidin-1-yl)-6-phenyl-pyrimidin-2-ylamino]-benzenesulfonamide;
3-(4-Morpholin-4-yl-6-phenyl-pyrimidin-2-ylamino)-benzenesulfonamide;
1-{4-[4-(4-Fluoro-phenyl)-6-morpholin-4-yl-pyrimidin-2-ylamino]-phenyl}-ethanone;
1-{4-[4-(4-Fluoro-phenyl)-6-(4-hydroxy-piperidin-1-yl)-pyrimidin-2-ylamino]-phenyl}-ethanone;
1-[6-Phenyl-2-(4-trifluoromethoxy-phenylamino)-pyrimidin-4-yl]-piperidin-4-ol;
(3-Chloro-4-methoxy-phenyl)-(4-phenyl-6-piperazin-1-yl-pyrimidin-2-yl)-amine;
Succinic acid mono-{1-[2-(3-chloro-4-methoxy-phenylamino)-6-phenyl-pyrimidin-4-yl]-piperidin-4-yl}ester;
(3-Chloro-4-methoxy-phenyl)-[4-(4-ethyl-piperazin-1-yl)-6-phenyl-pyrimid in-2-yl]-amine;
(3-Chloro-4-methoxy-phenyl)-[4-(4-methyl-piperazin-1-yl)-6-phenyl-pyrimidin-2-yl]-amine;
[4-(1,1-Dioxo-1-lambda-6-thiomorpholin-4-yl)-6-phenyl-pyrimidin-2-yl]-(3-fluoro-4-methoxy-phenyl)-amine;
1-[2-(4-Methanesulfonyl-phenylamino)-6-phenyl-pyrimidin-4-yl]-piperidin-4-ol;
[4,6-8 is-(4-fluoro-phenyl)-pyrimidin-2-yl]-(4-trifluoromethoxy-phenyl)-amine;
[4-(3-Methanesulfonyl-phenyl)-6-morpholin-4-yl-pyrimidin-2-yl]-(4-trifluoromethoxy-phenyl)-amine;
1-{4-[4-(4-Hydroxy-piperidin-1-yl)-6-phenyl-pyrimidin-2-ylamino]-phenyl}-ethanone;
1-[2-(4-methylsulfanyl-phenylamino)-6-phenyl-pyrimidin-4-yl]-piperidin-4-ol;
or any combination thereof;
or a pharmaceutically acceptable salt thereof.

7. The composition as claimed in claim 6, further comprising:
optionally, a pharmaceutically acceptable auxiliary;
optionally, a pharmaceutically acceptable preservative;
optionally, a pharmaceutically acceptable excipient;
optionally, a pharmaceutically acceptable diluent; and
optionally, a pharmaceutically acceptable solvate.

8. The composition as claimed in claim 6, wherein the composition is in the form of a tablet, a capsule, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash.

9. The compound of claim 3 wherein the compound is 1-{4-[4-(4Hydroxy-piperidin-1-yl)-6-phenyl-pyrimidine-2-ylamino]-phenyl)-ethanone.

* * * * *